(12) United States Patent
Farwell et al.

(10) Patent No.: US 10,501,762 B2
(45) Date of Patent: Dec. 10, 2019

(54) METHODS AND SYSTEMS FOR SULFIMIDATION OR SULFOXIMIDATION OF ORGANIC MOLECULES

(71) Applicant: The California Institute of Technology, Pasadena, CA (US)

(72) Inventors: Christopher C. Farwell, Thousand Oaks, CA (US); John A. McIntosh, Pasadena, CA (US); Frances H. Arnold, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 331 days.

(21) Appl. No.: 15/208,573

(22) Filed: Jul. 12, 2016

(65) Prior Publication Data

US 2016/0355852 A1 Dec. 8, 2016

Related U.S. Application Data

(62) Division of application No. 14/625,514, filed on Feb. 18, 2015, now Pat. No. 9,399,762.

(60) Provisional application No. 61/976,927, filed on Apr. 8, 2014, provisional application No. 61/941,197, filed on Feb. 18, 2014.

(51) Int. Cl.
*C12P 13/00* (2006.01)
*C12N 9/02* (2006.01)

(52) U.S. Cl.
CPC .......... *C12P 13/001* (2013.01); *C12N 9/0042* (2013.01); *C12P 13/00* (2013.01); *C12Y 106/02004* (2013.01); *C12Y 114/14001* (2013.01)

(58) Field of Classification Search
None
See application file for complete search history.

(56) References Cited

U.S. PATENT DOCUMENTS

| | | | |
|---|---|---|---|
| 3,965,204 A | 6/1976 | Lukas et al. | |
| 5,296,595 A | 3/1994 | Doyle | |
| 5,703,246 A | 12/1997 | Aggarwal et al. | |
| 7,267,949 B2 | 9/2007 | Richards et al. | |
| 7,625,642 B2 | 12/2009 | Matsutani et al. | |
| 7,662,969 B2 | 2/2010 | Doyle et al. | |
| 7,863,030 B2 | 1/2011 | Arnold et al. | |
| 8,247,430 B2 | 8/2012 | Yuan | |
| 2006/0030718 A1 | 2/2006 | Zhang et al. | |
| 2006/0111347 A1 | 5/2006 | Askew, Jr. et al. | |
| 2007/0276013 A1 | 11/2007 | Ebbinghaus et al. | |
| 2009/0238790 A2 | 9/2009 | Sommadossi et al. | |
| 2010/0056806 A1 | 3/2010 | Warren | |
| 2010/0168463 A1 | 7/2010 | Hirata et al. | |
| 2010/0240106 A1 | 9/2010 | Wong et al. | |
| 2011/0196086 A1 | 8/2011 | Matsushita et al. | |
| 2012/0237591 A1 | 9/2012 | Cullis et al. | |

FOREIGN PATENT DOCUMENTS

| | | |
|---|---|---|
| EP | 0 200 638 B1 | 4/1986 |
| WO | 2007/144599 A2 | 12/2007 |
| WO | 2011/159550 A3 | 12/2011 |

OTHER PUBLICATIONS

Adams, P.D. et al., "Phenix: a comprehensive Python-based system for macromolecular structure solution," Acta Crystallogr., Sect. D, Biol. Crystallogr., 2010, D66(2):213-221.
Ajikumar, P.K. et al., "Isoprenoid pathway optimization for taxol precursor overproduction in *Escherichia coli*", Science, 2010, 330:70-74.
Atschul, S.F. et al., "Basic local alignment search tool," J. Mol. Biol., 1990, 215(3): 403-10.
Bergman, R.G., "Organometallic chemistry: C-H activation," Nature, 2007, 446(7134):391-393.
Bloom, J.D. et al., "Protein stability promotes evolvability," Proc. Natl. Acad. Sci. USA, 2006, 103(15):5869-5874.
Bornscheur, U.T. and R.J. Kazlauskas, "Reaction specificity of enzymes: Catalytic promiscuity in biocatalysis: Using old enzymes to form new bonds and follow new pathways," Angew. Chem., Int. Ed., 2004, 43(45):6032-6040.
Boyce, M. and C.R. Bertozzi, "Bringing chemistry to life," Nat. Methods, 2011, 8(8):638-642.
Breslow, R., "Biomimetic chemistry: Biology as an inspiration," J. Biol. Chem., 2009, 284(3): 1337-1342.
Chen, M.S. and M.C. White, "A predictably selective aliphatic C-H oxidation reaction for complex molecule synthesis," Science, 2007, 318(5851):783-787.
Cirino, P.C. and F.H. Arnold, "A self-sufficient peroxide-driven hydroxylation biocatalyst," Angew. Chem., Int. Ed., 2003, 42(28):3299-3301.
Clark, J.P. et al., "The role of Thr268 and Phe393 in cytochrome P 450 BM3," J. Inorg. Biochem., 2006, 100(5-6): 1075-1090.
Coelho, P.S. et al., "A serine-substituted P450 catalyzes highly efficient carbene transfer to olefins in vivo," Nat. Chem. Biol., 2013, 9(8):485-487.
Coelho, P.S. et al., "Olefin Cyclopropanation via Carbene Transfer Catalyzed by Engineered Cytochrome P450 Enzymes," Science, 2013, 339(6117):307-310.
Davies, H.M.L. and J.R. Manning, "Catalytic C-H functionalization by metal carbenoid and nitrenoid insertion," Nature, 2008, 451(7177), 417-424.
Davies, H.M.L. and R.E.J. Beckwith, "Catalytic Enantioselective C-H Activation by Means of Metal-Carbenoid-Induced C-H Insertion," Chem. Rev., 2003, 103 (8), pp. 2861-2904.
Donaldson, W.A., "Synthesis of cyclopropane containing natural products," Tetrahedron, 2001, 57(41): 8589-8627.
Dunford, A.J. et al., "Probing the molecular determinants of coenzyme selectivity in the P450 BM3 FAD/NADPH domain," Biochim Biophys Acta., 2009,1794(8):1181-1189.
Emsley, P. and K. Cowtan, "Coot: model-building tools for molecular graphics," Acta Crystallogr., Sect. D., Biol. Crystallogr., 2004, D60(12, Pt. 1):2126-2132.

(Continued)

*Primary Examiner* — Paul J Holland

(74) *Attorney, Agent, or Firm* — Gavrilovich, Dodd & Lindsey LLP

(57) ABSTRACT

The disclosure generally relates to the fields of synthetic organic chemistry. In particular, the present disclosure relates to methods and systems for the imidation of sulfides.

12 Claims, 27 Drawing Sheets

Specification includes a Sequence Listing.

(56) References Cited

OTHER PUBLICATIONS

Evans, P., "Scaling and assessment of data quality," Acta Crystallogr., Sect. D, Biol. Crystallogr., 2006, D62(1):72-82.
Girvan et al., "Glutamate—haem ester bond formation is disfavoured in flavocytochrome P450 BM3: characterization of glutamate substitution mutants at the haem site of P450 BM3," Biochemical Journal, 2010, 455-466.
Groves, J.T., "The bioinorganic chemistry of iron in oxygenases and supramolecular assemblies," PNAS, Apr. 1, 2003, vol. 100, No. 7, 3569-3574.
Haines, D.C. et al., "Pivotal Role of Water in the Mechanism of P450BM-3+," Biochemistry, 2001, 40:13456-13465.
Hiraga, K. and F.H. Arnold, "General Method for Sequence-independent Site-directed Chimeragenesis," J. Mol. Biol. (2003) 330, 287-296.
Hüttinger, K., "Semi-synthetic proteins for catalytic and analytical applications," in Chemistry and Biochemistry, May 2009, Georgia Institute of Technology.
Hyster, T.K. et al., "Biotinylated Rh(III) Complex in Engineered Streptavidin for Accelerated Asymmetric C-H Activation," Science, 2012, 338(6106):500-503.
Isin, E.M. and F.P. Guengerich, "Complex reactions catalyzed by cytochrome P450 enzymes," Biochimica Biophysica Acta Gen. Subj., Mar. 2007, vol. 1770, Issue 3, pp. 314-329.
Kabsch, W., "Integration, scaling, space-group assignment and post-refinement," Acta Crystallogr., Sect. D, Biol. Crystallogr., Sect. D, Biol. Crystallogr., 2010, D66(2):133-144.
Kataoka, M. et al., "Novel bioreduction system for the production of chiral alcohols," Appl. Microbiol. Biotechnol. 2003, 62(5-6):437-45.
Lebel, H. et al., "Stereoselective cyclopropanation reactions", Chem. Rev., 2003, 103(4): 977-1050.
Lewis, J.C. and F.H. Arnold, "Catalysts on demand: selective oxidations by laboratory-evolved cytochrome P450 BM3," Chimia, 2009, 63(6):309-312.
Lewis, J.C. et al., "Chemoenzymatic elaboration of monosaccharides using engineered cytochrome P450BM3 demethylases," PNAS, 2009, 106(39), 16550-16555.
Lewis, J.C. et al., "Combinatorial Alanine Substitution Enables Rapid Optimization of Cytochrome P450BM3 for Selective Hydroxylation of Large Substrates," Chembiochem, 2010, 11(18), 2502-05.
Mansuy, D. et al., "Reaction of carbon tetrachloride with 5,10,15,20-tetraphenyl-porphinatoiron(II)[(TPP)FeII]: evidence for the formation of the carbene complex [(TPP)FeII(CCI2)]," J. Chem. Soc., Chem. Commun., 1977, 648-649.
Meinhold, P. et al., "Engineering Cytochrome P450 BM3 for Terminal Alkane Hydroxylation," Adv. Synth. Catal. 2006, 348, 763-772.
Morandi, B., and E.M. Carreira, "Iron-catalyzed cyclopropanation in 6 M KOH with in situ generation of diazomethane," Science, 2012, 335(6075): 1471-1474.
Nakagawa, S. et al., "Construction of Catalase Deficient *Escherichia coli* Strains for the Production of Uricase," Biosci. Biotechnol. Biochem., 1996, 60(3): 415-20.
Narhi, L.O. and A.J. Fulco, "Characterization of a catalytically self-sufficient 119,000-dalton cytochrome P-450 monooxygenase induced by barbiturates in *Bacillus megaterium*", J. Biol. Chem., 1986, 261(16):7160-9.
Nelson, D.R., "The cytochrome P450 homepage," Hum. Genomics, 2009, 4(1):59-65.
Omura, T. and R. Sato, "The carbon monoxide-binding pigment of liver microsomes. I. Evidence for its hemoprotein nature," J. Biol. Chem., 1964, 239(7):2370-8.
Ost, T.W.B. et al., "Phenylalanine 393 exerts thermodynamic control over the heme of flavocytochrome P450 BM3," Biochemistry, 2001, 40(45):13421-13429.
Otey, C.R. et al., "Structure-guided recombination creates an artificial family of cytochromes P450," PLoS Biol., 2006, 4(5)789-798.
Perera, R. et al., "Molecular basis for the inability of an oxygen atom donor ligand to replace the natural sulfur donor heme axial ligand in cytochrome P450 catalysis. Spectroscopic characterization of the Cys436Ser CYP2B4 mutant," Arch. Biochem. Biophys., 2011, 507(1):119-125.
Preissner, S. et al., "SuperCYP: a comprehensive database on Cytochrome P450 enzymes including a tool for analysis of CYP-drug interactions," Nucleic Acids Res., 2010, 38(Database issue):D237-43.
Raphael, A.L. and H.B. Gray, "Semisynthesis of axial-ligand (position 80) mutants of cytochrome c," J. Am. Chem. Soc., 1991, 113(3):1038-40.
Reedy, C.J. et al., "Development of a heme protein structure-electrochemical function database," Nucleic Acids Res., 2008, 36(Database Iss.):D307-D313.
Rosenberg, M.L. et al., "Highly cis-Selective Cyclopropanations with Ethyl Diazoacetate Using a Novel Rh(I) Catalyst with a Chelating N-Heterocyclic Iminocarbene Ligand," Org. Lett., 2009, 11(3), 547-50.
Ruppel, J.V. et al., "Cobalt-Catalyzed Intramolecular C-H Amination with Arylsulfonyl Azides," Org. Lett., 2007, 9(23):4889-4892.
Setsune, J.I. and D. Dolphin, "Organometallic aspects of cytochrome P-450 metabolism," Can. J. Chem., 1987, 65(3):459-67.
Siegel, J.B. et al., "Computational design of an enzyme catalyst for a stereoselective biomolecular Diels-Alder reaction," Science, 2010, 329(5989):309-313.
Sirim, D. et al., "The Cytochrome P450 Engineering Database: integration of biochemical properties," BMC Biochemistry 2009, 10:27.
Vagin, A. and A. Teplyakov, "MOLREP: an automated program for molecular replacement," J. Appl. Cryst., 1997, 30(6):1022-1025.
Vatsis, K.P. et al., "Replacement of active-site cysteine-436 by serine converts cytochrome P450 2B4 into an NADPH oxidase with negligible monooxygenase activity," Journal of Inorganic Biochemistry, 2002, 91(4): 542-553.
Westfall, P.J. et al., "Production of amorphadiene in yeast, and its conversion to dihydroartemisinic acid, precursor to the antimalarial agent artemisinin," Proc. Natl. Acad. Sci. USA, 2012, 109(3):E111-E-118.
Whitehouse, C.J.C. et al., "450BM3 (CYP102A1): connecting the dots," Chem. Soc. Rev., 2012, 41(3):1218-1260.
Wolf, J.R. et al., "Shape and stereoselective cyclopropanation of alkenes catalyzed by iron porphyrins," J. Am. Chem. Soc., 1995, 117(36):9194-9.
Wuttke, D.S. and H.B. Gray, "Protein engineering as a tool for understanding electron transfer," Curr. Opin. Struct. Biol., 1993, 3(4):555-563.
Yeom et al., "The Role of Thr268 in Oxygen Activation of Cytochrome P450BM3," Biochemistry, 1995, vol. 34, pp. 14733-14740.
Yoshioka, S. et al., Roles of the Proximal Hydrogen Bonding Network in Cytochrome P450cam-Catalyzed Oxygenation, J. Am. Chem. Soc., 2002, 124 (49), pp. 14571-14579.

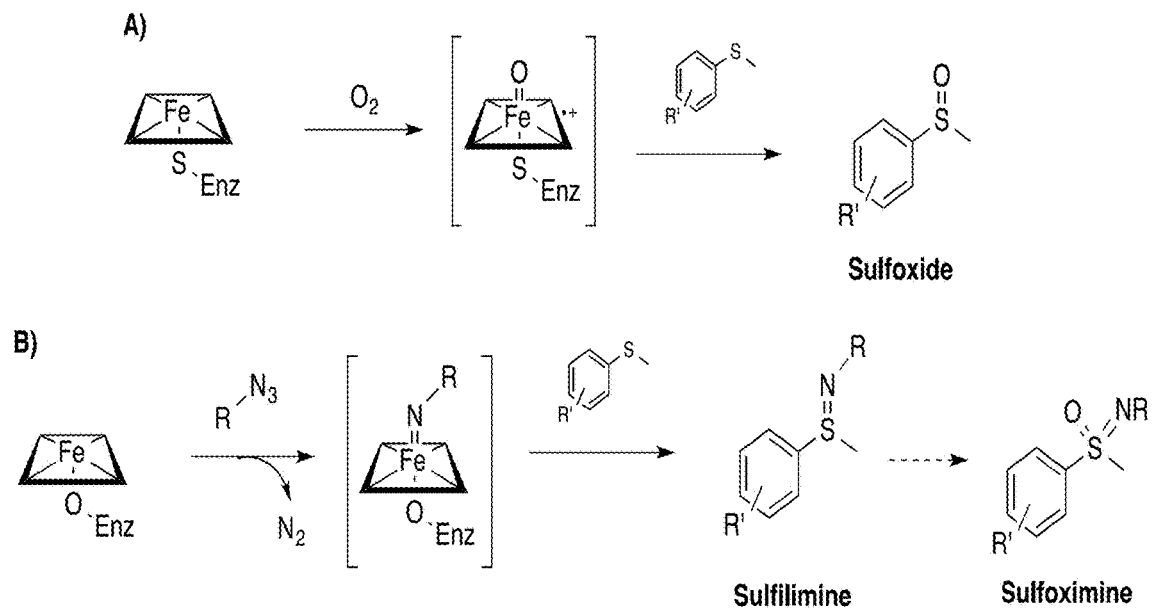
FIGURE 1A-B
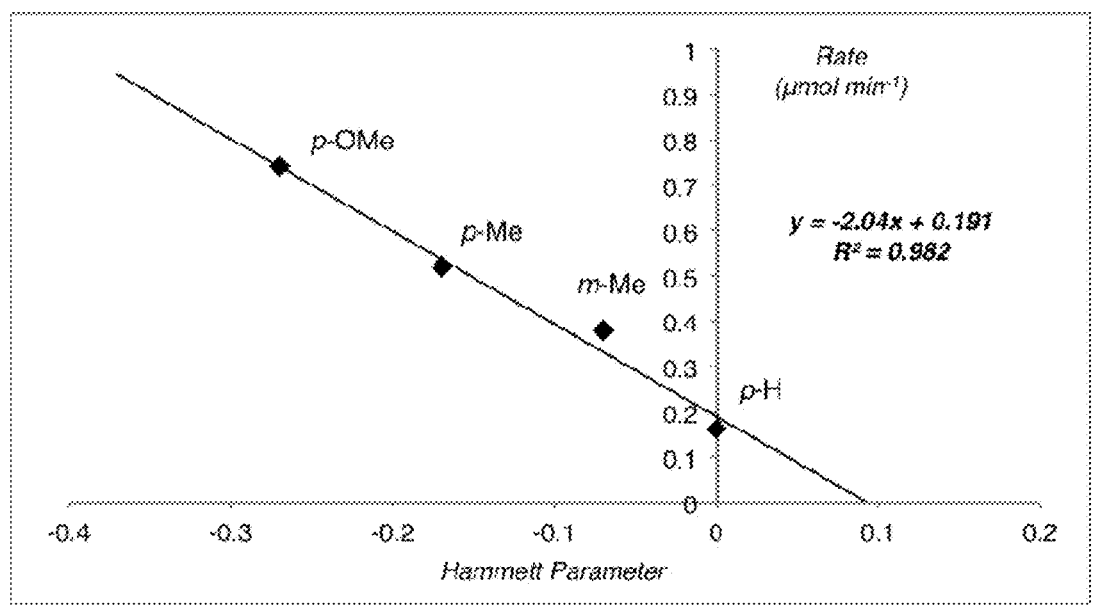
FIGURE 2

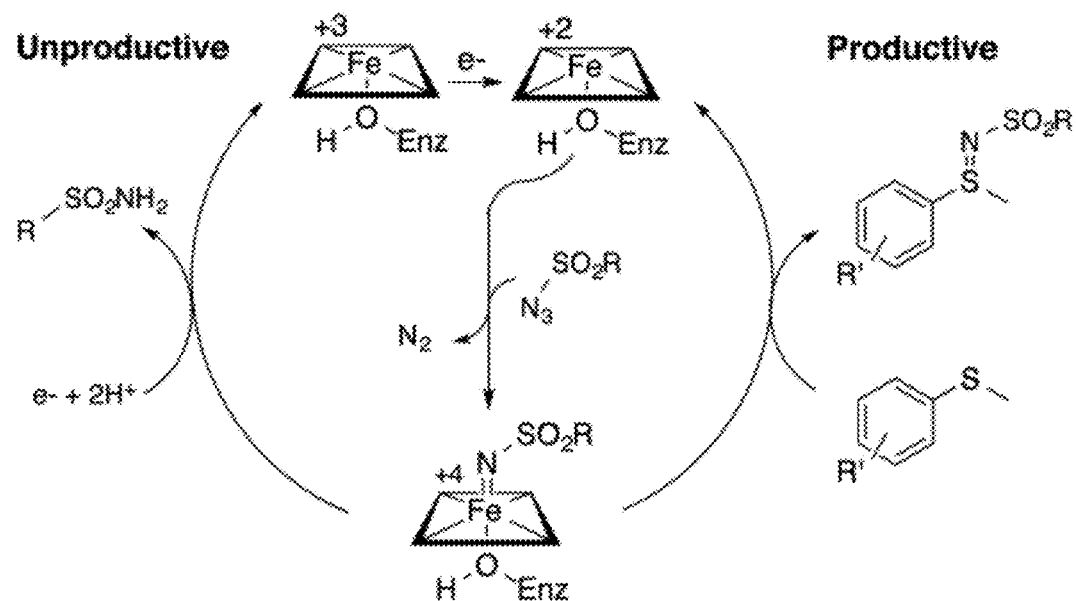
FIGURE 3
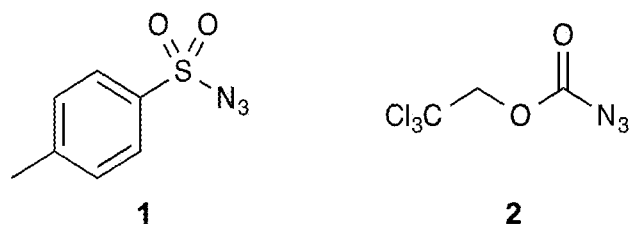
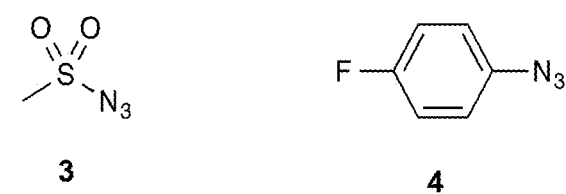
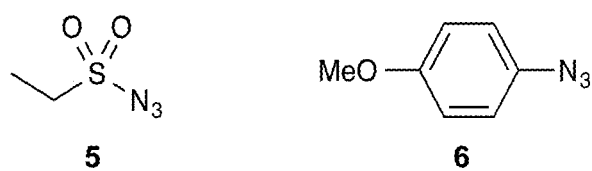
FIGURE 4

FIGURE 8A-D

SEQUENCE LISTING

<160> NUMBER OF SEQ ID NOS: 49

<210> SEQ ID NO 1
<211> LENGTH: 1048
<212> TYPE: PRT
<213> ORGANISM: Bacillus megaterium
<220> FEATURE:
<223> OTHER INFORMATION: cytochrome P450:NADPH-P-450 reductase
    precursor, cytochrome P450 (BM3), CYP102A1

<400> SEQUENCE: 1

```
Thr Ile Lys Glu Met Pro Gln Pro Lys Thr Phe Gly Glu Leu Lys Asn
1               5                   10                  15
Leu Pro Leu Leu Asn Thr Asp Lys Pro Val Gln Ala Leu Met Lys Ile
            20                  25                  30
Ala Asp Glu Leu Gly Glu Ile Phe Lys Phe Glu Ala Pro Gly Arg Val
        35                  40                  45
Thr Arg Tyr Leu Ser Ser Gln Arg Leu Ile Lys Glu Ala Cys Asp Glu
    50                  55                  60
Ser Arg Phe Asp Lys Asn Leu Ser Gln Ala Leu Lys Phe Val Arg Asp
65                  70                  75                  80
Phe Ala Gly Asp Gly Leu Phe Thr Ser Trp Thr His Glu Lys Asn Trp
                85                  90                  95
Lys Lys Ala His Asn Ile Leu Leu Pro Ser Phe Ser Gln Gln Ala Met
            100                 105                 110
Lys Gly Tyr His Ala Met Met Val Asp Ile Ala Val Gln Leu Val Gln
        115                 120                 125
Lys Trp Glu Arg Leu Asn Ala Asp Glu His Ile Glu Val Pro Glu Asp
    130                 135                 140
Met Thr Arg Leu Thr Leu Asp Thr Ile Gly Leu Cys Gly Phe Asn Tyr
145                 150                 155                 160
Arg Phe Asn Ser Phe Tyr Arg Asp Gln Pro His Pro Phe Ile Thr Ser
                165                 170                 175
Met Val Arg Ala Leu Asp Glu Ala Met Asn Lys Leu Gln Arg Ala Asn
            180                 185                 190
Pro Asp Asp Pro Ala Tyr Asp Glu Asn Lys Arg Gln Phe Gln Glu Asp
        195                 200                 205
Ile Lys Val Met Asn Asp Leu Val Asp Lys Ile Ile Ala Asp Arg Lys
    210                 215                 220
Ala Ser Gly Glu Gln Ser Asp Asp Leu Leu Thr His Met Leu Asn Gly
225                 230                 235                 240
Lys Asp Pro Glu Thr Gly Glu Pro Leu Asp Asp Glu Asn Ile Arg Tyr
                245                 250                 255
Gln Ile Ile Thr Phe Leu Ile Ala Gly His Glu Thr Thr Ser Gly Leu
            260                 265                 270
Leu Ser Phe Ala Leu Tyr Phe Leu Val Lys Asn Pro His Val Leu Gln
        275                 280                 285
Lys Ala Ala Glu Glu Ala Ala Arg Val Leu Val Asp Pro Val Pro Ser
    290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Leu Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
    370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
```

```
Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830
```

-continued

```
Ser Ser Pro Arg Val Asp Glu Lys Gln Ala Ser Ile Thr Val Ser Val
            835                 840                 845

Val Ser Gly Glu Ala Trp Ser Gly Tyr Gly Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val Ser
        1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 2
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V9,
      CYP102A1

<400> SEQUENCE: 2

Met Thr Ile Lys Glu Met Pro Gln Pro Lys Thr Phe Gly Glu Leu Lys
1               5                   10                  15

Asn Leu Pro Leu Leu Asn Thr Asp Lys Pro Ile Gln Thr Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Thr Asp Glu His Ile Glu Val Pro Glu
    130                 135                 140
```

-continued

```
Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
            165                 170                 175

Ser Met Val Arg Ala Leu Asp Glu Ala Met Asn Lys Leu Gln Arg Ala
        180                 185                 190

Asn Pro Asp Asp Pro Ala Tyr Asp Glu Asn Lys Arg Gln Phe Gln Glu
    195                 200                 205

Asp Ile Lys Val Met Asn Asp Leu Val Asp Lys Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Ala Ala Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
        340                 345                 350

Glu Leu Met Val Leu Ile Pro Gln Leu His Arg Asp Lys Thr Ile Trp
    355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
        420                 425                 430

Asp Ile Lys Glu Thr Leu Thr Leu Lys Pro Glu Gly Phe Val Val Lys
    435                 440                 445

Ala Lys Ser Lys Gln Ile Pro Leu Gly Gly Ile Pro Ser Pro Ser Arg
450                 455                 460

Glu Gln Ser Ala Lys Lys Glu Arg Lys Thr Val Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
        500                 505                 510

Gln Val Ala Thr Leu Asp Ser His Ala Gly Asn Leu Pro Arg Glu Gly
    515                 520                 525

Ala Val Leu Ile Val Thr Ala Ser Tyr Asn Gly His Pro Pro Asp Asn
530                 535                 540

Ala Lys Glu Phe Val Asp Trp Leu Asp Gln Ala Ser Ala Asp Glu Val
545                 550                 555                 560
```

-continued

```
Lys Gly Val Arg Tyr Ser Val Phe Gly Cys Gly Asp Lys Asn Trp Ala
            565                 570                 575
Thr Thr Tyr Gln Lys Val Pro Ala Phe Ile Asp Glu Thr Leu Ala Ala
            580                 585                 590
Lys Gly Ala Glu Asn Ile Ala Glu Arg Gly Glu Ala Asp Ala Ser Asp
            595                 600                 605
Asp Phe Glu Gly Thr Tyr Glu Glu Trp Arg Glu His Met Trp Ser Asp
610                 615                 620
Leu Ala Ala Tyr Phe Asn Leu Asp Ile Glu Asn Ser Glu Glu Asn Ala
625                 630                 635                 640
Ser Thr Leu Ser Leu Gln Phe Val Asp Ser Ala Ala Asp Met Pro Leu
            645                 650                 655
Ala Lys Met His Arg Ala Phe Ser Ala Asn Val Val Ala Ser Lys Glu
            660                 665                 670
Leu Gln Lys Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
            690                 695                 700
Pro Arg Asn Tyr Glu Gly Ile Val Asn Arg Val Ala Thr Arg Phe Gly
705                 710                 715                 720
Leu Asp Ala Ser Gln Gln Ile Arg Leu Glu Ala Glu Glu Lys Leu
            725                 730                 735
Ala His Leu Pro Leu Gly Lys Thr Val Ser Val Glu Leu Leu Gln
            740                 745                 750
Tyr Val Glu Leu Gln Asp Pro Val Thr Arg Thr Gln Leu Arg Ala Met
            755                 760                 765
Ala Ala Lys Thr Val Cys Pro Pro His Lys Val Glu Leu Glu Val Leu
            770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Glu Phe Ser
            805                 810                 815
Glu Phe Ile Ala Leu Leu Pro Ser Met Arg Pro Arg Tyr Tyr Ser Ile
            820                 825                 830
Ser Ser Ser Pro Arg Val Asp Glu Lys Gln Ala Ser Ile Thr Val Ser
            835                 840                 845
Val Val Ser Gly Glu Ala Trp Ser Gly Tyr Gly Glu Tyr Lys Gly Ile
            850                 855                 860
Ala Ser Asn Tyr Leu Ala Asn Leu Gln Glu Gly Asp Thr Ile Thr Cys
865                 870                 875                 880
Phe Val Ser Thr Pro Gln Ser Gly Phe Thr Leu Pro Lys Gly Pro Glu
            885                 890                 895
Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
            915                 920                 925
Gly Glu Ala His Leu Tyr Phe Gly Cys Arg Ser Pro His Glu Asp Tyr
            930                 935                 940
Leu Tyr Gln Lys Glu Leu Glu Asn Ala Gln Asn Glu Gly Ile Ile Thr
945                 950                 955                 960
Leu His Thr Ala Phe Ser Arg Val Pro Asn Gln Pro Lys Thr Tyr Val
            965                 970                 975
Gln His Val Met Glu Gln Asp Gly Lys Lys Leu Ile Glu Leu Leu Asp
```

```
            980             985              990
Gln Gly Ala His Phe Tyr Ile Cys Gly Asp Gly Ser Gln Met Ala Pro
            995              1000            1005

Asp Val Glu Ala Thr Leu Met Lys Ser Tyr Ala Glu Val His Gln Val
    1010             1015             1020

Ser Glu Ala Asp Ala Arg Leu Trp Leu Gln Gln Leu Glu Glu Lys Gly
1025             1030             1035             1040

Arg Tyr Ala Lys Asp Val Trp Ala Gly
            1045
```

<210> SEQ ID NO 3
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V10,
      CYP102A1

<400> SEQUENCE: 3

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Ile Gln Thr Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Thr Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285
```

-continued

```
Gln Lys Ala Ala Glu Glu Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Tyr Pro Leu Glu Lys Gly Asp
                340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Glu Gly Phe Val Val Lys
            435                 440                 445
Ala Lys Ser Lys Gln Ile Pro Leu Gly Gly Ile Pro Ser Pro Ser Arg
450                 455                 460
Glu Gln Ser Ala Lys Lys Glu Arg Lys Thr Val Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
        530                 535                 540
Ala Lys Glu Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Phe Ala Ala
                580                 585                 590
Lys Gly Ala Glu Asn Ile Ala Glu Arg Gly Glu Ala Asp Ala Ser Asp
            595                 600                 605
Asp Phe Glu Gly Thr Tyr Glu Glu Trp Arg Glu His Met Trp Ser Asp
        610                 615                 620
Leu Ala Ala Tyr Phe Asn Leu Asp Ile Glu Asn Ser Glu Glu Asn Ala
625                 630                 635                 640
Ser Thr Leu Ser Leu Gln Phe Val Asp Ser Ala Asp Met Pro Leu
                645                 650                 655
Ala Lys Met His Arg Ala Phe Ser Ala Asn Val Val Ala Ser Lys Glu
                660                 665                 670
Leu Gln Lys Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
        690                 695                 700
Pro Arg Asn Tyr Glu Gly Ile Val Asn Arg Val Ala Thr Arg Phe Gly
```

```
            705                 710                 715                 720
Leu Asp Ala Ser Gln Gln Ile Arg Leu Glu Ala Glu Glu Lys Leu
                    725                 730                 735

Ala His Leu Pro Leu Gly Lys Thr Val Ser Val Glu Glu Leu Leu Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Val Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Met Arg Pro Arg Tyr Tyr Ser Ile
                820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Gly Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Lys Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
            995                 1000                1005

Asp Val Glu Ala Thr Leu Met Lys Ser Tyr Ala Glu Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 4
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V4,
      CYP102A1

<400> SEQUENCE: 4

Met Thr Ile Lys Glu Met Pro Gln Pro Lys Thr Phe Gly Glu Leu Lys
1               5                   10                  15
```

```
Asn Leu Pro Leu Leu Asn Thr Asp Lys Pro Ile Gln Thr Leu Met Lys
             20                  25                  30

Ile Ala Asp Glu Leu Gly Glu Ile Phe Lys Phe Glu Ala Pro Gly Arg
         35                  40                  45

Val Thr Arg Tyr Leu Ser Ser Gln Arg Leu Ile Lys Glu Ala Cys Asp
     50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                 85                  90                  95

Trp Lys Lys Ala His Asn Ile Leu Leu Pro Ser Phe Ser Gln Gln Ala
             100                 105                 110

Met Lys Gly Tyr His Ala Met Met Val Asp Ile Ala Val Gln Leu Ile
         115                 120                 125

Gln Lys Trp Glu Arg Leu Asn Thr Asp Glu His Ile Glu Val Pro Glu
     130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                 165                 170                 175

Ser Met Val Arg Ala Leu Asp Glu Ala Met Asn Lys Leu Gln Arg Ala
             180                 185                 190

Asn Pro Asp Asp Pro Ala Tyr Asp Glu Asn Lys Arg Gln Phe Gln Glu
         195                 200                 205

Asp Ile Lys Val Met Asn Asp Leu Val Asp Lys Ile Ile Ala Asp Arg
     210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                 245                 250                 255

Tyr Gln Ile Ile Thr Phe Leu Ile Ala Gly His Glu Thr Thr Ser Gly
             260                 265                 270

Leu Leu Ser Phe Ala Leu Tyr Phe Leu Val Lys Asn Pro His Val Leu
         275                 280                 285

Gln Lys Ala Ala Glu Glu Ala Thr Arg Val Leu Val Asp Pro Val Pro
     290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                 325                 330                 335

Lys Glu Asp Thr Val Leu Gly Gly Glu Tyr Pro Leu Glu Lys Gly Asp
             340                 345                 350

Glu Leu Met Val Leu Ile Pro Gln Leu His Arg Asp Lys Thr Ile Trp
         355                 360                 365

Gly Glu Asp Val Glu Glu Phe Arg Pro Glu Arg Phe Glu Asn Pro Ser
     370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                 405                 410                 415

Met Met Leu Lys His Phe Asp Phe Glu Asp His Thr Asn Tyr Glu Leu
             420                 425                 430

Asp Ile Lys Glu Thr Leu Thr Leu Lys Pro Glu Gly Phe Val Val Lys
```

```
                435                 440                 445
Ala Lys Ser Lys Lys Ile Pro Leu Gly Gly Ile Pro Ser Pro Ser Thr
450                 455                 460
Glu Gln Ser Ala Lys Lys Val Arg Lys Lys Val Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
                515                 520                 525
Ala Val Leu Ile Val Thr Ala Ser Tyr Asn Gly His Pro Pro Asp Asn
530                 535                 540
Ala Lys Gln Phe Val Asp Trp Leu Asp Gln Ala Ser Ala Asp Asp Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
                595                 600                 605
Asp Phe Glu Gly Thr Tyr Glu Glu Trp Arg Glu His Met Trp Ser Asp
610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Ala Asn Val Val Ala Ser Lys Glu
                660                 665                 670
Leu Gln Gln Pro Gly Ser Glu Arg Ser Thr Arg His Leu Glu Ile Ala
                675                 680                 685
Leu Pro Lys Glu Ala Ser Tyr Gln Glu Gly Asp His Leu Gly Val Ile
                690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Gly Lys Thr Val Ser Val Glu Glu Leu Leu Gln
                740                 745                 750
Tyr Val Glu Leu Gln Asp Pro Val Thr Arg Thr Gln Leu Arg Ala Met
                755                 760                 765
Ala Ala Lys Thr Val Cys Pro Pro His Lys Val Glu Leu Glu Ala Leu
                770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Glu Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
                835                 840                 845
Val Val Ser Gly Glu Ala Trp Ser Gly Tyr Gly Glu Tyr Lys Gly Ile
                850                 855                 860
```

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Asp Ser Glu
            885                 890                 895

Thr Pro Leu Ile Met Val Gly Pro Gly Thr Gly Val Ala Pro Phe Arg
        900                 905                 910

Ser Phe Val Gln Ala Arg Lys Gln Leu Lys Glu Gln Gly Gln Ser Leu
    915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Asp Val Glu Ala Thr Leu Met Lys Ser Tyr Ala Asp Val Tyr Glu Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 5
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V8,
      CYP102A1

<400> SEQUENCE: 5

Met Thr Ile Lys Glu Met Pro Gln Pro Lys Thr Phe Gly Glu Leu Lys
1               5                   10                  15

Asn Leu Pro Leu Leu Asn Thr Asp Lys Pro Ile Gln Thr Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Thr Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr

```
                165                 170                 175
Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ile Ala Asp Arg
        210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Ala Ala Glu Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Gln Ile Pro Leu Gly Gly Ile Pro Ser Pro Ser Arg
        450                 455                 460

Glu Gln Ser Ala Lys Lys Glu Arg Lys Thr Val Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Arg Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
        530                 535                 540

Ala Lys Glu Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590
```

```
Lys Gly Ala Glu Asn Ile Ala Glu Arg Gly Glu Ala Asp Ala Ser Asp
        595                 600                 605

Asp Phe Glu Gly Thr Tyr Glu Glu Trp Arg Glu His Met Trp Ser Asp
610                 615                 620

Leu Ala Ala Tyr Phe Asn Leu Asp Ile Glu Asn Ser Glu Glu Asn Ala
625                 630                 635                 640

Ser Thr Leu Ser Leu Gln Phe Val Asp Ser Ala Ala Asp Met Pro Leu
            645                 650                 655

Ala Lys Met His Arg Ala Phe Ser Ala Asn Val Val Ala Ser Lys Glu
            660                 665                 670

Leu Gln Lys Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Ala Thr Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Val Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Met Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Gly Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
930                 935                 940

Leu Tyr Gln Lys Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005
```

-continued

```
Asp Val Glu Ala Thr Leu Met Lys Ser Tyr Ala Glu Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 6
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V3,
      CYP102A1

<400> SEQUENCE: 6

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320
```

```
Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Val Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Asp Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Ala Asn Val Val Ala Ser Lys Glu
            660                 665                 670

Leu Gln Gln Leu Gly Ser Glu Arg Ser Thr Arg His Leu Glu Ile Ala
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735
```

Ala His Leu Pro Leu Gly Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Ile Ser Pro Arg Tyr Tyr Ser Ile
            820                 825                 830

Ser Ser Ser Pro His Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Asp Ser Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Arg Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Asp Val Glu Ala Thr Leu Met Lys Ser Tyr Ala Asp Val Tyr Glu Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 7
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V7,
      CYP102A1

<400> SEQUENCE: 7

Met Thr Ile Lys Glu Met Pro Gln Pro Lys Thr Phe Gly Glu Leu Lys
1               5                   10                  15

Asn Leu Pro Leu Leu Asn Thr Asp Lys Pro Ile Gln Thr Leu Met Lys
            20                  25                  30

Ile Ala Asp Glu Leu Gly Glu Ile Phe Lys Phe Glu Ala Pro Gly Arg
        35                  40                  45

```
Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Leu Lys Phe Val Arg
 65                  70                  75                  80

Asp Phe Ala Gly Asp Gly Leu Phe Thr Ser Trp Thr His Glu Lys Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Ile
                115                 120                 125

Gln Lys Trp Glu Arg Leu Asn Thr Asp Glu His Ile Glu Val Pro Glu
                130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Glu
                195                 200                 205

Asp Ile Lys Val Met Asn Asp Leu Val Asp Lys Ile Ile Ala Asp Arg
                210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Ala Ala Glu Glu Ala Ala Arg Val Leu Val Asp Pro Val Pro
                290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
                370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
                435                 440                 445

Ala Lys Ser Lys Gln Ile Pro Leu Gly Gly Ile Pro Ser Pro Ser Arg
450                 455                 460
```

-continued

```
Glu Gln Ser Ala Lys Lys Glu Arg Lys Thr Val Asn Ala His Asn
465                 470                 475                 480

Thr Pro Leu Leu Val Leu Tyr Gly Ser Asn Met Gly Thr Ala Glu Gly
                    485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Pro Glu Gly
                515                 520                 525

Ala Val Leu Ile Val Thr Ala Ser Tyr Asn Gly His Pro Pro Asp Asn
            530                 535                 540

Ala Lys Glu Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Glu Arg Gly Glu Ala Asp Ala Ser Asp
                595                 600                 605

Asp Phe Glu Gly Thr Tyr Glu Glu Trp Arg Glu His Met Trp Ser Asp
            610                 615                 620

Leu Ala Ala Tyr Phe Asn Leu Asp Ile Glu Asn Ser Glu Glu Asn Ala
625                 630                 635                 640

Ser Thr Leu Ser Leu Gln Phe Val Asp Ser Ala Ala Asp Met Pro Leu
                    645                 650                 655

Ala Lys Met His Arg Ala Phe Ser Ala Asn Val Val Ala Ser Lys Glu
            660                 665                 670

Leu Gln Lys Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Ala Thr Arg Phe Gly
705                 710                 715                 720

Leu Asp Ala Ser Gln Gln Ile Arg Leu Glu Ala Glu Glu Lys Leu
                    725                 730                 735

Ala His Leu Pro Leu Gly Lys Thr Val Ser Val Glu Glu Leu Leu Gln
            740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Val Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                    805                 810                 815

Glu Phe Ile Ala Leu Leu Pro Ser Met Arg Pro Arg Tyr Tyr Ser Ile
            820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
            850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Gly Pro Glu
```

```
                        885                 890                 895
Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
        930                 935                 940

Leu Tyr Gln Lys Glu Leu Glu Asn Ala Gln Asn Glu Gly Ile Ile Thr
945                 950                 955                 960

Leu His Thr Ala Phe Ser Arg Val Pro Asn Glu Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Asp Val Glu Ala Thr Leu Met Lys Ser Tyr Ala Glu Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045
```

```
<210> SEQ ID NO 8
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V2,
      CYP102A1

<400> SEQUENCE: 8

Met Thr Ile Lys Glu Met Pro Gln Pro Lys Thr Phe Gly Glu Leu Lys
1               5                   10                  15

Asn Leu Pro Leu Leu Asn Thr Asp Lys Pro Ile Gln Thr Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Thr Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190
```

```
Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Thr Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Glu Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Val Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Asp Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
```

-continued

```
              610                 615                 620
Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Ala Asn Val Val Ala Ser Lys Glu
                    660                 665                 670

Leu Gln Gln Leu Gly Ser Glu Arg Ser Thr Arg His Leu Glu Ile Ala
                675                 680                 685

Leu Pro Lys Glu Ala Ser Tyr Gln Glu Gly Asp His Leu Gly Val Ile
                690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                    725                 730                 735

Ala His Leu Pro Leu Gly Lys Thr Val Ser Val Glu Glu Leu Leu Gln
                    740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                    805                 810                 815

Glu Phe Ile Ala Leu Leu Pro Ser Ile Ser Pro Arg Tyr Tyr Ser Ile
                820                 825                 830

Ser Ser Ser Pro His Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
                850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Asp Ser Glu
                    885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                    965                 970                 975

Gln His Val Met Glu Arg Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                 1000                1005

Asp Val Glu Ala Thr Leu Met Lys Ser Tyr Ala Asp Val Tyr Glu Val
        1010                1015                1020

Ser Glu Ala Asp Ala Arg Leu Trp Leu Gln Gln Leu Glu Glu Lys Gly
1025                1030                1035                1040
```

Arg Tyr Ala Lys Asp Val Trp Ala Gly
                1045

<210> SEQ ID NO 9
<211> LENGTH: 1049
<212> TYPE: PRT
<213> ORGANISM: Bacillus megaterium
<220> FEATURE:
<223> OTHER INFORMATION: cytochrome P450:NADPH P450 reductase, CYP102A1

<400> SEQUENCE: 9

Met Thr Ile Lys Glu Met Pro Gln Pro Lys Thr Phe Gly Glu Leu Lys
1               5                   10                  15

Asn Leu Pro Leu Leu Asn Thr Asp Lys Pro Ile Gln Thr Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Thr Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

```
Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Gln Ile Pro Leu Gly Gly Ile Pro Ser Pro Ser Arg
450                 455                 460

Glu Gln Ser Ala Lys Lys Glu Arg Lys Thr Val Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Glu Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Glu Arg Gly Glu Ala Asp Ala Ser Asp
            595                 600                 605

Asp Phe Glu Gly Thr Tyr Glu Glu Trp Arg Glu His Met Trp Ser Asp
    610                 615                 620

Leu Ala Ala Tyr Phe Asn Leu Asp Ile Glu Asn Ser Glu Glu Asn Ala
625                 630                 635                 640

Ser Thr Leu Ser Leu Gln Phe Val Asp Ser Ala Ala Asp Met Pro Leu
                645                 650                 655

Ala Lys Met His Arg Ala Phe Ser Ala Asn Val Val Ala Ser Lys Glu
            660                 665                 670

Leu Gln Lys Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Ala Thr Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Glu Leu Leu Gln
                740                 745                 750

Tyr Val Glu Leu Gln Asp Pro Val Thr Arg Thr Gln Leu Arg Ala Met
            755                 760                 765
```

```
Ala Ala Lys Thr Val Cys Pro Pro His Lys Val Glu Leu Glu Val Leu
    770             775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Glu Phe Ser
                805                 810                 815
Glu Phe Ile Ala Leu Leu Pro Ser Met Arg Pro Arg Tyr Tyr Ser Ile
            820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
    850                 855                 860
Ala Ser Asn Tyr Leu Ala Asn Leu Gln Glu Gly Asp Thr Ile Thr Cys
865                 870                 875                 880
Phe Val Ser Thr Pro Gln Ser Gly Phe Thr Leu Pro Lys Gly Pro Glu
                885                 890                 895
Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
        915                 920                 925
Gly Glu Ala His Leu Tyr Phe Gly Cys Arg Ser Pro His Glu Asp Tyr
    930                 935                 940
Leu Tyr Gln Lys Glu Leu Glu Asn Ala Gln Asn Glu Gly Ile Ile Thr
945                 950                 955                 960
Leu His Thr Ala Phe Ser Arg Val Pro Asn Gln Pro Lys Thr Tyr Val
                965                 970                 975
Gln His Val Met Glu Gln Asp Gly Lys Lys Leu Ile Glu Leu Leu Asp
            980                 985                 990
Gln Gly Ala His Phe Tyr Ile Cys Gly Asp Gly Ser Gln Met Ala Pro
        995                 1000                1005
Asp Val Glu Ala Thr Leu Met Lys Ser Tyr Ala Glu Val His Gln Val
    1010                1015                1020
Ser Glu Ala Asp Ala Arg Leu Trp Leu Gln Gln Leu Glu Glu Lys Gly
1025                1030                1035                1040
Arg Tyr Ala Lys Asp Val Trp Ala Gly
                1045

<210> SEQ ID NO 10
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V6,
      CYP102A1

<400> SEQUENCE: 10

Met Thr Ile Lys Glu Met Pro Gln Pro Lys Thr Phe Gly Glu Leu Lys
1               5                   10                  15
Asn Leu Pro Leu Leu Asn Thr Asp Lys Pro Val Gln Ala Leu Met Lys
            20                  25                  30
Ile Ala Asp Glu Leu Gly Glu Ile Phe Lys Phe Glu Ala Pro Gly Arg
        35                  40                  45
Val Thr Arg Tyr Leu Ser Ser Gln Arg Leu Ile Lys Glu Ala Cys Asp
    50                  55                  60
Glu Ser Arg Phe Asp Lys Asn Leu Ser Gln Ala Leu Lys Phe Val Arg
65                  70                  75                  80
```

```
Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Asp
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Gln Ile Pro Leu Gly Gly Ile Pro Ser Pro Ser Arg
    450                 455                 460

Glu Gln Ser Ala Lys Lys Glu Arg Lys Thr Val Glu Asn Ala His Asn
465                 470                 475                 480

Thr Pro Leu Leu Val Leu Tyr Gly Ser Asn Met Gly Thr Ala Glu Gly
                485                 490                 495
```

-continued

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ser Ala
                580                 585                 590

Lys Gly Ala Glu Asn Ile Ala Glu Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Leu Ala Ala Tyr Phe Asn Leu Asn Ile Glu Asn Ser Glu Asp Asn Ala
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Ala Asn Val Val Ala Ser Lys Glu
                660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Thr Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Glu Leu Leu Gln
                740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Thr Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Met Arg Pro Arg Tyr Tyr Ser Ile
                820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Val Ser Thr Pro Gln Ser Gly Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu

```
            915                 920                 925
Gly Glu Ala His Leu Tyr Phe Gly Cys Arg Ser Pro His Glu Asp Tyr
            930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Val Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Asp Val Glu Ala Thr Leu Met Lys Ser Tyr Ala Glu Val His Lys Val
            1010                1015                1020

Ser Glu Ala Asp Ala Arg Leu Trp Leu Gln Gln Leu Glu Glu Lys Ser
1025                1030                1035                1040

Arg Tyr Ala Lys Asp Val Trp Ala Gly
                1045
```

<210> SEQ ID NO 11
<211> LENGTH: 1049
<212> TYPE: PRT
<213> ORGANISM: Bacillus megaterium
<220> FEATURE:
<223> OTHER INFORMATION: NADPH-cytochrome P450 reductase 102A1V5, CYP102A1

<400> SEQUENCE: 11

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Asp
        195                 200                 205

Asp Ile Lys Val Met Asn Asp Leu Val Asp Lys Ile Ile Ala Asp Arg
    210                 215                 220
```

```
Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Ala Ala Glu Glu Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
        420                 425                 430

Asp Ile Lys Glu Thr Leu Thr Leu Lys Pro Glu Gly Phe Val Val Lys
        435                 440                 445

Ala Lys Ser Lys Gln Ile Pro Leu Gly Gly Ile Pro Ser Pro Ser Arg
    450                 455                 460

Glu Gln Ser Ala Lys Lys Glu Arg Lys Thr Val Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ser Ala
            580                 585                 590

Lys Gly Ala Glu Asn Ile Ala Glu Arg Gly Glu Ala Asp Ala Ser Asp
        595                 600                 605

Asp Phe Glu Gly Thr Tyr Glu Glu Trp Arg Glu His Met Trp Ser Asp
        610                 615                 620

Leu Ala Ala Tyr Phe Asn Leu Asn Ile Glu Asn Ser Glu Asp Asn Ala
625                 630                 635                 640

Ser Thr Leu Ser Leu Gln Phe Val Asp Ser Ala Ala Asp Met Pro Leu
```

```
            645                 650                 655
Ala Lys Met His Gly Ala Phe Ser Ala Asn Val Val Ala Ser Lys Glu
            660                 665                 670
Leu Gln Gln Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
            690                 695                 700
Pro Arg Asn Tyr Glu Gly Ile Val Asn Arg Val Thr Thr Arg Phe Gly
705                 710                 715                 720
Leu Asp Ala Ser Gln Gln Ile Arg Leu Glu Ala Glu Glu Lys Leu
                    725                 730                 735
Ala His Leu Pro Leu Gly Lys Thr Val Ser Val Glu Leu Leu Gln
                    740                 745                 750
Tyr Val Glu Leu Gln Asp Pro Val Thr Arg Thr Gln Leu Arg Ala Met
                    755                 760                 765
Ala Ala Lys Thr Val Cys Pro His Lys Val Glu Leu Glu Ala Leu
                    770                 775                 780
Leu Glu Lys Gln Ala Tyr Lys Glu Gln Val Leu Thr Lys Arg Leu Thr
785                 790                 795                 800
Met Leu Glu Leu Leu Glu Lys Tyr Pro Ala Cys Glu Met Glu Phe Ser
                    805                 810                 815
Glu Phe Ile Ala Leu Leu Pro Ser Met Arg Pro Arg Tyr Tyr Ser Ile
                    820                 825                 830
Ser Ser Ser Pro Arg Val Asp Glu Lys Gln Ala Ser Ile Thr Val Ser
                    835                 840                 845
Val Val Ser Gly Glu Ala Trp Ser Gly Tyr Gly Glu Tyr Lys Gly Ile
                    850                 855                 860
Ala Ser Asn Tyr Leu Ala Glu Leu Gln Glu Gly Asp Thr Ile Thr Cys
865                 870                 875                 880
Phe Val Ser Thr Pro Gln Ser Gly Phe Thr Leu Pro Lys Asp Pro Glu
                    885                 890                 895
Thr Pro Leu Ile Met Val Gly Pro Gly Thr Gly Val Ala Pro Phe Arg
                    900                 905                 910
Gly Phe Val Gln Ala Arg Lys Gln Leu Lys Glu Gln Gly Gln Ser Leu
                    915                 920                 925
Gly Glu Ala His Leu Tyr Phe Gly Cys Arg Ser Pro His Glu Asp Tyr
                    930                 935                 940
Leu Tyr Gln Glu Glu Leu Glu Asn Ala Gln Asn Glu Gly Ile Ile Thr
945                 950                 955                 960
Leu His Thr Ala Phe Ser Arg Val Pro Asn Gln Pro Lys Thr Tyr Val
                    965                 970                 975
Gln His Val Val Glu Gln Asp Gly Lys Lys Leu Ile Glu Leu Leu Asp
                    980                 985                 990
Gln Gly Ala His Phe Tyr Ile Cys Gly Asp Gly Ser Gln Met Ala Pro
                    995                 1000                1005
Asp Val Glu Ala Thr Leu Met Lys Ser Tyr Ala Glu Val His Lys Val
            1010                1015                1020
Ser Glu Ala Asp Ala Arg Leu Trp Leu Gln Gln Leu Glu Glu Lys Ser
1025                1030                1035                1040
Arg Tyr Ala Lys Asp Val Trp Ala Gly
                    1045

<210> SEQ ID NO 12
```

<211> LENGTH: 420
<212> TYPE: PRT
<213> ORGANISM: Mycobacterium sp. HXN-1500
<220> FEATURE:
<223> OTHER INFORMATION: cytochrome P450 alkane hydroxylase, CYP153A6

<400> SEQUENCE: 12

```
Met Thr Glu Met Thr Val Ala Ala Ser Asp Ala Thr Asn Ala Ala Tyr
 1               5                  10                  15

Gly Met Ala Leu Glu Asp Ile Asp Val Ser Asn Pro Val Leu Phe Arg
                20                  25                  30

Asp Asn Thr Trp His Pro Tyr Phe Lys Arg Leu Arg Glu Glu Asp Pro
            35                  40                  45

Val His Tyr Cys Lys Ser Ser Met Phe Gly Pro Tyr Trp Ser Val Thr
        50                  55                  60

Lys Tyr Arg Asp Ile Met Ala Val Glu Thr Asn Pro Lys Val Phe Ser
 65                  70                  75                  80

Ser Glu Ala Lys Ser Gly Gly Ile Thr Ile Met Asp Asp Asn Ala Ala
                85                  90                  95

Ala Ser Leu Pro Met Phe Ile Ala Met Asp Pro Pro Lys His Asp Val
            100                 105                 110

Gln Arg Lys Thr Val Ser Pro Ile Val Ala Pro Glu Asn Leu Ala Thr
        115                 120                 125

Met Glu Ser Val Ile Arg Gln Arg Thr Ala Asp Leu Leu Asp Gly Leu
130                 135                 140

Pro Ile Asn Glu Glu Phe Asp Trp Val His Arg Val Ser Ile Glu Leu
145                 150                 155                 160

Thr Thr Lys Met Leu Ala Thr Leu Phe Asp Phe Pro Trp Asp Asp Arg
                165                 170                 175

Ala Lys Leu Thr Arg Trp Ser Asp Val Thr Thr Ala Leu Pro Gly Gly
            180                 185                 190

Gly Ile Ile Asp Ser Glu Glu Gln Arg Met Ala Glu Leu Met Glu Cys
        195                 200                 205

Ala Thr Tyr Phe Thr Glu Leu Trp Asn Gln Arg Val Asn Ala Glu Pro
    210                 215                 220

Lys Asn Asp Leu Ile Ser Met Met Ala His Ser Glu Ser Thr Arg His
225                 230                 235                 240

Met Ala Pro Glu Glu Tyr Leu Gly Asn Ile Val Leu Leu Ile Val Gly
                245                 250                 255

Gly Asn Asp Thr Thr Arg Asn Ser Met Thr Gly Gly Val Leu Ala Leu
            260                 265                 270

Asn Glu Phe Pro Asp Glu Tyr Arg Lys Leu Ser Ala Asn Pro Ala Leu
        275                 280                 285

Ile Ser Ser Met Val Ser Glu Ile Ile Arg Trp Gln Thr Pro Leu Ser
    290                 295                 300

His Met Arg Arg Thr Ala Leu Glu Asp Ile Glu Phe Gly Gly Lys His
305                 310                 315                 320

Ile Arg Gln Gly Asp Lys Val Val Met Trp Tyr Val Ser Gly Asn Arg
                325                 330                 335

Asp Pro Glu Ala Ile Asp Asn Pro Asp Thr Phe Ile Ile Asp Arg Ala
            340                 345                 350

Lys Pro Arg Gln His Leu Ser Phe Gly Phe Gly Ile His Arg Cys Val
        355                 360                 365

Gly Asn Arg Leu Ala Glu Leu Gln Leu Asn Ile Leu Trp Glu Glu Ile
    370                 375                 380
```

```
Leu Lys Arg Trp Pro Asp Pro Leu Gln Ile Gln Val Leu Gln Glu Pro
385                 390                 395                 400

Thr Arg Val Leu Ser Pro Phe Val Lys Gly Tyr Glu Ser Leu Pro Val
                405                 410                 415

Arg Ile Asn Ala
            420

<210> SEQ ID NO 13
<211> LENGTH: 496
<212> TYPE: PRT
<213> ORGANISM: Tetrahymena thermophile
<220> FEATURE:
<223> OTHER INFORMATION: cytochrome P450 monooxygenase CYP5013C2

<400> SEQUENCE: 13

Met Ile Phe Glu Leu Ile Leu Ile Ala Val Ala Leu Phe Ala Tyr Phe
1               5                   10                  15

Lys Ile Ala Lys Pro Tyr Phe Ser Tyr Leu Lys Tyr Arg Lys Tyr Gly
            20                  25                  30

Lys Gly Phe Tyr Tyr Pro Ile Leu Gly Glu Met Ile Glu Gln Glu Gln
        35                  40                  45

Asp Leu Lys Gln His Ala Asp Ala Asp Tyr Ser Val His His Ala Leu
    50                  55                  60

Asp Lys Asp Pro Asp Gln Lys Leu Phe Val Thr Asn Leu Gly Thr Lys
65                  70                  75                  80

Val Lys Leu Arg Leu Ile Glu Pro Glu Ile Ile Lys Asp Phe Phe Ser
                85                  90                  95

Lys Ser Gln Tyr Tyr Gln Lys Asp Gln Thr Phe Ile Gln Asn Ile Thr
            100                 105                 110

Arg Phe Leu Lys Asn Gly Ile Val Phe Ser Glu Gly Asn Thr Trp Lys
        115                 120                 125

Glu Ser Arg Lys Leu Phe Ser Pro Ala Phe His Tyr Glu Tyr Ile Gln
130                 135                 140

Lys Leu Thr Pro Leu Ile Asn Asp Ile Thr Asp Thr Ile Phe Asn Leu
145                 150                 155                 160

Ala Val Lys Asn Gln Glu Leu Lys Asn Phe Asp Pro Ile Ala Gln Ile
                165                 170                 175

Gln Glu Ile Thr Gly Arg Val Ile Ala Ser Phe Phe Gly Glu Val
            180                 185                 190

Ile Glu Gly Glu Lys Phe Gln Gly Leu Thr Ile Ile Gln Cys Leu Ser
        195                 200                 205

His Ile Ile Asn Thr Leu Gly Asn Gln Thr Tyr Ser Ile Met Tyr Phe
210                 215                 220

Leu Phe Gly Ser Lys Tyr Phe Glu Leu Gly Val Thr Glu Glu His Arg
225                 230                 235                 240

Lys Phe Asn Lys Phe Ile Ala Glu Phe Asn Lys Tyr Leu Leu Gln Lys
                245                 250                 255

Ile Asp Gln Gln Ile Glu Ile Met Ser Asn Glu Leu Gln Thr Lys Gly
            260                 265                 270

Tyr Ile Gln Asn Pro Cys Ile Leu Ala Gln Leu Ile Ser Thr His Lys
        275                 280                 285

Ile Asp Glu Ile Thr Arg Asn Gln Leu Phe Asp Phe Lys Thr Phe
290                 295                 300

Tyr Ile Ala Gly Met Asp Thr Thr Gly His Leu Leu Gly Met Thr Ile
305                 310                 315                 320
```

```
Tyr Tyr Val Ser Gln Asn Lys Asp Ile Tyr Thr Lys Leu Gln Ser Glu
                325                 330                 335

Ile Asp Ser Asn Thr Asp Gln Ser Ala His Gly Leu Ile Lys Asn Leu
            340                 345                 350

Pro Tyr Leu Asn Ala Val Ile Lys Glu Thr Leu Arg Tyr Tyr Gly Pro
        355                 360                 365

Gly Asn Ile Leu Phe Asp Arg Ile Ala Ile Lys Asp His Glu Leu Ala
    370                 375                 380

Gly Ile Pro Ile Lys Lys Gly Thr Ile Val Thr Pro Tyr Ala Met Ser
385                 390                 395                 400

Met Gln Arg Asn Ser Lys Tyr Tyr Gln Asp Pro His Lys Tyr Asn Pro
                405                 410                 415

Ser Arg Trp Leu Glu Lys Gln Ser Ser Asp Leu His Pro Asp Ala Asn
            420                 425                 430

Ile Pro Phe Ser Ala Gly Gln Arg Lys Cys Ile Gly Glu Gln Leu Ala
        435                 440                 445

Leu Leu Glu Ala Arg Ile Ile Leu Asn Lys Phe Ile Lys Met Phe Asp
    450                 455                 460

Phe Thr Cys Pro Gln Asp Tyr Lys Leu Met Met Asn Tyr Lys Phe Leu
465                 470                 475                 480

Ser Glu Pro Val Asn Pro Leu Pro Leu Gln Leu Thr Leu Arg Lys Gln
                485                 490                 495

<210> SEQ ID NO 14
<211> LENGTH: 394
<212> TYPE: PRT
<213> ORGANISM: Nonomuraea dietziae
<220> FEATURE:
<223> OTHER INFORMATION: cytochrome P450 hydroxylase sb8

<400> SEQUENCE: 14

Val Asn Ile Asp Leu Val Asp Gln Asp His Tyr Ala Thr Phe Gly Pro
1               5                   10                  15

Pro His Glu Gln Met Arg Trp Leu Arg Glu His Ala Pro Val Tyr Trp
                20                  25                  30

His Glu Gly Glu Pro Gly Phe Trp Ala Val Thr Arg His Glu Asp Val
            35                  40                  45

Val His Val Ser Arg His Ser Asp Leu Phe Ser Ser Ala Arg Arg Leu
        50                  55                  60

Ala Leu Phe Asn Glu Met Pro Glu Gln Arg Glu Leu Gln Arg Met
65                  70                  75                  80

Met Met Leu Asn Gln Asp Pro Pro Glu His Thr Arg Arg Ser Leu
                85                  90                  95

Val Asn Arg Gly Phe Thr Pro Arg Thr Ile Arg Ala Leu Glu Gln His
            100                 105                 110

Ile Arg Asp Ile Cys Asp Asp Leu Leu Asp Gln Cys Ser Gly Glu Gly
        115                 120                 125

Asp Phe Val Thr Asp Leu Ala Ala Pro Leu Pro Leu Tyr Val Ile Cys
    130                 135                 140

Glu Leu Leu Gly Ala Pro Val Ala Asp Arg Asp Lys Ile Phe Ala Trp
145                 150                 155                 160

Ser Asn Arg Met Ile Gly Ala Gln Asp Pro Asp Tyr Ala Ala Ser Pro
                165                 170                 175

Glu Glu Gly Gly Ala Ala Ala Met Glu Val Tyr Ala Tyr Ala Ser Glu
            180                 185                 190
```

```
Leu Ala Ala Gln Arg Arg Ala Ala Pro Arg Asp Asp Ile Val Thr Lys
            195                 200                 205

Leu Leu Gln Ser Asp Glu Asn Gly Glu Ser Leu Thr Glu Asn Glu Phe
    210                 215                 220

Glu Leu Phe Val Leu Leu Val Val Ala Gly Asn Glu Thr Thr Arg
225                 230                 235                 240

Asn Ala Ala Ser Gly Gly Met Leu Thr Leu Phe Glu His Pro Asp Gln
                245                 250                 255

Trp Asp Arg Leu Val Ala Asp Pro Ser Leu Ala Ala Thr Ala Ala Asp
                260                 265                 270

Glu Ile Val Arg Trp Val Ser Pro Val Asn Leu Phe Arg Arg Thr Ala
                275                 280                 285

Thr Ala Asp Leu Thr Leu Gly Gly Gln Gln Val Lys Ala Asp Asp Lys
                290                 295                 300

Val Val Val Phe Tyr Ser Ser Ala Asn Arg Asp Ala Ser Val Phe Ser
305                 310                 315                 320

Asp Pro Glu Val Phe Asp Ile Gly Arg Ser Pro Asn Pro His Ile Gly
                325                 330                 335

Phe Gly Gly Gly Gly Ala His Phe Cys Leu Gly Asn His Leu Ala Lys
                340                 345                 350

Leu Glu Leu Arg Val Leu Phe Glu Gln Leu Ala Arg Arg Phe Pro Arg
                355                 360                 365

Met Arg Gln Thr Gly Glu Ala Arg Arg Leu Arg Ser Asn Phe Ile Asn
                370                 375                 380

Gly Ile Lys Thr Leu Pro Val Thr Leu Gly
385                 390

<210> SEQ ID NO 15
<211> LENGTH: 501
<212> TYPE: PRT
<213> ORGANISM: Homo sapiens
<220> FEATURE:
<223> OTHER INFORMATION: human vitamin D 25-hydroxylase, CYP2R1

<400> SEQUENCE: 15

Met Trp Lys Leu Trp Arg Ala Glu Glu Gly Ala Ala Ala Leu Gly Gly
1               5                   10                  15

Ala Leu Phe Leu Leu Phe Ala Leu Gly Val Arg Gln Leu Leu Lys
                20                  25                  30

Gln Arg Arg Pro Met Gly Phe Pro Pro Gly Pro Pro Gly Leu Pro Phe
                35                  40                  45

Ile Gly Asn Ile Tyr Ser Leu Ala Ala Ser Ser Glu Leu Pro His Val
    50                  55                  60

Tyr Met Arg Lys Gln Ser Gln Val Tyr Gly Glu Ile Phe Ser Leu Asp
65                  70                  75                  80

Leu Gly Gly Ile Ser Thr Val Val Leu Asn Gly Tyr Asp Val Val Lys
                85                  90                  95

Glu Cys Leu Val His Gln Ser Glu Ile Phe Ala Asp Arg Pro Cys Leu
                100                 105                 110

Pro Leu Phe Met Lys Met Thr Lys Met Gly Gly Leu Leu Asn Ser Arg
                115                 120                 125

Tyr Gly Arg Gly Trp Val Asp His Arg Arg Leu Ala Val Asn Ser Phe
                130                 135                 140

Arg Tyr Phe Gly Tyr Gly Gln Lys Ser Phe Glu Ser Lys Ile Leu Glu
145                 150                 155                 160
```

Glu Thr Lys Phe Phe Asn Asp Ala Ile Glu Thr Tyr Lys Gly Arg Pro
            165                 170                 175

Phe Asp Phe Lys Gln Leu Ile Thr Asn Ala Val Ser Asn Ile Thr Asn
            180                 185                 190

Leu Ile Ile Phe Gly Glu Arg Phe Thr Tyr Glu Asp Thr Asp Phe Gln
            195                 200                 205

His Met Ile Glu Leu Phe Ser Glu Asn Val Glu Leu Ala Ala Ser Ala
            210                 215                 220

Ser Val Phe Leu Tyr Asn Ala Phe Pro Trp Ile Gly Ile Leu Pro Phe
225                 230                 235                 240

Gly Lys His Gln Gln Leu Phe Arg Asn Ala Ala Val Val Tyr Asp Phe
            245                 250                 255

Leu Ser Arg Leu Ile Glu Lys Ala Ser Val Asn Arg Lys Pro Gln Leu
            260                 265                 270

Pro Gln His Phe Val Asp Ala Tyr Leu Asp Glu Met Asp Gln Gly Lys
            275                 280                 285

Asn Asp Pro Ser Ser Thr Phe Ser Lys Glu Asn Leu Ile Phe Ser Val
            290                 295                 300

Gly Glu Leu Ile Ile Ala Gly Thr Glu Thr Thr Thr Asn Val Leu Arg
305                 310                 315                 320

Trp Ala Ile Leu Phe Met Ala Leu Tyr Pro Asn Ile Gln Gly Gln Val
            325                 330                 335

Gln Lys Glu Ile Asp Leu Ile Met Gly Pro Asn Gly Lys Pro Ser Trp
            340                 345                 350

Asp Asp Lys Cys Lys Met Pro Tyr Thr Glu Ala Val Leu His Glu Val
            355                 360                 365

Leu Arg Phe Cys Asn Ile Val Pro Leu Gly Ile Phe His Ala Thr Ser
            370                 375                 380

Glu Asp Ala Val Val Arg Gly Tyr Ser Ile Pro Lys Gly Thr Thr Val
385                 390                 395                 400

Ile Thr Asn Leu Tyr Ser Val His Phe Asp Glu Lys Tyr Trp Arg Asp
            405                 410                 415

Pro Glu Val Phe His Pro Glu Arg Phe Leu Asp Ser Ser Gly Tyr Phe
            420                 425                 430

Ala Lys Lys Glu Ala Leu Val Pro Phe Ser Leu Gly Arg Arg His Cys
            435                 440                 445

Leu Gly Glu His Leu Ala Arg Met Glu Met Phe Leu Phe Phe Thr Ala
            450                 455                 460

Leu Leu Gln Arg Phe His Leu His Phe Pro His Glu Leu Val Pro Asp
465                 470                 475                 480

Leu Lys Pro Arg Leu Gly Met Thr Leu Gln Pro Gln Pro Tyr Leu Ile
            485                 490                 495

Cys Ala Glu Arg Arg
            500

<210> SEQ ID NO 16
<211> LENGTH: 501
<212> TYPE: PRT
<213> ORGANISM: Macaca mulatta
<220> FEATURE:
<223> OTHER INFORMATION: Rhesus monkey vitamin D 25-hydroxylase, CYP2R1

<400> SEQUENCE: 16

Met Trp Lys Leu Trp Gly Gly Glu Glu Gly Ala Ala Ala Leu Gly Gly
1               5                   10                  15

```
Ala Leu Phe Leu Leu Phe Ala Leu Gly Val Arg Gln Leu Leu Lys
            20                  25                  30

Leu Arg Arg Pro Met Gly Phe Pro Gly Pro Gly Leu Pro Phe
        35                  40                  45

Ile Gly Asn Ile Tyr Ser Leu Ala Ala Ser Ala Glu Leu Pro His Val
50                  55                  60

Tyr Met Arg Lys Gln Ser Gln Val Tyr Gly Glu Ile Phe Ser Leu Asp
65                  70                  75                  80

Leu Gly Gly Ile Ser Thr Val Val Leu Asn Gly Tyr Asp Val Val Lys
                85                  90                  95

Glu Cys Leu Val His Gln Ser Gly Ile Phe Ala Asp Arg Pro Cys Leu
                100                 105                 110

Pro Leu Phe Met Lys Met Thr Lys Met Gly Gly Leu Leu Asn Ser Arg
                115                 120                 125

Tyr Gly Gln Gly Trp Val Glu His Arg Arg Leu Ala Val Asn Ser Phe
130                 135                 140

Arg Tyr Phe Gly Tyr Gly Gln Lys Ser Phe Glu Ser Lys Ile Leu Glu
145                 150                 155                 160

Glu Thr Lys Phe Phe Thr Asp Ala Ile Glu Thr Tyr Lys Gly Arg Pro
                165                 170                 175

Phe Asp Phe Lys Gln Leu Ile Thr Ser Ala Val Ser Asn Ile Thr Asn
                180                 185                 190

Leu Ile Ile Phe Gly Glu Arg Phe Thr Tyr Glu Asp Thr Asp Phe Gln
            195                 200                 205

His Met Ile Glu Leu Phe Ser Glu Asn Val Glu Leu Ala Ala Ser Ala
            210                 215                 220

Ser Val Phe Leu Tyr Asn Ala Phe Pro Trp Ile Gly Ile Leu Pro Phe
225                 230                 235                 240

Gly Lys His Gln Gln Leu Phe Arg Asn Ala Ser Val Val Tyr Asp Phe
                245                 250                 255

Leu Ser Arg Leu Ile Glu Lys Ala Ser Val Asn Arg Lys Pro Gln Leu
                260                 265                 270

Pro Gln His Phe Val Asp Ala Tyr Phe Asp Glu Met Asp Gln Gly Lys
            275                 280                 285

Asn Asp Pro Ser Ser Thr Phe Ser Lys Glu Asn Leu Ile Phe Ser Val
            290                 295                 300

Gly Glu Leu Ile Ile Ala Gly Thr Glu Thr Thr Thr Asn Val Leu Arg
305                 310                 315                 320

Trp Ala Ile Leu Phe Met Ala Leu Tyr Pro Asn Ile Gln Gly Gln Val
                325                 330                 335

Gln Lys Glu Ile Asp Leu Ile Met Gly Pro Asn Gly Lys Pro Ser Trp
            340                 345                 350

Asp Asp Lys Phe Lys Met Pro Tyr Thr Glu Ala Val Leu His Glu Val
            355                 360                 365

Leu Arg Phe Cys Asn Ile Val Pro Leu Gly Ile Phe His Ala Thr Ser
            370                 375                 380

Glu Asp Ala Val Val Arg Gly Tyr Ser Ile Pro Lys Gly Thr Thr Val
385                 390                 395                 400

Ile Thr Asn Leu Tyr Ser Val His Phe Asp Glu Lys Tyr Trp Arg Asp
                405                 410                 415

Pro Glu Val Phe His Pro Glu Arg Phe Leu Asp Ser Ser Gly Tyr Phe
                420                 425                 430
```

-continued

```
Ala Lys Lys Glu Ala Leu Val Pro Phe Ser Leu Gly Arg Arg His Cys
            435                 440                 445

Leu Gly Glu Gln Leu Ala Arg Met Glu Met Phe Leu Phe Phe Thr Ala
450                 455                 460

Leu Leu Gln Arg Phe His Leu His Phe Pro His Glu Leu Val Pro Asp
465                 470                 475                 480

Leu Lys Pro Arg Leu Gly Met Thr Leu Gln Pro Gln Pro Tyr Leu Ile
                485                 490                 495

Cys Ala Glu Arg Arg
                500
```

<210> SEQ ID NO 17
<211> LENGTH: 501
<212> TYPE: PRT
<213> ORGANISM: Canis familiaris
<220> FEATURE:
<223> OTHER INFORMATION: dog vitamin D 25-hydroxylase, CYP2R1

<400> SEQUENCE: 17

```
Met Arg Gly Pro Pro Gly Ala Glu Ala Cys Ala Ala Gly Leu Gly Ala
1               5                   10                  15

Ala Leu Leu Leu Leu Phe Val Leu Gly Val Arg Gln Leu Leu Lys
                20                  25                  30

Gln Arg Arg Pro Ala Gly Phe Pro Pro Gly Pro Ser Gly Leu Pro Phe
            35                  40                  45

Ile Gly Asn Ile Tyr Ser Leu Ala Ala Ser Gly Glu Leu Ala His Val
        50                  55                  60

Tyr Met Arg Lys Gln Ser Arg Val Tyr Gly Glu Ile Phe Ser Leu Asp
65                  70                  75                  80

Leu Gly Gly Ile Ser Ala Val Val Leu Asn Gly Tyr Asp Val Val Lys
                85                  90                  95

Glu Cys Leu Val His Gln Ser Glu Ile Phe Ala Asp Arg Pro Cys Leu
            100                 105                 110

Pro Leu Phe Met Lys Met Thr Lys Met Gly Gly Leu Leu Asn Ser Arg
        115                 120                 125

Tyr Gly Arg Gly Trp Val Asp His Arg Lys Leu Ala Val Asn Ser Phe
    130                 135                 140

Arg Cys Phe Gly Tyr Gly Gln Lys Ser Phe Glu Ser Lys Ile Leu Glu
145                 150                 155                 160

Glu Thr Asn Phe Phe Ile Asp Ala Ile Glu Thr Tyr Lys Gly Arg Pro
                165                 170                 175

Phe Asp Leu Lys Gln Leu Ile Thr Asn Ala Val Ser Asn Ile Thr Asn
            180                 185                 190

Leu Ile Ile Phe Gly Glu Arg Phe Thr Tyr Glu Asp Thr Asp Phe Gln
        195                 200                 205

His Met Ile Glu Leu Phe Ser Glu Asn Val Glu Leu Ala Ala Ser Ala
    210                 215                 220

Ser Val Phe Leu Tyr Asn Ala Phe Pro Trp Ile Gly Ile Pro Phe
225                 230                 235                 240

Gly Lys His Gln Gln Leu Phe Arg Asn Ala Ala Val Val Tyr Asp Phe
                245                 250                 255

Leu Ser Arg Leu Ile Glu Lys Ala Ser Ile Asn Arg Lys Pro Gln Ser
            260                 265                 270

Pro Gln His Phe Val Asp Ala Tyr Leu Asn Glu Met Asp Gln Gly Lys
        275                 280                 285
```

```
Asn Asp Pro Ser Cys Thr Phe Ser Lys Glu Asn Leu Ile Phe Ser Val
    290                 295                 300

Gly Glu Leu Ile Ile Ala Gly Thr Glu Thr Thr Thr Asn Val Leu Arg
305                 310                 315                 320

Trp Ala Ile Leu Phe Met Ala Leu Tyr Pro Asn Ile Gln Gly Gln Val
                325                 330                 335

Gln Lys Glu Ile Asp Leu Ile Met Gly Pro Thr Gly Lys Pro Ser Trp
            340                 345                 350

Asp Asp Lys Cys Lys Met Pro Tyr Thr Glu Ala Val Leu His Glu Val
            355                 360                 365

Leu Arg Phe Cys Asn Ile Val Pro Leu Gly Ile Phe His Ala Thr Ser
    370                 375                 380

Glu Asp Ala Val Val Arg Gly Tyr Ser Ile Pro Lys Gly Thr Thr Val
385                 390                 395                 400

Ile Thr Asn Leu Tyr Ser Val His Phe Asp Glu Lys Tyr Trp Arg Asn
                405                 410                 415

Pro Glu Ile Phe Tyr Pro Glu Arg Phe Leu Asp Ser Ser Gly Tyr Phe
            420                 425                 430

Ala Lys Lys Glu Ala Leu Val Pro Phe Ser Leu Gly Lys Arg His Cys
            435                 440                 445

Leu Gly Glu Gln Leu Ala Arg Met Glu Met Phe Leu Phe Thr Ala
450                 455                 460

Leu Leu Gln Arg Phe His Leu His Phe Pro His Gly Leu Val Pro Asp
465                 470                 475                 480

Leu Lys Pro Arg Leu Gly Met Thr Leu Gln Pro Gln Pro Tyr Leu Ile
                485                 490                 495

Cys Ala Glu Arg Arg
                500

<210> SEQ ID NO 18
<211> LENGTH: 222
<212> TYPE: PRT
<213> ORGANISM: Mus musculus
<220> FEATURE:
<223> OTHER INFORMATION: mouse Cyp2r1 protein, CYP2R1

<400> SEQUENCE: 18

Met Gly Asp Glu Met Asp Gln Gly Gln Asn Asp Pro Leu Ser Thr Phe
1               5                   10                  15

Ser Lys Glu Asn Leu Ile Phe Ser Val Gly Glu Leu Ile Ile Ala Gly
                20                  25                  30

Thr Glu Thr Thr Thr Asn Val Leu Arg Trp Ala Ile Leu Phe Met Ala
            35                  40                  45

Leu Tyr Pro Asn Ile Gln Gly Gln Val His Lys Glu Ile Asp Leu Ile
    50                  55                  60

Val Gly His Asn Arg Arg Pro Ser Trp Glu Tyr Lys Cys Lys Met Pro
65                  70                  75                  80

Tyr Thr Glu Ala Val Leu His Glu Val Leu Arg Phe Cys Asn Ile Val
                85                  90                  95

Pro Leu Gly Ile Phe His Ala Thr Ser Glu Asp Ala Val Val Arg Gly
            100                 105                 110

Tyr Ser Ile Pro Lys Gly Thr Thr Val Ile Thr Asn Leu Tyr Ser Val
        115                 120                 125

His Phe Asp Glu Lys Tyr Trp Lys Asp Pro Asp Met Phe Tyr Pro Glu
    130                 135                 140
```

```
Arg Phe Leu Asp Ser Asn Gly Tyr Phe Thr Lys Lys Glu Ala Leu Ile
145                 150                 155                 160

Pro Phe Ser Leu Gly Arg Arg His Cys Leu Gly Glu Gln Leu Ala Arg
                165                 170                 175

Met Glu Met Phe Leu Phe Phe Thr Ser Leu Leu Gln Gln Phe His Leu
            180                 185                 190

His Phe Pro His Glu Leu Val Pro Asn Leu Lys Pro Arg Leu Gly Met
        195                 200                 205

Thr Leu Gln Pro Gln Pro Tyr Leu Ile Cys Ala Glu Arg Arg
    210                 215                 220

<210> SEQ ID NO 19
<211> LENGTH: 422
<212> TYPE: PRT
<213> ORGANISM: Bacillus halodurans
<220> FEATURE:
<223> OTHER INFORMATION: Bacillus halodurans strain C-125 fatty acid
      alpha hydroxylase, CYP152A6

<400> SEQUENCE: 19

Met Lys Ser Asn Asp Pro Ile Pro Lys Asp Ser Pro Leu Asp His Thr
1               5                   10                  15

Met Asn Leu Met Arg Glu Gly Tyr Glu Phe Leu Ser His Arg Met Glu
            20                  25                  30

Arg Phe Gln Thr Asp Leu Phe Glu Thr Arg Val Met Gly Gln Lys Val
        35                  40                  45

Leu Cys Ile Arg Gly Ala Glu Ala Val Lys Leu Phe Tyr Asp Pro Glu
    50                  55                  60

Arg Phe Lys Arg His Arg Ala Thr Pro Lys Arg Ile Gln Lys Ser Leu
65                  70                  75                  80

Phe Gly Glu Asn Ala Ile Gln Thr Met Asp Asp Lys Ala His Leu His
                85                  90                  95

Arg Lys Gln Leu Phe Leu Ser Met Met Lys Pro Glu Asp Glu Gln Glu
            100                 105                 110

Leu Ala Arg Leu Thr His Glu Thr Trp Arg Arg Val Ala Glu Gly Trp
        115                 120                 125

Lys Lys Ser Arg Pro Ile Val Leu Phe Asp Glu Ala Lys Arg Val Leu
130                 135                 140

Cys Gln Val Ala Cys Glu Trp Ala Glu Val Pro Leu Lys Ser Thr Glu
145                 150                 155                 160

Ile Asp Arg Arg Ala Glu Asp Phe His Ala Met Val Asp Ala Phe Gly
                165                 170                 175

Ala Val Gly Pro Arg His Trp Arg Gly Arg Lys Gly Arg Arg Arg Thr
            180                 185                 190

Glu Arg Trp Ile Gln Ser Ile Ile His Gln Val Arg Thr Gly Ser Leu
        195                 200                 205

Gln Ala Arg Glu Gly Ser Pro Leu Tyr Lys Val Ser Tyr His Arg Glu
    210                 215                 220

Leu Asn Gly Lys Leu Leu Asp Glu Arg Met Ala Ala Ile Glu Leu Ile
225                 230                 235                 240

Asn Val Leu Arg Pro Ile Val Ala Ile Ala Thr Phe Ile Ser Phe Ala
                245                 250                 255

Ala Ile Ala Leu Gln Glu His Pro Glu Trp Gln Glu Arg Leu Lys Asn
            260                 265                 270

Gly Ser Asn Glu Glu Phe His Met Phe Val Gln Glu Val Arg Arg Tyr
        275                 280                 285
```

```
Tyr Pro Phe Ala Pro Leu Ile Gly Ala Lys Val Arg Lys Ser Phe Thr
        290                 295                 300

Trp Lys Gly Val Arg Phe Lys Lys Gly Arg Leu Val Phe Leu Asp Met
305                 310                 315                 320

Tyr Gly Thr Asn His Asp Pro Lys Leu Trp Asp Glu Pro Asp Ala Phe
                325                 330                 335

Arg Pro Glu Arg Phe Gln Glu Arg Lys Asp Ser Leu Tyr Asp Phe Ile
                340                 345                 350

Pro Gln Gly Gly Gly Asp Pro Thr Lys Gly His Arg Cys Pro Gly Glu
                355                 360                 365

Gly Ile Thr Val Glu Val Met Lys Thr Thr Met Asp Phe Leu Val Asn
        370                 375                 380

Asp Ile Asp Tyr Asp Val Pro Asp Gln Asp Ile Ser Tyr Ser Leu Ser
385                 390                 395                 400

Arg Met Pro Thr Arg Pro Glu Ser Gly Tyr Ile Met Ala Asn Ile Glu
                405                 410                 415

Arg Lys Tyr Glu His Ala
                420

<210> SEQ ID NO 20
<211> LENGTH: 389
<212> TYPE: PRT
<213> ORGANISM: Streptomyces parvus
<220> FEATURE:
<223> OTHER INFORMATION: cytochrome P450, aryC

<400> SEQUENCE: 20

Met Tyr Leu Gly Gly Arg Arg Gly Thr Glu Ala Val Gly Glu Ser Arg
1               5                   10                  15

Glu Pro Gly Val Trp Glu Val Phe Arg Tyr Asp Glu Ala Val Gln Val
                20                  25                  30

Leu Gly Asp His Arg Thr Phe Ser Ser Asp Met Asn His Phe Ile Pro
            35                  40                  45

Glu Glu Gln Arg Gln Leu Ala Arg Ala Ala Arg Gly Asn Phe Val Gly
        50                  55                  60

Ile Asp Pro Pro Asp His Thr Gln Leu Arg Gly Leu Val Ser Gln Ala
65                  70                  75                  80

Phe Ser Pro Arg Val Thr Ala Ala Leu Glu Pro Arg Ile Gly Arg Leu
                85                  90                  95

Ala Glu Gln Leu Leu Asp Asp Ile Val Ala Glu Arg Gly Asp Lys Ala
                100                 105                 110

Ser Cys Asp Leu Val Gly Glu Phe Ala Gly Pro Leu Ser Ala Ile Val
            115                 120                 125

Ile Ala Glu Leu Phe Gly Ile Pro Glu Ser Asp His Thr Met Ile Ala
        130                 135                 140

Glu Trp Ala Lys Ala Leu Leu Gly Ser Arg Pro Ala Gly Glu Leu Ser
145                 150                 155                 160

Ile Ala Asp Glu Ala Ala Met Gln Asn Thr Ala Asp Leu Val Arg Arg
                165                 170                 175

Ala Gly Glu Tyr Leu Val His His Ile Thr Glu Arg Arg Ala Arg Pro
            180                 185                 190

Gln Asp Asp Leu Thr Ser Arg Leu Ala Thr Thr Glu Val Asp Gly Lys
        195                 200                 205

Arg Leu Asp Asp Glu Glu Ile Val Gly Val Ile Gly Met Phe Leu Ile
        210                 215                 220
```

Ala Gly Tyr Leu Pro Ala Ser Val Leu Thr Ala Asn Thr Val Met Ala
225                 230                 235                 240

Leu Asp Glu His Pro Ala Ala Leu Ala Glu Val Arg Ser Asp Pro Ala
            245                 250                 255

Leu Leu Pro Gly Ala Ile Glu Glu Val Leu Arg Trp Arg Pro Pro Leu
            260                 265                 270

Val Arg Asp Gln Arg Leu Thr Thr Arg Asp Ala Asp Leu Gly Gly Arg
        275                 280                 285

Thr Val Pro Ala Gly Ser Met Val Cys Val Trp Leu Ala Ser Ala His
        290                 295                 300

Arg Asp Pro Phe Arg Phe Glu Asn Pro Asp Leu Phe Asp Ile His Arg
305                 310                 315                 320

Asn Ala Gly Arg His Leu Ala Phe Gly Lys Gly Ile His Tyr Cys Leu
                325                 330                 335

Gly Ala Pro Leu Ala Arg Leu Glu Ala Arg Ile Ala Val Glu Thr Leu
            340                 345                 350

Leu Arg Arg Phe Glu Arg Ile Glu Ile Pro Arg Asp Glu Ser Val Glu
        355                 360                 365

Phe His Glu Ser Ile Gly Val Leu Gly Pro Val Arg Leu Pro Thr Thr
    370                 375                 380

Leu Phe Ala Arg Arg
385

<210> SEQ ID NO 21
<211> LENGTH: 414
<212> TYPE: PRT
<213> ORGANISM: Pseudomonas putida
<220> FEATURE:
<223> OTHER INFORMATION: camphor 5-monooxygenase, camC, cyp101, locus
    CPXA_PSEPU, CYP101A1

<400> SEQUENCE: 21

Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Tyr
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr

```
                180             185             190
Phe Ala Glu Ala Lys Glu Ala Leu Tyr Asp Tyr Leu Ile Pro Ile Ile
            195                 200                 205
Glu Gln Arg Arg Gln Lys Pro Gly Thr Asp Ala Ile Ser Ile Val Ala
            210                 215                 220
Asn Gly Gln Val Asn Gly Arg Pro Ile Thr Ser Asp Glu Ala Lys Arg
225                 230                 235                 240
Met Cys Gly Leu Leu Val Gly Gly Leu Asp Thr Val Val Asn Phe
                    245                 250                 255
Leu Ser Phe Ser Met Glu Phe Leu Ala Lys Ser Pro Glu His Arg Gln
                260                 265                 270
Glu Leu Ile Glu Arg Pro Glu Arg Ile Pro Ala Ala Cys Glu Glu Leu
            275                 280                 285
Leu Arg Arg Phe Ser Leu Val Ala Asp Gly Arg Ile Leu Thr Ser Asp
            290                 295                 300
Tyr Glu Phe His Gly Val Gln Leu Lys Lys Gly Asp Gln Ile Leu Leu
305                 310                 315                 320
Pro Gln Met Leu Ser Gly Leu Asp Glu Arg Glu Asn Ala Cys Pro Met
                    325                 330                 335
His Val Asp Phe Ser Arg Gln Lys Val Ser His Thr Thr Phe Gly His
                340                 345                 350
Gly Ser His Leu Cys Leu Gly Gln His Leu Ala Arg Arg Glu Ile Ile
                355                 360                 365
Val Thr Leu Lys Glu Trp Leu Thr Arg Ile Pro Asp Phe Ser Ile Ala
            370                 375                 380
Pro Gly Ala Gln Ile Gln His Lys Ser Gly Ile Val Ser Gly Val Gln
385                 390                 395                 400
Ala Leu Pro Leu Val Trp Asp Pro Ala Thr Thr Lys Ala Val
                    405                 410

<210> SEQ ID NO 22
<211> LENGTH: 515
<212> TYPE: PRT
<213> ORGANISM: Homo sapiens
<220> FEATURE:
<223> OTHER INFORMATION: human cytochrome P450, CYP2D7

<400> SEQUENCE: 22

Gly Leu Glu Ala Leu Val Pro Leu Ala Met Ile Val Ala Ile Phe Leu
1               5                   10                  15
Leu Leu Val Asp Leu Met His Arg His Gln Arg Trp Ala Ala Arg Tyr
                20                  25                  30
Pro Pro Gly Pro Leu Pro Leu Pro Gly Leu Gly Asn Leu Leu His Val
            35                  40                  45
Asp Phe Gln Asn Thr Pro Tyr Cys Phe Asp Gln Leu Arg Arg Arg Phe
    50                  55                  60
Gly Asp Val Phe Asn Leu Gln Leu Ala Trp Thr Pro Val Val Val Leu
65                  70                  75                  80
Asn Gly Leu Ala Ala Val Arg Glu Ala Met Val Thr Arg Gly Glu Asp
                85                  90                  95
Thr Ala Asp Arg Pro Pro Ala Pro Ile Tyr Gln Val Leu Gly Phe Gly
            100                 105                 110
Pro Arg Ser Gln Gly Val Ile Leu Ser Arg Tyr Gly Pro Ala Trp Arg
            115                 120                 125
Glu Gln Arg Arg Phe Ser Val Ser Thr Leu Arg Asn Leu Gly Leu Gly
```

```
            130              135              140
Lys Lys Ser Leu Glu Gln Trp Val Thr Glu Glu Ala Ala Cys Leu Cys
145                 150                 155                 160

Ala Ala Phe Ala Asp Gln Ala Gly Arg Pro Phe Arg Pro Asn Gly Leu
                165                 170                 175

Leu Asp Lys Ala Val Ser Asn Val Ile Ala Ser Leu Thr Cys Gly Arg
            180                 185                 190

Arg Phe Glu Tyr Asp Asp Pro Arg Phe Leu Arg Leu Leu Asp Leu Ala
        195                 200                 205

Gln Glu Gly Leu Lys Glu Ser Gly Phe Leu Arg Glu Val Leu Asn
210                 215                 220

Ala Val Pro Val Leu Pro His Ile Pro Ala Leu Ala Gly Lys Val Leu
225                 230                 235                 240

Arg Phe Gln Lys Ala Phe Leu Thr Gln Leu Asp Glu Leu Leu Thr Glu
                245                 250                 255

His Arg Met Thr Trp Asp Pro Ala Gln Pro Pro Arg Asp Leu Thr Glu
                260                 265                 270

Ala Phe Leu Ala Lys Lys Glu Lys Ala Lys Gly Ser Pro Glu Ser Ser
            275                 280                 285

Phe Asn Asp Glu Asn Leu Arg Ile Val Val Gly Asn Leu Phe Leu Ala
        290                 295                 300

Gly Met Val Thr Thr Leu Thr Thr Leu Ala Trp Gly Leu Leu Leu Met
305                 310                 315                 320

Ile Leu His Leu Asp Val Gln Arg Gly Arg Arg Val Ser Pro Gly Cys
                325                 330                 335

Ser Pro Ile Val Gly Thr His Val Cys Pro Val Arg Val Gln Gln Glu
                340                 345                 350

Ile Asp Asp Val Ile Gly Gln Val Arg Arg Pro Glu Met Gly Asp Gln
            355                 360                 365

Val His Met Pro Tyr Thr Thr Ala Val Ile His Glu Val Gln Arg Phe
        370                 375                 380

Gly Asp Ile Val Pro Leu Gly Val Thr His Met Thr Ser Arg Asp Ile
385                 390                 395                 400

Glu Val Gln Gly Phe Arg Ile Pro Lys Gly Thr Thr Leu Ile Thr Asn
                405                 410                 415

Leu Ser Ser Val Leu Lys Asp Glu Ala Val Trp Glu Lys Pro Phe Arg
            420                 425                 430

Phe His Pro Glu His Phe Leu Asp Ala Gln Gly His Phe Val Lys Pro
        435                 440                 445

Glu Ala Phe Leu Pro Phe Ser Ala Gly Arg Arg Ala Cys Leu Gly Glu
    450                 455                 460

Pro Leu Ala Arg Met Glu Leu Phe Leu Phe Thr Ser Leu Leu Gln
465                 470                 475                 480

His Phe Ser Phe Ser Val Ala Ala Gly Gln Pro Arg Pro Ser His Ser
                485                 490                 495

Arg Val Val Ser Phe Leu Val Thr Pro Ser Pro Tyr Glu Leu Cys Ala
            500                 505                 510

Val Pro Arg
        515

<210> SEQ ID NO 23
<211> LENGTH: 532
<212> TYPE: PRT
<213> ORGANISM: Rattus norvegicus
```

<220> FEATURE:
<223> OTHER INFORMATION: rat cytochrome P450, CYPC27

<400> SEQUENCE: 23

```
Ala Val Leu Ser Arg Met Arg Leu Arg Trp Ala Leu Leu Asp Thr Arg
1               5                   10                  15

Val Met Gly His Gly Leu Cys Pro Gln Gly Ala Arg Ala Lys Ala Ala
            20                  25                  30

Ile Pro Ala Ala Leu Arg Asp His Glu Ser Thr Glu Gly Pro Gly Thr
        35                  40                  45

Gly Gln Asp Arg Pro Arg Leu Arg Ser Leu Ala Glu Leu Pro Gly Pro
    50                  55                  60

Gly Thr Leu Arg Phe Leu Phe Gln Leu Phe Leu Arg Gly Tyr Val Leu
65                  70                  75                  80

His Leu His Glu Leu Gln Ala Leu Asn Lys Ala Lys Tyr Gly Pro Met
                85                  90                  95

Trp Thr Thr Thr Phe Gly Thr Arg Thr Asn Val Asn Leu Ala Ser Ala
            100                 105                 110

Pro Leu Leu Glu Gln Val Met Arg Gln Glu Gly Lys Tyr Pro Ile Arg
        115                 120                 125

Asp Ser Met Glu Gln Trp Lys Glu His Arg Asp His Lys Gly Leu Ser
    130                 135                 140

Tyr Gly Ile Phe Ile Thr Gln Gly Gln Gln Trp Tyr His Leu Arg His
145                 150                 155                 160

Ser Leu Asn Gln Arg Met Leu Lys Pro Ala Glu Ala Ala Leu Tyr Thr
                165                 170                 175

Asp Ala Leu Asn Glu Val Ile Ser Asp Phe Ile Ala Arg Leu Asp Gln
            180                 185                 190

Val Arg Thr Glu Ser Ala Ser Gly Asp Gln Val Pro Asp Val Ala His
        195                 200                 205

Leu Leu Tyr His Leu Ala Leu Glu Ala Ile Cys Tyr Ile Leu Phe Glu
    210                 215                 220

Lys Arg Val Gly Cys Leu Glu Pro Ser Ile Pro Glu Asp Thr Ala Thr
225                 230                 235                 240

Phe Ile Arg Ser Val Gly Leu Met Phe Lys Asn Ser Val Tyr Val Thr
                245                 250                 255

Phe Leu Pro Lys Trp Ser Arg Pro Leu Leu Pro Phe Trp Lys Arg Tyr
            260                 265                 270

Met Asn Asn Trp Asp Asn Ile Phe Ser Phe Gly Glu Lys Met Ile His
        275                 280                 285

Gln Lys Val Gln Glu Ile Glu Ala Gln Leu Gln Ala Ala Gly Pro Asp
    290                 295                 300

Gly Val Gln Val Ser Gly Tyr Leu His Phe Leu Thr Lys Glu Leu
305                 310                 315                 320

Leu Ser Pro Gln Glu Thr Val Gly Thr Phe Pro Glu Leu Ile Leu Ala
                325                 330                 335

Gly Val Asp Thr Thr Ser Asn Thr Leu Thr Trp Ala Leu Tyr His Leu
            340                 345                 350

Ser Lys Asn Pro Glu Ile Gln Glu Ala Leu His Lys Glu Val Thr Gly
        355                 360                 365

Val Val Pro Phe Gly Lys Val Pro Gln Asn Lys Asp Phe Ala His Met
    370                 375                 380

Pro Leu Leu Lys Ala Val Ile Lys Glu Thr Leu Arg Leu Tyr Pro Val
385                 390                 395                 400
```

```
Val Pro Thr Asn Ser Arg Ile Ile Thr Glu Lys Thr Glu Ile Asn
                405                 410                 415

Gly Phe Leu Phe Pro Lys Asn Thr Gln Phe Val Leu Cys Thr Tyr Val
            420                 425                 430

Val Ser Arg Asp Pro Ser Val Phe Pro Glu Pro Glu Ser Phe Gln Pro
        435                 440                 445

His Arg Trp Leu Arg Lys Arg Glu Asp Asn Ser Gly Ile Gln His
    450                 455                 460

Pro Phe Gly Ser Val Pro Phe Gly Tyr Gly Val Arg Ser Cys Leu Gly
465                 470                 475                 480

Arg Arg Ile Ala Glu Leu Glu Met Gln Leu Leu Ser Arg Leu Ile
                485                 490                 495

Gln Lys Tyr Glu Val Val Leu Ser Pro Gly Met Gly Glu Val Lys Ser
            500                 505                 510

Val Ser Arg Ile Val Leu Val Pro Ser Lys Lys Val Ser Leu Arg Phe
        515                 520                 525

Leu Gln Arg Gln
    530

<210> SEQ ID NO 24
<211> LENGTH: 491
<212> TYPE: PRT
<213> ORGANISM: Oryctolagus cuniculus
<220> FEATURE:
<223> OTHER INFORMATION: rabbit cytochrome P450, CYP2B4

<400> SEQUENCE: 24

Met Glu Phe Ser Leu Leu Leu Leu Ala Phe Leu Ala Gly Leu Leu
1               5                   10                  15

Leu Leu Leu Phe Arg Gly His Pro Lys Ala His Gly Arg Leu Pro Pro
                20                  25                  30

Gly Pro Ser Pro Leu Pro Val Leu Gly Asn Leu Leu Gln Met Asp Arg
            35                  40                  45

Lys Gly Leu Leu Arg Ser Phe Leu Arg Leu Arg Glu Lys Tyr Gly Asp
        50                  55                  60

Val Phe Thr Val Tyr Leu Gly Ser Arg Pro Val Val Leu Cys Gly
65              70                  75                  80

Thr Asp Ala Ile Arg Glu Ala Leu Val Asp Gln Ala Glu Ala Phe Ser
                85                  90                  95

Gly Arg Gly Lys Ile Ala Val Val Asp Pro Ile Phe Gln Gly Tyr Gly
            100                 105                 110

Val Ile Phe Ala Asn Gly Glu Arg Trp Arg Ala Leu Arg Arg Phe Ser
        115                 120                 125

Leu Ala Thr Met Arg Asp Phe Gly Met Gly Lys Arg Ser Val Glu Glu
    130                 135                 140

Arg Ile Gln Glu Glu Ala Arg Cys Leu Val Glu Glu Leu Arg Lys Ser
145                 150                 155                 160

Lys Gly Ala Leu Leu Asp Asn Thr Leu Leu Phe His Ser Ile Thr Ser
                165                 170                 175

Asn Ile Ile Cys Ser Ile Val Phe Gly Lys Arg Phe Asp Tyr Lys Asp
            180                 185                 190

Pro Val Phe Leu Arg Leu Leu Asp Leu Phe Phe Gln Ser Phe Ser Leu
        195                 200                 205

Ile Ser Ser Phe Ser Ser Gln Val Phe Glu Leu Phe Pro Gly Phe Leu
    210                 215                 220
```

Lys His Phe Pro Gly Thr His Arg Gln Ile Tyr Arg Asn Leu Gln Glu
225                 230                 235                 240

Ile Asn Thr Phe Ile Gly Gln Ser Val Glu Lys His Arg Ala Thr Leu
            245                 250                 255

Asp Pro Ser Asn Pro Arg Asp Phe Ile Asp Val Tyr Leu Leu Arg Met
            260                 265                 270

Glu Lys Asp Lys Ser Asp Pro Ser Ser Glu Phe His His Gln Asn Leu
        275                 280                 285

Ile Leu Thr Val Leu Ser Leu Phe Phe Ala Gly Thr Glu Thr Thr Ser
290                 295                 300

Thr Thr Leu Arg Tyr Gly Phe Leu Leu Met Leu Lys Tyr Pro His Val
305                 310                 315                 320

Thr Glu Arg Val Gln Lys Glu Ile Glu Gln Val Ile Gly Ser His Arg
                325                 330                 335

Pro Pro Ala Leu Asp Asp Arg Ala Lys Met Pro Tyr Thr Asp Ala Val
            340                 345                 350

Ile His Glu Ile Gln Arg Leu Gly Asp Leu Ile Pro Phe Gly Val Pro
        355                 360                 365

His Thr Val Thr Lys Asp Thr Gln Phe Arg Gly Tyr Val Ile Pro Lys
370                 375                 380

Asn Thr Glu Val Phe Pro Val Leu Ser Ser Ala Leu His Asp Pro Arg
385                 390                 395                 400

Tyr Phe Glu Thr Pro Asn Thr Phe Asn Pro Gly His Phe Leu Asp Ala
                405                 410                 415

Asn Gly Ala Leu Lys Arg Asn Glu Gly Phe Met Pro Phe Ser Leu Gly
            420                 425                 430

Lys Arg Ile Cys Leu Gly Glu Gly Ile Ala Arg Thr Glu Leu Phe Leu
        435                 440                 445

Phe Phe Thr Thr Ile Leu Gln Asn Phe Ser Ile Ala Ser Pro Val Pro
450                 455                 460

Pro Glu Asp Ile Asp Leu Thr Pro Arg Glu Ser Gly Val Gly Asn Val
465                 470                 475                 480

Pro Pro Ser Tyr Gln Ile Arg Phe Leu Ala Arg
                485                 490

<210> SEQ ID NO 25
<211> LENGTH: 1061
<212> TYPE: PRT
<213> ORGANISM: Bacillus subtilis
<220> FEATURE:
<223> OTHER INFORMATION: Bacillus subtilis strain 168 probable
      bifunctional P-450/NADPH-P450 reductase 1, cypD, locus
      CYPD_BACSU, CYP102A2

<400> SEQUENCE: 25

Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
            20                  25                  30

Lys Leu Ala Glu Glu Gln Gly Pro Ile Phe Gln Ile His Thr Pro Ala
        35                  40                  45

Gly Thr Thr Ile Val Val Ser Gly His Glu Leu Val Lys Glu Val Cys
    50                  55                  60

Asp Glu Glu Arg Phe Asp Lys Ser Ile Glu Gly Ala Leu Glu Lys Val
65                  70                  75                  80

```
Arg Ala Phe Ser Gly Asp Gly Leu Phe Thr Ser Trp Thr His Glu Pro
             85                  90                  95
Asn Trp Arg Lys Ala His Asn Ile Leu Met Pro Thr Phe Ser Gln Arg
        100                 105                 110
Ala Met Lys Asp Tyr His Glu Lys Met Val Asp Ile Ala Val Gln Leu
        115                 120                 125
Ile Gln Lys Trp Ala Arg Leu Asn Pro Asn Glu Ala Val Asp Val Pro
        130                 135                 140
Gly Asp Met Thr Arg Leu Thr Leu Asp Thr Ile Gly Leu Cys Gly Phe
145                 150                 155                 160
Asn Tyr Arg Phe Asn Ser Tyr Tyr Arg Glu Thr Pro His Pro Phe Ile
                165                 170                 175
Asn Ser Met Val Arg Ala Leu Asp Glu Ala Met His Gln Met Gln Arg
            180                 185                 190
Leu Asp Val Gln Asp Lys Leu Met Val Arg Thr Lys Arg Gln Phe Arg
        195                 200                 205
His Asp Ile Gln Thr Met Phe Ser Leu Val Asp Ser Ile Ile Ala Glu
        210                 215                 220
Arg Arg Ala Asn Gly Asp Gln Asp Glu Lys Asp Leu Leu Ala Arg Met
225                 230                 235                 240
Leu Asn Val Glu Asp Pro Glu Thr Gly Glu Lys Leu Asp Asp Glu Asn
                245                 250                 255
Ile Arg Phe Gln Ile Ile Thr Phe Leu Ile Ala Gly His Glu Thr Thr
                260                 265                 270
Ser Gly Leu Leu Ser Phe Ala Thr Tyr Phe Leu Leu Lys His Pro Asp
        275                 280                 285
Lys Leu Lys Lys Ala Tyr Glu Glu Val Asp Arg Val Leu Thr Asp Ala
        290                 295                 300
Ala Pro Thr Tyr Lys Gln Val Leu Glu Leu Thr Tyr Ile Arg Met Ile
305                 310                 315                 320
Leu Asn Glu Ser Leu Arg Leu Trp Pro Thr Ala Pro Ala Phe Ser Leu
                325                 330                 335
Tyr Pro Lys Glu Asp Thr Val Ile Gly Gly Lys Phe Pro Ile Thr Thr
                340                 345                 350
Asn Asp Arg Ile Ser Val Leu Ile Pro Gln Leu His Arg Asp Arg Asp
            355                 360                 365
Ala Trp Gly Lys Asp Ala Glu Glu Phe Arg Pro Glu Arg Phe Glu His
        370                 375                 380
Gln Asp Gln Val Pro His His Ala Tyr Lys Pro Phe Gly Asn Gly Gln
385                 390                 395                 400
Arg Ala Cys Ile Gly Met Gln Phe Ala Leu His Glu Ala Thr Leu Val
                405                 410                 415
Leu Gly Met Ile Leu Lys Tyr Phe Thr Leu Ile Asp His Glu Asn Tyr
                420                 425                 430
Glu Leu Asp Ile Lys Gln Thr Leu Thr Leu Lys Pro Gly Asp Phe His
        435                 440                 445
Ile Arg Val Gln Ser Arg Asn Gln Asp Ala Ile His Ala Asp Val Gln
        450                 455                 460
Ala Val Glu Lys Ala Ala Ser Asp Glu Gln Lys Glu Lys Thr Glu Ala
465                 470                 475                 480
Lys Gly Thr Ser Val Ile Gly Leu Asn Asn Arg Pro Leu Leu Val Leu
                485                 490                 495
Tyr Gly Ser Asp Thr Gly Thr Ala Glu Gly Val Ala Arg Glu Leu Ala
```

```
                500                 505                 510
Asp Thr Ala Ser Leu His Gly Val Arg Thr Glu Thr Ala Pro Leu Asn
            515                 520                 525
Asp Arg Ile Gly Lys Leu Pro Lys Glu Gly Ala Val Ile Val Thr
            530                 535                 540
Ser Ser Tyr Asn Gly Lys Pro Pro Ser Asn Ala Gly Gln Phe Val Gln
545                 550                 555                 560
Trp Leu Gln Glu Ile Lys Pro Gly Glu Leu Glu Gly Val His Tyr Ala
                565                 570                 575
Val Phe Gly Cys Gly Asp His Asn Trp Ala Ser Thr Tyr Gln Tyr Val
                580                 585                 590
Pro Arg Phe Ile Asp Glu Gln Leu Ala Glu Lys Gly Ala Thr Arg Phe
            595                 600                 605
Ser Ala Arg Gly Glu Gly Asp Val Ser Gly Asp Phe Glu Gly Gln Leu
            610                 615                 620
Asp Glu Trp Lys Lys Ser Met Trp Ala Asp Ala Ile Lys Ala Phe Gly
625                 630                 635                 640
Leu Glu Leu Asn Glu Asn Ala Asp Lys Glu Arg Ser Thr Leu Ser Leu
                645                 650                 655
Gln Phe Val Arg Gly Leu Gly Glu Ser Pro Leu Ala Arg Ser Tyr Glu
                660                 665                 670
Ala Ser His Ala Ser Ile Ala Glu Asn Arg Glu Leu Gln Ser Ala Asp
            675                 680                 685
Ser Asp Arg Ser Thr Arg His Ile Glu Ile Ala Leu Pro Pro Asp Val
            690                 695                 700
Glu Tyr Gln Glu Gly Asp His Leu Gly Val Leu Pro Lys Asn Ser Gln
705                 710                 715                 720
Thr Asn Val Ser Arg Ile Leu His Arg Phe Gly Leu Lys Gly Thr Asp
                725                 730                 735
Gln Val Thr Leu Ser Ala Ser Gly Arg Ser Ala Gly His Leu Pro Leu
                740                 745                 750
Gly Arg Pro Val Ser Leu His Asp Leu Leu Ser Tyr Ser Val Glu Val
            755                 760                 765
Gln Glu Ala Ala Thr Arg Ala Gln Ile Arg Glu Leu Ala Ala Phe Thr
            770                 775                 780
Val Cys Pro Pro His Arg Arg Glu Leu Glu Leu Ser Ala Glu Gly
785                 790                 795                 800
Val Tyr Gln Glu Gln Ile Leu Lys Lys Arg Ile Ser Met Leu Asp Leu
                805                 810                 815
Leu Glu Lys Tyr Glu Ala Cys Asp Met Pro Phe Glu Arg Phe Leu Glu
                820                 825                 830
Leu Leu Arg Pro Leu Lys Pro Arg Tyr Tyr Ser Ile Ser Ser Ser Pro
            835                 840                 845
Arg Val Asn Pro Arg Gln Ala Ser Ile Thr Val Gly Val Val Arg Gly
            850                 855                 860
Pro Ala Trp Ser Gly Arg Gly Glu Tyr Arg Gly Val Ala Ser Asn Asp
865                 870                 875                 880
Leu Ala Glu Arg Gln Ala Gly Asp Asp Val Val Met Phe Ile Arg Thr
                885                 890                 895
Pro Glu Ser Arg Phe Gln Leu Pro Lys Asp Pro Glu Thr Pro Ile Ile
            900                 905                 910
Met Val Gly Pro Gly Thr Gly Val Ala Pro Phe Arg Gly Phe Leu Gln
            915                 920                 925
```

```
Ala Arg Asp Val Leu Lys Arg Glu Gly Lys Thr Leu Gly Glu Ala His
        930                 935                 940

Leu Tyr Phe Gly Cys Arg Asn Asp Arg Asp Phe Ile Tyr Arg Asp Glu
945                 950                 955                 960

Leu Glu Arg Phe Glu Lys Asp Gly Ile Val Thr Val His Thr Ala Phe
                965                 970                 975

Ser Arg Lys Glu Gly Met Pro Lys Thr Tyr Val Gln His Leu Met Ala
            980                 985                 990

Asp Gln Ala Asp Thr Leu Ile Ser Ile Leu Asp Arg Gly Gly Arg Leu
        995                 1000                1005

Tyr Val Cys Gly Asp Gly Ser Lys Met Ala Pro Asp Val Glu Ala Ala
    1010                1015                1020

Leu Gln Lys Ala Tyr Gln Ala Val His Gly Thr Gly Glu Gln Glu Ala
1025                1030                1035                1040

Gln Asn Trp Leu Arg His Leu Gln Asp Thr Gly Met Tyr Ala Lys Asp
                1045                1050                1055

Val Trp Ala Gly Ile
            1060

<210> SEQ ID NO 26
<211> LENGTH: 1054
<212> TYPE: PRT
<213> ORGANISM: Bacillus subtilis
<220> FEATURE:
<223> OTHER INFORMATION: Bacillus subtilis strain 168 probable
      bifunctional P-450/NADPH-P450 reductase 2, cypE, CYP102A3

<400> SEQUENCE: 26

Met Lys Gln Ala Ser Ala Ile Pro Gln Pro Lys Thr Tyr Gly Pro Leu
1               5                   10                  15

Lys Asn Leu Pro His Leu Glu Lys Glu Gln Leu Ser Gln Ser Leu Trp
            20                  25                  30

Arg Ile Ala Asp Glu Leu Gly Pro Ile Phe Arg Phe Asp Phe Pro Gly
        35                  40                  45

Val Ser Ser Val Phe Val Ser Gly His Asn Leu Val Ala Glu Val Cys
    50                  55                  60

Asp Glu Ser Arg Phe Asp Lys Asn Leu Gly Lys Gly Leu Gln Lys Val
65                  70                  75                  80

Arg Glu Phe Gly Gly Asp Gly Leu Phe Thr Ser Trp Thr His Glu Pro
                85                  90                  95

Asn Trp Gln Lys Ala His Arg Ile Leu Leu Pro Ser Phe Ser Gln Lys
            100                 105                 110

Ala Met Lys Gly Tyr His Ser Met Met Leu Asp Ile Ala Thr Gln Leu
        115                 120                 125

Ile Gln Lys Trp Ser Arg Leu Asn Pro Asn Glu Glu Ile Asp Val Ala
    130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Ser Gln His Pro Phe Ile
                165                 170                 175

Thr Ser Met Leu Arg Ala Leu Lys Glu Ala Met Asn Gln Ser Lys Arg
            180                 185                 190

Leu Gly Leu Gln Asp Lys Met Met Val Lys Thr Lys Leu Gln Phe Gln
        195                 200                 205

Lys Asp Ile Glu Val Met Asn Ser Leu Val Asp Arg Met Ile Ala Glu
```

```
            210                 215                 220
Arg Lys Ala Asn Pro Asp Asp Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
290                 295                 300

Thr Pro Glu Tyr Lys Gln Ile Gln Gln Leu Lys Tyr Thr Arg Met Val
305                 310                 315                 320

Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Glu Tyr Pro Ile Ser Lys
                340                 345                 350

Gly Gln Pro Val Thr Val Leu Ile Pro Lys Leu His Arg Asp Gln Asn
                355                 360                 365

Ala Trp Gly Pro Asp Ala Glu Asp Phe Arg Pro Glu Arg Phe Glu Asp
                370                 375                 380

Pro Ser Ser Ile Pro His His Ala Tyr Lys Pro Phe Gly Asn Gly Gln
385                 390                 395                 400

Arg Ala Cys Ile Gly Met Gln Phe Ala Leu Gln Glu Ala Thr Met Val
                405                 410                 415

Leu Gly Leu Val Leu Lys His Phe Glu Leu Ile Asn His Thr Gly Tyr
                420                 425                 430

Glu Leu Lys Ile Lys Glu Ala Leu Thr Ile Lys Pro Asp Asp Phe Lys
                435                 440                 445

Ile Thr Val Lys Pro Arg Lys Thr Ala Ala Ile Asn Val Gln Arg Lys
                450                 455                 460

Glu Gln Ala Asp Ile Lys Ala Glu Thr Lys Pro Lys Glu Thr Lys Pro
465                 470                 475                 480

Lys His Gly Thr Pro Leu Leu Val Leu Tyr Gly Ser Asn Leu Gly Thr
                485                 490                 495

Ala Glu Gly Ile Ala Gly Glu Leu Ala Ala Gln Gly Arg Gln Met Gly
                500                 505                 510

Phe Thr Ala Glu Thr Ala Pro Leu Asp Asp Tyr Ile Gly Lys Leu Pro
                515                 520                 525

Glu Glu Gly Ala Val Val Ile Val Thr Ala Ser Tyr Asn Gly Ser Pro
530                 535                 540

Pro Asp Asn Ala Ala Gly Phe Val Glu Trp Leu Lys Glu Leu Glu Glu
545                 550                 555                 560

Gly Gln Leu Lys Gly Val Ser Tyr Ala Val Phe Gly Cys Gly Asn Arg
                565                 570                 575

Ser Trp Ala Ser Thr Tyr Gln Arg Ile Pro Arg Leu Ile Asp Asp Met
                580                 585                 590

Met Lys Ala Lys Gly Ala Ser Arg Leu Thr Glu Ile Gly Glu Gly Asp
                595                 600                 605

Ala Ala Asp Asp Phe Glu Ser His Arg Glu Ser Trp Glu Asn Arg Phe
                610                 615                 620

Trp Lys Glu Thr Met Asp Ala Phe Asp Ile Asn Glu Ile Ala Gln Lys
625                 630                 635                 640
```

```
Glu Asp Arg Pro Ser Leu Ser Ile Ala Phe Leu Ser Glu Ala Thr Glu
            645                 650                 655

Thr Pro Val Ala Lys Ala Tyr Gly Ala Phe Glu Gly Val Val Leu Glu
            660                 665                 670

Asn Arg Glu Leu Gln Thr Ala Asp Ser Thr Arg Ser Thr Arg His Ile
            675                 680                 685

Glu Leu Glu Ile Pro Ala Gly Lys Thr Tyr Lys Glu Gly Asp His Ile
            690                 695                 700

Gly Ile Met Pro Lys Asn Ser Arg Glu Leu Val Gln Arg Val Leu Ser
705                 710                 715                 720

Arg Phe Gly Leu Gln Ser Asn His Val Ile Lys Val Ser Gly Ser Ala
            725                 730                 735

His Met Ser His Leu Pro Met Asp Arg Pro Ile Lys Val Ala Asp Leu
            740                 745                 750

Leu Ser Ser Tyr Val Glu Leu Gln Glu Pro Ala Ser Arg Leu Gln Leu
            755                 760                 765

Arg Glu Leu Ala Ser Tyr Thr Val Cys Pro Pro His Gln Lys Glu Leu
            770                 775                 780

Glu Gln Leu Val Leu Asp Asp Gly Ile Tyr Lys Glu Gln Val Leu Ala
785                 790                 795                 800

Lys Arg Leu Thr Met Leu Asp Phe Leu Glu Asp Tyr Pro Ala Cys Glu
            805                 810                 815

Met Pro Phe Glu Arg Phe Leu Ala Leu Leu Pro Ser Leu Lys Pro Arg
            820                 825                 830

Tyr Tyr Ser Ile Ser Ser Ser Pro Lys Val His Ala Asn Ile Val Ser
            835                 840                 845

Met Thr Val Gly Val Val Lys Ala Ser Ala Trp Ser Gly Arg Gly Glu
850                 855                 860

Tyr Arg Gly Val Ala Ser Asn Tyr Leu Ala Glu Leu Asn Thr Gly Asp
865                 870                 875                 880

Ala Ala Ala Cys Phe Ile Arg Thr Pro Gln Ser Gly Phe Gln Met Pro
            885                 890                 895

Asp Glu Pro Glu Thr Pro Met Ile Met Val Gly Pro Gly Thr Gly Ile
            900                 905                 910

Ala Pro Phe Arg Gly Phe Ile Gln Ala Arg Ser Val Leu Lys Lys Glu
            915                 920                 925

Gly Ser Thr Leu Gly Glu Ala Leu Leu Tyr Phe Gly Cys Arg Arg Pro
930                 935                 940

Asp His Asp Asp Leu Tyr Arg Glu Glu Leu Asp Gln Ala Glu Gln Glu
945                 950                 955                 960

Gly Leu Val Thr Ile Arg Arg Cys Tyr Ser Arg Val Glu Asn Glu Ser
            965                 970                 975

Lys Gly Tyr Val Gln His Leu Leu Lys Gln Asp Ser Gln Lys Leu Met
            980                 985                 990

Thr Leu Ile Glu Lys Gly Ala His Ile Tyr Val Cys Gly Asp Gly Ser
            995                 1000                1005

Gln Met Ala Pro Asp Val Glu Lys Thr Leu Arg Trp Ala Tyr Glu Thr
            1010                1015                1020

Glu Lys Gly Ala Ser Gln Glu Glu Ser Ala Asp Trp Leu Gln Lys Leu
1025                1030                1035                1040

Gln Asp Gln Lys Arg Tyr Ile Lys Asp Val Trp Thr Gly Asn
            1045                1050
```

<210> SEQ ID NO 27
<211> LENGTH: 1049
<212> TYPE: PRT
<213> ORGANISM: Bacillus megaterium
<220> FEATURE:
<223> OTHER INFORMATION: bifunctional P-450/NADPH-P450 reductase, cyp102A1, locus CPXB_BACME, CYP102A1

<400> SEQUENCE: 27

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365
```

```
Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780
```

-continued

```
Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 28
<211> LENGTH: 1065
<212> TYPE: PRT
<213> ORGANISM: Bacillus cereus
<220> FEATURE:
<223> OTHER INFORMATION: Bacillus cereus strain ATCC 14579 NADPH-
      cytochrome P450 reductase, CYP102A5

<400> SEQUENCE: 28

Met Glu Lys Lys Val Ser Ala Ile Pro Gln Pro Lys Thr Tyr Gly Pro
1               5                   10                  15

Leu Gly Asn Leu Pro Leu Ile Asp Lys Asp Lys Pro Thr Leu Ser Phe
            20                  25                  30

Ile Lys Ile Ala Glu Glu Tyr Gly Pro Ile Phe Gln Ile Gln Thr Leu
        35                  40                  45

Ser Asp Thr Ile Ile Val Val Ser Gly His Glu Leu Val Ala Glu Val
    50                  55                  60

Cys Asp Glu Thr Arg Phe Asp Lys Ser Ile Glu Gly Ala Leu Ala Lys
65                  70                  75                  80

Val Arg Ala Phe Ala Gly Asp Gly Leu Phe Thr Ser Glu Thr His Glu
                85                  90                  95
```

```
Pro Asn Trp Lys Lys Ala His Asn Ile Leu Met Pro Thr Phe Ser Gln
            100                 105                 110

Arg Ala Met Lys Asp Tyr His Ala Met Met Val Asp Ile Ala Val Gln
            115                 120                 125

Leu Val Gln Lys Trp Ala Arg Leu Asn Pro Asn Glu Asn Val Asp Val
    130                 135                 140

Pro Glu Asp Met Thr Arg Leu Thr Leu Asp Thr Ile Gly Leu Cys Gly
145                 150                 155                 160

Phe Asn Tyr Arg Phe Asn Ser Phe Tyr Arg Glu Thr Pro His Pro Phe
                165                 170                 175

Ile Thr Ser Met Thr Arg Ala Leu Asp Glu Ala Met His Gln Leu Gln
            180                 185                 190

Arg Leu Asp Ile Glu Asp Lys Leu Met Trp Arg Thr Lys Arg Gln Phe
    195                 200                 205

Gln His Asp Ile Gln Ser Met Phe Ser Leu Val Asp Asn Ile Ile Ala
210                 215                 220

Glu Arg Lys Ser Ser Gly Asp Gln Glu Glu Asn Asp Leu Leu Ser Arg
225                 230                 235                 240

Met Leu Asn Val Pro Asp Pro Glu Thr Gly Glu Lys Leu Asp Asp Glu
                245                 250                 255

Asn Ile Arg Phe Gln Ile Ile Thr Phe Leu Ile Ala Gly His Glu Thr
            260                 265                 270

Thr Ser Gly Leu Leu Ser Phe Ala Ile Tyr Phe Leu Leu Lys Asn Pro
            275                 280                 285

Asp Lys Leu Lys Lys Ala Tyr Glu Glu Val Asp Arg Val Leu Thr Asp
    290                 295                 300

Pro Thr Pro Thr Tyr Gln Gln Val Met Lys Leu Lys Tyr Met Arg Met
305                 310                 315                 320

Ile Leu Asn Glu Ser Leu Arg Leu Trp Pro Thr Ala Pro Ala Phe Ser
                325                 330                 335

Leu Tyr Ala Lys Glu Asp Thr Val Ile Gly Gly Lys Tyr Pro Ile Lys
            340                 345                 350

Lys Gly Glu Asp Arg Ile Ser Val Leu Ile Pro Gln Leu His Arg Asp
            355                 360                 365

Lys Asp Ala Trp Gly Asp Asn Val Glu Glu Phe Gln Pro Glu Arg Phe
    370                 375                 380

Glu Glu Leu Asp Lys Val Pro His His Ala Tyr Lys Pro Phe Gly Asn
385                 390                 395                 400

Gly Gln Arg Ala Cys Ile Gly Met Gln Phe Ala Leu His Glu Ala Thr
                405                 410                 415

Leu Val Met Gly Met Leu Leu Gln His Phe Glu Leu Ile Asp Tyr Gln
            420                 425                 430

Asn Tyr Gln Leu Asp Val Lys Gln Thr Leu Thr Leu Lys Pro Gly Asp
            435                 440                 445

Phe Lys Ile Arg Ile Leu Pro Arg Lys Gln Thr Ile Ser His Pro Thr
    450                 455                 460

Val Leu Ala Pro Thr Glu Asp Lys Leu Lys Asn Asp Glu Ile Lys Gln
465                 470                 475                 480

His Val Gln Lys Thr Pro Ser Ile Ile Gly Ala Asp Asn Leu Ser Leu
                485                 490                 495

Leu Val Leu Tyr Gly Ser Asp Thr Gly Val Ala Glu Gly Ile Ala Arg
            500                 505                 510
```

```
Glu Leu Ala Asp Thr Ala Ser Leu Glu Gly Val Gln Thr Glu Val Val
            515                 520                 525
Ala Leu Asn Asp Arg Ile Gly Ser Leu Pro Lys Glu Gly Ala Val Leu
        530                 535                 540
Ile Val Thr Ser Ser Tyr Asn Gly Lys Pro Pro Ser Asn Ala Gly Gln
545                 550                 555                 560
Phe Val Gln Trp Leu Glu Leu Lys Pro Asp Glu Leu Lys Gly Val
                565                 570                 575
Gln Tyr Ala Val Phe Gly Cys Gly Asp His Asn Trp Ala Ser Thr Tyr
                580                 585                 590
Gln Arg Ile Pro Arg Tyr Ile Asp Glu Gln Met Ala Gln Lys Gly Ala
            595                 600                 605
Thr Arg Phe Ser Lys Arg Gly Glu Ala Asp Ala Ser Gly Asp Phe Glu
            610                 615                 620
Glu Gln Leu Glu Gln Trp Lys Gln Asn Met Trp Ser Asp Ala Met Lys
625                 630                 635                 640
Ala Phe Gly Leu Glu Leu Asn Lys Asn Met Glu Lys Glu Arg Ser Thr
                645                 650                 655
Leu Ser Leu Gln Phe Val Ser Arg Leu Gly Gly Ser Pro Leu Ala Arg
            660                 665                 670
Thr Tyr Glu Ala Val Tyr Ala Ser Ile Leu Glu Asn Arg Glu Leu Gln
            675                 680                 685
Ser Ser Ser Ser Asp Arg Ser Thr Arg His Ile Glu Val Ser Leu Pro
        690                 695                 700
Glu Gly Ala Thr Tyr Lys Glu Gly Asp His Leu Gly Val Leu Pro Val
705                 710                 715                 720
Asn Ser Glu Lys Asn Ile Asn Arg Ile Leu Lys Arg Phe Gly Leu Asn
                725                 730                 735
Gly Lys Asp Gln Val Ile Leu Ser Ala Ser Gly Arg Ser Ile Asn His
            740                 745                 750
Ile Pro Leu Asp Ser Pro Val Ser Leu Leu Ala Leu Leu Ser Tyr Ser
                755                 760                 765
Val Glu Val Gln Glu Ala Ala Thr Arg Ala Gln Ile Arg Glu Met Val
        770                 775                 780
Thr Phe Thr Ala Cys Pro Pro His Lys Lys Glu Leu Glu Ala Leu Leu
785                 790                 795                 800
Glu Glu Gly Val Tyr His Glu Gln Ile Leu Lys Lys Arg Ile Ser Met
                805                 810                 815
Leu Asp Leu Leu Glu Lys Tyr Glu Ala Cys Glu Ile Arg Phe Glu Arg
            820                 825                 830
Phe Leu Glu Leu Leu Pro Ala Leu Lys Pro Arg Tyr Tyr Ser Ile Ser
            835                 840                 845
Ser Ser Pro Leu Val Ala His Asn Arg Leu Ser Ile Thr Val Gly Val
        850                 855                 860
Val Asn Ala Pro Ala Trp Ser Gly Glu Gly Thr Tyr Glu Gly Val Ala
865                 870                 875                 880
Ser Asn Tyr Leu Ala Gln Arg His Asn Lys Asp Glu Ile Ile Cys Phe
                885                 890                 895
Ile Arg Thr Pro Gln Ser Asn Phe Glu Leu Pro Lys Asp Pro Glu Thr
            900                 905                 910
Pro Ile Ile Met Val Gly Pro Gly Thr Gly Ile Ala Pro Phe Arg Gly
            915                 920                 925
Phe Leu Gln Ala Arg Arg Val Gln Lys Gln Lys Gly Met Asn Leu Gly
```

```
            930                 935                 940
Gln Ala His Leu Tyr Phe Gly Cys Arg His Pro Glu Lys Asp Tyr Leu
945                 950                 955                 960

Tyr Arg Thr Glu Leu Glu Asn Asp Glu Arg Asp Gly Leu Ile Ser Leu
                965                 970                 975

His Thr Ala Phe Ser Arg Leu Glu Gly His Pro Lys Thr Tyr Val Gln
                980                 985                 990

His Leu Ile Lys Gln Asp Arg Ile Asn Leu Ile Ser Leu Leu Asp Asn
                995                 1000                1005

Gly Ala His Leu Tyr Ile Cys Gly Asp Gly Ser Lys Met Ala Pro Asp
                1010                1015                1020

Val Glu Asp Thr Leu Cys Gln Ala Tyr Gln Glu Ile His Glu Val Ser
1025                1030                1035                1040

Glu Gln Glu Ala Arg Asn Trp Leu Asp Arg Val Gln Asp Glu Gly Arg
                1045                1050                1055

Tyr Gly Lys Asp Val Trp Ala Gly Ile
                1060                1065
```

<210> SEQ ID NO 29
<211> LENGTH: 1074
<212> TYPE: PRT
<213> ORGANISM: Bacillus licheniformis
<220> FEATURE:
<223> OTHER INFORMATION: Bacillus licheniformis strain DSM 13 = ATCC
      14580 cytochrome P450/NADPH-ferrihemoproteinreductase, CYP102A7

<400> SEQUENCE: 29

```
Met Asn Lys Leu Asp Gly Ile Pro Ile Pro Lys Thr Tyr Gly Pro Leu
1               5                   10                  15

Gly Asn Leu Pro Leu Leu Asp Lys Asn Arg Val Ser Gln Ser Leu Trp
                20                  25                  30

Lys Ile Ala Asp Glu Met Gly Pro Ile Phe Gln Phe Lys Phe Ala Asp
            35                  40                  45

Ala Ile Gly Val Phe Val Ser Ser His Glu Leu Val Lys Glu Val Ser
        50                  55                  60

Glu Glu Ser Arg Phe Asp Lys Asn Met Gly Lys Gly Leu Leu Lys Val
65                  70                  75                  80

Arg Glu Phe Ser Gly Asp Gly Leu Phe Thr Ser Trp Thr Glu Glu Pro
                85                  90                  95

Asn Trp Arg Lys Ala His Asn Ile Leu Leu Pro Ser Phe Ser Gln Lys
                100                 105                 110

Ala Met Lys Gly Tyr His Pro Met Met Gln Asp Ile Ala Val Gln Leu
            115                 120                 125

Ile Gln Lys Trp Ser Arg Leu Asn Gln Asp Glu Ser Ile Asp Val Pro
        130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Glu Gly Gln His Pro Phe Ile
                165                 170                 175

Glu Ser Met Val Arg Gly Leu Ser Glu Ala Met Arg Gln Thr Lys Arg
            180                 185                 190

Phe Pro Leu Gln Asp Lys Leu Met Ile Gln Thr Lys Arg Arg Phe Asn
        195                 200                 205

Ser Asp Val Glu Ser Met Phe Ser Leu Val Asp Arg Ile Ile Ala Asp
    210                 215                 220
```

```
Arg Lys Gln Ala Glu Ser Glu Ser Gly Asn Asp Leu Leu Ser Leu Met
225                 230                 235                 240

Leu His Ala Lys Asp Pro Glu Thr Gly Glu Lys Leu Asp Asp Glu Asn
                245                 250                 255

Ile Arg Tyr Gln Ile Ile Thr Phe Leu Ile Ala Gly His Glu Thr Thr
                260                 265                 270

Ser Gly Leu Leu Ser Phe Ala Ile Tyr Leu Leu Leu Lys His Pro Asp
                275                 280                 285

Lys Leu Lys Lys Ala Tyr Glu Glu Ala Asp Arg Val Leu Thr Asp Pro
290                 295                 300

Val Pro Ser Tyr Lys Gln Val Gln Gln Leu Lys Tyr Ile Arg Met Ile
305                 310                 315                 320

Leu Asn Glu Ser Ile Arg Leu Trp Pro Thr Ala Pro Ala Phe Ser Leu
                325                 330                 335

Tyr Ala Lys Glu Glu Thr Val Ile Gly Gly Lys Tyr Leu Ile Pro Lys
                340                 345                 350

Gly Gln Ser Val Thr Val Leu Ile Pro Lys Leu His Arg Asp Gln Ser
                355                 360                 365

Val Trp Gly Glu Asp Ala Glu Ala Phe Arg Pro Glu Arg Phe Glu Gln
370                 375                 380

Met Asp Ser Ile Pro Ala His Ala Tyr Lys Pro Phe Gly Asn Gly Gln
385                 390                 395                 400

Arg Ala Cys Ile Gly Met Gln Phe Ala Leu His Glu Ala Thr Leu Val
                405                 410                 415

Leu Gly Met Ile Leu Gln Tyr Phe Asp Leu Glu Asp His Ala Asn Tyr
                420                 425                 430

Gln Leu Lys Ile Lys Glu Ser Leu Thr Leu Lys Pro Asp Gly Phe Thr
                435                 440                 445

Ile Arg Val Arg Pro Arg Lys Lys Glu Ala Met Thr Ala Met Pro Gly
                450                 455                 460

Ala Gln Pro Glu Glu Asn Gly Arg Gln Glu Arg Pro Ser Ala Pro
465                 470                 475                 480

Ala Ala Glu Asn Thr His Gly Thr Pro Leu Leu Val Leu Tyr Gly Ser
                485                 490                 495

Asn Leu Gly Thr Ala Glu Glu Ile Ala Lys Glu Leu Ala Glu Glu Ala
                500                 505                 510

Arg Glu Gln Gly Phe His Ser Arg Thr Ala Glu Leu Asp Gln Tyr Ala
                515                 520                 525

Gly Ala Ile Pro Ala Glu Gly Ala Val Ile Ile Val Thr Ala Ser Tyr
530                 535                 540

Asn Gly Asn Pro Pro Asp Cys Ala Lys Glu Phe Val Asn Trp Leu Glu
545                 550                 555                 560

His Asp Gln Thr Asp Asp Leu Arg Gly Val Lys Tyr Ala Val Phe Gly
                565                 570                 575

Cys Gly Asn Arg Ser Trp Ala Ser Thr Tyr Gln Arg Ile Pro Arg Leu
                580                 585                 590

Ile Asp Ser Val Leu Glu Lys Lys Gly Ala Gln Arg Leu His Lys Leu
                595                 600                 605

Gly Glu Gly Asp Ala Gly Asp Asp Phe Glu Gly Gln Phe Glu Ser Trp
                610                 615                 620

Lys Tyr Asp Leu Trp Pro Leu Leu Arg Thr Glu Phe Ser Leu Ala Glu
625                 630                 635                 640

Pro Glu Pro Asn Gln Thr Glu Thr Asp Arg Gln Ala Leu Ser Val Glu
```

```
                645                 650                 655
Phe Val Asn Ala Pro Ala Ser Pro Leu Ala Lys Ala Tyr Gln Val
                660                 665                 670

Phe Thr Ala Lys Ile Ser Ala Asn Arg Glu Leu Gln Cys Glu Lys Ser
                675                 680                 685

Gly Arg Ser Thr Arg His Ile Glu Ile Ser Leu Pro Glu Gly Ala Ala
                690                 695                 700

Tyr Gln Glu Gly Asp His Leu Gly Val Leu Pro Gln Asn Ser Glu Val
705                 710                 715                 720

Leu Ile Gly Arg Val Phe Gln Arg Phe Gly Leu Asn Gly Asn Glu Gln
                725                 730                 735

Ile Leu Ile Ser Gly Arg Asn Gln Ala Ser His Leu Pro Leu Glu Arg
                740                 745                 750

Pro Val His Val Lys Asp Leu Phe Gln His Cys Val Glu Leu Gln Glu
                755                 760                 765

Pro Ala Thr Arg Ala Gln Ile Arg Glu Leu Ala Ala His Thr Val Cys
                770                 775                 780

Pro Pro His Gln Arg Glu Leu Glu Asp Leu Leu Lys Asp Asp Val Tyr
785                 790                 795                 800

Lys Asp Gln Val Leu Asn Lys Arg Leu Thr Met Leu Asp Leu Leu Glu
                805                 810                 815

Gln Tyr Pro Ala Cys Glu Leu Pro Phe Ala Arg Phe Leu Ala Leu Leu
                820                 825                 830

Pro Pro Leu Lys Pro Arg Tyr Tyr Ser Ile Ser Ser Ser Pro Gln Leu
                835                 840                 845

Asn Pro Arg Gln Thr Ser Ile Thr Val Ser Val Val Ser Gly Pro Ala
                850                 855                 860

Leu Ser Gly Arg Gly His Tyr Lys Gly Val Ala Ser Asn Tyr Leu Ala
865                 870                 875                 880

Gly Leu Glu Pro Gly Asp Ala Ile Ser Cys Phe Ile Arg Glu Pro Gln
                885                 890                 895

Ser Gly Phe Arg Leu Pro Glu Asp Pro Glu Thr Pro Val Ile Met Val
                900                 905                 910

Gly Pro Gly Thr Gly Ile Ala Pro Tyr Arg Gly Phe Leu Gln Ala Arg
                915                 920                 925

Arg Ile Gln Arg Asp Ala Gly Val Lys Leu Gly Glu Ala His Leu Tyr
                930                 935                 940

Phe Gly Cys Arg Arg Pro Asn Glu Asp Phe Leu Tyr Arg Asp Glu Leu
945                 950                 955                 960

Glu Gln Ala Glu Lys Asp Gly Ile Val His Leu His Thr Ala Phe Ser
                965                 970                 975

Arg Leu Glu Gly Arg Pro Lys Thr Tyr Val Gln Asp Leu Leu Arg Glu
                980                 985                 990

Asp Ala Ala Leu Leu Ile His Leu Leu Asn Glu Gly Gly Arg Leu Tyr
                995                 1000                1005

Val Cys Gly Asp Gly Ser Arg Met Ala Pro Ala Val Glu Gln Ala Leu
                1010                1015                1020

Cys Glu Ala Tyr Arg Ile Val Gln Gly Ala Ser Arg Glu Glu Ser Gln
1025                1030                1035                1040

Ser Trp Leu Ser Ala Leu Leu Glu Glu Gly Arg Tyr Ala Lys Asp Val
                1045                1050                1055

Trp Asp Gly Gly Val Ser Gln His Asn Val Lys Ala Asp Cys Ile Ala
                1060                1065                1070
```

Arg Thr

<210> SEQ ID NO 30
<211> LENGTH: 1065
<212> TYPE: PRT
<213> ORGANISM: Bacillus thuringiensis
<220> FEATURE:
<223> OTHER INFORMATION: Bacillus thuringiensis serovar konkukian strain
      97-27 NADPH-cytochrome P450 reductase, CYPX

<400> SEQUENCE: 30

```
Met Asp Lys Lys Val Ser Ala Ile Pro Gln Pro Lys Thr Tyr Gly Pro
1               5                   10                  15

Leu Gly Asn Leu Pro Leu Ile Asp Lys Asp Lys Pro Thr Leu Ser Phe
            20                  25                  30

Ile Lys Leu Ala Glu Glu Tyr Gly Pro Ile Phe Gln Ile Gln Thr Leu
        35                  40                  45

Ser Asp Thr Ile Ile Val Val Ser Gly His Glu Leu Val Ala Glu Val
    50                  55                  60

Cys Asp Glu Thr Arg Phe Asp Lys Ser Ile Glu Gly Ala Leu Ala Lys
65                  70                  75                  80

Val Arg Ala Phe Ala Gly Asp Gly Leu Phe Thr Ser Glu Thr Asp Glu
                85                  90                  95

Pro Asn Trp Lys Lys Ala His Asn Ile Leu Met Pro Thr Phe Ser Gln
            100                 105                 110

Arg Ala Met Lys Asp Tyr His Ala Met Met Val Asp Ile Ala Val Gln
        115                 120                 125

Leu Val Gln Lys Trp Ala Arg Leu Asn Pro Asn Glu Asn Val Asp Val
    130                 135                 140

Pro Glu Asp Met Thr Arg Leu Thr Leu Asp Thr Ile Gly Leu Cys Gly
145                 150                 155                 160

Phe Asn Tyr Arg Phe Asn Ser Phe Tyr Arg Glu Thr Pro His Pro Phe
                165                 170                 175

Ile Thr Ser Met Thr Arg Ala Leu Asp Glu Ala Met His Gln Leu Gln
            180                 185                 190

Arg Leu Asp Ile Glu Asp Lys Leu Met Trp Arg Thr Lys Arg Gln Phe
        195                 200                 205

Gln His Asp Ile Gln Ser Met Phe Ser Leu Val Asp Asn Ile Ile Ala
    210                 215                 220

Glu Arg Lys Ser Ser Glu Asn Gln Glu Asn Asp Leu Leu Ser Arg
225                 230                 235                 240

Met Leu Asn Val Gln Asp Pro Glu Thr Gly Glu Lys Leu Asp Asp Glu
                245                 250                 255

Asn Ile Arg Phe Gln Ile Ile Thr Phe Leu Ile Ala Gly His Glu Thr
            260                 265                 270

Thr Ser Gly Leu Leu Ser Phe Ala Ile Tyr Phe Leu Leu Lys Asn Pro
        275                 280                 285

Asp Lys Leu Lys Lys Ala Tyr Glu Glu Val Asp Arg Val Leu Thr Asp
    290                 295                 300

Ser Thr Pro Thr Tyr Gln Gln Val Met Lys Leu Lys Tyr Ile Arg Met
305                 310                 315                 320

Ile Leu Asn Glu Ser Leu Arg Leu Trp Pro Thr Ala Pro Ala Phe Ser
                325                 330                 335

Leu Tyr Ala Lys Glu Asp Thr Val Ile Gly Gly Lys Tyr Pro Ile Lys
            340                 345                 350
```

```
Lys Gly Glu Asp Arg Ile Ser Val Leu Ile Pro Gln Leu His Arg Asp
        355                 360                 365

Lys Asp Ala Trp Gly Asp Asp Val Glu Glu Phe Gln Pro Glu Arg Phe
    370                 375                 380

Glu Glu Leu Asp Lys Val Pro His His Ala Tyr Lys Pro Phe Gly Asn
385                 390                 395                 400

Gly Gln Arg Ala Cys Ile Gly Met Gln Phe Ala Leu His Glu Ala Thr
                405                 410                 415

Leu Val Met Gly Met Leu Leu Gln His Phe Glu Phe Ile Asp Tyr Glu
            420                 425                 430

Asp Tyr Gln Leu Asp Val Lys Gln Thr Leu Thr Leu Lys Pro Gly Asp
        435                 440                 445

Phe Lys Ile Arg Ile Val Pro Arg Asn Gln Thr Ile Ser His Thr Thr
    450                 455                 460

Val Leu Ala Pro Thr Glu Glu Lys Leu Lys Lys His Glu Ile Lys Lys
465                 470                 475                 480

Gln Val Gln Lys Thr Pro Ser Ile Ile Gly Ala Asp Asn Leu Ser Leu
                485                 490                 495

Leu Val Leu Tyr Gly Ser Asp Thr Gly Val Ala Glu Gly Ile Ala Arg
            500                 505                 510

Glu Leu Ala Asp Thr Ala Ser Leu Glu Gly Val Gln Thr Glu Val Val
        515                 520                 525

Ala Leu Asn Asp Arg Ile Gly Ser Leu Pro Lys Glu Gly Ala Val Leu
    530                 535                 540

Ile Val Thr Ser Ser Tyr Asn Gly Lys Pro Pro Ser Asn Ala Gly Gln
545                 550                 555                 560

Phe Val Gln Trp Leu Glu Glu Leu Lys Pro Asp Glu Leu Lys Gly Val
                565                 570                 575

Gln Tyr Ala Val Phe Gly Cys Gly Asp His Asn Trp Ala Ser Thr Tyr
            580                 585                 590

Gln Arg Ile Pro Arg Tyr Ile Asp Glu Gln Met Ala Gln Lys Gly Ala
        595                 600                 605

Thr Arg Phe Ser Thr Arg Gly Glu Ala Asp Ala Ser Gly Asp Phe Glu
    610                 615                 620

Glu Gln Leu Glu Gln Trp Lys Gln Ser Met Trp Ser Asp Ala Met Lys
625                 630                 635                 640

Ala Phe Gly Leu Glu Leu Asn Lys Asn Met Glu Lys Glu Arg Ser Thr
                645                 650                 655

Leu Ser Leu Gln Phe Val Ser Arg Leu Gly Gly Ser Pro Leu Ala Arg
            660                 665                 670

Thr Tyr Glu Ala Val Tyr Ala Ser Ile Leu Glu Asn Arg Glu Leu Gln
        675                 680                 685

Ser Ser Ser Ser Glu Arg Ser Thr Arg His Ile Glu Ile Ser Leu Pro
    690                 695                 700

Glu Gly Ala Thr Tyr Lys Glu Gly Asp His Leu Gly Val Leu Pro Ile
705                 710                 715                 720

Asn Asn Glu Lys Asn Val Asn Arg Ile Leu Lys Arg Phe Gly Leu Asn
                725                 730                 735

Gly Lys Asp Gln Val Ile Leu Ser Ala Ser Gly Arg Ser Val Asn His
            740                 745                 750

Ile Pro Leu Asp Ser Pro Val Arg Leu Tyr Asp Leu Leu Ser Tyr Ser
        755                 760                 765
```

| | | | | | | | | | | | | |
|---|---|---|---|---|---|---|---|---|---|---|---|---|
|Val|Glu|Val|Gln|Glu|Ala|Ala|Thr|Arg|Ala|Gln|Ile|Arg|Glu|Met|Val|
|770| | | | |775| | | | |780| | | | |

Thr Phe Thr Ala Cys Pro Pro His Lys Lys Glu Leu Glu Ser Leu Leu
785                 790                 795                 800

Glu Asp Gly Val Tyr Gln Glu Gln Ile Leu Lys Lys Arg Ile Ser Met
                805                 810                 815

Leu Asp Leu Leu Glu Lys Tyr Glu Ala Cys Glu Ile Arg Phe Glu Arg
            820                 825                 830

Phe Leu Glu Leu Leu Pro Ala Leu Lys Pro Arg Tyr Tyr Ser Ile Ser
        835                 840                 845

Ser Ser Pro Leu Val Ala Gln Asp Arg Leu Ser Ile Thr Val Gly Val
850                 855                 860

Val Asn Ala Pro Ala Trp Ser Gly Glu Gly Thr Tyr Glu Gly Val Ala
865                 870                 875                 880

Ser Asn Tyr Leu Ala Gln Arg His Asn Lys Asp Glu Ile Ile Cys Phe
                885                 890                 895

Ile Arg Thr Pro Gln Ser Asn Phe Gln Leu Pro Glu Asn Pro Glu Thr
            900                 905                 910

Pro Ile Ile Met Val Gly Pro Gly Thr Gly Ile Ala Pro Phe Arg Gly
        915                 920                 925

Phe Leu Gln Ala Arg Arg Val Gln Lys Gln Lys Gly Met Lys Val Gly
    930                 935                 940

Glu Ala His Leu Tyr Phe Gly Cys Arg His Pro Glu Lys Asp Tyr Leu
945                 950                 955                 960

Tyr Arg Thr Glu Leu Glu Asn Asp Glu Arg Asp Gly Leu Ile Ser Leu
                965                 970                 975

His Thr Ala Phe Ser Arg Leu Glu Gly His Pro Lys Thr Tyr Val Gln
            980                 985                 990

His Val Ile Lys Glu Asp Arg Ile His Leu Ile Ser Leu Leu Asp Asn
        995                 1000                1005

Gly Ala His Leu Tyr Ile Cys Gly Asp Gly Ser Lys Met Ala Pro Asp
    1010                1015                1020

Val Glu Asp Thr Leu Cys Gln Ala Tyr Gln Glu Ile His Glu Val Ser
1025                1030                1035                1040

Glu Gln Glu Ala Arg Asn Trp Leu Asp Arg Leu Gln Glu Gly Arg
                1045                1050                1055

Tyr Gly Lys Asp Val Trp Ala Gly Ile
            1060                1065

<210> SEQ ID NO 31
<211> LENGTH: 1064
<212> TYPE: PRT
<213> ORGANISM: Cupriavidus metallidurans
<220> FEATURE:
<223> OTHER INFORMATION: Cupriavidus metallidurans (R. metallidurans)
      strain CH34putative bifunctional P-450:NADPH-450
      reductase 2, CYP102E1

<400> SEQUENCE: 31

Met Ser Thr Ala Thr Pro Ala Ala Ala Leu Glu Pro Ile Pro Arg Asp
1               5                   10                  15

Pro Gly Trp Pro Ile Phe Gly Asn Leu Phe Gln Ile Thr Pro Gly Glu
                20                  25                  30

Val Gly Gln His Leu Leu Ala Arg Ser Arg His His Asp Gly Ile Phe
            35                  40                  45

Glu Leu Asp Phe Ala Gly Lys Arg Val Pro Phe Val Ser Ser Val Ala

-continued

```
            50                  55                  60
Leu Ala Ser Glu Leu Cys Asp Ala Thr Arg Phe Arg Lys Ile Ile Gly
 65                  70                  75                  80

Pro Pro Leu Ser Tyr Leu Arg Asp Met Ala Gly Asp Gly Leu Phe Thr
                 85                  90                  95

Ala His Ser Asp Glu Pro Asn Trp Gly Cys Ala His Arg Ile Leu Met
                100                 105                 110

Pro Ala Phe Ser Gln Arg Ala Met Lys Ala Tyr Phe Asp Val Met Leu
                115                 120                 125

Arg Val Ala Asn Arg Leu Val Asp Lys Trp Asp Arg Gln Gly Pro Asp
            130                 135                 140

Ala Asp Ile Ala Val Ala Asp Asp Met Thr Arg Leu Thr Leu Asp Thr
145                 150                 155                 160

Ile Ala Leu Ala Gly Phe Gly Tyr Asp Phe Ala Ser Phe Ala Ser Asp
                165                 170                 175

Glu Leu Asp Pro Phe Val Met Ala Met Val Gly Ala Leu Gly Glu Ala
                180                 185                 190

Met Gln Lys Leu Thr Arg Leu Pro Ile Gln Asp Arg Phe Met Gly Arg
            195                 200                 205

Ala His Arg Gln Ala Ala Glu Asp Ile Ala Tyr Met Arg Asn Leu Val
            210                 215                 220

Asp Asp Val Ile Arg Gln Arg Val Ser Pro Thr Ser Gly Met Asp
225                 230                 235                 240

Leu Leu Asn Leu Met Leu Glu Ala Arg Asp Pro Glu Thr Asp Arg Arg
                245                 250                 255

Leu Asp Asp Ala Asn Ile Arg Asn Gln Val Ile Thr Phe Leu Ile Ala
                260                 265                 270

Gly His Glu Thr Thr Ser Gly Leu Leu Thr Phe Ala Leu Tyr Glu Leu
            275                 280                 285

Leu Arg Asn Pro Gly Val Leu Ala Gln Ala Tyr Ala Glu Val Asp Thr
            290                 295                 300

Val Leu Pro Gly Asp Ala Leu Pro Val Tyr Ala Asp Leu Ala Arg Met
305                 310                 315                 320

Pro Val Leu Asp Arg Val Leu Lys Glu Thr Leu Arg Leu Trp Pro Thr
                325                 330                 335

Ala Pro Ala Phe Ala Val Ala Pro Phe Asp Asp Val Val Leu Gly Gly
                340                 345                 350

Arg Tyr Arg Leu Arg Lys Asp Arg Arg Ile Ser Val Val Leu Thr Ala
            355                 360                 365

Leu His Arg Asp Pro Lys Val Trp Ala Asn Pro Glu Arg Phe Asp Ile
            370                 375                 380

Asp Arg Phe Leu Pro Glu Asn Glu Ala Lys Leu Pro Ala His Ala Tyr
385                 390                 395                 400

Met Pro Phe Gly Gln Gly Glu Arg Ala Cys Ile Gly Arg Gln Phe Ala
                405                 410                 415

Leu Thr Glu Ala Lys Leu Ala Leu Ala Leu Met Leu Arg Asn Phe Ala
                420                 425                 430

Phe Gln Asp Pro His Asp Tyr Gln Phe Arg Leu Lys Glu Thr Leu Thr
            435                 440                 445

Ile Lys Pro Asp Gln Phe Val Leu Arg Val Arg Arg Arg Pro His
            450                 455                 460

Glu Arg Phe Val Thr Arg Gln Ala Ser Gln Ala Val Ala Asp Ala Ala
465                 470                 475                 480
```

-continued

```
Gln Thr Asp Val Arg Gly His Gly Gln Ala Met Thr Val Leu Cys Ala
            485                 490                 495
Ser Ser Leu Gly Thr Ala Arg Glu Leu Ala Glu Gln Ile His Ala Gly
            500                 505                 510
Ala Ile Ala Ala Gly Phe Asp Ala Lys Leu Ala Asp Leu Asp Asp Ala
            515                 520                 525
Val Gly Val Leu Pro Thr Ser Gly Leu Val Val Val Ala Ala Thr
530                 535                 540
Tyr Asn Gly Arg Ala Pro Asp Ser Ala Arg Lys Phe Glu Ala Met Leu
545                 550                 555                 560
Asp Ala Asp Ala Ser Gly Tyr Arg Ala Asn Gly Met Arg Leu Ala
            565                 570                 575
Leu Leu Gly Cys Gly Asn Ser Gln Trp Ala Thr Tyr Gln Ala Phe Pro
            580                 585                 590
Arg Arg Val Phe Asp Phe Phe Ile Thr Ala Gly Ala Val Pro Leu Leu
            595                 600                 605
Pro Arg Gly Glu Ala Asp Gly Asn Gly Asp Phe Asp Gln Ala Ala Glu
            610                 615                 620
Arg Trp Leu Ala Gln Leu Trp Gln Ala Leu Gln Ala Asp Gly Ala Gly
625                 630                 635                 640
Thr Gly Gly Leu Gly Val Asp Val Gln Val Arg Ser Met Ala Ala Ile
            645                 650                 655
Arg Ala Glu Thr Leu Pro Ala Gly Thr Gln Ala Phe Thr Val Leu Ser
            660                 665                 670
Asn Asp Glu Leu Val Gly Asp Pro Ser Gly Leu Trp Asp Phe Ser Ile
            675                 680                 685
Glu Ala Pro Arg Thr Ser Thr Arg Asp Ile Arg Leu Gln Leu Pro Pro
            690                 695                 700
Gly Ile Thr Tyr Arg Thr Gly Asp His Ile Ala Val Trp Pro Gln Asn
705                 710                 715                 720
Asp Ala Gln Leu Val Ser Glu Leu Cys Glu Arg Leu Asp Leu Asp Pro
            725                 730                 735
Asp Ala Gln Ala Thr Ile Ser Ala Pro His Gly Met Gly Arg Gly Leu
            740                 745                 750
Pro Ile Asp Gln Ala Leu Pro Val Arg Gln Leu Leu Thr His Phe Ile
            755                 760                 765
Glu Leu Gln Asp Val Val Ser Arg Gln Thr Leu Arg Ala Leu Ala Gln
            770                 775                 780
Ala Thr Arg Cys Pro Phe Thr Lys Gln Ser Ile Glu Gln Leu Ala Ser
785                 790                 795                 800
Asp Asp Ala Glu His Gly Tyr Ala Thr Lys Val Val Ala Arg Arg Leu
            805                 810                 815
Gly Ile Leu Asp Val Leu Val Glu His Pro Ala Ile Ala Leu Thr Leu
            820                 825                 830
Gln Glu Leu Leu Ala Cys Thr Val Pro Met Arg Pro Arg Leu Tyr Ser
            835                 840                 845
Ile Ala Ser Ser Pro Leu Val Ser Pro Asp Val Ala Thr Leu Leu Val
850                 855                 860
Gly Thr Val Cys Ala Pro Ala Leu Ser Gly Arg Gly Gln Phe Arg Gly
865                 870                 875                 880
Val Ala Ser Thr Trp Leu Gln His Leu Pro Pro Gly Ala Arg Val Ser
            885                 890                 895
```

```
Ala Ser Ile Arg Thr Pro Asn Pro Pro Phe Ala Pro Asp Pro Asp Pro
                900                 905                 910

Ala Ala Pro Met Leu Leu Ile Gly Pro Gly Thr Gly Ile Ala Pro Phe
            915                 920                 925

Arg Gly Phe Leu Glu Glu Arg Ala Leu Arg Lys Met Ala Gly Asn Ala
        930                 935                 940

Val Thr Pro Ala Gln Leu Tyr Phe Gly Cys Arg His Pro Gln His Asp
945                 950                 955                 960

Trp Leu Tyr Arg Glu Asp Ile Glu Arg Trp Ala Gly Gln Gly Val Val
                965                 970                 975

Glu Val His Pro Ala Tyr Ser Val Val Pro Asp Ala Pro Arg Tyr Val
            980                 985                 990

Gln Asp Leu Leu Trp Gln Arg Glu Gln Val Trp Ala Gln Val Arg
        995                 1000                1005

Asp Gly Ala Thr Ile Tyr Val Cys Gly Asp Gly Arg Arg Met Ala Pro
    1010                1015                1020

Ala Val Arg Gln Thr Leu Ile Glu Ile Gly Met Ala Gln Gly Gly Met
1025                1030                1035                1040

Thr Asp Lys Ala Ala Ser Asp Trp Phe Gly Gly Leu Val Ala Gln Gly
                1045                1050                1055

Arg Tyr Arg Gln Asp Val Phe Asn
            1060

<210> SEQ ID NO 32
<211> LENGTH: 1120
<212> TYPE: PRT
<213> ORGANISM: Aspergillus fumigatus
<220> FEATURE:
<223> OTHER INFORMATION: Aspergillus fumigatus strain Af293 putative
      P450 family fatty acid hydroxylase, CYP505X

<400> SEQUENCE: 32

Met Ser Glu Ser Lys Thr Val Pro Ile Pro Gly Pro Arg Gly Val Pro
1               5                   10                  15

Leu Leu Gly Asn Ile Tyr Asp Ile Glu Gln Glu Val Pro Leu Arg Ser
                20                  25                  30

Ile Asn Leu Met Ala Asp Gln Tyr Gly Pro Ile Tyr Arg Leu Thr Thr
            35                  40                  45

Phe Gly Trp Ser Arg Val Phe Val Ser Thr His Glu Leu Val Asp Glu
        50                  55                  60

Val Cys Asp Glu Glu Arg Phe Thr Lys Val Val Thr Ala Gly Leu Asn
65                  70                  75                  80

Gln Ile Arg Asn Gly Val His Asp Gly Leu Phe Thr Ala Asn Phe Pro
                85                  90                  95

Gly Glu Glu Asn Trp Ala Ile Ala His Arg Val Leu Val Pro Ala Phe
            100                 105                 110

Gly Pro Leu Ser Ile Arg Gly Met Phe Asp Glu Met Tyr Asp Ile Ala
        115                 120                 125

Thr Gln Leu Val Met Lys Trp Ala Arg His Gly Pro Thr Val Pro Ile
    130                 135                 140

Met Val Thr Asp Asp Phe Thr Arg Leu Thr Leu Asp Thr Ile Ala Leu
145                 150                 155                 160

Cys Ala Met Gly Thr Arg Phe Asn Ser Phe Tyr His Glu Glu Met His
                165                 170                 175

Pro Phe Val Glu Ala Met Val Gly Leu Leu Gln Gly Ser Gly Asp Arg
            180                 185                 190
```

```
Ala Arg Arg Pro Ala Leu Leu Asn Asn Leu Pro Thr Ser Glu Asn Ser
            195                 200                 205

Lys Tyr Trp Asp Asp Ile Ala Phe Leu Arg Asn Leu Ala Gln Glu Leu
    210                 215                 220

Val Glu Ala Arg Arg Lys Asn Pro Glu Asp Lys Lys Asp Leu Leu Asn
225                 230                 235                 240

Ala Leu Ile Leu Gly Arg Asp Pro Lys Thr Gly Lys Gly Leu Thr Asp
                245                 250                 255

Glu Ser Ile Ile Asp Asn Met Ile Thr Phe Leu Ile Ala Gly His Glu
                260                 265                 270

Thr Thr Ser Gly Leu Leu Ser Phe Leu Phe Tyr Tyr Leu Leu Lys Thr
            275                 280                 285

Pro Asn Ala Tyr Lys Lys Ala Gln Glu Glu Val Asp Ser Val Val Gly
            290                 295                 300

Arg Arg Lys Ile Thr Val Glu Asp Met Ser Arg Leu Pro Tyr Leu Asn
305                 310                 315                 320

Ala Val Met Arg Glu Thr Leu Arg Leu Arg Ser Thr Ala Pro Leu Ile
                325                 330                 335

Ala Val His Ala His Pro Glu Lys Asn Lys Glu Asp Pro Val Thr Leu
                340                 345                 350

Gly Gly Gly Lys Tyr Val Leu Asn Lys Asp Glu Pro Ile Val Ile Ile
            355                 360                 365

Leu Asp Lys Leu His Arg Asp Pro Gln Val Tyr Gly Pro Asp Ala Glu
            370                 375                 380

Glu Phe Lys Pro Glu Arg Met Leu Asp Glu Asn Phe Glu Lys Leu Pro
385                 390                 395                 400

Lys Asn Ala Trp Lys Pro Phe Gly Asn Gly Met Arg Ala Cys Ile Gly
                405                 410                 415

Arg Pro Phe Ala Trp Gln Glu Ala Leu Leu Val Val Ala Ile Leu Leu
                420                 425                 430

Gln Asn Phe Asn Phe Gln Met Asp Asp Pro Ser Tyr Asn Leu His Ile
            435                 440                 445

Lys Gln Thr Leu Thr Ile Lys Pro Lys Asp Phe His Met Arg Ala Thr
            450                 455                 460

Leu Arg His Gly Leu Asp Ala Thr Lys Leu Gly Ile Ala Leu Ser Gly
465                 470                 475                 480

Ser Ala Asp Arg Ala Pro Pro Glu Ser Ser Gly Ala Ala Ser Arg Val
                485                 490                 495

Arg Lys Gln Ala Thr Pro Pro Ala Gly Gln Leu Lys Pro Met His Ile
            500                 505                 510

Phe Phe Gly Ser Asn Thr Gly Thr Cys Glu Thr Phe Ala Arg Arg Leu
            515                 520                 525

Ala Asp Asp Ala Val Gly Tyr Gly Phe Ala Ala Asp Val Gln Ser Leu
530                 535                 540

Asp Ser Ala Met Gln Asn Val Pro Lys Asp Glu Pro Val Val Phe Ile
545                 550                 555                 560

Thr Ala Ser Tyr Glu Gly Gln Pro Pro Asp Asn Ala Ala His Phe Phe
                565                 570                 575

Glu Trp Leu Ser Ala Leu Lys Glu Asn Glu Leu Glu Gly Val Asn Tyr
            580                 585                 590

Ala Val Phe Gly Cys Gly His His Asp Trp Gln Ala Thr Phe His Arg
            595                 600                 605
```

```
Ile Pro Lys Ala Val Asn Gln Leu Val Ala Glu His Gly Gly Asn Arg
610                 615                 620

Leu Cys Asp Leu Gly Leu Ala Asp Ala Ala Asn Ser Asp Met Phe Thr
625                 630                 635                 640

Asp Phe Asp Ser Trp Gly Glu Ser Thr Phe Trp Pro Ala Ile Thr Ser
                645                 650                 655

Lys Phe Gly Gly Gly Lys Ser Asp Glu Pro Lys Pro Ser Ser Ser Leu
                660                 665                 670

Gln Val Glu Val Ser Thr Gly Met Arg Ala Ser Thr Leu Gly Leu Gln
                675                 680                 685

Leu Gln Glu Gly Leu Val Ile Asp Asn Gln Leu Leu Ser Ala Pro Asp
690                 695                 700

Val Pro Ala Lys Arg Met Ile Arg Phe Lys Leu Pro Ser Asp Met Ser
705                 710                 715                 720

Tyr Arg Cys Gly Asp Tyr Leu Ala Val Leu Pro Val Asn Pro Thr Ser
                725                 730                 735

Val Val Arg Arg Ala Ile Arg Arg Phe Asp Leu Pro Trp Asp Ala Met
                740                 745                 750

Leu Thr Ile Arg Lys Pro Ser Gln Ala Pro Lys Gly Ser Thr Ser Ile
    755                 760                 765

Pro Leu Asp Thr Pro Ile Ser Ala Phe Glu Leu Leu Ser Thr Tyr Val
770                 775                 780

Glu Leu Ser Gln Pro Ala Ser Lys Arg Asp Leu Thr Ala Leu Ala Asp
785                 790                 795                 800

Ala Ala Ile Thr Asp Ala Asp Ala Gln Ala Glu Leu Arg Tyr Leu Ala
                805                 810                 815

Ser Ser Pro Thr Arg Phe Thr Glu Glu Ile Val Lys Lys Arg Met Ser
                820                 825                 830

Pro Leu Asp Leu Leu Ile Arg Tyr Pro Ser Ile Lys Leu Pro Val Gly
                835                 840                 845

Asp Phe Leu Ala Met Leu Pro Pro Met Arg Val Arg Gln Tyr Ser Ile
    850                 855                 860

Ser Ser Ser Pro Leu Ala Asp Pro Ser Glu Cys Ser Ile Thr Phe Ser
865                 870                 875                 880

Val Leu Asn Ala Pro Ala Leu Ala Ala Ser Leu Pro Pro Ala Glu
                885                 890                 895

Arg Ala Glu Ala Glu Gln Tyr Met Gly Val Ala Ser Thr Tyr Leu Ser
                900                 905                 910

Glu Leu Lys Pro Gly Glu Arg Ala His Ile Ala Val Arg Pro Ser His
                915                 920                 925

Ser Gly Phe Lys Pro Pro Met Asp Leu Lys Ala Pro Met Ile Met Ala
    930                 935                 940

Cys Ala Gly Ser Gly Leu Ala Pro Phe Arg Gly Phe Ile Met Asp Arg
945                 950                 955                 960

Ala Glu Lys Ile Arg Gly Arg Ser Ser Val Gly Ala Asp Gly Gln
                965                 970                 975

Leu Pro Glu Val Glu Gln Pro Ala Lys Ala Ile Leu Tyr Val Gly Cys
                980                 985                 990

Arg Thr Lys Gly Lys Asp Asp Ile His Ala Thr Glu Leu Ala Glu Trp
                995                 1000                1005

Ala Gln Leu Gly Ala Val Asp Val Arg Trp Ala Tyr Ser Arg Pro Glu
    1010                1015                1020

Asp Gly Ser Lys Gly Arg His Val Gln Asp Leu Met Leu Glu Asp Arg
```

| | | | |
|---|---|---|---|
| 1025 | 1030 | 1035 | 1040 |

Glu Glu Leu Val Ser Leu Phe Asp Gln Gly Ala Arg Ile Tyr Val Cys
                1045                1050                1055

Gly Ser Thr Gly Val Gly Asn Gly Val Arg Gln Ala Cys Lys Asp Ile
                1060                1065                1070

Tyr Leu Glu Arg Arg Arg Gln Leu Arg Gln Ala Ala Arg Glu Arg Gly
                1075                1080                1085

Glu Glu Val Pro Ala Glu Glu Asp Glu Asp Ala Ala Ala Glu Gln Phe
    1090                1095                1100

Leu Asp Asn Leu Arg Thr Lys Glu Arg Tyr Ala Thr Asp Val Phe Thr
1105                1110                1115                1120

<210> SEQ ID NO 33
<211> LENGTH: 1083
<212> TYPE: PRT
<213> ORGANISM: Aspergillus nidulans
<220> FEATURE:
<223> OTHER INFORMATION: Aspergillus nidulans strain FGSC A4
     hypothetical protein AN6835.2, CYP505A8

<400> SEQUENCE: 33

Met Ala Glu Ile Pro Glu Pro Lys Gly Leu Pro Leu Ile Gly Asn Ile
1                 5                  10                 15

Gly Thr Ile Asp Gln Glu Phe Pro Leu Gly Ser Met Val Ala Leu Ala
            20                 25                 30

Glu Glu His Gly Glu Ile Tyr Arg Leu Arg Phe Pro Gly Arg Thr Val
         35                 40                 45

Val Val Val Ser Thr His Ala Leu Val Asn Glu Thr Cys Asp Glu Lys
  50                  55                 60

Arg Phe Arg Lys Ser Val Asn Ser Ala Leu Ala His Val Arg Glu Gly
65                 70                 75                 80

Val His Asp Gly Leu Phe Thr Ala Lys Met Gly Glu Val Asn Trp Glu
            85                 90                 95

Ile Ala His Arg Val Leu Met Pro Ala Phe Gly Pro Leu Ser Ile Arg
         100                105               110

Gly Met Phe Asp Glu Met His Asp Ile Ala Ser Gln Leu Ala Leu Lys
        115                120               125

Trp Ala Arg Tyr Gly Pro Asp Cys Pro Ile Met Val Thr Asp Asp Phe
130                135                140

Thr Arg Leu Thr Leu Asp Thr Leu Ala Leu Cys Ser Met Gly Tyr Arg
145               150                155               160

Phe Asn Ser Tyr Tyr Ser Pro Val Leu His Pro Phe Ile Glu Ala Met
        165                170               175

Gly Asp Phe Leu Thr Glu Ala Gly Glu Lys Pro Arg Arg Pro Pro Leu
        180                185               190

Pro Ala Val Phe Phe Arg Asn Arg Asp Gln Lys Phe Gln Asp Asp Ile
        195                200               205

Ala Val Leu Arg Asp Thr Ala Gln Gly Val Leu Gln Ala Arg Lys Glu
210                215                220

Gly Lys Ser Asp Arg Asn Asp Leu Leu Ser Ala Met Leu Arg Gly Val
225               230                235               240

Asp Ser Gln Thr Gly Gln Lys Met Thr Asp Glu Ser Ile Met Asp Asn
        245                250               255

Leu Ile Thr Phe Leu Ile Ala Gly His Glu Thr Thr Ser Gly Leu Leu
        260                265               270

```
Ser Phe Val Phe Tyr Gln Leu Leu Lys His Pro Glu Thr Tyr Arg Thr
            275                 280                 285

Ala Gln Gln Glu Val Asp Asn Val Val Gly Gln Gly Val Ile Glu Val
290                 295                 300

Ser His Leu Ser Lys Leu Pro Tyr Ile Asn Ser Val Leu Arg Glu Thr
305                 310                 315                 320

Leu Arg Leu Asn Ala Thr Ile Pro Leu Phe Thr Val Glu Ala Phe Glu
                325                 330                 335

Asp Thr Leu Leu Ala Gly Lys Tyr Pro Val Lys Ala Gly Glu Thr Ile
            340                 345                 350

Val Asn Leu Leu Ala Lys Ser His Leu Asp Pro Glu Val Tyr Gly Glu
        355                 360                 365

Asp Ala Leu Glu Phe Lys Pro Glu Arg Met Ser Asp Glu Leu Phe Asn
    370                 375                 380

Ala Arg Leu Lys Gln Phe Pro Ser Ala Trp Lys Pro Phe Gly Asn Gly
385                 390                 395                 400

Met Arg Ala Cys Ile Gly Arg Pro Phe Ala Trp Gln Glu Ala Leu Leu
                405                 410                 415

Val Met Ala Met Leu Leu Gln Asn Phe Asp Phe Ser Leu Ala Asp Pro
            420                 425                 430

Asn Tyr Asp Leu Lys Phe Lys Gln Thr Leu Thr Ile Lys Pro Lys Asp
        435                 440                 445

Met Phe Met Lys Ala Arg Leu Arg His Gly Leu Thr Pro Thr Thr Leu
    450                 455                 460

Glu Arg Arg Leu Ala Gly Leu Ala Val Glu Ser Ala Thr Gln Asp Lys
465                 470                 475                 480

Ile Val Thr Asn Pro Ala Asp Asn Ser Val Thr Gly Thr Arg Leu Thr
                485                 490                 495

Ile Leu Tyr Gly Ser Asn Ser Gly Thr Cys Glu Thr Leu Ala Arg Arg
            500                 505                 510

Ile Ala Ala Asp Ala Pro Ser Lys Gly Phe His Val Met Arg Phe Asp
        515                 520                 525

Gly Leu Asp Ser Gly Arg Ser Ala Leu Pro Thr Asp His Pro Val Val
    530                 535                 540

Ile Val Thr Ser Ser Tyr Glu Gly Gln Pro Pro Glu Asn Ala Lys Gln
545                 550                 555                 560

Phe Val Ser Trp Leu Glu Glu Leu Glu Gln Gln Asn Glu Ser Leu Gln
                565                 570                 575

Leu Lys Gly Val Asp Phe Ala Val Phe Gly Cys Phe Lys Glu Trp Ala
            580                 585                 590

Gln Thr Phe His Arg Ile Pro Lys Leu Val Asp Ser Leu Leu Glu Lys
        595                 600                 605

Leu Gly Gly Ser Arg Leu Thr Asp Leu Gly Leu Ala Asp Val Ser Thr
    610                 615                 620

Asp Glu Leu Phe Ser Thr Phe Glu Thr Trp Ala Asp Asp Val Leu Trp
625                 630                 635                 640

Pro Arg Leu Val Ala Gln Tyr Gly Ala Asp Gly Lys Thr Gln Ala His
                645                 650                 655

Gly Ser Ser Ala Gly His Glu Ala Ser Asn Ala Ala Val Glu Val
            660                 665                 670

Thr Val Ser Asn Ser Arg Thr Gln Ala Leu Arg Gln Asp Val Gly Gln
        675                 680                 685

Ala Met Val Val Glu Thr Arg Leu Leu Thr Ala Glu Ser Glu Lys Glu
```

```
            690                 695                 700
Arg Arg Lys Lys His Leu Glu Ile Arg Leu Pro Asp Gly Val Ser Tyr
705                 710                 715                 720

Thr Ala Gly Asp Tyr Leu Ala Val Leu Pro Ile Asn Pro Pro Glu Thr
                725                 730                 735

Val Arg Arg Ala Met Arg Gln Phe Lys Leu Ser Trp Asp Ala Gln Ile
                740                 745                 750

Thr Ile Ala Pro Ser Gly Pro Thr Thr Ala Leu Pro Thr Asp Gly Pro
            755                 760                 765

Ile Ala Ala Asn Asp Ile Phe Ser Thr Tyr Val Glu Leu Ser Gln Pro
770                 775                 780

Ala Thr Arg Lys Asp Leu Arg Ile Met Ala Asp Ala Thr Thr Asp Pro
785                 790                 795                 800

Asp Val Gln Lys Ile Leu Arg Thr Tyr Ala Asn Glu Thr Tyr Thr Ala
                805                 810                 815

Glu Ile Leu Thr Lys Ser Ile Ser Val Leu Asp Ile Leu Glu Gln His
                820                 825                 830

Pro Ala Ile Asp Leu Pro Leu Gly Thr Phe Leu Leu Met Leu Pro Ser
            835                 840                 845

Met Arg Met Arg Gln Tyr Ser Ile Ser Ser Ser Pro Leu Leu Thr Pro
850                 855                 860

Thr Thr Ala Thr Ile Thr Ile Ser Val Leu Asp Ala Pro Ser Arg Ser
865                 870                 875                 880

Arg Ser Asn Gly Ser Arg His Leu Gly Val Ala Thr Ser Tyr Leu Asp
                885                 890                 895

Ser Leu Ser Val Gly Asp His Leu Gln Val Thr Val Arg Lys Asn Pro
                900                 905                 910

Ser Ser Gly Phe Arg Leu Pro Ser Glu Pro Glu Thr Thr Pro Met Ile
            915                 920                 925

Cys Ile Ala Ala Gly Ser Gly Ile Ala Pro Phe Arg Ala Phe Leu Gln
930                 935                 940

Glu Arg Ala Val Met Met Glu Gln Asp Lys Asp Arg Lys Leu Ala Pro
945                 950                 955                 960

Ala Leu Leu Phe Phe Gly Cys Arg Ala Pro Gly Ile Asp Asp Leu Tyr
                965                 970                 975

Arg Glu Gln Leu Glu Glu Trp Gln Ala Arg Gly Val Val Asp Ala Arg
                980                 985                 990

Trp Ala Phe Ser Arg Gln Ser Asp Asp Thr Lys Gly Cys Arg His Val
            995                 1000                1005

Asp Asp Arg Ile Leu Ala Asp Arg Glu Asp Val Val Lys Leu Trp Arg
    1010                1015                1020

Asp Gly Ala Arg Val Tyr Val Cys Gly Ser Gly Ala Leu Ala Gln Ser
1025                1030                1035                1040

Val Arg Ser Ala Met Val Thr Val Leu Arg Asp Glu Met Glu Thr Thr
                1045                1050                1055

Gly Asp Gly Ser Asp Asn Gly Lys Ala Glu Lys Trp Phe Asp Glu Gln
            1060                1065                1070

Arg Asn Val Arg Tyr Val Met Asp Val Phe Asp
            1075                1080

<210> SEQ ID NO 34
<211> LENGTH: 1054
<212> TYPE: PRT
<213> ORGANISM: Aspergillus oryzae
```

<220> FEATURE:
<223> OTHER INFORMATION: Aspergillus oryzae strain ATCC 42149 cytochrome
      P450, locus Q2U4F1_ASPOR, CYP505A3

<400> SEQUENCE: 34

```
Met Arg Gln Asn Asp Asn Glu Lys Gln Ile Cys Pro Ile Pro Gly Pro
1               5                   10                  15

Gln Gly Leu Pro Phe Leu Gly Asn Ile Leu Asp Ile Asp Leu Asp Asn
            20                  25                  30

Gly Thr Met Ser Thr Leu Lys Ile Ala Lys Thr Tyr Tyr Pro Ile Phe
        35                  40                  45

Lys Phe Thr Phe Ala Gly Glu Thr Ser Ile Val Ile Asn Ser Val Ala
50                  55                  60

Leu Leu Ser Glu Leu Cys Asp Glu Thr Arg Phe His Lys His Val Ser
65                  70                  75                  80

Phe Gly Leu Glu Leu Leu Arg Ser Gly Thr His Asp Gly Leu Phe Thr
                85                  90                  95

Ala Tyr Asp His Glu Lys Asn Trp Glu Leu Ala His Arg Leu Leu Val
            100                 105                 110

Pro Ala Phe Gly Pro Leu Arg Ile Arg Glu Met Phe Pro Gln Met His
        115                 120                 125

Asp Ile Ala Gln Gln Leu Cys Leu Lys Trp Gln Arg Tyr Gly Pro Arg
130                 135                 140

Arg Pro Leu Asn Leu Val Asp Asp Phe Thr Arg Thr Thr Leu Asp Thr
145                 150                 155                 160

Ile Ala Leu Cys Ala Met Gly Tyr Arg Phe Asn Ser Phe Tyr Ser Glu
                165                 170                 175

Gly Asp Phe His Pro Phe Ile Lys Ser Met Val Arg Phe Leu Lys Glu
            180                 185                 190

Ala Glu Thr Gln Ala Thr Leu Pro Ser Phe Ile Ser Asn Leu Arg Val
        195                 200                 205

Arg Ala Lys Arg Arg Thr Gln Leu Asp Ile Asp Leu Met Arg Thr Val
210                 215                 220

Cys Arg Glu Ile Val Thr Glu Arg Arg Gln Thr Asn Leu Asp His Lys
225                 230                 235                 240

Asn Asp Leu Leu Asp Thr Met Leu Thr Ser Arg Asp Ser Leu Ser Gly
                245                 250                 255

Asp Ala Leu Ser Asp Glu Ser Ile Ile Asp Asn Ile Leu Thr Phe Leu
            260                 265                 270

Val Ala Gly His Glu Thr Thr Ser Gly Leu Leu Ser Phe Ala Val Tyr
        275                 280                 285

Tyr Leu Leu Thr Thr Pro Asp Ala Met Ala Lys Ala Ala His Glu Val
290                 295                 300

Asp Asp Val Val Gly Asp Gln Glu Leu Thr Ile Glu His Leu Ser Met
305                 310                 315                 320

Leu Lys Tyr Leu Asn Ala Ile Leu Arg Glu Thr Leu Arg Leu Met Pro
                325                 330                 335

Thr Ala Pro Gly Phe Ser Val Thr Pro Tyr Lys Pro Glu Ile Ile Gly
            340                 345                 350

Gly Lys Tyr Glu Val Lys Pro Gly Asp Ser Leu Asp Val Phe Leu Ala
        355                 360                 365

Ala Val His Arg Asp Pro Ala Val Tyr Gly Ser Asp Ala Asp Glu Phe
370                 375                 380

Arg Pro Glu Arg Met Ser Asp Glu His Phe Gln Lys Leu Pro Ala Asn
```

-continued

```
            385                 390                 395                 400
Ser Trp Lys Pro Phe Gly Asn Gly Lys Arg Ser Cys Ile Gly Arg Ala
                    405                 410                 415

Phe Ala Trp Gln Glu Ala Leu Met Ile Leu Ala Leu Ile Leu Gln Ser
                420                 425                 430

Phe Ser Leu Asn Leu Val Asp Arg Gly Tyr Thr Leu Lys Leu Lys Glu
            435                 440                 445

Ser Leu Thr Ile Lys Pro Asp Asn Leu Trp Ala Tyr Ala Thr Pro Arg
    450                 455                 460

Pro Gly Arg Asn Val Leu His Thr Arg Leu Ala Leu Gln Thr Asn Ser
465                 470                 475                 480

Thr His Pro Glu Gly Leu Met Ser Leu Lys His Glu Thr Val Glu Ser
                485                 490                 495

Gln Pro Ala Thr Ile Leu Tyr Gly Ser Asn Ser Gly Thr Cys Glu Ala
                500                 505                 510

Leu Ala His Arg Leu Ala Ile Glu Met Ser Ser Lys Gly Arg Phe Val
            515                 520                 525

Cys Lys Val Gln Pro Met Asp Ala Ile Glu His Arg Arg Leu Pro Arg
530                 535                 540

Gly Gln Pro Val Ile Ile Thr Gly Ser Tyr Asp Gly Arg Pro Pro
545                 550                 555                 560

Glu Asn Ala Arg His Phe Val Lys Trp Leu Gln Ser Leu Lys Gly Asn
                565                 570                 575

Asp Leu Glu Gly Ile Gln Tyr Ala Val Phe Gly Cys Gly Leu Pro Gly
                580                 585                 590

His His Asp Trp Ser Thr Thr Phe Tyr Lys Ile Pro Thr Leu Ile Asp
            595                 600                 605

Thr Ile Met Ala Glu His Gly Gly Ala Arg Leu Ala Pro Arg Gly Ser
    610                 615                 620

Ala Asp Thr Ala Glu Asp Pro Phe Ala Glu Leu Glu Ser Trp Ser
625                 630                 635                 640

Glu Arg Ser Val Trp Pro Gly Leu Glu Ala Ala Phe Asp Leu Val Arg
                645                 650                 655

His Asn Ser Ser Asp Gly Thr Gly Lys Ser Thr Arg Ile Thr Ile Arg
            660                 665                 670

Ser Pro Tyr Thr Leu Arg Ala Ala His Glu Thr Ala Val Val His Gln
    675                 680                 685

Val Arg Val Leu Thr Ser Ala Glu Thr Thr Lys Lys Val His Val Glu
    690                 695                 700

Leu Ala Leu Pro Asp Thr Ile Asn Tyr Arg Pro Gly Asp His Leu Ala
705                 710                 715                 720

Ile Leu Pro Leu Asn Ser Arg Gln Ser Val Gln Arg Val Leu Ser Leu
                725                 730                 735

Phe Gln Ile Gly Ser Asp Thr Ile Leu Tyr Met Thr Ser Ser Ser Ala
                740                 745                 750

Thr Ser Leu Pro Thr Asp Thr Pro Ile Ser Ala His Asp Leu Leu Ser
            755                 760                 765

Gly Tyr Val Glu Leu Asn Gln Val Ala Thr Pro Thr Ser Leu Arg Ser
    770                 775                 780

Leu Ala Ala Lys Ala Thr Asp Glu Lys Thr Ala Glu Tyr Leu Glu Ala
785                 790                 795                 800

Leu Ala Thr Asp Arg Tyr Thr Thr Glu Val Arg Gly Asn His Leu Ser
                805                 810                 815
```

```
Leu Leu Asp Ile Leu Glu Ser Tyr Ser Val Pro Ser Ile Glu Ile Gln
                820                 825                 830

His Tyr Ile Gln Met Leu Pro Leu Arg Pro Arg Gln Tyr Thr Ile
                835                 840                 845

Ser Ser Ser Pro Arg Leu Asn Arg Gly Gln Ala Ser Leu Thr Val Ser
850                 855                 860

Val Met Glu Arg Ala Asp Val Gly Pro Arg Asn Cys Ala Gly Val
865                 870                 875                 880

Ala Ser Asn Tyr Leu Ala Ser Cys Thr Pro Gly Ser Ile Leu Arg Val
                885                 890                 895

Ser Leu Arg Gln Ala Asn Pro Asp Phe Arg Leu Pro Asp Glu Ser Cys
                900                 905                 910

Ser His Pro Ile Ile Met Val Ala Ala Gly Ser Gly Ile Ala Pro Phe
                915                 920                 925

Arg Ala Phe Val Gln Glu Arg Ser Val Arg Gln Lys Glu Gly Ile Ile
 930                 935                 940

Leu Pro Pro Ala Phe Leu Phe Phe Gly Cys Arg Arg Ala Asp Leu Asp
945                 950                 955                 960

Asp Leu Tyr Arg Glu Glu Leu Asp Ala Phe Glu Glu Gln Gly Val Val
                965                 970                 975

Thr Leu Phe Arg Ala Phe Ser Arg Ala Gln Ser Glu Ser His Gly Cys
                980                 985                 990

Lys Tyr Val Gln Asp Leu Leu Trp Met Glu Arg Val Arg Val Lys Thr
                995                 1000                1005

Leu Trp Gly Gln Asp Ala Lys Val Phe Val Cys Gly Ser Val Arg Met
    1010                1015                1020

Asn Glu Gly Val Lys Ala Ile Ile Ser Lys Ile Val Ser Pro Thr Pro
1025                1030                1035                1040

Thr Glu Glu Leu Ala Arg Arg Tyr Ile Ala Glu Thr Phe Ile
                1045                1050

<210> SEQ ID NO 35
<211> LENGTH: 1103
<212> TYPE: PRT
<213> ORGANISM: Aspergillus oryzae
<220> FEATURE:
<223> OTHER INFORMATION: Aspergillus oryzae strain ATCC 42149 cytochrome
      P450, locus Q2UNA2_ASPOR, CYPX

<400> SEQUENCE: 35

Met Ser Thr Pro Lys Ala Glu Pro Val Pro Ile Pro Gly Pro Arg Gly
1               5                   10                  15

Val Pro Leu Met Gly Asn Ile Leu Asp Ile Glu Ser Glu Ile Pro Leu
                20                  25                  30

Arg Ser Leu Glu Met Met Ala Asp Thr Tyr Gly Pro Ile Tyr Arg Leu
            35                  40                  45

Thr Thr Phe Gly Phe Ser Arg Cys Met Ile Ser Ser His Glu Leu Ala
        50                  55                  60

Ala Glu Val Phe Asp Glu Glu Arg Phe Thr Lys Lys Ile Met Ala Gly
65              70                  75                  80

Leu Ser Glu Leu Arg His Gly Ile His Asp Gly Leu Phe Thr Ala His
                85                  90                  95

Met Gly Glu Glu Asn Trp Glu Ile Ala His Arg Val Leu Met Pro Ala
                100                 105                 110

Phe Gly Pro Leu Asn Ile Gln Asn Met Phe Asp Glu Met His Asp Ile
```

-continued

```
                115                 120                 125
Ala Thr Gln Leu Val Met Lys Trp Ala Arg Gln Gly Pro Lys Gln Lys
            130                 135                 140
Ile Met Val Thr Asp Asp Phe Thr Arg Leu Thr Leu Asp Thr Ile Ala
145                 150                 155                 160
Leu Cys Ala Met Gly Thr Arg Phe Asn Ser Phe Tyr Ser Glu Glu Met
                165                 170                 175
His Pro Phe Val Asp Ala Met Val Gly Met Leu Lys Thr Ala Gly Asp
            180                 185                 190
Arg Ser Arg Arg Pro Gly Leu Val Asn Asn Leu Pro Thr Thr Glu Asn
            195                 200                 205
Asn Lys Tyr Trp Glu Asp Ile Asp Tyr Leu Arg Asn Leu Cys Lys Glu
        210                 215                 220
Leu Val Asp Thr Arg Lys Lys Asn Pro Thr Asp Lys Lys Asp Leu Leu
225                 230                 235                 240
Asn Ala Leu Ile Asn Gly Arg Asp Pro Lys Thr Gly Lys Gly Met Ser
                245                 250                 255
Tyr Asp Ser Ile Ile Asp Asn Met Ile Thr Phe Leu Ile Ala Gly His
            260                 265                 270
Glu Thr Thr Ser Gly Ser Leu Ser Phe Ala Phe Tyr Asn Met Leu Lys
            275                 280                 285
Asn Pro Gln Ala Tyr Gln Lys Ala Gln Glu Glu Val Asp Arg Val Ile
        290                 295                 300
Gly Arg Arg Arg Ile Thr Val Glu Asp Leu Gln Lys Leu Pro Tyr Ile
305                 310                 315                 320
Thr Ala Val Met Arg Glu Thr Leu Arg Leu Thr Pro Thr Ala Pro Ala
                325                 330                 335
Ile Ala Val Gly Pro His Pro Thr Lys Asn His Glu Asp Pro Val Thr
            340                 345                 350
Leu Gly Asn Gly Lys Tyr Val Leu Gly Lys Asp Glu Pro Cys Ala Leu
            355                 360                 365
Leu Leu Gly Lys Ile Gln Arg Asp Pro Lys Val Tyr Gly Pro Asp Ala
        370                 375                 380
Glu Glu Phe Lys Pro Glu Arg Met Leu Asp Glu His Phe Asn Lys Leu
385                 390                 395                 400
Pro Lys His Ala Trp Lys Pro Phe Gly Asn Gly Met Arg Ala Cys Ile
                405                 410                 415
Gly Arg Pro Phe Ala Trp Gln Glu Ala Leu Leu Val Ile Ala Met Leu
            420                 425                 430
Leu Gln Asn Phe Asn Phe Gln Met Asp Asp Pro Ser Tyr Asn Ile Gln
            435                 440                 445
Leu Lys Gln Thr Leu Thr Ile Lys Pro Asn His Phe Tyr Met Arg Ala
        450                 455                 460
Ala Leu Arg Glu Gly Leu Asp Ala Val His Leu Gly Ser Ala Leu Ser
465                 470                 475                 480
Ala Ser Ser Ser Glu His Ala Asp His Ala Ala Gly His Gly Lys Ala
                485                 490                 495
Gly Ala Ala Lys Lys Gly Ala Asp Leu Lys Pro Met His Val Tyr Tyr
            500                 505                 510
Gly Ser Asn Thr Gly Thr Cys Glu Ala Phe Ala Arg Arg Leu Ala Asp
            515                 520                 525
Asp Ala Thr Ser Tyr Gly Tyr Ser Ala Glu Val Glu Ser Leu Asp Ser
        530                 535                 540
```

```
Ala Lys Asp Ser Ile Pro Lys Asn Gly Pro Val Phe Ile Thr Ala
545                 550                 555                 560

Ser Tyr Glu Gly Gln Pro Pro Asp Asn Ala Ala His Phe Phe Glu Trp
        565                 570                 575

Leu Ser Ala Leu Lys Gly Asp Lys Pro Leu Asp Gly Val Asn Tyr Ala
            580                 585                 590

Val Phe Gly Cys Gly His His Asp Trp Gln Thr Thr Phe Tyr Arg Ile
                595                 600                 605

Pro Lys Glu Val Asn Arg Leu Val Gly Glu Asn Gly Ala Asn Arg Leu
            610                 615                 620

Cys Glu Ile Gly Leu Ala Asp Thr Ala Asn Ala Asp Ile Val Thr Asp
625                 630                 635                 640

Phe Asp Thr Trp Gly Glu Thr Ser Phe Trp Pro Ala Val Ala Ala Lys
                645                 650                 655

Phe Gly Ser Asn Thr Gln Gly Ser Gln Lys Ser Ser Thr Phe Arg Val
            660                 665                 670

Glu Val Ser Ser Gly His Arg Ala Thr Thr Leu Gly Leu Gln Leu Gln
        675                 680                 685

Glu Gly Leu Val Val Glu Asn Thr Leu Leu Thr Gln Ala Gly Val Pro
690                 695                 700

Ala Lys Arg Thr Ile Arg Phe Lys Leu Pro Thr Asp Thr Gln Tyr Lys
705                 710                 715                 720

Cys Gly Asp Tyr Leu Ala Ile Leu Pro Val Asn Pro Ser Thr Val Val
                725                 730                 735

Arg Lys Val Met Ser Arg Phe Asp Leu Pro Trp Asp Ala Val Leu Arg
            740                 745                 750

Ile Glu Lys Ala Ser Pro Ser Ser Lys His Ile Ser Ile Pro Met
            755                 760                 765

Asp Thr Gln Val Ser Ala Tyr Asp Leu Phe Ala Thr Tyr Val Glu Leu
    770                 775                 780

Ser Gln Pro Ala Ser Lys Arg Asp Leu Ala Val Leu Ala Asp Ala Ala
785                 790                 795                 800

Ala Val Asp Pro Glu Thr Gln Ala Glu Leu Gln Ala Ile Ala Ser Asp
                805                 810                 815

Pro Ala Arg Phe Ala Glu Ile Ser Gln Lys Arg Ile Ser Val Leu Asp
                820                 825                 830

Leu Leu Leu Gln Tyr Pro Ser Ile Asn Leu Ala Ile Gly Asp Phe Val
            835                 840                 845

Ala Met Leu Pro Pro Met Arg Val Arg Gln Tyr Ser Ile Ser Ser Ser
850                 855                 860

Pro Leu Val Asp Pro Thr Glu Cys Ser Ile Thr Phe Ser Val Leu Lys
865                 870                 875                 880

Ala Pro Ser Leu Ala Ala Leu Thr Lys Glu Asp Glu Tyr Leu Gly Val
                885                 890                 895

Ala Ser Thr Tyr Leu Ser Glu Leu Arg Ser Gly Glu Arg Val Gln Leu
                900                 905                 910

Ser Val Arg Pro Ser His Thr Gly Phe Lys Pro Pro Thr Glu Leu Ser
            915                 920                 925

Thr Pro Met Ile Met Ala Cys Ala Gly Ser Gly Leu Ala Pro Phe Arg
    930                 935                 940

Gly Phe Val Met Asp Arg Ala Glu Lys Ile Arg Gly Arg Ser Ser
945                 950                 955                 960
```

Gly Ser Met Pro Glu Gln Pro Ala Lys Ala Ile Leu Tyr Ala Gly Cys
                    965                 970                 975

Arg Thr Gln Gly Lys Asp Asp Ile His Ala Asp Glu Leu Ala Glu Trp
                980                 985                 990

Glu Lys Ile Gly Ala Val Glu Val Arg Arg Ala Tyr Ser Arg Pro Ser
                995                 1000                1005

Asp Gly Ser Lys Gly Thr His Val Gln Asp Leu Met Met Glu Asp Lys
            1010                1015                1020

Lys Glu Leu Ile Asp Leu Phe Glu Ser Gly Ala Arg Ile Tyr Val Cys
1025                1030                1035                1040

Gly Thr Pro Gly Val Gly Asn Ala Val Arg Asp Ser Ile Lys Ser Met
                1045                1050                1055

Phe Leu Glu Arg Arg Glu Glu Ile Arg Arg Ile Ala Lys Glu Lys Gly
                1060                1065                1070

Glu Pro Val Ser Asp Asp Glu Glu Thr Ala Phe Glu Lys Phe Leu
            1075                1080                1085

Asp Asp Met Lys Thr Lys Glu Arg Tyr Thr Thr Asp Ile Phe Ala
            1090                1095                1100

<210> SEQ ID NO 36
<211> LENGTH: 1066
<212> TYPE: PRT
<213> ORGANISM: Fusarium oxysporum
<220> FEATURE:
<223> OTHER INFORMATION: bifunctional P-450:NADPH-P450 reductase,
      cytochrome P450foxy, fatty acid omega-hydrolxylase, cytochrome
      P450 505, NADPH-cytochrome P450 reductase, locus C505_FUSOX,
      CYP505A1

<400> SEQUENCE: 36

Met Ala Glu Ser Val Pro Ile Pro Glu Pro Pro Gly Tyr Pro Leu Ile
1               5                   10                  15

Gly Asn Leu Gly Glu Phe Thr Ser Asn Pro Leu Ser Asp Leu Asn Arg
                20                  25                  30

Leu Ala Asp Thr Tyr Gly Pro Ile Phe Arg Leu Arg Leu Gly Ala Lys
            35                  40                  45

Ala Pro Ile Phe Val Ser Asn Ser Leu Ile Asn Glu Val Cys Asp
        50                  55                  60

Glu Lys Arg Phe Lys Lys Thr Leu Lys Ser Val Leu Ser Gln Val Arg
65                  70                  75                  80

Glu Gly Val His Asp Gly Leu Phe Thr Ala Phe Glu Asp Glu Pro Asn
                85                  90                  95

Trp Gly Lys Ala His Arg Ile Leu Val Pro Ala Phe Gly Pro Leu Ser
                100                 105                 110

Ile Arg Gly Met Phe Pro Glu Met His Asp Ile Ala Thr Gln Leu Cys
            115                 120                 125

Met Lys Phe Ala Arg His Gly Pro Arg Thr Pro Ile Asp Thr Ser Asp
130                 135                 140

Asn Phe Thr Arg Leu Ala Leu Asp Thr Leu Ala Leu Cys Ala Met Asp
145                 150                 155                 160

Phe Arg Phe Tyr Ser Tyr Tyr Lys Glu Glu Leu His Pro Phe Ile Glu
                165                 170                 175

Ala Met Gly Asp Phe Leu Thr Glu Ser Gly Asn Arg Asn Arg Arg Pro
            180                 185                 190

Pro Phe Ala Pro Asn Phe Leu Tyr Arg Ala Ala Asn Glu Lys Phe Tyr
        195                 200                 205

```
Gly Asp Ile Ala Leu Met Lys Ser Val Ala Asp Glu Val Val Ala Ala
210                 215                 220
Arg Lys Ala Ser Pro Ser Asp Arg Lys Asp Leu Leu Ala Ala Met Leu
225                 230                 235                 240
Asn Gly Val Asp Pro Gln Thr Gly Glu Lys Leu Ser Asp Glu Asn Ile
                245                 250                 255
Thr Asn Gln Leu Ile Thr Phe Leu Ile Ala Gly His Glu Thr Thr Ser
            260                 265                 270
Gly Thr Leu Ser Phe Ala Met Tyr Gln Leu Leu Lys Asn Pro Glu Ala
            275                 280                 285
Tyr Ser Lys Val Gln Lys Glu Val Asp Glu Val Val Gly Arg Gly Pro
        290                 295                 300
Val Leu Val Glu His Leu Thr Lys Leu Pro Tyr Ile Ser Ala Val Leu
305                 310                 315                 320
Arg Glu Thr Leu Arg Leu Asn Ser Pro Ile Thr Ala Phe Gly Leu Glu
                325                 330                 335
Ala Ile Asp Asp Thr Phe Leu Gly Gly Lys Tyr Leu Val Lys Lys Gly
            340                 345                 350
Glu Ile Val Thr Ala Leu Leu Ser Arg Gly His Val Asp Pro Val Val
            355                 360                 365
Tyr Gly Asn Asp Ala Asp Lys Phe Ile Pro Glu Arg Met Leu Asp Asp
        370                 375                 380
Glu Phe Ala Arg Leu Asn Lys Glu Tyr Pro Asn Cys Trp Lys Pro Phe
385                 390                 395                 400
Gly Asn Gly Lys Arg Ala Cys Ile Gly Arg Pro Phe Ala Trp Gln Glu
                405                 410                 415
Ser Leu Leu Ala Met Val Val Leu Phe Gln Asn Phe Asn Phe Thr Met
            420                 425                 430
Thr Asp Pro Asn Tyr Ala Leu Glu Ile Lys Gln Thr Leu Thr Ile Lys
        435                 440                 445
Pro Asp His Phe Tyr Ile Asn Ala Thr Leu Arg His Gly Met Thr Pro
        450                 455                 460
Thr Glu Leu Glu His Val Leu Ala Gly Asn Gly Ala Thr Ser Ser Ser
465                 470                 475                 480
Thr His Asn Ile Lys Ala Ala Ala Asn Leu Asp Ala Lys Ala Gly Ser
                485                 490                 495
Gly Lys Pro Met Ala Ile Phe Tyr Gly Ser Asn Ser Gly Thr Cys Glu
            500                 505                 510
Ala Leu Ala Asn Arg Leu Ala Ser Asp Ala Pro Ser His Gly Phe Ser
        515                 520                 525
Ala Thr Thr Val Gly Pro Leu Asp Gln Ala Lys Gln Asn Leu Pro Glu
        530                 535                 540
Asp Arg Pro Val Val Ile Val Thr Ala Ser Tyr Glu Gly Gln Pro Pro
545                 550                 555                 560
Ser Asn Ala Ala His Phe Ile Lys Trp Met Glu Asp Leu Asp Gly Asn
                565                 570                 575
Asp Met Glu Lys Val Ser Tyr Ala Val Phe Ala Cys Gly His His Asp
            580                 585                 590
Trp Val Glu Thr Phe His Arg Ile Pro Lys Leu Val Asp Ser Thr Leu
        595                 600                 605
Glu Lys Arg Gly Gly Thr Arg Leu Val Pro Met Gly Ser Ala Asp Ala
        610                 615                 620
Ala Thr Ser Asp Met Phe Ser Asp Phe Glu Ala Trp Glu Asp Ile Val
```

```
                625                 630                 635                 640
        Leu Trp Pro Gly Leu Lys Glu Lys Tyr Lys Ile Ser Asp Glu Glu Ser
                        645                 650                 655

Gly Gly Gln Lys Gly Leu Leu Val Glu Val Ser Thr Pro Arg Lys Thr
                        660                 665                 670

Ser Leu Arg Gln Asp Val Glu Ala Leu Val Val Ala Glu Lys Thr
                675                 680                 685

Leu Thr Lys Ser Gly Pro Ala Lys Lys His Ile Glu Ile Gln Leu Pro
                690                 695                 700

Ser Ala Met Thr Tyr Lys Ala Gly Asp Tyr Leu Ala Ile Leu Pro Leu
        705                 710                 715                 720

Asn Pro Lys Ser Thr Val Ala Arg Val Phe Arg Phe Ser Leu Ala
                        725                 730                 735

Trp Asp Ser Phe Leu Lys Ile Gln Ser Glu Gly Pro Thr Thr Leu Pro
                        740                 745                 750

Thr Asn Val Ala Ile Ser Ala Phe Asp Val Phe Ser Ala Tyr Val Glu
                        755                 760                 765

Leu Ser Gln Pro Ala Thr Lys Arg Asn Ile Leu Ala Leu Ala Glu Ala
                770                 775                 780

Thr Glu Asp Lys Asp Thr Ile Gln Glu Leu Glu Arg Leu Ala Gly Asp
        785                 790                 795                 800

Ala Tyr Gln Ala Glu Ile Ser Pro Lys Arg Val Ser Val Leu Asp Leu
                        805                 810                 815

Leu Glu Lys Phe Pro Ala Val Ala Leu Pro Ile Ser Ser Tyr Leu Ala
                        820                 825                 830

Met Leu Pro Pro Met Arg Val Arg Gln Tyr Ser Ile Ser Ser Ser Pro
                        835                 840                 845

Phe Ala Asp Pro Ser Lys Leu Thr Leu Thr Tyr Ser Leu Leu Asp Ala
                850                 855                 860

Pro Ser Leu Ser Gly Gln Gly Arg His Val Gly Val Ala Thr Asn Phe
        865                 870                 875                 880

Leu Ser His Leu Thr Ala Gly Asp Lys Leu His Val Ser Val Arg Ala
                        885                 890                 895

Ser Ser Glu Ala Phe His Leu Pro Ser Asp Ala Glu Lys Thr Pro Ile
                        900                 905                 910

Ile Cys Val Ala Ala Gly Thr Gly Leu Ala Pro Leu Arg Gly Phe Ile
                        915                 920                 925

Gln Glu Arg Ala Ala Met Leu Ala Ala Gly Arg Thr Leu Ala Pro Ala
                930                 935                 940

Leu Leu Phe Phe Gly Cys Arg Asn Pro Glu Ile Asp Asp Leu Tyr Ala
        945                 950                 955                 960

Glu Glu Phe Glu Arg Trp Glu Lys Met Gly Ala Val Asp Val Arg Arg
                        965                 970                 975

Ala Tyr Ser Arg Ala Thr Asp Lys Ser Glu Gly Cys Lys Tyr Val Gln
                        980                 985                 990

Asp Arg Val Tyr His Asp Arg Ala Asp Val Phe Lys Val Trp Asp Gln
                        995                 1000                1005

Gly Ala Lys Val Phe Ile Cys Gly Ser Arg Glu Ile Gly Lys Ala Val
                1010                1015                1020

Glu Asp Val Cys Val Arg Leu Ala Ile Glu Lys Ala Gln Gln Asn Gly
        1025                1030                1035                1040

Arg Asp Val Thr Glu Glu Met Ala Arg Ala Trp Phe Glu Arg Ser Arg
                        1045                1050                1055
```

-continued

```
Asn Glu Arg Phe Ala Thr Asp Val Phe Asp
            1060                1065

<210> SEQ ID NO 37
<211> LENGTH: 1115
<212> TYPE: PRT
<213> ORGANISM: Fusarium verticillioides
<220> FEATURE:
<223> OTHER INFORMATION: Fusarium verticillioides (G. moniliformis)
      Fum6p, CYPX

<400> SEQUENCE: 37

Met Ser Ala Thr Ala Leu Phe Thr Arg Arg Ser Val Ser Thr Ser Asn
1               5                   10                  15

Pro Glu Leu Arg Pro Ile Pro Gly Pro Lys Pro Leu Pro Leu Leu Gly
            20                  25                  30

Asn Leu Phe Asp Phe Asp Phe Asp Asn Leu Thr Lys Ser Leu Gly Glu
        35                  40                  45

Leu Gly Lys Ile His Gly Pro Ile Tyr Ser Ile Thr Phe Gly Ala Ser
    50                  55                  60

Thr Glu Ile Met Val Thr Ser Arg Glu Ile Ala Gln Glu Leu Cys Asp
65                  70                  75                  80

Glu Thr Arg Phe Cys Lys Leu Pro Gly Gly Ala Leu Asp Val Met Lys
                85                  90                  95

Ala Val Val Gly Asp Gly Leu Phe Thr Ala Glu Thr Ser Asn Pro Lys
            100                 105                 110

Trp Ala Ile Ala His Arg Ile Ile Thr Pro Leu Phe Gly Ala Met Arg
        115                 120                 125

Ile Arg Gly Met Phe Asp Asp Met Lys Asp Ile Cys Glu Gln Met Cys
    130                 135                 140

Leu Arg Trp Ala Arg Phe Gly Pro Asp Glu Pro Leu Asn Val Cys Asp
145                 150                 155                 160

Asn Met Thr Lys Leu Thr Leu Asp Thr Ile Ala Leu Cys Thr Ile Asp
                165                 170                 175

Tyr Arg Phe Asn Ser Phe Tyr Arg Glu Asn Gly Ala Ala His Pro Phe
            180                 185                 190

Ala Glu Ala Val Val Asp Val Met Thr Glu Ser Phe Asp Gln Ser Asn
        195                 200                 205

Leu Pro Asp Phe Val Asn Asn Tyr Val Arg Phe Arg Ala Met Ala Lys
    210                 215                 220

Phe Lys Arg Gln Ala Ala Glu Leu Arg Arg Gln Thr Glu Glu Leu Ile
225                 230                 235                 240

Ala Ala Arg Arg Gln Asn Pro Val Asp Arg Asp Asp Leu Leu Asn Ala
                245                 250                 255

Met Leu Ser Ala Lys Asp Pro Lys Thr Gly Glu Gly Leu Ser Pro Glu
            260                 265                 270

Ser Ile Val Asp Asn Leu Leu Thr Phe Leu Ile Ala Gly His Glu Thr
        275                 280                 285

Thr Ser Ser Leu Leu Ser Phe Cys Phe Tyr Tyr Leu Leu Glu Asn Pro
    290                 295                 300

His Val Leu Arg Arg Val Gln Gln Glu Val Asp Thr Val Val Gly Ser
305                 310                 315                 320

Asp Thr Ile Thr Val Asp His Leu Ser Ser Met Pro Tyr Leu Glu Ala
                325                 330                 335

Val Leu Arg Glu Thr Leu Arg Leu Arg Asp Pro Gly Pro Gly Phe Tyr
```

```
              340                 345                 350
Val Lys Pro Leu Lys Asp Glu Val Ala Gly Lys Tyr Ala Val Asn
            355                 360                 365

Lys Asp Gln Pro Leu Phe Ile Val Phe Asp Ser Val His Arg Asp Gln
    370                 375                 380

Ser Thr Tyr Gly Ala Asp Ala Asp Glu Phe Arg Pro Glu Arg Met Leu
385                 390                 395                 400

Lys Asp Gly Phe Asp Lys Leu Pro Pro Cys Ala Trp Lys Pro Phe Gly
                405                 410                 415

Asn Gly Val Arg Ala Cys Val Gly Arg Pro Phe Ala Met Gln Gln Ala
                420                 425                 430

Ile Leu Ala Val Ala Met Val Leu His Lys Phe Asp Leu Val Lys Asp
                435                 440                 445

Glu Ser Tyr Thr Leu Lys Tyr His Val Thr Met Thr Val Arg Pro Val
    450                 455                 460

Gly Phe Thr Met Lys Val Arg Leu Arg Gln Gly Gln Arg Ala Thr Asp
465                 470                 475                 480

Leu Ala Met Gly Leu His Arg Gly His Ser Gln Glu Ala Ser Ala Ala
                485                 490                 495

Ala Ser Pro Ser Arg Ala Ser Leu Lys Arg Leu Ser Ser Asp Val Asn
                500                 505                 510

Gly Asp Asp Thr Asp His Lys Ser Gln Ile Ala Val Leu Tyr Ala Ser
                515                 520                 525

Asn Ser Gly Ser Cys Glu Ala Leu Ala Tyr Arg Leu Ala Ala Glu Ala
                530                 535                 540

Thr Glu Arg Gly Phe Gly Ile Arg Ala Val Asp Val Val Asn Asn Ala
545                 550                 555                 560

Ile Asp Arg Ile Pro Val Gly Ser Pro Val Leu Ile Thr Ala Ser
                565                 570                 575

Tyr Asn Gly Glu Pro Ala Asp Asp Ala Gln Glu Phe Val Pro Trp Leu
                580                 585                 590

Lys Ser Leu Glu Ser Gly Arg Leu Asn Gly Val Lys Phe Ala Val Phe
                595                 600                 605

Gly Asn Gly His Arg Asp Trp Ala Asn Thr Leu Phe Ala Val Pro Arg
                610                 615                 620

Leu Ile Asp Ser Glu Leu Ala Arg Cys Gly Ala Glu Arg Val Ser Leu
625                 630                 635                 640

Met Gly Val Ser Asp Thr Cys Asp Ser Ser Asp Pro Phe Ser Asp Phe
                645                 650                 655

Glu Arg Trp Ile Asp Glu Lys Leu Phe Pro Glu Leu Glu Thr Pro His
                660                 665                 670

Gly Pro Gly Gly Val Lys Asn Gly Asp Arg Ala Val Pro Arg Gln Glu
                675                 680                 685

Leu Gln Val Ser Leu Gly Gln Pro Pro Arg Ile Thr Met Arg Lys Gly
                690                 695                 700

Tyr Val Arg Ala Ile Val Thr Glu Ala Arg Ser Leu Ser Ser Pro Gly
705                 710                 715                 720

Val Pro Glu Lys Arg His Leu Glu Leu Leu Pro Lys Asp Phe Asn
                725                 730                 735

Tyr Lys Ala Gly Asp His Val Tyr Ile Leu Pro Arg Asn Ser Pro Arg
                740                 745                 750

Asp Val Val Arg Ala Leu Ser Tyr Phe Gly Leu Gly Glu Asp Thr Leu
                755                 760                 765
```

```
Ile Thr Ile Arg Asn Thr Ala Arg Lys Leu Ser Leu Gly Leu Pro Leu
    770                 775                 780

Asp Thr Pro Ile Thr Ala Thr Asp Leu Leu Gly Ala Tyr Val Glu Leu
785                 790                 795                 800

Gly Arg Thr Ala Ser Leu Lys Asn Leu Trp Thr Leu Val Asp Ala Ala
                805                 810                 815

Gly His Gly Ser Arg Ala Ala Leu Leu Ser Leu Thr Glu Pro Glu Arg
            820                 825                 830

Phe Arg Ala Glu Val Gln Asp Arg His Val Ser Ile Leu Asp Leu Leu
        835                 840                 845

Glu Arg Phe Pro Asp Ile Asp Leu Ser Leu Ser Cys Phe Leu Pro Met
    850                 855                 860

Leu Ala Gln Ile Arg Pro Arg Ala Tyr Ser Phe Ser Ser Ala Pro Asp
865                 870                 875                 880

Trp Lys Pro Gly His Ala Thr Leu Thr Tyr Thr Val Val Asp Phe Ala
                885                 890                 895

Thr Pro Ala Thr Gln Gly Ile Asn Gly Ser Ser Lys Ser Lys Ala Val
            900                 905                 910

Gly Asp Gly Thr Ala Val Val Gln Arg Gln Gly Leu Ala Ser Ser Tyr
        915                 920                 925

Leu Ser Ser Leu Gly Pro Gly Thr Ser Leu Tyr Val Ser Leu His Arg
    930                 935                 940

Ala Ser Pro Tyr Phe Cys Leu Gln Lys Ser Thr Ser Leu Pro Val Ile
945                 950                 955                 960

Met Val Gly Ala Gly Thr Gly Leu Ala Pro Phe Arg Ala Phe Leu Gln
                965                 970                 975

Glu Arg Arg Met Ala Ala Glu Gly Ala Lys Gln Arg Phe Gly Pro Ala
            980                 985                 990

Leu Leu Phe Phe Gly Cys Arg Gly Pro Arg Leu Asp Ser Leu Tyr Ser
        995                 1000                1005

Val Glu Leu Glu Ala Tyr Glu Thr Ile Gly Leu Val Gln Val Arg Arg
    1010                1015                1020

Ala Tyr Ser Arg Asp Pro Ser Ala Gln Asp Ala Gln Gly Cys Lys Tyr
1025                1030                1035                1040

Val Thr Asp Arg Leu Gly Lys Cys Arg Asp Glu Val Ala Arg Leu Trp
                1045                1050                1055

Met Asp Gly Ala Gln Val Leu Val Cys Gly Gly Lys Lys Met Ala Asn
            1060                1065                1070

Asp Val Leu Glu Val Leu Gly Pro Met Leu Leu Glu Ile Asp Gln Lys
        1075                1080                1085

Arg Gly Glu Thr Thr Ala Lys Thr Val Val Glu Trp Arg Ala Arg Leu
    1090                1095                1100

Asp Lys Ser Arg Tyr Val Glu Glu Val Tyr Val
1105                1110                1115
```

<210> SEQ ID NO 38
<211> LENGTH: 1069
<212> TYPE: PRT
<213> ORGANISM: Gibberella zeae
<220> FEATURE:
<223> OTHER INFORMATION: Gibberella zeae strain PH1 bifuctional
      P-450:NADPH-P450 reductase, fatty acid
      omega-hyroxylase, P450foxy, locus C505_FUSOX,
      CYP505A7

<400> SEQUENCE: 38

```
Met Ala Glu Ser Val Pro Ile Pro Glu Pro Pro Gly Tyr Pro Leu Ile
1               5                   10                  15
Gly Asn Leu Gly Glu Phe Lys Thr Asn Pro Leu Asn Asp Leu Asn Arg
            20                  25                  30
Leu Ala Asp Thr Tyr Gly Pro Ile Phe Arg Leu His Leu Gly Ser Lys
        35                  40                  45
Thr Pro Thr Phe Val Ser Ser Asn Ala Phe Ile Asn Glu Val Cys Asp
    50                  55                  60
Glu Lys Arg Phe Lys Lys Thr Leu Lys Ser Val Leu Ser Val Val Arg
65                  70                  75                  80
Glu Gly Val His Asp Gly Leu Phe Thr Ala Phe Glu Asp Glu Pro Asn
                85                  90                  95
Trp Gly Lys Ala His Arg Ile Leu Ile Pro Ala Phe Gly Pro Leu Ser
            100                 105                 110
Ile Arg Asn Met Phe Pro Glu Met His Glu Ile Ala Asn Gln Leu Cys
            115                 120                 125
Met Lys Leu Ala Arg His Gly Pro His Thr Pro Val Asp Ala Ser Asp
    130                 135                 140
Asn Phe Thr Arg Leu Ala Leu Asp Thr Leu Ala Leu Cys Ala Met Asp
145                 150                 155                 160
Phe Arg Phe Asn Ser Tyr Tyr Lys Glu Glu Leu His Pro Phe Ile Glu
                165                 170                 175
Ala Met Gly Asp Phe Leu Leu Glu Ser Gly Asn Arg Asn Arg Arg Pro
            180                 185                 190
Ala Phe Ala Pro Asn Phe Leu Tyr Arg Ala Ala Asn Asp Lys Phe Tyr
        195                 200                 205
Ala Asp Ile Ala Leu Met Lys Ser Val Ala Asp Glu Val Val Ala Thr
    210                 215                 220
Arg Lys Gln Asn Pro Thr Asp Arg Lys Asp Leu Leu Ala Ala Met Leu
225                 230                 235                 240
Glu Gly Val Asp Pro Gln Thr Gly Glu Lys Leu Ser Asp Asp Asn Ile
                245                 250                 255
Thr Asn Gln Leu Ile Thr Phe Leu Ile Ala Gly His Glu Thr Thr Ser
            260                 265                 270
Gly Thr Leu Ser Phe Ala Met Tyr His Leu Leu Lys Asn Pro Glu Ala
        275                 280                 285
Tyr Asn Lys Leu Gln Lys Glu Ile Asp Glu Val Ile Gly Arg Asp Pro
    290                 295                 300
Val Thr Val Glu His Leu Thr Lys Leu Pro Tyr Leu Ser Ala Val Leu
305                 310                 315                 320
Arg Glu Thr Leu Arg Ile Ser Ser Pro Ile Thr Gly Phe Gly Val Glu
                325                 330                 335
Ala Ile Glu Asp Thr Phe Leu Gly Gly Lys Tyr Leu Ile Lys Lys Gly
            340                 345                 350
Glu Thr Val Leu Ser Val Leu Ser Arg Gly His Val Asp Pro Val Val
        355                 360                 365
Tyr Gly Pro Asp Ala Glu Lys Phe Val Pro Glu Arg Met Leu Asp Asp
    370                 375                 380
Glu Phe Ala Arg Leu Asn Lys Glu Phe Pro Asn Cys Trp Lys Pro Phe
385                 390                 395                 400
Gly Asn Gly Lys Arg Ala Cys Ile Gly Arg Pro Phe Ala Trp Gln Glu
                405                 410                 415
```

```
Ser Leu Leu Ala Met Ala Leu Leu Phe Gln Asn Phe Asn Phe Thr Gln
            420                 425                 430

Thr Asp Pro Asn Tyr Glu Leu Gln Ile Lys Gln Asn Leu Thr Ile Lys
        435                 440                 445

Pro Asp Asn Phe Phe Phe Asn Cys Thr Leu Arg His Gly Met Thr Pro
    450                 455                 460

Thr Asp Leu Glu Gly Gln Leu Ala Gly Lys Gly Ala Thr Thr Ser Ile
465                 470                 475                 480

Ala Ser His Ile Lys Ala Pro Ala Ala Ser Lys Gly Ala Lys Ala Ser
                485                 490                 495

Asn Gly Lys Pro Met Ala Ile Tyr Tyr Gly Ser Asn Ser Gly Thr Cys
            500                 505                 510

Glu Ala Leu Ala Asn Arg Leu Ala Ser Asp Ala Ala Gly His Gly Phe
            515                 520                 525

Ser Ala Ser Val Ile Gly Thr Leu Asp Gln Ala Lys Gln Asn Leu Pro
            530                 535                 540

Glu Asp Arg Pro Val Val Ile Val Thr Ala Ser Tyr Glu Gly Gln Pro
545                 550                 555                 560

Pro Ser Asn Ala Ala His Phe Ile Lys Trp Met Glu Asp Leu Ala Gly
                565                 570                 575

Asn Glu Met Glu Lys Val Ser Tyr Ala Val Phe Gly Cys Gly His His
            580                 585                 590

Asp Trp Val Asp Thr Phe Leu Arg Ile Pro Lys Leu Val Asp Thr Thr
            595                 600                 605

Leu Glu Gln Arg Gly Gly Thr Arg Leu Val Pro Met Gly Ser Ala Asp
610                 615                 620

Ala Ala Thr Ser Asp Met Phe Ser Asp Phe Glu Ala Trp Glu Asp Thr
625                 630                 635                 640

Val Leu Trp Pro Ser Leu Lys Glu Lys Tyr Asn Val Thr Asp Asp Glu
            645                 650                 655

Ala Ser Gly Gln Arg Gly Leu Leu Val Glu Val Thr Thr Pro Arg Lys
            660                 665                 670

Thr Thr Leu Arg Gln Asp Val Glu Glu Ala Leu Val Val Ser Glu Lys
            675                 680                 685

Thr Leu Thr Lys Thr Gly Pro Ala Lys Lys His Ile Glu Ile Gln Leu
            690                 695                 700

Pro Ser Gly Met Thr Tyr Lys Ala Gly Asp Tyr Leu Ala Ile Leu Pro
705                 710                 715                 720

Leu Asn Pro Arg Lys Thr Val Ser Arg Val Phe Arg Arg Phe Ser Leu
            725                 730                 735

Ala Trp Asp Ser Phe Leu Lys Ile Gln Ser Asp Gly Pro Thr Thr Leu
            740                 745                 750

Pro Ile Asn Ile Ala Ile Ser Ala Phe Asp Val Phe Ser Ala Tyr Val
    755                 760                 765

Glu Leu Ser Gln Pro Ala Thr Lys Arg Asn Ile Leu Ala Leu Ser Glu
    770                 775                 780

Ala Thr Glu Asp Lys Ala Thr Ile Gln Glu Leu Glu Lys Leu Ala Gly
785                 790                 795                 800

Asp Ala Tyr Gln Glu Asp Val Ser Ala Lys Lys Val Ser Val Leu Asp
                805                 810                 815

Leu Leu Glu Lys Tyr Pro Ala Val Ala Leu Pro Ile Ser Ser Tyr Leu
            820                 825                 830

Ala Met Leu Pro Pro Met Arg Val Arg Gln Tyr Ser Ile Ser Ser Ser
```

```
                835                 840                 845
Pro Phe Ala Asp Pro Ser Lys Leu Thr Leu Thr Tyr Ser Leu Leu Asp
850                 855                 860

Ala Pro Ser Leu Ser Gly Gln Gly Arg His Val Gly Val Ala Thr Asn
865                 870                 875                 880

Phe Leu Ser Gln Leu Ile Ala Gly Asp Lys Leu His Ile Ser Val Arg
                885                 890                 895

Ala Ser Ser Ala Ala Phe His Leu Pro Ser Asp Pro Glu Thr Thr Pro
                900                 905                 910

Ile Ile Cys Val Ala Ala Gly Thr Gly Leu Ala Pro Phe Arg Gly Phe
                915                 920                 925

Ile Gln Glu Arg Ala Ala Met Leu Ala Ala Gly Arg Lys Leu Ala Pro
            930                 935                 940

Ala Leu Leu Phe Phe Gly Cys Arg Asp Pro Glu Asn Asp Asp Leu Tyr
945                 950                 955                 960

Ala Glu Glu Leu Ala Arg Trp Glu Gln Met Gly Ala Val Asp Val Arg
                965                 970                 975

Arg Ala Tyr Ser Arg Ala Thr Asp Lys Ser Glu Gly Cys Lys Tyr Val
                980                 985                 990

Gln Asp Arg Ile Tyr His Asp Arg Ala Asp Val Phe Lys Val Trp Asp
                995                 1000                1005

Gln Gly Ala Lys Val Phe Ile Cys Gly Ser Arg Glu Ile Gly Lys Ala
            1010                1015                1020

Val Glu Asp Ile Cys Val Arg Leu Ala Met Glu Arg Ser Glu Ala Thr
1025                1030                1035                1040

Gln Glu Gly Lys Gly Ala Thr Glu Glu Lys Ala Arg Glu Trp Phe Glu
                1045                1050                1055

Arg Ser Arg Asn Glu Arg Phe Ala Thr Asp Val Phe Asp
                1060                1065

<210> SEQ ID NO 39
<211> LENGTH: 1066
<212> TYPE: PRT
<213> ORGANISM: Gibberella zeae
<220> FEATURE:
<223> OTHER INFORMATION: Gibberella zeae strain PH1a hypothetical
      protein FG07596.1, CYP505C2

<400> SEQUENCE: 39

Met Ala Ile Lys Asp Gly Gly Lys Ser Gly Gln Ile Pro Gly Pro
1               5                   10                  15

Lys Gly Leu Pro Val Leu Gly Asn Leu Phe Asp Leu Asp Leu Ser Asp
                20                  25                  30

Ser Leu Thr Ser Leu Ile Asn Ile Gly Gln Lys Tyr Ala Pro Ile Phe
            35                  40                  45

Ser Leu Glu Leu Gly Gly His Arg Glu Val Met Ile Cys Ser Arg Asp
50                  55                  60

Leu Leu Asp Glu Leu Cys Asp Glu Thr Arg Phe His Lys Ile Val Thr
65                  70                  75                  80

Gly Gly Val Asp Lys Leu Arg Pro Leu Ala Gly Asp Gly Leu Phe Thr
                85                  90                  95

Ala Gln His Gly Asn His Asp Trp Gly Ile Ala His Arg Ile Leu Met
            100                 105                 110

Pro Leu Phe Gly Pro Leu Lys Ile Arg Glu Met Phe Asp Asp Met Gln
            115                 120                 125
```

-continued

```
Asp Val Ser Glu Gln Leu Cys Leu Lys Trp Ala Arg Leu Gly Pro Ser
    130                 135                 140
Ala Thr Ile Asp Val Ala Asn Asp Phe Thr Arg Leu Thr Leu Asp Thr
145                 150                 155                 160
Ile Ala Leu Cys Thr Met Gly Tyr Arg Phe Asn Ser Phe Tyr Ser Asn
                165                 170                 175
Asp Lys Met His Pro Phe Val Asp Ser Met Val Ala Ala Leu Ile Asp
                180                 185                 190
Ala Asp Lys Gln Ser Met Phe Pro Asp Phe Ile Gly Ala Cys Arg Val
            195                 200                 205
Lys Ala Leu Ser Ala Phe Arg Lys His Ala Ala Ile Met Lys Gly Thr
210                 215                 220
Cys Asn Glu Leu Ile Gln Glu Arg Arg Lys Asn Pro Ile Glu Gly Thr
225                 230                 235                 240
Asp Leu Leu Thr Ala Met Met Glu Gly Lys Asp Pro Lys Thr Gly Glu
                245                 250                 255
Gly Met Ser Asp Asp Leu Ile Val Gln Asn Leu Ile Thr Phe Leu Ile
                260                 265                 270
Ala Gly His Glu Thr Thr Ser Gly Leu Leu Ser Phe Ala Phe Tyr Tyr
            275                 280                 285
Leu Leu Glu Asn Pro His Thr Leu Glu Lys Ala Arg Ala Glu Val Asp
290                 295                 300
Glu Val Val Gly Asp Gln Ala Leu Asn Val Asp His Leu Thr Lys Met
305                 310                 315                 320
Pro Tyr Val Asn Met Ile Leu Arg Glu Thr Leu Arg Leu Met Pro Thr
                325                 330                 335
Ala Pro Gly Phe Phe Val Thr Pro His Lys Asp Glu Ile Ile Gly Gly
                340                 345                 350
Lys Tyr Ala Val Pro Ala Asn Glu Ser Leu Phe Cys Phe Leu His Leu
            355                 360                 365
Ile His Arg Asp Pro Lys Val Trp Gly Ala Asp Ala Glu Glu Phe Arg
370                 375                 380
Pro Glu Arg Met Ala Asp Glu Phe Phe Glu Ala Leu Pro Lys Asn Ala
385                 390                 395                 400
Trp Lys Pro Phe Gly Asn Gly Met Arg Gly Cys Ile Gly Arg Glu Phe
                405                 410                 415
Ala Trp Gln Glu Ala Lys Leu Ile Thr Val Met Ile Leu Gln Asn Phe
            420                 425                 430
Glu Leu Ser Lys Ala Asp Pro Ser Tyr Lys Leu Lys Ile Lys Gln Ser
            435                 440                 445
Leu Thr Ile Lys Pro Asp Gly Phe Asn Met His Ala Lys Leu Arg Asn
450                 455                 460
Asp Arg Lys Val Ser Gly Leu Phe Lys Ala Pro Ser Leu Ser Ser Gln
465                 470                 475                 480
Gln Pro Ser Leu Ser Ser Arg Gln Ser Ile Asn Ala Ile Asn Ala Lys
                485                 490                 495
Asp Leu Lys Pro Ile Ser Ile Phe Tyr Gly Ser Asn Thr Gly Thr Cys
                500                 505                 510
Glu Ala Leu Ala Gln Lys Leu Ser Ala Asp Cys Val Ala Ser Gly Phe
            515                 520                 525
Met Pro Ser Lys Pro Leu Pro Leu Asp Met Ala Thr Lys Asn Leu Ser
530                 535                 540
Lys Asp Gly Pro Asn Ile Leu Leu Ala Ala Ser Tyr Asp Gly Arg Pro
```

```
                545                 550                 555                 560
Ser Asp Asn Ala Glu Glu Phe Thr Lys Trp Ala Glu Ser Leu Lys Pro
                    565                 570                 575
Gly Glu Leu Glu Gly Val Gln Phe Ala Val Phe Gly Cys Gly His Lys
                580                 585                 590
Asp Trp Val Ser Thr Tyr Phe Lys Ile Pro Lys Ile Leu Asp Lys Cys
                595                 600                 605
Leu Ala Asp Ala Gly Ala Glu Arg Leu Val Glu Ile Gly Leu Thr Asp
            610                 615                 620
Ala Ser Thr Gly Arg Leu Tyr Ser Asp Phe Asp Asp Trp Glu Asn Gln
625                 630                 635                 640
Lys Leu Phe Thr Glu Leu Ser Lys Arg Gln Gly Val Thr Pro Thr Asp
                    645                 650                 655
Asp Ser His Leu Glu Leu Asn Val Thr Val Ile Gln Pro Gln Asn Asn
                660                 665                 670
Asp Met Gly Gly Asn Phe Lys Arg Ala Glu Val Val Glu Asn Thr Leu
                675                 680                 685
Leu Thr Tyr Pro Gly Val Ser Arg Lys His Ser Leu Leu Leu Lys Leu
            690                 695                 700
Pro Lys Asp Met Glu Tyr Thr Pro Gly Asp His Val Leu Val Leu Pro
705                 710                 715                 720
Lys Asn Pro Pro Gln Leu Val Glu Gln Ala Met Ser Cys Phe Gly Val
                    725                 730                 735
Asp Ser Asp Thr Ala Leu Thr Ile Ser Ser Lys Arg Pro Thr Phe Leu
                740                 745                 750
Pro Thr Asp Thr Pro Ile Leu Ile Ser Ser Leu Leu Ser Ser Leu Val
            755                 760                 765
Glu Leu Ser Gln Thr Val Ser Arg Thr Ser Leu Lys Arg Leu Ala Asp
            770                 775                 780
Phe Ala Asp Asp Asp Thr Lys Ala Cys Val Glu Arg Ile Ala Gly
785                 790                 795                 800
Asp Asp Tyr Thr Val Glu Val Glu Glu Gln Arg Met Ser Leu Leu Asp
                805                 810                 815
Ile Leu Arg Lys Tyr Pro Gly Ile Asn Met Pro Leu Ser Thr Phe Leu
            820                 825                 830
Ser Met Leu Pro Gln Met Arg Pro Arg Thr Tyr Ser Phe Ala Ser Ala
            835                 840                 845
Pro Glu Trp Lys Gln Gly His Gly Met Leu Leu Phe Ser Val Val Glu
850                 855                 860
Ala Glu Glu Gly Thr Val Ser Arg Pro Gly Gly Leu Ala Thr Asn Tyr
865                 870                 875                 880
Met Ala Gln Leu Arg Gln Gly Asp Ser Ile Leu Val Glu Pro Arg Pro
                    885                 890                 895
Cys Arg Pro Glu Leu Arg Thr Thr Met Met Leu Pro Glu Pro Lys Val
                    900                 905                 910
Pro Ile Ile Met Ile Ala Val Gly Ala Gly Leu Ala Pro Phe Leu Gly
            915                 920                 925
Tyr Leu Gln Lys Arg Phe Leu Gln Ala Gln Ser Gln Arg Thr Ala Leu
            930                 935                 940
Pro Pro Cys Thr Leu Leu Phe Gly Cys Arg Gly Ala Lys Met Asp Asp
945                 950                 955                 960
Ile Cys Arg Ala Gln Leu Asp Glu Tyr Ser Arg Ala Gly Val Val Ser
                    965                 970                 975
```

Val His Arg Ala Tyr Ser Arg Asp Pro Asp Ser Gln Cys Lys Tyr Val
              980                 985                 990

Gln Gly Leu Val Thr Lys His Ser Glu Thr Leu Ala Lys Gln Trp Ala
         995                1000                1005

Gln Gly Ala Ile Val Met Val Cys Ser Gly Lys Lys Val Ser Asp Gly
    1010                1015                1020

Val Met Asn Val Leu Ser Pro Ile Leu Phe Ala Glu Glu Lys Arg Ser
1025                1030                1035                1040

Gly Met Thr Gly Ala Asp Ser Val Asp Val Trp Arg Gln Asn Val Pro
              1045                1050                1055

Lys Glu Arg Met Ile Leu Glu Val Phe Gly
         1060                1065

<210> SEQ ID NO 40
<211> LENGTH: 1130
<212> TYPE: PRT
<213> ORGANISM: Magnaporthe oryzae
<220> FEATURE:
<223> OTHER INFORMATION: Magnaporthe oryzae (M. grisea) strain 70-15
      hypothetical protein MGG_01925, CYP505A5

<400> SEQUENCE: 40

Met Phe Phe Leu Ser Ser Ser Leu Ala Tyr Met Ala Ala Thr Gln Ser
1               5                   10                  15

Arg Asp Trp Ala Ser Phe Gly Val Ser Leu Pro Ser Thr Ala Leu Gly
            20                  25                  30

Arg His Leu Gln Ala Ala Met Pro Phe Leu Ser Glu Glu Asn His Lys
        35                  40                  45

Ser Gln Gly Thr Val Leu Ile Pro Asp Ala Gln Gly Pro Ile Pro Phe
    50                  55                  60

Leu Gly Ser Val Pro Leu Val Asp Pro Glu Leu Pro Ser Gln Ser Leu
65                  70                  75                  80

Gln Arg Leu Ala Arg Gln Tyr Gly Glu Ile Tyr Arg Phe Val Ile Pro
                85                  90                  95

Gly Arg Gln Ser Pro Ile Leu Val Ser Thr His Ala Leu Val Asn Glu
            100                 105                 110

Leu Cys Asp Glu Lys Arg Phe Lys Lys Val Ala Ala Ala Leu Leu
        115                 120                 125

Gly Leu Arg Glu Ala Ile His Asp Gly Leu Phe Thr Ala His Asn Asp
    130                 135                 140

Glu Pro Asn Trp Gly Ile Ala His Arg Ile Leu Met Pro Ala Phe Gly
145                 150                 155                 160

Pro Met Ala Ile Lys Gly Met Phe Asp Glu Met His Asp Val Ala Ser
                165                 170                 175

Gln Met Ile Leu Lys Trp Ala Arg His Gly Ser Thr Thr Pro Ile Met
            180                 185                 190

Val Ser Asp Asp Phe Thr Arg Leu Thr Leu Asp Thr Ile Ala Leu Cys
        195                 200                 205

Ser Met Gly Tyr Arg Phe Asn Ser Phe His Asp Ser Met His Glu
    210                 215                 220

Phe Ile Glu Ala Met Thr Cys Trp Met Lys Glu Ser Gly Asn Lys Thr
225                 230                 235                 240

Arg Arg Leu Leu Pro Asp Val Phe Tyr Arg Thr Thr Asp Lys Lys Trp
                245                 250                 255

His Asp Asp Ala Glu Ile Leu Arg Arg Thr Ala Asp Glu Val Leu Lys

```
                260             265             270
Ala Arg Lys Glu Asn Pro Ser Gly Arg Lys Asp Leu Leu Thr Ala Met
            275             280             285
Ile Glu Gly Val Asp Pro Lys Thr Gly Lys Leu Ser Asp Ser Ser
        290             295             300
Ile Ile Asp Asn Leu Ile Thr Phe Leu Ile Ala Gly His Glu Thr Thr
305             310             315             320
Ser Gly Met Leu Ser Phe Ala Phe Tyr Leu Leu Leu Lys Asn Pro Thr
                325             330             335
Ala Tyr Arg Lys Ala Gln Gln Glu Ile Asp Asp Leu Cys Gly Arg Glu
            340             345             350
Pro Ile Thr Val Glu His Leu Ser Lys Met Pro Tyr Ile Thr Ala Val
            355             360             365
Leu Arg Glu Thr Leu Arg Leu Tyr Ser Thr Ile Pro Ala Phe Val Val
        370             375             380
Glu Ala Ile Glu Asp Thr Val Val Gly Gly Lys Tyr Ala Ile Pro Lys
385             390             395             400
Asn His Pro Ile Phe Leu Met Ile Ala Glu Ser His Arg Asp Pro Lys
                405             410             415
Val Tyr Gly Asp Asp Ala Gln Glu Phe Glu Pro Glu Arg Met Leu Asp
            420             425             430
Gly Gln Phe Glu Arg Arg Asn Arg Glu Phe Pro Asn Ser Trp Lys Pro
            435             440             445
Phe Gly Asn Gly Met Arg Gly Cys Ile Gly Arg Ala Phe Ala Trp Gln
        450             455             460
Glu Ala Leu Leu Ile Thr Ala Met Leu Leu Gln Asn Phe Asn Phe Val
465             470             475             480
Met His Asp Pro Ala Tyr Gln Leu Ser Ile Lys Glu Asn Leu Thr Leu
                485             490             495
Lys Pro Asp Asn Phe Tyr Met Arg Ala Ile Leu Arg His Gly Met Ser
            500             505             510
Pro Thr Glu Leu Glu Arg Ser Ile Ser Gly Val Ala Pro Thr Gly Asn
            515             520             525
Lys Thr Pro Pro Arg Asn Ala Thr Arg Thr Ser Ser Pro Asp Pro Glu
            530             535             540
Asp Gly Gly Ile Pro Met Ser Ile Tyr Tyr Gly Ser Asn Ser Gly Thr
545             550             555             560
Cys Glu Ser Leu Ala His Lys Leu Ala Val Asp Ala Ser Ala Gln Gly
            565             570             575
Phe Lys Ala Glu Thr Val Asp Val Leu Asp Ala Ala Asn Gln Lys Leu
            580             585             590
Pro Ala Gly Asn Arg Gly Pro Val Val Leu Ile Thr Ala Ser Tyr Glu
            595             600             605
Gly Leu Pro Pro Asp Asn Ala Lys His Phe Val Glu Trp Leu Glu Asn
            610             615             620
Leu Lys Gly Gly Asp Glu Leu Val Asp Thr Ser Tyr Ala Val Phe Gly
625             630             635             640
Cys Gly His Gln Asp Trp Thr Lys Thr Phe His Arg Ile Pro Lys Leu
                645             650             655
Val Asp Glu Lys Leu Ala Glu His Gly Ala Val Arg Leu Ala Pro Leu
            660             665             670
Gly Leu Ser Asn Ala Ala His Gly Asp Met Phe Val Asp Phe Glu Thr
            675             680             685
```

```
Trp Glu Phe Glu Thr Leu Trp Pro Ala Leu Ala Asp Arg Tyr Lys Thr
690                 695                 700

Gly Ala Gly Arg Gln Asp Ala Ala Ala Thr Asp Leu Thr Ala Ala Leu
705                 710                 715                 720

Ser Gln Leu Ser Val Glu Val Ser His Pro Arg Ala Ala Asp Leu Arg
            725                 730                 735

Gln Asp Val Gly Glu Ala Val Val Ala Ala Arg Asp Leu Thr Ala
                740                 745                 750

Pro Gly Ala Pro Pro Lys Arg His Met Glu Ile Arg Leu Pro Lys Thr
        755                 760                 765

Gly Gly Arg Val His Tyr Ser Ala Gly Asp Tyr Leu Ala Val Leu Pro
770                 775                 780

Val Asn Pro Lys Ser Thr Val Glu Arg Ala Met Arg Arg Phe Gly Leu
785                 790                 795                 800

Ala Trp Asp Ala His Val Thr Ile Arg Ser Gly Gly Arg Thr Thr Leu
            805                 810                 815

Pro Thr Gly Ala Pro Val Ser Ala Arg Glu Val Leu Ser Ser Tyr Val
                820                 825                 830

Glu Leu Thr Gln Pro Ala Thr Lys Arg Gly Ile Ala Val Leu Ala Gly
        835                 840                 845

Ala Val Thr Gly Gly Pro Ala Ala Glu Gln Glu Gln Ala Lys Ala Ala
850                 855                 860

Leu Leu Asp Leu Ala Gly Asp Ser Tyr Ala Leu Glu Val Ser Ala Lys
865                 870                 875                 880

Arg Val Gly Val Leu Asp Leu Leu Glu Arg Phe Pro Ala Cys Ala Val
            885                 890                 895

Pro Phe Gly Thr Phe Leu Ala Leu Leu Pro Pro Met Arg Val Arg Gln
                900                 905                 910

Tyr Ser Ile Ser Ser Ser Pro Leu Trp Asn Asp Glu His Ala Thr Leu
        915                 920                 925

Thr Tyr Ser Val Leu Ser Ala Pro Ser Leu Ala Asp Pro Ala Arg Thr
930                 935                 940

His Val Gly Val Ala Ser Ser Tyr Leu Ala Gly Leu Gly Glu Gly Asp
945                 950                 955                 960

His Leu His Val Ala Leu Arg Pro Ser His Val Ala Phe Arg Leu Pro
            965                 970                 975

Ser Pro Glu Thr Pro Val Val Cys Val Cys Ala Gly Ser Gly Met Ala
                980                 985                 990

Pro Phe Arg Ala Phe Ala Gln Glu Arg Ala Ala Leu Val Gly Ala Gly
        995                 1000                1005

Arg Lys Val Ala Pro Leu Leu Leu Phe Phe Gly Cys Arg Glu Pro Gly
    1010                1015                1020

Val Asp Asp Leu Tyr Arg Glu Glu Leu Glu Gly Trp Glu Ala Lys Gly
1025                1030                1035                1040

Val Leu Ser Val Arg Arg Ala Tyr Ser Arg Arg Thr Glu Gln Ser Glu
                1045                1050                1055

Gly Cys Arg Tyr Val Gln Asp Arg Leu Leu Lys Asn Arg Ala Glu Val
        1060                1065                1070

Lys Ser Leu Trp Ser Gln Asp Ala Lys Val Phe Val Cys Gly Ser Arg
    1075                1080                1085

Glu Val Ala Glu Gly Val Lys Glu Ala Met Phe Lys Val Val Ala Gly
        1090                1095                1100
```

-continued

```
Lys Glu Gly Ser Ser Glu Glu Val Gln Ala Trp Tyr Glu Glu Val Arg
1105                1110                1115                1120

Asn Val Arg Tyr Ala Ser Asp Ile Phe Asp
            1125                1130

<210> SEQ ID NO 41
<211> LENGTH: 1108
<212> TYPE: PRT
<213> ORGANISM: Neurospora crassa
<220> FEATURE:
<223> OTHER INFORMATION: Neurospora crassa strain OR74A bifunctional
      P-450:NADPH-P450 reductase, CYP505A2

<400> SEQUENCE: 41

Met Ser Ser Asp Glu Thr Pro Gln Thr Ile Pro Ile Pro Gly Pro Pro
1               5                   10                  15

Gly Leu Pro Leu Val Gly Asn Ser Phe Asp Ile Asp Thr Glu Phe Pro
            20                  25                  30

Leu Gly Ser Met Leu Asn Phe Ala Asp Gln Tyr Gly Glu Ile Phe Arg
        35                  40                  45

Leu Asn Phe Pro Gly Arg Asn Thr Val Phe Val Thr Ser Gln Ala Leu
    50                  55                  60

Val His Glu Leu Cys Asp Glu Lys Arg Phe Gln Lys Thr Val Asn Ser
65                  70                  75                  80

Ala Leu His Glu Ile Arg His Gly Ile His Asp Gly Leu Phe Thr Ala
                85                  90                  95

Arg Asn Asp Glu Pro Asn Trp Gly Ile Ala His Arg Ile Leu Met Pro
            100                 105                 110

Ala Phe Gly Pro Met Ala Ile Gln Asn Met Phe Pro Glu Met His Glu
        115                 120                 125

Ile Ala Ser Gln Leu Ala Leu Lys Trp Ala Arg His Gly Pro Asn Gln
    130                 135                 140

Ser Ile Lys Val Thr Asp Asp Phe Thr Arg Leu Thr Leu Asp Thr Ile
145                 150                 155                 160

Ala Leu Cys Ser Met Asp Tyr Arg Phe Asn Ser Tyr Tyr His Asp Asp
                165                 170                 175

Met His Pro Phe Ile Asp Ala Met Ala Ser Phe Leu Val Glu Ser Gly
            180                 185                 190

Asn Arg Ser Arg Arg Pro Ala Leu Pro Ala Phe Met Tyr Ser Lys Val
        195                 200                 205

Asp Arg Lys Phe Tyr Asp Ile Arg Val Leu Arg Glu Thr Ala Glu
    210                 215                 220

Gly Val Leu Lys Ser Arg Lys Glu His Pro Ser Glu Arg Lys Asp Leu
225                 230                 235                 240

Leu Thr Ala Met Leu Asp Gly Val Asp Pro Lys Thr Gly Gly Lys Leu
                245                 250                 255

Ser Asp Asp Ser Ile Ile Asp Asn Leu Ile Thr Phe Leu Ile Ala Gly
            260                 265                 270

His Glu Thr Thr Ser Gly Leu Leu Ser Phe Ala Phe Val Gln Leu Leu
        275                 280                 285

Lys Asn Pro Glu Thr Tyr Arg Lys Ala Gln Lys Glu Val Asp Asp Val
    290                 295                 300

Cys Gly Lys Gly Pro Ile Lys Leu Glu His Met Asn Lys Leu His Tyr
305                 310                 315                 320

Ile Ala Ala Val Leu Arg Glu Thr Leu Arg Leu Cys Pro Thr Ile Pro
                325                 330                 335
```

```
Val Ile Gly Val Glu Ser Lys Glu Asp Thr Val Ile Gly Gly Lys Tyr
            340                 345                 350

Glu Val Ser Lys Gly Gln Pro Phe Ala Leu Leu Phe Ala Lys Ser His
            355                 360                 365

Val Asp Pro Ala Val Tyr Gly Asp Thr Ala Asn Asp Phe Asp Pro Glu
            370                 375                 380

Arg Met Leu Asp Glu Asn Phe Glu Arg Leu Asn Lys Glu Phe Pro Asp
385                 390                 395                 400

Cys Trp Lys Pro Phe Gly Asn Gly Met Arg Ala Cys Ile Gly Arg Pro
                405                 410                 415

Phe Ala Trp Gln Glu Ala Leu Leu Val Met Ala Val Cys Leu Gln Asn
            420                 425                 430

Phe Asn Phe Met Pro Glu Asp Pro Asn Tyr Thr Leu Gln Tyr Lys Gln
            435                 440                 445

Thr Leu Thr Thr Lys Pro Lys Gly Phe Tyr Met Arg Ala Met Leu Arg
            450                 455                 460

Asp Gly Met Ser Ala Leu Asp Leu Glu Arg Arg Leu Lys Gly Glu Leu
465                 470                 475                 480

Val Ala Pro Lys Pro Thr Ala Gln Gly Pro Val Ser Gly Gln Pro Lys
            485                 490                 495

Lys Ser Gly Glu Gly Lys Pro Ile Ser Ile Tyr Tyr Gly Ser Asn Thr
            500                 505                 510

Gly Thr Cys Glu Thr Phe Ala Gln Arg Leu Ala Ser Asp Ala Glu Ala
            515                 520                 525

His Gly Phe Thr Ala Thr Ile Ile Asp Ser Leu Asp Ala Ala Asn Gln
            530                 535                 540

Asn Leu Pro Lys Asp Arg Pro Val Val Phe Ile Thr Ala Ser Tyr Glu
545                 550                 555                 560

Gly Gln Pro Pro Asp Asn Ala Ala Leu Phe Val Gly Trp Leu Glu Ser
                565                 570                 575

Leu Thr Gly Asn Glu Leu Glu Gly Val Gln Tyr Ala Val Phe Gly Cys
            580                 585                 590

Gly His His Asp Trp Ala Gln Thr Phe His Arg Ile Pro Lys Leu Val
            595                 600                 605

Asp Asn Thr Val Ser Glu Arg Gly Gly Asp Arg Ile Cys Ser Leu Gly
610                 615                 620

Leu Ala Asp Ala Gly Lys Gly Glu Met Phe Thr Glu Phe Glu Gln Trp
625                 630                 635                 640

Glu Asp Glu Val Phe Trp Pro Ala Met Glu Lys Tyr Glu Val Ser
                645                 650                 655

Arg Lys Glu Asp Asp Asn Glu Ala Leu Leu Gln Ser Gly Leu Thr Val
            660                 665                 670

Asn Phe Ser Lys Pro Arg Ser Ser Thr Leu Arg Gln Asp Val Gln Glu
            675                 680                 685

Ala Val Val Asp Ala Lys Thr Ile Thr Ala Pro Gly Ala Pro Pro
            690                 695                 700

Lys Arg His Ile Glu Val Gln Leu Ser Ser Asp Ser Gly Ala Tyr Arg
705                 710                 715                 720

Ser Gly Asp Tyr Leu Ala Val Leu Pro Ile Asn Pro Lys Glu Thr Val
                725                 730                 735

Asn Arg Val Met Arg Arg Phe Gln Leu Ala Trp Asp Thr Asn Ile Thr
            740                 745                 750
```

```
Ile Glu Ala Ser Arg Gln Thr Thr Ile Leu Pro Thr Gly Val Pro Met
            755                 760                 765

Pro Val His Asp Val Leu Gly Ala Tyr Val Glu Leu Ser Gln Pro Ala
    770                 775                 780

Thr Lys Lys Asn Ile Leu Ala Leu Ala Glu Ala Ala Asp Asn Ala Glu
785                 790                 795                 800

Thr Lys Ala Thr Leu Arg Gln Leu Ala Gly Pro Glu Tyr Thr Glu Lys
                805                 810                 815

Ile Thr Ser Arg Arg Val Ser Ile Leu Asp Leu Leu Glu Gln Phe Pro
            820                 825                 830

Ser Ile Pro Leu Pro Phe Ser Ser Phe Leu Ser Leu Leu Pro Pro Met
    835                 840                 845

Arg Val Arg Gln Tyr Ser Ile Ser Ser Ser Pro Leu Trp Asn Pro Ser
850                 855                 860

His Val Thr Leu Thr Tyr Ser Leu Leu Glu Ser Pro Ser Leu Ser Asn
865                 870                 875                 880

Pro Asp Lys Lys His Val Gly Val Ala Thr Ser Tyr Leu Ala Ser Leu
                885                 890                 895

Glu Ala Gly Asp Lys Leu Asn Val Ser Ile Arg Pro Ser His Lys Ala
            900                 905                 910

Phe His Leu Pro Val Asp Ala Asp Lys Thr Pro Leu Ile Met Ile Ala
    915                 920                 925

Ala Gly Ser Gly Leu Ala Pro Phe Arg Gly Phe Val Gln Glu Arg Ala
    930                 935                 940

Ala Gln Ile Ala Ala Gly Arg Ser Leu Ala Pro Ala Met Leu Phe Tyr
945                 950                 955                 960

Gly Cys Arg His Pro Glu Gln Asp Asp Leu Tyr Arg Asp Glu Phe Asp
                965                 970                 975

Lys Trp Glu Ser Ile Gly Ala Val Ser Val Arg Arg Ala Phe Ser Arg
            980                 985                 990

Cys Pro Glu Ser Gln Glu Thr Lys Gly Cys Lys Tyr Val Gly Asp Arg
    995                 1000                1005

Leu Trp Glu Asp Arg Glu Glu Val Thr Gly Leu Trp Asp Arg Gly Ala
    1010                1015                1020

Lys Val Tyr Val Cys Gly Ser Arg Glu Val Gly Glu Ser Val Lys Lys
1025                1030                1035                1040

Val Val Val Arg Ile Ala Leu Glu Arg Gln Lys Met Ile Val Glu Ala
                1045                1050                1055

Arg Glu Lys Gly Glu Leu Asp Ser Leu Pro Glu Gly Ile Val Glu Gly
    1060                1065                1070

Leu Lys Leu Lys Gly Leu Thr Val Glu Asp Val Glu Val Ser Glu Glu
        1075                1080                1085

Arg Ala Leu Lys Trp Phe Glu Gly Ile Arg Asn Glu Arg Tyr Ala Thr
    1090                1095                1100

Asp Val Phe Asp
1105

<210> SEQ ID NO 42
<211> LENGTH: 561
<212> TYPE: PRT
<213> ORGANISM: Oryza sativa
<220> FEATURE:
<223> OTHER INFORMATION: Oryza sativa Japonica group cytochrome P450
      family protein, CYP97C

<400> SEQUENCE: 42
```

```
Met Ala Ala Ala Ala Ala Ala Val Pro Cys Val Pro Phe Leu Cys
1               5                   10                  15

Pro Pro Pro Pro Pro Leu Val Ser Pro Arg Leu Arg Arg Gly His Val
                20                  25                  30

Arg Leu Arg Leu Arg Pro Pro Arg Ser Ser Gly Gly Gly Gly Gly Gly
        35                  40                  45

Gly Ala Gly Gly Asp Glu Pro Pro Ile Thr Thr Ser Trp Val Ser Pro
    50                  55                  60

Asp Trp Leu Thr Ala Leu Ser Arg Ser Val Ala Thr Arg Leu Gly Gly
65                  70                  75                  80

Gly Asp Asp Ser Gly Ile Pro Val Ala Ser Ala Lys Leu Asp Asp Val
                85                  90                  95

Arg Asp Leu Leu Gly Gly Ala Leu Phe Leu Pro Leu Phe Lys Trp Phe
                100                 105                 110

Arg Glu Glu Gly Pro Val Tyr Arg Leu Ala Ala Gly Pro Arg Asp Leu
                115                 120                 125

Val Val Val Ser Asp Pro Ala Val Ala Arg His Val Leu Arg Gly Tyr
        130                 135                 140

Gly Ser Arg Tyr Glu Lys Gly Leu Val Ala Glu Val Ser Glu Phe Leu
145                 150                 155                 160

Phe Gly Ser Gly Phe Ala Ile Ala Glu Gly Ala Leu Trp Thr Val Arg
                165                 170                 175

Arg Arg Ser Val Val Pro Ser Leu His Lys Arg Phe Leu Ser Val Met
                180                 185                 190

Val Asp Arg Val Phe Cys Lys Cys Ala Glu Arg Leu Val Glu Lys Leu
        195                 200                 205

Glu Thr Ser Ala Leu Ser Gly Lys Pro Val Asn Met Glu Ala Arg Phe
210                 215                 220

Ser Gln Met Thr Leu Asp Val Ile Gly Leu Ser Leu Phe Asn Tyr Asn
225                 230                 235                 240

Phe Asp Ser Leu Thr Ser Asp Ser Pro Val Ile Asp Ala Val Tyr Thr
                245                 250                 255

Ala Leu Lys Glu Ala Glu Leu Arg Ser Thr Asp Leu Leu Pro Tyr Trp
                260                 265                 270

Lys Ile Asp Leu Leu Cys Lys Ile Val Pro Arg Gln Ile Lys Ala Glu
                275                 280                 285

Lys Ala Val Asn Ile Ile Arg Asn Thr Val Glu Asp Leu Ile Thr Lys
                290                 295                 300

Cys Lys Lys Ile Val Asp Ala Glu Asn Glu Gln Ile Glu Gly Glu Glu
305                 310                 315                 320

Tyr Val Asn Glu Ala Asp Pro Ser Ile Leu Arg Phe Leu Leu Ala Ser
                325                 330                 335

Arg Glu Glu Val Thr Ser Val Gln Leu Arg Asp Asp Leu Leu Ser Met
                340                 345                 350

Leu Val Ala Gly His Glu Thr Thr Gly Ser Val Leu Thr Trp Thr Ile
                355                 360                 365

Tyr Leu Leu Ser Lys Asp Pro Ala Ala Leu Arg Ala Gln Ala Glu
                370                 375                 380

Val Asp Arg Val Leu Gln Gly Arg Leu Pro Arg Tyr Glu Asp Leu Lys
385                 390                 395                 400

Glu Leu Lys Tyr Leu Met Arg Cys Ile Asn Glu Ser Met Arg Leu Tyr
                405                 410                 415
```

-continued

```
Pro His Pro Pro Val Leu Ile Arg Arg Ala Ile Val Asp Asp Val Leu
            420                 425                 430

Pro Gly Asn Tyr Lys Ile Lys Ala Gly Gln Asp Ile Met Ile Ser Val
            435                 440                 445

Tyr Asn Ile His Arg Ser Pro Glu Val Trp Asp Arg Ala Asp Asp Phe
450                 455                 460

Ile Pro Glu Arg Phe Asp Leu Glu Gly Pro Val Pro Asn Glu Thr Asn
465                 470                 475                 480

Thr Glu Tyr Arg Phe Ile Pro Phe Ser Gly Gly Pro Arg Lys Cys Val
                485                 490                 495

Gly Asp Gln Phe Ala Leu Leu Glu Ala Ile Val Ala Leu Ala Val Val
            500                 505                 510

Leu Gln Lys Met Asp Ile Glu Leu Val Pro Asp Gln Lys Ile Asn Met
            515                 520                 525

Thr Thr Gly Ala Thr Ile His Thr Thr Asn Gly Leu Tyr Met Asn Val
            530                 535                 540

Ser Leu Arg Lys Val Asp Arg Glu Pro Asp Phe Ala Leu Ser Gly Ser
545                 550                 555                 560

Arg

<210> SEQ ID NO 43
<211> LENGTH: 467
<212> TYPE: PRT
<213> ORGANISM: Artificial Sequence
<220> FEATURE:
<223> OTHER INFORMATION: synthetic chimeric heme enzyme C2G9, chimeric
      cytochrome P450 enzyme C2G9

<400> SEQUENCE: 43

Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
            20                  25                  30

Lys Leu Ala Glu Glu Gln Gly Pro Ile Phe Gln Ile His Thr Pro Ala
        35                  40                  45

Gly Thr Thr Ile Val Val Ser Gly His Glu Leu Val Lys Glu Val Cys
    50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Ala Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Val Gln Leu
        115                 120                 125

Ile Gln Lys Trp Ala Arg Leu Asn Pro Asn Glu Ala Val Asp Val Pro
    130                 135                 140

Gly Asp Met Thr Arg Leu Thr Leu Asp Thr Ile Gly Leu Cys Gly Phe
145                 150                 155                 160

Asn Tyr Arg Phe Asn Ser Tyr Tyr Arg Glu Thr Pro His Pro Phe Ile
                165                 170                 175

Asn Ser Met Val Arg Ala Leu Asp Glu Ala Met His Gln Met Gln Arg
            180                 185                 190

Leu Asp Val Gln Asp Lys Leu Met Val Arg Thr Lys Arg Gln Phe Arg
        195                 200                 205
```

Tyr Asp Ile Gln Thr Met Phe Ser Leu Val Asp Arg Met Ile Ala Glu
    210                 215                 220

Arg Lys Ala Asn Pro Asp Glu Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
                260                 265                 270

Ser Gly Leu Leu Ser Phe Ala Leu Tyr Phe Leu Val Lys Asn Pro His
            275                 280                 285

Val Leu Gln Lys Ala Ala Glu Glu Ala Ala Arg Val Leu Val Asp Pro
    290                 295                 300

Val Pro Ser Tyr Lys Gln Val Lys Gln Leu Lys Tyr Val Gly Met Val
305                 310                 315                 320

Leu Asn Glu Ala Leu Arg Leu Trp Pro Thr Ala Pro Ala Phe Ser Leu
                325                 330                 335

Tyr Ala Lys Glu Asp Thr Val Leu Gly Gly Tyr Pro Ile Ser Lys
                340                 345                 350

Gly Gln Pro Val Thr Val Leu Ile Pro Lys Leu His Arg Asp Gln Asn
            355                 360                 365

Ala Trp Gly Pro Asp Ala Glu Asp Phe Arg Pro Glu Arg Phe Glu Asp
    370                 375                 380

Pro Ser Ser Ile Pro His His Ala Tyr Lys Pro Phe Gly Asn Gly Gln
385                 390                 395                 400

Arg Ala Cys Ile Gly Met Gln Phe Ala Leu His Glu Ala Thr Leu Val
                405                 410                 415

Leu Gly Met Ile Leu Lys Tyr Phe Thr Leu Ile Asp His Glu Asn Tyr
                420                 425                 430

Glu Leu Asp Ile Lys Gln Thr Leu Thr Leu Lys Pro Gly Asp Phe His
            435                 440                 445

Ile Ser Val Gln Ser Arg His Gln Glu Ala Ile His Ala Asp Val Gln
    450                 455                 460

Ala Ala Glu
465

<210> SEQ ID NO 44
<211> LENGTH: 467
<212> TYPE: PRT
<213> ORGANISM: Artificial Sequence
<220> FEATURE:
<223> OTHER INFORMATION: synthetic chimeric heme enzyme X7, chimeric
      cytochrome P450 enzyme X7

<400> SEQUENCE: 44

Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
                20                  25                  30

Lys Leu Ala Glu Glu Gln Gly Pro Ile Phe Gln Ile His Thr Pro Ala
            35                  40                  45

Gly Thr Thr Ile Val Val Ser Gly His Glu Leu Val Lys Glu Val Cys
        50                  55                  60

Asp Glu Glu Arg Phe Ala Lys Ser Ile Glu Gly Ala Leu Glu Lys Val
65                  70                  75                  80

Arg Ala Phe Ser Gly Asp Gly Leu Ala Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Thr Gln Leu
        115                 120                 125

Ile Gln Lys Trp Ser Arg Leu Asn Pro Asn Glu Glu Ile Asp Val Ala
    130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Gln Pro His Pro Phe Ile
                165                 170                 175

Thr Ser Met Val Arg Ala Leu Asp Glu Ala Met Asn Lys Leu Gln Arg
            180                 185                 190

Ala Asn Pro Asp Asp Pro Ala Tyr Asp Glu Asn Lys Arg Gln Phe Gln
        195                 200                 205

Glu Asp Ile Lys Val Met Asn Asp Leu Val Asp Ser Ile Ile Ala Glu
    210                 215                 220

Arg Arg Ala Asn Gly Asp Gln Asp Glu Lys Asp Leu Leu Ala Arg Met
225                 230                 235                 240

Leu Asn Val Glu Asp Pro Glu Thr Gly Glu Lys Leu Asp Asp Glu Asn
                245                 250                 255

Ile Arg Phe Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
    290                 295                 300

Thr Pro Glu Tyr Lys Gln Ile Gln Gln Leu Lys Tyr Ile Arg Met Val
305                 310                 315                 320

Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Glu Tyr Pro Ile Ser Lys
            340                 345                 350

Gly Gln Pro Val Thr Val Leu Ile Pro Lys Leu His Arg Asp Gln Asn
        355                 360                 365

Ala Trp Gly Pro Asp Ala Glu Asp Phe Arg Pro Glu Arg Phe Glu Asp
    370                 375                 380

Pro Ser Ser Ile Pro His His Ala Tyr Lys Pro Phe Gly Asn Gly Gln
385                 390                 395                 400

Arg Ala Cys Ile Gly Met Gln Phe Ala Leu Gln Glu Ala Thr Met Val
                405                 410                 415

Leu Gly Leu Val Leu Lys His Phe Glu Leu Ile Asn His Thr Gly Tyr
            420                 425                 430

Glu Leu Lys Ile Lys Glu Ala Leu Thr Ile Lys Pro Asp Asp Phe Lys
        435                 440                 445

Ile Thr Val Lys Pro Arg Lys Thr Ala Ala Ile Asn Val Gln Arg Lys
    450                 455                 460

Glu Gln Ala
465

<210> SEQ ID NO 45
<211> LENGTH: 466
<212> TYPE: PRT
<213> ORGANISM: Artificial Sequence
<220> FEATURE:

<223> OTHER INFORMATION: synthetic chimeric heme enzyme X7-12, chimeric cytochrome P450 enzyme X7-12

<400> SEQUENCE: 45

| | | | | | | | | | | | | | | |
|---|---|---|---|---|---|---|---|---|---|---|---|---|---|---|
| Met | Thr | Ile | Lys | Glu | Met | Pro | Gln | Pro | Lys | Thr | Phe | Gly | Glu | Leu | Lys |
| 1 | | | | 5 | | | | | 10 | | | | | 15 |

| Asn | Leu | Pro | Leu | Leu | Asn | Thr | Asp | Lys | Pro | Val | Gln | Ala | Leu | Met | Lys |
| 20 | 25 | 30 |

| Ile | Ala | Asp | Glu | Leu | Gly | Glu | Ile | Phe | Lys | Phe | Glu | Ala | Pro | Gly | Arg |
| 35 | 40 | 45 |

| Val | Thr | Arg | Tyr | Leu | Ser | Ser | Gln | Arg | Leu | Ile | Lys | Glu | Ala | Cys | Asp |
| 50 | 55 | 60 |

| Glu | Glu | Arg | Phe | Asp | Lys | Ser | Ile | Glu | Gly | Ala | Leu | Glu | Lys | Val | Arg |
| 65 | 70 | 75 | 80 |

| Ala | Phe | Ser | Gly | Asp | Gly | Leu | Ala | Thr | Ser | Trp | Thr | His | Glu | Pro | Asn |
| 85 | 90 | 95 |

| Trp | Arg | Lys | Ala | His | Asn | Ile | Leu | Met | Pro | Thr | Phe | Ser | Gln | Arg | Ala |
| 100 | 105 | 110 |

| Met | Lys | Asp | Tyr | His | Glu | Lys | Met | Val | Asp | Ile | Ala | Val | Gln | Leu | Val |
| 115 | 120 | 125 |

| Gln | Lys | Trp | Glu | Arg | Leu | Asn | Ala | Asp | Glu | His | Ile | Glu | Val | Pro | Glu |
| 130 | 135 | 140 |

| Asp | Met | Thr | Arg | Leu | Thr | Leu | Asp | Thr | Ile | Gly | Leu | Cys | Gly | Phe | Asn |
| 145 | 150 | 155 | 160 |

| Tyr | Arg | Phe | Asn | Ser | Phe | Tyr | Arg | Asp | Gln | Pro | His | Pro | Phe | Ile | Thr |
| 165 | 170 | 175 |

| Ser | Met | Val | Arg | Ala | Leu | Asp | Glu | Ala | Met | Asn | Lys | Leu | Gln | Arg | Ala |
| 180 | 185 | 190 |

| Asn | Pro | Asp | Asp | Pro | Ala | Tyr | Asp | Glu | Asn | Lys | Arg | Gln | Phe | Gln | Glu |
| 195 | 200 | 205 |

| Asp | Ile | Lys | Val | Met | Asn | Asp | Leu | Val | Asp | Ser | Ile | Ile | Ala | Glu | Arg |
| 210 | 215 | 220 |

| Arg | Ala | Asn | Gly | Asp | Gln | Asp | Glu | Lys | Asp | Leu | Leu | Ala | Arg | Met | Leu |
| 225 | 230 | 235 | 240 |

| Asn | Val | Glu | Asp | Pro | Glu | Thr | Gly | Glu | Lys | Leu | Asp | Asp | Glu | Asn | Ile |
| 245 | 250 | 255 |

| Arg | Phe | Gln | Ile | Ile | Thr | Phe | Leu | Ile | Ala | Gly | His | Glu | Thr | Thr | Ser |
| 260 | 265 | 270 |

| Gly | Leu | Leu | Ser | Phe | Ala | Ile | Tyr | Cys | Leu | Leu | Thr | His | Pro | Glu | Lys |
| 275 | 280 | 285 |

| Leu | Lys | Lys | Ala | Gln | Glu | Glu | Ala | Asp | Arg | Val | Leu | Thr | Asp | Asp | Thr |
| 290 | 295 | 300 |

| Pro | Glu | Tyr | Lys | Gln | Ile | Gln | Gln | Leu | Lys | Tyr | Ile | Arg | Met | Val | Leu |
| 305 | 310 | 315 | 320 |

| Asn | Glu | Thr | Leu | Arg | Leu | Tyr | Pro | Thr | Ala | Pro | Ala | Phe | Ser | Leu | Tyr |
| 325 | 330 | 335 |

| Ala | Lys | Glu | Asp | Thr | Val | Leu | Gly | Gly | Glu | Tyr | Pro | Ile | Ser | Lys | Gly |
| 340 | 345 | 350 |

| Gln | Pro | Val | Thr | Val | Leu | Ile | Pro | Lys | Leu | His | Arg | Asp | Gln | Asn | Ala |
| 355 | 360 | 365 |

| Trp | Gly | Pro | Asp | Ala | Glu | Asp | Phe | Arg | Pro | Glu | Arg | Phe | Glu | Asp | Pro |
| 370 | 375 | 380 |

| Ser | Ser | Ile | Pro | His | His | Ala | Tyr | Lys | Pro | Phe | Gly | Asn | Gly | Gln | Arg |
| 385 | 390 | 395 | 400 |

Ala Cys Ile Gly Met Gln Phe Ala Leu Gln Glu Ala Thr Met Val Leu
            405                 410                 415

Gly Leu Val Leu Lys His Phe Glu Leu Ile Asn His Thr Gly Tyr Glu
            420                 425                 430

Leu Lys Ile Lys Glu Ala Leu Thr Ile Lys Pro Asp Asp Phe Lys Ile
            435                 440                 445

Thr Val Lys Pro Arg Lys Thr Ala Ala Ile Asn Val Gln Arg Lys Glu
    450                 455                 460

Gln Ala
465

<210> SEQ ID NO 46
<211> LENGTH: 465
<212> TYPE: PRT
<213> ORGANISM: Artificial Sequence
<220> FEATURE:
<223> OTHER INFORMATION: synthetic chimeric heme enzyme C2E6, chimeric
      cytochrome P450 enzyme C2E6

<400> SEQUENCE: 46

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Arg Met Ile Ala Glu Arg
    210                 215                 220

Lys Ala Asn Pro Asp Glu Asn Ile Lys Asp Leu Leu Ser Leu Met Leu
225                 230                 235                 240

Tyr Ala Lys Asp Pro Val Thr Gly Glu Thr Leu Asp Asp Glu Asn Ile
                245                 250                 255

Arg Tyr Gln Ile Ile Thr Phe Leu Ile Ala Gly His Glu Thr Thr Ser
            260                 265                 270

Gly Leu Leu Ser Phe Ala Ile Tyr Cys Leu Leu Thr His Pro Glu Lys

```
            275                 280                 285
Leu Lys Lys Ala Gln Glu Glu Ala Asp Arg Val Leu Thr Asp Asp Thr
        290                 295                 300

Pro Glu Tyr Lys Gln Ile Gln Gln Leu Lys Tyr Ile Arg Met Val Leu
305                 310                 315                 320

Asn Glu Thr Leu Arg Leu Tyr Pro Thr Ala Pro Ala Phe Ser Leu Tyr
                325                 330                 335

Ala Lys Glu Asp Thr Val Leu Gly Gly Glu Tyr Pro Leu Glu Lys Gly
            340                 345                 350

Asp Glu Leu Met Val Leu Ile Pro Gln Leu His Arg Asp Lys Thr Ile
        355                 360                 365

Trp Gly Asp Asp Val Glu Glu Phe Arg Pro Glu Arg Phe Glu Asn Pro
    370                 375                 380

Ser Ala Ile Pro Gln His Ala Phe Lys Pro Phe Gly Asn Gly Gln Arg
385                 390                 395                 400

Ala Cys Ile Gly Gln Gln Phe Ala Leu His Glu Ala Thr Leu Val Leu
                405                 410                 415

Gly Met Met Leu Lys His Phe Asp Phe Glu Asp His Thr Asn Tyr Glu
            420                 425                 430

Leu Asp Ile Lys Glu Thr Leu Thr Leu Lys Pro Glu Gly Phe Val Val
        435                 440                 445

Lys Ala Lys Ser Lys Lys Ile Pro Leu Gly Gly Ile Pro Ser Pro Ser
    450                 455                 460

Thr
465

<210> SEQ ID NO 47
<211> LENGTH: 467
<212> TYPE: PRT
<213> ORGANISM: Artificial Sequence
<220> FEATURE:
<223> OTHER INFORMATION: synthetic chimeric heme enzyme X7-9, chimeric
      cytochrome P450 enzyme X7-9

<400> SEQUENCE: 47

Met Lys Gln Ala Ser Ala Ile Pro Gln Pro Lys Thr Tyr Gly Pro Leu
1               5                   10                  15

Lys Asn Leu Pro His Leu Glu Lys Glu Gln Leu Ser Gln Ser Leu Trp
            20                  25                  30

Arg Ile Ala Asp Glu Leu Gly Pro Ile Phe Arg Phe Asp Phe Pro Gly
        35                  40                  45

Val Ser Ser Val Phe Val Ser Gly His Asn Leu Val Ala Glu Val Cys
    50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Ala Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Thr Gln Leu
        115                 120                 125

Ile Gln Lys Trp Ser Arg Leu Asn Pro Asn Glu Glu Ile Asp Val Ala
    130                 135                 140

Asp Asp Met Thr Arg Leu Thr Leu Asp Thr Ile Gly Leu Cys Gly Phe
145                 150                 155                 160
```

```
Asn Tyr Arg Phe Asn Ser Phe Tyr Arg Asp Gln Pro His Pro Phe Ile
                165                 170                 175

Thr Ser Met Val Arg Ala Leu Asp Glu Ala Met Asn Lys Leu Gln Arg
            180                 185                 190

Ala Asn Pro Asp Asp Pro Ala Tyr Asp Glu Asn Lys Arg Gln Phe Gln
        195                 200                 205

Glu Asp Ile Lys Val Met Asn Asp Leu Val Asp Ser Ile Ile Ala Glu
    210                 215                 220

Arg Arg Ala Asn Gly Asp Gln Asp Glu Lys Asp Leu Leu Ala Arg Met
225                 230                 235                 240

Leu Asn Val Glu Asp Pro Glu Thr Gly Glu Lys Leu Asp Asp Glu Asn
                245                 250                 255

Ile Arg Phe Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
    290                 295                 300

Thr Pro Glu Tyr Lys Gln Ile Gln Gln Leu Lys Tyr Ile Arg Met Val
305                 310                 315                 320

Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Tyr Pro Ile Ser Lys
            340                 345                 350

Gly Gln Pro Val Thr Val Leu Ile Pro Lys Leu His Arg Asp Gln Asn
        355                 360                 365

Ala Trp Gly Pro Asp Ala Glu Asp Phe Arg Pro Glu Arg Phe Glu Asp
    370                 375                 380

Pro Ser Ser Ile Pro His His Ala Tyr Lys Pro Phe Gly Asn Gly Gln
385                 390                 395                 400

Arg Ala Cys Ile Gly Met Gln Phe Ala Leu Gln Glu Ala Thr Met Val
                405                 410                 415

Leu Gly Leu Val Leu Lys His Phe Glu Leu Ile Asn His Thr Gly Tyr
            420                 425                 430

Glu Leu Lys Ile Lys Glu Ala Leu Thr Ile Lys Pro Asp Asp Phe Lys
        435                 440                 445

Ile Thr Val Lys Pro Arg Lys Thr Ala Ala Ile Asn Val Gln Arg Lys
    450                 455                 460

Glu Gln Ala
465

<210> SEQ ID NO 48
<211> LENGTH: 467
<212> TYPE: PRT
<213> ORGANISM: Artificial Sequence
<220> FEATURE:
<223> OTHER INFORMATION: synthetic chimeric heme enzyme C2B12, chimeric
      cytochrome P450 enzyme C2B12

<400> SEQUENCE: 48

Met Lys Gln Ala Ser Ala Ile Pro Gln Pro Lys Thr Tyr Gly Pro Leu
1               5                   10                  15

Lys Asn Leu Pro His Leu Glu Lys Glu Gln Leu Ser Gln Ser Leu Trp
            20                  25                  30

Arg Ile Ala Asp Glu Leu Gly Pro Ile Phe Arg Phe Asp Phe Pro Gly
        35                  40                  45
```

```
Val Ser Ser Val Phe Val Ser Gly His Asn Leu Val Ala Glu Val Cys
 50                  55                  60

Asp Glu Glu Arg Phe Asp Lys Ser Ile Glu Gly Ala Leu Glu Lys Val
 65                  70                  75                  80

Arg Ala Phe Ser Gly Asp Gly Leu Ala Thr Ser Trp Thr His Glu Pro
                 85                  90                  95

Asn Trp Arg Lys Ala His Asn Ile Leu Met Pro Thr Phe Ser Gln Arg
             100                 105                 110

Ala Met Lys Asp Tyr His Glu Lys Met Val Asp Ile Ala Thr Gln Leu
         115                 120                 125

Ile Gln Lys Trp Ser Arg Leu Asn Pro Asn Glu Glu Ile Asp Val Ala
     130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Gln Pro His Pro Phe Ile
                165                 170                 175

Thr Ser Met Val Arg Ala Leu Asp Glu Ala Met Asn Lys Leu Gln Arg
            180                 185                 190

Ala Asn Pro Asp Asp Pro Ala Tyr Asp Glu Asn Lys Arg Gln Phe Gln
        195                 200                 205

Glu Asp Ile Lys Val Met Asn Asp Leu Val Asp Arg Met Ile Ala Glu
    210                 215                 220

Arg Lys Ala Asn Pro Asp Glu Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
                260                 265                 270

Ser Gly Leu Leu Ser Phe Ala Thr Tyr Phe Leu Leu Lys His Pro Asp
            275                 280                 285

Lys Leu Lys Lys Ala Tyr Glu Glu Val Asp Arg Val Leu Thr Asp Ala
    290                 295                 300

Ala Pro Thr Tyr Lys Gln Val Leu Glu Leu Thr Tyr Ile Arg Met Ile
305                 310                 315                 320

Leu Asn Glu Ser Leu Arg Leu Trp Pro Thr Ala Pro Ala Phe Ser Leu
                325                 330                 335

Tyr Ala Lys Glu Asp Thr Val Leu Gly Gly Glu Tyr Pro Ile Ser Lys
            340                 345                 350

Gly Gln Pro Val Thr Val Leu Ile Pro Lys Leu His Arg Asp Gln Asn
    355                 360                 365

Ala Trp Gly Pro Asp Ala Glu Asp Phe Arg Pro Glu Arg Phe Glu Asp
370                 375                 380

Pro Ser Ser Ile Pro His His Ala Tyr Lys Pro Phe Gly Asn Gly Gln
385                 390                 395                 400

Arg Ala Cys Ile Gly Met Gln Phe Ala Leu Gln Glu Ala Thr Met Val
                405                 410                 415

Leu Gly Leu Val Leu Lys His Phe Glu Leu Ile Asn His Thr Gly Tyr
            420                 425                 430

Glu Leu Lys Ile Lys Glu Ala Leu Thr Ile Lys Pro Asp Asp Phe Lys
    435                 440                 445

Ile Thr Val Lys Pro Arg Lys Thr Ala Ala Ile Asn Val Gln Arg Lys
450                 455                 460
```

-continued

Glu Gln Ala
465

<210> SEQ ID NO 49
<211> LENGTH: 467
<212> TYPE: PRT
<213> ORGANISM: Artificial Sequence
<220> FEATURE:
<223> OTHER INFORMATION: synthetic chimeric heme enzyme TSP234, chimeric cytochrome P450 enzyme TSP234

<400> SEQUENCE: 49

Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
                20                  25                  30

Lys Leu Ala Glu Glu Gln Gly Pro Ile Phe Gln Ile His Thr Pro Ala
            35                  40                  45

Gly Thr Thr Ile Val Val Ser Gly His Glu Leu Val Lys Glu Val Cys
        50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Ala Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Thr Gln Leu
        115                 120                 125

Ile Gln Lys Trp Ser Arg Leu Asn Pro Asn Glu Glu Ile Asp Val Ala
    130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Gln Pro His Pro Phe Ile
                165                 170                 175

Thr Ser Met Val Arg Ala Leu Asp Glu Ala Met Asn Lys Leu Gln Arg
            180                 185                 190

Ala Asn Pro Asp Asp Pro Ala Tyr Asp Glu Asn Lys Arg Gln Phe Gln
        195                 200                 205

Glu Asp Ile Lys Val Met Asn Asp Leu Val Asp Arg Met Ile Ala Glu
    210                 215                 220

Arg Lys Ala Asn Pro Asp Glu Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
    290                 295                 300

Thr Pro Glu Tyr Lys Gln Ile Gln Gln Leu Lys Tyr Ile Arg Met Val
305                 310                 315                 320

Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Glu Tyr Pro Ile Ser Lys
            340                 345                 350

```
Gly Gln Pro Val Thr Val Leu Ile Pro Lys Leu His Arg Asp Gln Asn
        355             360             365

Ala Trp Gly Pro Asp Ala Glu Asp Phe Arg Pro Glu Arg Phe Glu Asp
    370             375             380

Pro Ser Ser Ile Pro His His Ala Tyr Lys Pro Phe Gly Asn Gly Gln
385             390             395             400

Arg Ala Cys Ile Gly Met Gln Phe Ala Leu Gln Glu Ala Thr Met Val
                405             410             415

Leu Gly Leu Val Leu Lys His Phe Glu Leu Ile Asn His Thr Gly Tyr
                420             425             430

Glu Leu Lys Ile Lys Glu Ala Leu Thr Ile Lys Pro Asp Asp Phe Lys
        435             440             445

Ile Thr Val Lys Pro Arg Lys Thr Ala Ala Ile Asn Val Gln Arg Lys
        450             455             460

Glu Gln Ala
465
```

METHODS AND SYSTEMS FOR SULFIMIDATION OR SULFOXIMIDATION OF ORGANIC MOLECULES

CROSS REFERENCE TO RELATED APPLICATIONS

This application is a divisional of U.S. application Ser. No. 14/625,514, filed Feb. 18, 2015 (now U.S. Pat. No. 9,399,762), which claims priority to U.S. Provisional Application No. 61/941,197, filed Feb. 18, 2014 and claims priority to U.S. Provisional Application No. 61/976,927, filed Apr. 8, 2014, the disclosures of each of the foregoing application are incorporated herein by reference in their entirety.

STATEMENT REGARDING FEDERALLY SPONSORED RESEARCH

This invention was made with government support under GM101792 awarded by the National Institutes of Health and under N00014-11-1-0205 awarded by the Office of Naval Research. The government has certain rights in the invention.

TECHNICAL FIELD

The present disclosure generally relates to the fields of synthetic organic chemistry. In particular, the present disclosure relates to methods and systems for the imidation of sulfides.

BACKGROUND

Enzymes offer appealing alternatives to traditional chemical catalysts due to their ability to function in aqueous media at ambient temperature and pressure. In addition, the ability of enzymes to orient substrate binding for defined regio- and stereo-chemical outcomes is highly valuable. This property is exemplified by the cytochrome P450 monooxygenase family of enzymes that catalyze insertion of oxygen atoms into unactivated C—H bonds (P. R. O. d. Montellano, Cytochrome P450: Structure, Mechanism and Biochemistry. Kluwer Academic/Plenum Publishers, New York, ed. 3rd Edition, 2005).

Cytochrome P450s catalyze monooxygenation with high degrees of regio- and stereo-selectivity, a property that makes them attractive for use in chemical synthesis. This broad enzyme class is capable of oxygenating a wide variety of organic molecules including aromatic compounds, fatty acids, alkanes and alkenes. Diverse substrate selectivity is a hallmark of this enzyme family and is exemplified in the natural world by their importance in natural product oxidation as well as xenobiotic metabolism (F. P. Guengerich, Chem. Res. Toxicol. 14, 611 (2001)). Limitations to this enzyme class in synthesis include their large size, need for expensive reducing equivalents (e.g., NADPH) and cellular distribution—many cytochrome P450s are membrane bound and therefore difficult to handle (Montellano, Cytochrome P450: Structure, Mechanism and Biochemistry. Kluwer Academic/Plenum Publishers, New York, ed. 3rd Edition, 2005). Several soluble bacterial cytochrome P450s have been isolated, however, that show excellent properties and behavior for chemical synthesis and protein engineering applications.

SUMMARY

The disclosure provides method and compositions comprising one or more heme enzymes that catalyze the nitrene transfer or insertion into an organosulfur compounds comprising an —S— target site to form a new S—N bond. In particular embodiments, the disclosure provides heme enzyme variants comprising at least one or more amino acid mutations therein that catalyze sulfoxidation and/or sulfimidation, making products described herein with high stereoselectivity. In some embodiments, the heme enzyme variants of the disclosure have the ability to catalyze nitrene transfer reactions efficiently, display increased total turnover numbers, and/or demonstrate highly regio- and/or enantioselective product formation compared to the corresponding wild-type enzymes.

The disclosure provides a method for catalyzing the intermolecular insertion of nitrogen into thioethers, sulfur-organo compounds or sulfoxides to produce a product having a new S—N bond, the method comprising providing a nitrene source, a thioether or sulfoxide precursor and a heme enzyme or an engineered heme enzyme; and allowing the reaction to proceed for a time sufficient to form a product having a new S—N bond. In one embodiment, the nitrene source is an azide. In a further embodiment, the azide has the general formula $R^1$—$N_3$, wherein $R^1$ is (i) a substituted or unsubstituted aryl, a substitute or unsubstituted alkyl, —$OR^2$, or —$NR^2$, wherein $R^2$ is a substituted or unsubstituted aryl, a substitute or unsubstituted alkyl; (ii) —$SO_2R^3$, wherein $R^3$ a substituted or unsubstituted aryl, a substitute or unsubstituted alkyl, —$OR^2$ or $NR^2$, wherein $R^2$ are any alkyl or aryl; (iii) —$COR^4$ wherein $R^4$ is a substituted or unsubstituted aryl, a substitute or unsubstituted alkyl, —$OR^2$ or $NR^2$, wherein $R^2$ are any alkyl or aryl; or (iv) —$P(O)(OR^5)(OR^6)$, wherein $R^5$ and $R^6$ are independently H, a substituted or unsubstituted aryl, a substitute or unsubstituted alkyl. In a further embodiment, the azide has a structure selected from the group consisting of:

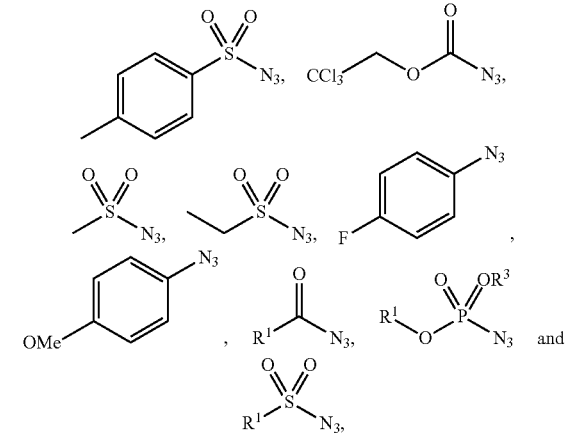

wherein $R^1$ is any alkyl, aryl, —OR, $NR^2$, wherein R, $R^2$ and $R^3$ are any alkyl, or aryl. In another embodiment, the nitrene source is selected from the group consisting of:

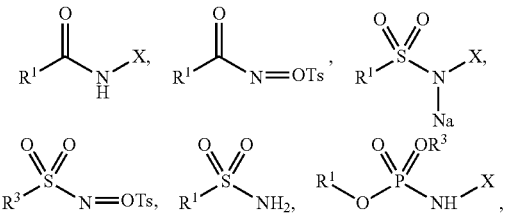

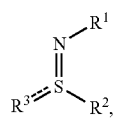 and 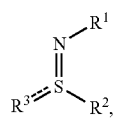, wherein $R^1$ is any alkyl, aryl, —OR, $NR^2$, wherein R, $R^2$ and $R^3$ are any alkyl, or aryl. In another embodiment, the S—N containing product is an aliphatic amine and the nitrene precursor is tosyl azide. In yet another embodiment, the product is generated through a nitrenoid intermediate. In still yet another embodiment, the engineered heme enzyme is a cytochrome P450 enzyme or a variant thereof. In a further embodiment, the cytochrome P450 enzyme is expressed in a bacterial, archaeal or fungal host organism. In yet another embodiment, the cytochrome P450 enzyme is a P450 BM3 enzyme or a variant thereof. In a further embodiment, the cytochrome P450 BM3 enzyme comprises the amino acid sequence set forth in SEQ ID NO: 1 or a variant thereof. In yet other embodiments of the foregoing the cytochrome P450 enzyme variant comprises a mutation at the axial position of the heme coordination site. In a further embodiment, the mutation is an amino acid substitution of Cys with a member selected from the group consisting of Ala, Asp, Arg, Asn, Glu, Gln, Gly, His, He, Lys, Leu, Met, Phe, Pro, Ser, Thr, Trp, Tyr and Val at the axial position. In still a further embodiment, the mutation is an amino acid substitution of Cys with Asp or Ser at the axial position. In another embodiment of any of the foregoing, the P450 BM3 enzyme variant comprises at least one, two, three, four, five, six, seven, eight, nine, ten, eleven, twelve, or all thirteen of the following amino acid substitutions in SEQ ID NO: 1: V78A, F87V, P142S, T175I, A184V, S226R, H236Q, E252G, T268A, A290V, L353V, I366V, and E442K. In another embodiment of any of the foregoing the cytochrome P450 enzyme variant comprises a T268A mutation and/or a C400X mutation in SEQ ID NO: 1, wherein X is any amino acid other than Cys. In still another embodiment, the cytochrome P450 enzyme variant comprises a T438S mutation and/or a C400X mutation in SEQ ID NO: 1, wherein X is any amino acid other than Cys. In yet another embodiment, the cytochrome P450 enzyme variant comprises a T268A mutation, a C400X mutation and a T438S mutation in SEQ ID NO:1, wherein X is any amino acid other than Cys. In another embodiment, the engineered heme enzyme comprises a fragment of the cytochrome P450 enzyme or variant thereof. In yet another embodiment, the engineered heme enzyme is a cytochrome P450 BM3 enzyme variant selected from Table 4, Table 5 and Table 6. In yet another embodiment, the product is a compound of Formula 1a:

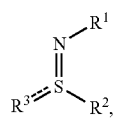

wherein $R^1$ is a sulfoxide, a carbonyl or a phosphonate; wherein $R^2$ is H or any alkyl or aryl; and wherein $R^3$ is H, O or an optionally substituted aryl group. In a further embodiment, $R^1$ is a sulfoxide of formula $SO_2R^5$, wherein $R^5$ any alkyl, any aryl, —$OR^6$ or $NR^7$, wherein $R^6$ and $R^7$ are any alkyl or any aryl. In a further embodiment, $R^2$ is any alkyl or aryl. In still a further embodiment, $R^3$ is H. In yet another embodiment of Formula 1a $R^1$ is a phosphonate of formula $P(O)(OR^8)(OR^9)$, wherein $R^8$ and $R^9$ are independently any aryl or any alkyl. In a further embodiment, $R^2$ is any alkyl or any aryl. In still a further embodiment, $R^3$ is any alkyl or aryl. In yet another embodiment of Formula 1a, $R^1$ is a carbonyl group. In a further embodiment, $R^2$ is any alkyl or any aryl. In a further embodiment, $R^3$ is any alkyl or any aryl. In another embodiment of Formula 1a, $R^3$ is an optionally substituted aryl group. In a further embodiment, $R^1$ is any alkyl or any aryl. In a further embodiment, $R^2$ is H or any alkyl or any aryl. In another embodiment of Formula 1a, $R^1$ is a carbonyl group. In a further embodiment, $R^2$ is any alkyl or any aryl. In a further embodiment, $R^3$ is O.

The disclosure also provides products made by any of the foregoing methods.

Also provided is a reaction mixture comprising a nitrene source, a thioether or sulfoxide substrate and an engineered heme enzyme for producing a product having a new S—N bond. In one embodiment, the nitrene source is an azide. In a further embodiment, the azide has the general formula $R^1$—$N_3$, wherein $R^1$ is (i) a substituted or unsubstituted aryl, a substitute or unsubstituted alkyl, —$OR^2$, or —$NR^2$, wherein $R^2$ is a substituted or unsubstituted aryl, a substitute or unsubstituted alkyl; (ii) —$SO_2R^3$, wherein $R^3$ a substituted or unsubstituted aryl, a substitute or unsubstituted alkyl, —$OR^2$ or $NR^2$, wherein $R^2$ are any alkyl or aryl; (iii) —$COR^4$ wherein $R^4$ is a substituted or unsubstituted aryl, a substitute or unsubstituted alkyl, —$OR^2$ or $NR^2$, wherein $R^2$ are any alkyl or aryl; or (iv) —$P(O)(OR^5)(OR^6)$, wherein $R^5$ and $R^6$ are independently H, a substituted or unsubstituted aryl, a substitute or unsubstituted alkyl. In a further embodiment, the azide has a structure selected from the group consisting of:

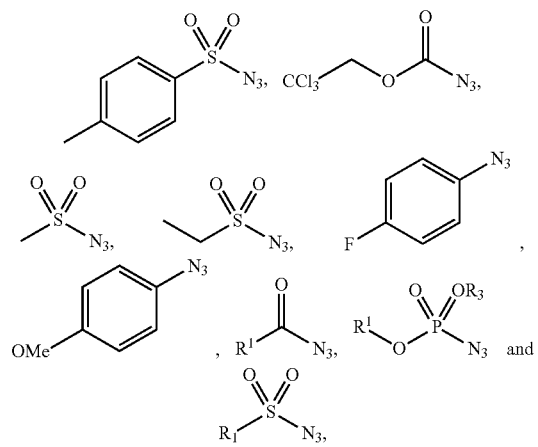

wherein $R^1$ is any alkyl, aryl, —OR, $NR^2$, wherein R, $R^2$ and $R^3$ are any alkyl, or aryl. In another embodiment, the nitrene source is selected from the group consisting of:

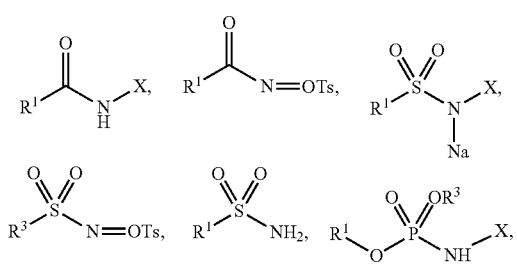

-continued

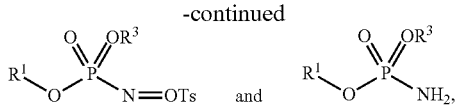

wherein $R^1$ is any alkyl, aryl, —OR, $NR^2$, wherein R, $R^2$ and $R^3$ are any alkyl, or aryl. In another embodiment, the S—N containing product is an aliphatic amine and the nitrene precursor is tosyl azide. In yet another embodiment, the product is generated through a nitrenoid intermediate. In still yet another embodiment, the engineered heme enzyme is a cytochrome P450 enzyme or a variant thereof. In a further embodiment, the cytochrome P450 enzyme is expressed in a bacterial, archaeal or fungal host organism. In yet another embodiment, the cytochrome P450 enzyme is a P450 BM3 enzyme or a variant thereof. In a further embodiment, the cytochrome P450 BM3 enzyme comprises the amino acid sequence set forth in SEQ ID NO: 1 or a variant thereof. In yet other embodiments of the foregoing the cytochrome P450 enzyme variant comprises a mutation at the axial position of the heme coordination site. In a further embodiment, the mutation is an amino acid substitution of Cys with a member selected from the group consisting of Ala, Asp, Arg, Asn, Glu, Gln, Gly, His, He, Lys, Leu, Met, Phe, Pro, Ser, Thr, Trp, Tyr and Val at the axial position. In still a further embodiment, the mutation is an amino acid substitution of Cys with Asp or Ser at the axial position. In another embodiment of any of the foregoing, the P450 BM3 enzyme variant comprises at least one, two, three, four, five, six, seven, eight, nine, ten, eleven, twelve, or all thirteen of the following amino acid substitutions in SEQ ID NO: 1: V78A, F87V, P142S, T175I, A184V, S226R, H236Q, E252G, T268A, A290V, L353V, I366V, and E442K. In another embodiment of any of the foregoing the cytochrome P450 enzyme variant comprises a T268A mutation and/or a C400X mutation in SEQ ID NO: 1, wherein X is any amino acid other than Cys. In still another embodiment, the cytochrome P450 enzyme variant comprises a T438S mutation and/or a C400X mutation in SEQ ID NO: 1, wherein X is any amino acid other than Cys. In yet another embodiment, the cytochrome P450 enzyme variant comprises a T268A mutation, a C400X mutation and a T438S mutation in SEQ ID NO:1, wherein X is any amino acid other than Cys. In another embodiment, the engineered heme enzyme comprises a fragment of the cytochrome P450 enzyme or variant thereof. In yet another embodiment, the engineered heme enzyme is a cytochrome P450 BM3 enzyme variant selected from Table 4, Table 5 and Table 6. In yet another embodiment, the product is a compound of Formula 1a:

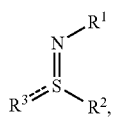

wherein $R^1$ is a sulfoxide, a carbonyl or a phosphonate; wherein $R^2$ is H or any alkyl or aryl; and wherein $R^3$ is H, O or an optionally substituted aryl group. In a further embodiment, $R^1$ is a sulfoxide of formula $SO_2R^5$, wherein $R^5$ any alkyl, any aryl, —$OR^6$ or $NR^7$, wherein $R^6$ and $R^7$ are any alkyl or any aryl. In a further embodiment, $R^2$ is any alkyl or any aryl. In still a further embodiment, $R^3$ is H. In yet another embodiment of Formula 1a $R^1$ is a phosphonate of formula $P(O)(OR^8)(OR^9)$, wherein $R^8$ and $R^9$ are independently any aryl or any alkyl. In a further embodiment, $R^2$ is any alkyl or any aryl. In still a further embodiment, $R^3$ is any alkyl or aryl. In yet another embodiment of Formula 1a, $R^1$ is a carbonyl group. In a further embodiment, $R^2$ is any alkyl or any aryl. In a further embodiment, $R^3$ is any alkyl or any aryl. In another embodiment of Formula 1a, $R^3$ is an optionally substituted aryl group. In a further embodiment, $R^1$ is any alkyl or any aryl. In a further embodiment, $R^2$ is H or any alkyl or any aryl. In another embodiment of Formula 1a, $R^1$ is a carbonyl group. In a further embodiment, $R^2$ is any alkyl or any aryl. In a further embodiment, $R^3$ is O.

The disclosure demonstrates the intermolecular nitrene transfer catalyzed by an enzyme, allowing for a mechanistic analysis of this new enzyme activity. Similar to P450-catalyzed sulfoxidation, the electronic properties of the sulfide substrates influence reactivity, though the magnitude of the substituent effects is greater for nitrene transfer, possibly owing to the less oxidizing nature of the presumed nitrenoid intermediate.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the disclosure.

FIG. 1A-B shows P450-catalyzed sulfoxidation and P450-catalyzed sulfimination. (A) P450-catalyzed sulfoxidation, shown proceeding through compound I. This reaction can also be mediated by compound 0 (hydroperoxy intermediate). (B) P411-catalyzed sulfimination proceeding through a nitrenoid intermediate formed from the azide with $N_2$ as a byproduct. Subsequent oxidation of the sulfilimine can result in sulfoximine formation.

FIG. 2 shows a plot of reaction rate versus Hammett parameter of substituted aryl sulfides in reactions using P411-CIS enzyme and tosyl azide as nitrogen source. Data points are labeled with aryl substituent and position (p-=para, m-=meta).

FIG. 3 shows proposed mechanisms of sulfimide ("productive") and sulfonamide ("unproductive") formation.

FIG. 4 shows examples of azides tested as nitrene sources for sulfimidation of thioanisole using the $P411_{BM3}$-CIS T438S enzyme.

As shown in FIG. 13, the Soret peak for the Fe(III) state is obscured by NADPH. Therefore the Q-band region (enlarged box from 530-640 nm) was used to assess the transition from Fe(III) to Fe(II) as reaction proceeds.

FIG. 16 shows TTN values measured for slow addition vs. adding substrates simultaneously, using $P411_{BM3}$-CIS T438S enzyme and the substrates shown in FIG. S10. Light gray bar shows TTN for sulfonamide, 9, dark gray shows TTN for the sulfimide, 8a.

DETAILED DESCRIPTION

Figure 5:
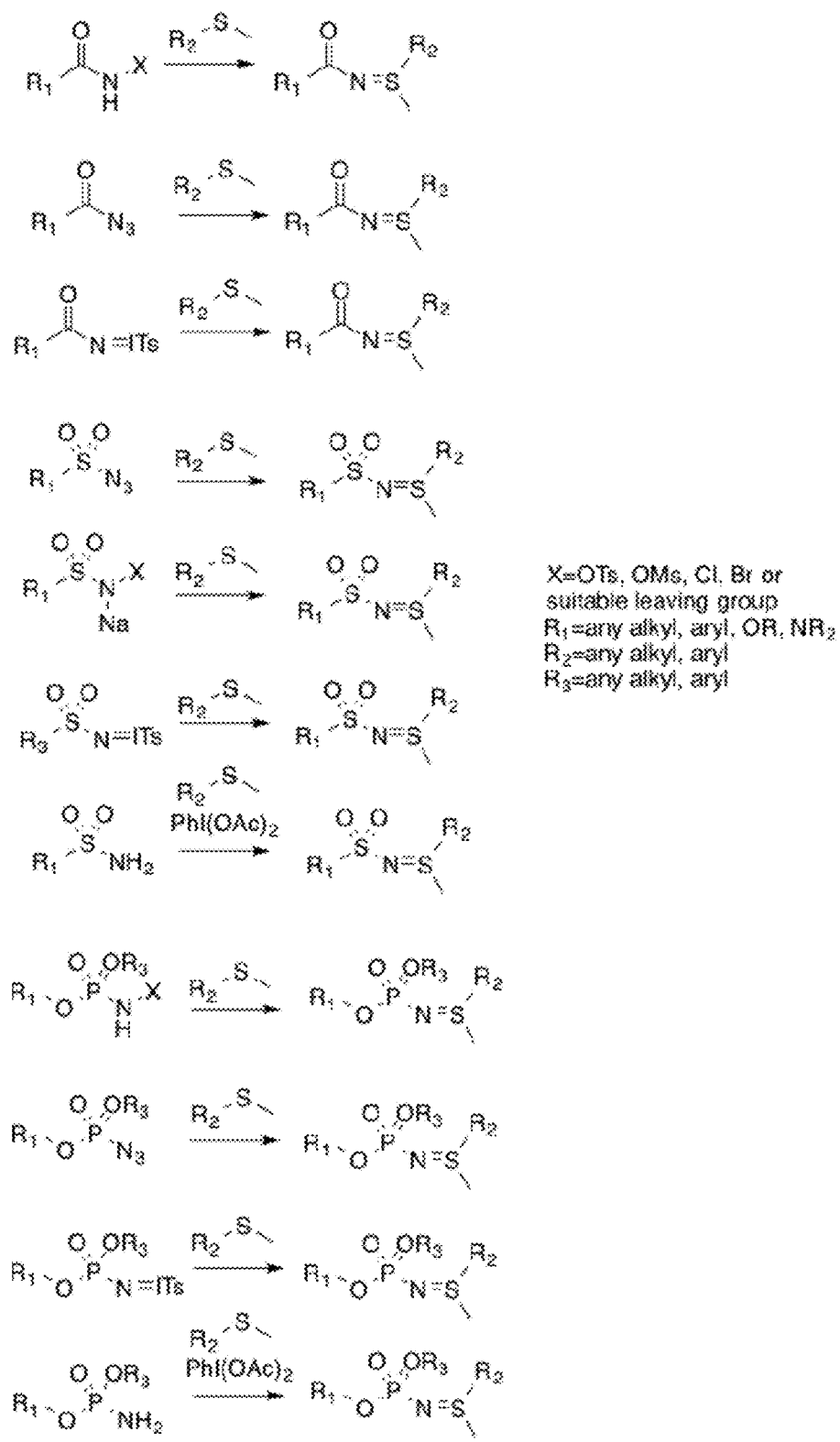
FIG. 5 shows examples of appropriate nitrene sources and generalized reactions for the formation of sulfilimines.

As used herein and in the appended claims, the singular forms "a," "and," and "the" include plural referents unless the context clearly dictates otherwise. Thus, for example, reference to "a species" includes a plurality of such species and reference to "the enzyme" includes reference to one or more enzymes and equivalents thereof, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Enzymes offer many advantages over traditional catalysts, such as selectivity, mild reaction conditions, convenient production, and use in whole cells. Cytochrome P450 enzymes are known to be able to carry out monooxygenations of diverse substrates, and exemplify the mild operating conditions that enzymes can afford. Many of the small molecule catalysts developed for C—H amination reaction have been designed in an effort to mimic these enzymes, but with the goal of activating nitrene equivalents rather than the oxene equivalents activated by cytochrome P450 enzymes (Bennett, R. D. & Heftmann, Phytochemistry 4, 873-879 (1965)). Cytochrome P450 enzymes bind to a cofactor comprising a catalytic transition metal (iron heme) that forms a reactive intermediate similar in electronic and steric features to metallonitrenoid intermediates used for synthetic C—N bond forming reactions.

The disclosure is based on the surprising discovery that engineered heme enzymes such as cytochrome P450BM3 enzymes, including a serine-heme-ligated P411 enzyme, efficiently catalyze nitrene insertion and transfer reactions. Suitable reactions include, but are not limited to, transfer of a nitrogen atom derived from an appropriate nitrene precursor to sulfur atoms with formation of an S—N bond. For example, in certain aspects, the present disclosure provides engineered heme enzymes such as cytochrome P450BM3 enzymes, including the serine-heme-ligated 'P411', which efficiently catalyze the sulfimidation of various organsulfur molecules. Significant enhancements in catalytic activity and enantioselectivity are observed in vivo, using intact bacterial cells expressing the engineered enzymes. The results presented here underscore the utility of enzymes in catalyzing new reaction types with the aid of synthetic reagents. The ability to genetically encode catalysts for formal nitrene transfers opens up new biosynthetic pathways to amines and expands the scope of transformations accessible to biocatalysis.

The term "S—N sulfimidation" includes a transfer of a nitrogen atom derived from an appropriate nitrene precursor to sulfur atoms with formation of an S—N bond, yielding a sulfimide.

The term "S—N sulfimidation (enzyme) catalyst" or "enzyme with S—N suflimidation activity" includes any and all chemical processes catalyzed by enzymes, by which substrates containing at least one carbon-sulfur bond can be converted into sulfimide products by using nitrene precursors such as sulfonyl azides, carbonyl azides, aryl azides, azidoformates, phosphoryl azides, azide phosphonates, iminoiodanes, or haloamine derivatives.

This disclosure describes enzyme catalysts based for the transfer of nitrogen atoms to aryl sulfides and other organosulfur compounds. This reaction is presumed to take place through a metal-nitrenoid intermediate, the reactivity of which is modulated by both the enzyme and substrates.

In some embodiments the organosulfur molecule has the structure of formula (I):

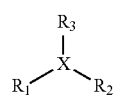
(I)

in which X=S atom is a target site for addition of a nitrogen, and $R_1$, $R_2$, and $R_3$ are independently selected from the group consisting of hydrogen, oxygen, aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy, and functional groups (FG) or are taken together to form a ring.

The term "aliphatic" is used in the conventional sense to refer to an open-chain or cyclic, linear or branched, saturated or unsaturated hydrocarbon group, including but not limited to alkyl group, alkenyl group and alkynyl groups. The term "heteroatom-containing aliphatic" as used herein refer to an aliphatic moiety where at least one carbon atom is replaced with a heteroatom.

The term "alkyl" and "alkyl group" as used herein refers to a linear, branched, or cyclic saturated hydrocarbon typically containing 1 to 24 carbon atoms, preferably 1 to 12 carbon atoms, such as methyl, ethyl, n-propyl, isopropyl, n-butyl, isobutyl, t-butyl, octyl, decyl and the like. The term "heteroatom-containing alkyl" as used herein refers to an alkyl moiety where at least one carbon atom is replaced with a heteroatom, e.g. oxygen, nitrogen, sulphur, phosphorus, or silicon, and typically oxygen, nitrogen, or sulphur.

The term "alkenyl" and "alkenyl group" as used herein refers to a linear, branched, or cyclic hydrocarbon group of 2 to 24 carbon atoms, preferably of 2 to 12 carbon atoms, containing at least one double bond, such as ethenyl, n-propenyl, isopropenyl, n-butenyl, isobutenyl, octenyl, decenyl, and the like. The term "heteroatom-containing alkenyl" as used herein refer to an alkenyl moiety where at least one carbon atom is replaced with a heteroatom.

The term "alkynyl" and "alkynyl group" as used herein refers to a linear, branched, or cyclic hydrocarbon group of 2 to 24 carbon atoms, preferably of 2 to 12 carbon atoms, containing at least one triple bond, such as ethynyl, n-propynyl, and the like. The term "heteroatom-containing alkynyl" as used herein refer to an alkynyl moiety where at least one carbon atom is replaced with a heteroatom.

The term "aryl" and "aryl group" as used herein refers to an aromatic substituent containing a single aromatic or multiple aromatic rings that are fused together, directly linked, or indirectly linked (such as linked through a methylene or an ethylene moiety). Preferred aryl groups contain 5 to 24 carbon atoms, and particularly preferred aryl groups contain 5 to 14 carbon atoms. The term "heteroatom-containing aryl" as used herein refer to an aryl moiety where at least one carbon atom is replaced with a heteroatom.

The term "alkoxy" and "alkoxy group" as used herein refers to an aliphatic group or a heteroatom-containing aliphatic group bound through a single, terminal ether linkage. Preferred aryl alkoxy groups contain 1 to 24 carbon atoms, and particularly preferred alkoxy groups contain 1 to 14 carbon atoms.

The term "aryloxy" and "aryloxy group" as used herein refers to an aryl group or a heteroatom-containing aryl group bound through a single, terminal ether linkage. Preferred aryloxy groups contain 5 to 24 carbon atoms, and particularly preferred aryloxy groups contain 5 to 14 carbon atoms.

The terms "halo" and "halogen" are used in the conventional sense to refer to a fluoro, chloro, bromo or iodo substituent.

By "substituted" it is intended that in the alkyl, alkenyl, alkynyl, aryl, or other moiety, at least one hydrogen atom is replaced with one or more non-hydrogen atoms. Examples of such substituents include, without limitation: functional groups referred to herein as "FG", such as alkoxy, aryloxy, alkyl, heteroatom-containing alkyl, alkenyl, heteroatom-containing alkenyl, alkynyl, heteroatom-containing alkynyl, aryl, heteroatom-containing aryl, alkoxy, heteroatom-containing alkoxy, aryloxy, heteroatom-containing aryloxy, halo, hydroxyl (—OH), sulfhydryl (—SH), substituted sulfhydryl, carbonyl (—CO—), thiocarbonyl, (—CS—), carboxy (—COOH), amino (—$NH_2$), substituted amino, nitro (—$NO_2$), nitroso (—NO), sulfo (—$SO_2$—OH), cyano (—C≡N), cyanato (—O—C≡N), thiocyanato (—S—C≡N), formyl (—CO—H), thioformyl (—CS—H), phosphono (—P(O)$OH_2$), substituted phosphono, and phospho (—$PO_2$).

In particular, the substituents $R_1$, $R_2$ and $R_3$ of formula I can be independently selected from hydrogen, $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy, carbonyl, thiocarbonyl, and carboxy. More in particular, $R_1$, $R_2$ and $R_3$ of formula I can be independently selected from hydrogen, $C_1$-$C_{12}$ alkyl, $C_1$-$C_{12}$ substituted alkyl, $C_1$-$C_{12}$ substituted heteroatom-containing alkyl, $C_1$-$C_{12}$ substituted heteroatom-containing alkyl, $C_2$-$C_{12}$ alkenyl, $C_2$-$C_{12}$ substituted alkenyl, $C_2$-$C_{12}$ substituted heteroatom-containing alkenyl, $C_2$-$C_{12}$ substituted heteroatom-containing alkenyl, $C_5$-$C_{14}$ aryl, $C_5$-$C_{14}$ substituted aryl, $C_5$-$C_{14}$ substituted heteroatom-containing aryl, $C_5$-$C_{14}$ substituted heteroatom-containing aryl, $C_2$-$C_{14}$ alkoxy, $C_5$-$C_{14}$ aryloxy, carbonyl, thiocarbonyl, and carboxy.

As used herein, the term "alkylthio" refers to an alkyl group having a sulfur atom that connects the alkyl group to the point of attachment: i.e., alkyl-S—. As for alkyl groups, alkylthio groups can have any suitable number of carbon atoms, such as $C_{1-6}$ or $C_{1-4}$. Alkylthio groups include, for example, methoxy, ethoxy, propoxy, iso-propoxy, butoxy, 2-butoxy, iso-butoxy, sec-butoxy, tert-butoxy, pentoxy, hexoxy, etc. Alkylthio groups can be optionally substituted with one or more moieties selected from halo, hydroxy, amino, alkylamino, alkoxy, haloalkyl, carboxy, amido, nitro, oxo, and cyano. Thioethers have the generals structure R—S—R, wherein R is any alkyl, alkynyl, alkenyl, aryl (substituted or unsubstituted).

As used herein, the term "haloalkyl" refers to an alkyl moiety as defined above substituted with at least one halogen atom.

As used herein, the term "acyl" refers to a moiety —C(O)R, wherein R is an alkyl group.

As used herein, the term "oxo" refers to an oxygen atom that is double-bonded to a compound (i.e., O=).

As used herein, the term "carboxy" refers to a moiety —C(O)OH. The carboxy moiety can be ionized to form the carboxylate anion.

As used herein, the term "amino" refers to a moiety —$NR^3$, wherein each R group is H or alkyl.

As used herein, the term "amido" refers to a moiety —NRC(O)R or —C(O)$NR^2$, wherein each R group is H or alkyl.

The terms "engineered heme enzyme" and "heme enzyme variant" include any heme-containing enzyme comprising at least one amino acid mutation with respect to wild-type and also include any chimeric protein comprising recombined sequences or blocks of amino acids from two, three, or more different heme-containing enzymes that will improve its S—N sulfimidation activity or other reactions disclosed herein.

The terms "engineered cytochrome P450" and "cytochrome P450 variant" include any cytochrome P450 enzyme comprising at least one amino acid mutation with respect to wild-type and also include any chimeric protein comprising recombined sequences or blocks of amino acids from two, three, or more different cytochrome P450 enzymes.

As used herein, the term "whole cell catalyst" includes microbial cells expressing heme containing enzymes, engineered cytochrome P450, or a cytochrome P450 variant, where the whole cell displays sulfimidation activity or sulfoximdation activity.

As used herein, the term "nitrene equivalent" or "nitrene precursor" includes molecules that can be decomposed in the presence of metal (or enzyme) catalysts to structures that contain at least one monovalent nitrogen atom with only 6 valence shell electrons and that can be transferred to a sulfur to form sulfilimines or sulfoximines.

As used herein, the terms "microbial," "microbial organism" and "microorganism" include any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. Also included are cell cultures of any species that can be cultured for the production of a chemical.

As used herein, the term "non-naturally occurring," when used in reference to a microbial organism or enzyme activity of the disclosure, is intended to mean that the microbial organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon.

As used herein, the term "anaerobic", when used in reference to a reaction, culture or growth condition, is intended to mean that the concentration of oxygen is less than about 25 μM, typically less than about 5 μM, and commonly less than 1 μM. The term is also intended to include sealed chambers of liquid or solid medium maintained with an atmosphere of less than about 1% oxygen. Typically, anaerobic conditions are achieved by sparging a reaction mixture with an inert gas such as nitrogen or argon.

As used herein, the term "exogenous" is intended to mean that the referenced molecule or the referenced activity is introduced into the host microbial organism. The term as it is used in reference to expression of an encoding nucleic acid refers to the introduction of the encoding nucleic acid in an expressible form into the microbial organism using recombinant DNA techniques. When used in reference to a biosynthetic activity, the term refers to an activity that is introduced into the host reference organism.

The term "heterologous" as used herein with reference to molecules, and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the term "native" or "endogenous" as used herein with reference to molecules, and in particular enzymes and polynucleotides, indicates molecules that are expressed in the organism in which they originated or are found in nature, independently of the level of expression that can be lower equal or higher than the level of expression of the molecule in the native microorganism. It is understood that expression of native enzymes or polynucleotides may be modified in recombinant microorganisms.

The term "homolog," as used herein with respect to an original enzyme or gene of a first family or species, refers to distinct enzymes or genes of a second family or species which are determined by functional, structural and/or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In particular embodiments, the homology between two proteins is indicative of its shared ancestry, related by evolution.

The terms "analog" and "analogous" include nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

The term "contact" as used herein with reference to interactions of chemical units indicates that the chemical units are at a distance that allows short range non-covalent interactions (such as Van der Waals forces, hydrogen bonding, hydrophobic interactions, electrostatic interactions, dipole-dipole interactions) to dominate the interaction of the chemical units. For example, when an oxygenase enzyme is 'contacted' with a target molecule, the enzyme is allowed to interact with and bind to the organic molecule through non-covalent interactions so that a reaction between the enzyme and the target molecule can occur.

The term "introducing" as used herein with reference to the interaction between two chemical units, such as a functional groups and a target site, indicates a reaction resulting in the formation of a bond between the two chemical units, e.g. the functional group and the target site.

The disclosure provides an enzymatic process for the suflimidation or sulfoximidation of a atarget sulfur atom b a nitrene precursor. The methods and compositions of the disclosure includes a heme enzyme (e.g., an engineered P450BM3 of variant) an nitrene precursor (e.g., an azide or other compound that comprises a nitrogen atom that can be used as a nitrene) and a target organosulfur compound, wherein the compound comprises a sulfur atom that is linked to a nitrogen to form a new N-C bond using the enzymatic process of the disclosure.

In some embodiments, the enzyme is a heme-containing enzyme or a variant thereof. The wording "heme" or "heme domain" as used herein refers to an amino acid sequence within an enzyme, which is capable of binding an iron-complexing structure such as a porphyrin. Compounds of iron are typically complexed in a porphyrin (tetrapyrrole) ring that may differ in side chain composition. Heme groups can be the prosthetic groups of cytochromes and are found in most oxygen carrier proteins. Exemplary heme domains include that of $P450_{BM3}$ as well as truncated or mutated versions of these that retain the capability to bind the iron-complexing structure. A skilled person can identify the heme domain of a specific protein using methods known in the art.

The terms "heme enzyme" and "heme protein" are used herein to include any member of a group of proteins containing heme as a prosthetic group. Non-limiting examples of heme enzymes include globins, cytochromes, oxidoreductases, any other protein containing a heme as a prosthetic group, and combinations thereof. Heme-containing globins include, but are not limited to, hemoglobin, myoglobin, and combinations thereof. Heme-containing cytochromes include, but are not limited to, cytochrome P450, cytochrome b, cytochrome cl, cytochrome c, and combinations thereof. Heme-containing oxidoreductases include, but are not limited to, a catalase, an oxidase, an oxygenase, a haloperoxidase, a peroxidase, and combinations thereof.

In certain instances, the heme enzymes are metal-substituted heme enzymes containing protoporphyrin IX or other porphyrin molecules containing metals other than iron, including, but not limited to, cobalt, rhodium, copper, ruthenium, and manganese, which are active sulfimidation or sulfoximidation catalysts.

In some embodiments, the heme enzyme is a member of one of the enzyme classes set forth in Table 1. In other embodiments, the heme enzyme is a variant or homolog of a member of one of the enzyme classes set forth in Table 1. In yet other embodiments, the heme enzyme comprises or consists of the heme domain of a member of one of the enzyme classes set forth in Table 1 or a fragment thereof (e.g., a truncated heme domain) that is capable of carrying out the nitrene insertion and nitrene transfer reactions described herein.

TABLE 1

Heme enzymes identified by their enzyme classification number (EC number) and classification name.

| EC Number | Name |
|---|---|
| 1.1.2.3 | L-lactate dehydrogenase |
| 1.1.2.6 | polyvinyl alcohol dehydrogenase (cytochrome) |
| 1.1.2.7 | methanol dehydrogenase (cytochrome c) |
| 1.1.5.5 | alcohol dehydrogenase (quinone) |
| 1.1.5.6 | formate dehydrogenase-N: |
| 1.1.9.1 | alcohol dehydrogenase (azurin): |
| 1.1.99.3 | gluconate 2-dehydrogenase (acceptor) |
| 1.1.99.11 | fructose 5-dehydrogenase |
| 1.1.99.18 | cellobiose dehydrogenase (acceptor) |
| 1.1.99.20 | alkan-1-ol dehydrogenase (acceptor) |
| 1.2.1.70 | glutamyl-tRNA reductase |
| 1.2.3.7 | indole-3-acetaldehyde oxidase |
| 1.2.99.3 | aldehyde dehydrogenase (pyrroloquinoline-quinone) |
| 1.3.1.6 | fumarate reductase (NADH): |
| 1.3.5.1 | succinate dehydrogenase (ubiquinone) |
| 1.3.5.4 | fumarate reductase (menaquinone) |
| 1.3.99.1 | succinate dehydrogenase |
| 1.4.9.1 | methylamine dehydrogenase (amicyanin) |
| 1.4.9.2. | aralkylamine dehydrogenase (azurin) |
| 1.5.1.20 | methylenetetrahydrofolate reductase [NAD(P)H] |
| 1.5.99.6 | spermidine dehydrogenase |
| 1.6.3.1 | NAD(P)H oxidase |
| 1.7.1.1 | nitrate reductase (NADH) |
| 1.7.1.2 | Nitrate reductase [NAD(P)H] |
| 1.7.1.3 | nitrate reductase (NADPH) |
| 1.7.1.4 | nitrite reductase [NAD(P)H] |
| 1.7.1.14 | nitric oxide reductase [NAD(P), nitrous oxide-forming] |

TABLE 1-continued

Heme enzymes identified by their enzyme classification number (EC number) and classification name.

| EC Number | Name |
| --- | --- |
| 1.7.2.1 | nitrite reductase (NO-forming) |
| 1.7.2.2 | nitrite reductase (cytochrome; ammonia-forming) |
| 1.7.2.3 | trimethylamine-N-oxide reductase (cytochrome c) |
| 1.7.2.5 | nitric oxide reductase (cytochrome c) |
| 1.7.2.6 | hydroxylamine dehydrogenase |
| 1.7.3.6 | hydroxylamine oxidase (cytochrome) |
| 1.7.5.1 | nitrate reductase (quinone) |
| 1.7.5.2 | nitric oxide reductase (menaquinol) |
| 1.7.6.1 | nitrite dismutase |
| 1.7.7.1 | ferredoxin-nitrite reductase |
| 1.7.7.2 | ferredoxin-nitrate reductase |
| 1.7.99.4 | nitrate reductase |
| 1.7.99.8 | hydrazine oxidoreductase |
| 1.8.1.2 | sulfite reductase (NADPH) |
| 1.8.2.1 | sulfite dehydrogenase |
| 1.8.2.2 | thiosulfate dehydrogenase |
| 1.8.2.3 | sulfide-cytochrome-c reductase (flavocytochrome c) |
| 1.8.2.4 | dimethyl sulfide:cytochrome c2 reductase |
| 1.8.3.1 | sulfite oxidase |
| 1.8.7.1 | sulfite reductase (ferredoxin) |
| 1.8.98.1 | CoB-CoM heterodisulfide reductase |
| 1.8.99.1 | sulfite reductase |
| 1.8.99.2 | adenylyl-sulfate reductase |
| 1.8.99.3 | hydrogensulfite reductase |
| 1.9.3.1 | cytochrome-c oxidase |
| 1.9.6.1 | nitrate reductase (cytochrome) |
| 1.10.2.2 | ubiquinol-cytochrome-c reductase |
| 1.10.3.1 | catechol oxidase |
| 1.10.3.B1 | caldariellaquinol oxidase (H+-transporting) |
| 1.10.3.3 | L-ascorbate oxidase |
| 1.10.3.9 | photosystem II |
| 1.10.3.10 | ubiquinol oxidase (H+-transporting) |
| 1.10.3.11 | ubiquinol oxidase |
| 1.10.3.12 | menaquinol oxidase (H+-transporting) |
| 1.10.9.1 | plastoquinol-plastocyanin reductase |
| 1.11.1.5 | cytochrome-c peroxidase |
| 1.11.1.6 | catalase |
| 1.11.1.7 | peroxidase |
| 1.11.1.B2 | chloride peroxidase (vanadium-containing) |
| 1.11.1.B7 | bromide peroxidase (heme-containing) |
| 1.11.1.8 | iodide peroxidase |
| 1.11.1.10 | chloride peroxidase |
| 1.11.1.11 | L-ascorbate peroxidase |
| 1.11.1.13 | manganese peroxidase |
| 1.11.1.14 | lignin peroxidase |
| 1.11.1.16 | versatile peroxidase |
| 1.11.1.19 | dye decolorizing peroxidase |
| 1.11.1.21 | catalase-peroxidase |
| 1.11.2.1 | unspecific peroxygenase |
| 1.11.2.2 | myeloperoxidase |
| 1.11.2.3 | plant seed peroxygenase |
| 1.11.2.4 | fatty-acid peroxygenase |
| 1.12.2.1 | cytochrome-c3 hydrogenase |
| 1.12.5.1 | hydrogen:quinone oxidoreductase |
| 1.12.99.6 | hydrogenase (acceptor) |
| 1.13.11.9 | 2,5-dihydroxypyridine 5,6-dioxygenase |
| 1.13.11.11 | tryptophan 2,3-dioxygenase |
| 1.13.11.49 | chlorite O2-lyase |
| 1.13.11.50 | acetylacetone-cleaving enzyme |
| 1.13.11.52 | indoleamine 2,3-dioxygenase |
| 1.13.11.60 | linoleate 8R-lipoxygenase |
| 1.13.99.3 | tryptophan 2'-dioxygenase |
| 1.14.11.9 | flavanone 3-dioxygenase |
| 1.14.12.17 | nitric oxide dioxygenase |
| 1.14.13.39 | nitric-oxide synthase (NADPH dependent) |
| 1.14.13.17 | cholesterol 7alpha-monooxygenase |
| 1.14.13.41 | tyrosine N-monooxygenase |
| 1.14.13.70 | sterol 14alpha-demethylase |
| 1.14.13.71 | N-methylcoclaurine 3'-monooxygenase |
| 1.14.13.81 | magnesium-protoporphyrin IX monomethyl ester (oxidative) cyclase |
| 1.14.13.86 | 2-hydroxyisoflavanone synthase |
| 1.14.13.98 | cholesterol 24-hydroxylase |
| 1.14.13.119 | 5-epiaristolochene 1,3-dihydroxylase |
| 1.14.13.126 | vitamin D3 24-hydroxylase |
| 1.14.13.129 | beta-carotene 3-hydroxylase |
| 1.14.13.141 | cholest-4-en-3-one 26-monooxygenase |
| 1.14.13.142 | 3-ketosteroid 9alpha-monooxygenase |
| 1.14.13.151 | linalool 8-monooxygenase |
| 1.14.13.156 | 1,8-cineole 2-endo-monooxygenase |
| 1.14.13.159 | vitamin D 25-hydroxylase |
| 1.14.14.1 | unspecific monooxygenase |
| 1.14.15.1 | camphor 5-monooxygenase |
| 1.14.15.6 | cholesterol monooxygenase (side-chain-cleaving) |
| 1.14.15.8 | steroid 15beta-monooxygenase |
| 1.14.15.9 | spheroidene monooxygenase |
| 1.14.18.1 | tyrosinase |
| 1.14.19.1 | stearoyl-CoA 9-desaturase |
| 1.14.19.3 | linoleoyl-CoA desaturase |
| 1.14.21.7 | biflaviolin synthase |
| 1.14.99.1 | prostaglandin-endoperoxide synthase |
| 1.14.99.3 | heme oxygenase |
| 1.14.99.9 | steroid 17alpha-monooxygenase |
| 1.14.99.10 | steroid 21-monooxygenase |
| 1.14.99.15 | 4-methoxybenzoate monooxygenase (O-demethylating) |
| 1.14.99.45 | carotene epsilon-monooxygenase |
| 1.16.5.1 | ascorbate ferrireductase (transmembrane) |
| 1.16.9.1 | iron:rusticyanin reductase |
| 1.17.1.4 | xanthine dehydrogenase |
| 1.17.2.2 | lupanine 17-hydroxylase (cytochrome c) |
| 1.17.99.1 | 4-methylphenol dehydrogenase (hydroxylating) |
| 1.17.99.2 | ethylbenzene hydroxylase |
| 1.97.1.1 | chlorate reductase |
| 1.97.1.9 | selenate reductase |
| 2.7.7.65 | diguanylate cyclase |
| 2.7.13.3 | histidine kinase |
| 3.1.4.52 | cyclic-guanylate-specific phosphodiesterase |
| 4.2.1.B9 | colneleic acid/etheroleic acid synthase |
| 4.2.1.22 | Cystathionine beta-synthase |
| 4.2.1.92 | hydroperoxide dehydratase |
| 4.2.1.212 | colneleate synthase |
| 4.3.1.26 | chromopyrrolate synthase |
| 4.6.1.2 | guanylate cyclase |
| 4.99.1.3 | sirohydrochlorin cobaltochelatase |
| 4.99.1.5 | aliphatic aldoxime dehydratase |
| 4.99.1.7 | phenylacetaldoxime dehydratase |
| 5.3.99.3 | prostaglandin-E synthase |
| 5.3.99.4 | prostaglandin-I synthase |
| 5.3.99.5 | Thromboxane-A synthase |
| 5.4.4.5 | 9,12-octadecadienoate 8-hydroperoxide 8R-isomerase |
| 5.4.4.6 | 9,12-octadecadienoate 8-hydroperoxide 8S-isomerase |
| 6.6.1.2 | cobaltochelatase |

In some embodiments, the heme enzyme is a variant or a fragment thereof (e.g., a truncated variant containing the heme domain) comprising at least one mutation such as, e.g., a mutation at the axial position of the heme coordination site. In some instances, the mutation is a substitution of the native residue with Ala, Asp, Arg, Asn, Cys, Glu, Gln, Gly, His, Ile, Lys, Leu, Met, Phe, Pro, Ser, Thr, Trp, Tyr, or Val at the axial position. In certain instances, the mutation is a substitution of Cys with any other amino acid such as Ser at the axial position.

In certain embodiments, the in vitro methods for producing a product described herein comprise providing a heme enzyme, variant, or homolog thereof with a reducing agent such as NADPH or a dithionite salt (e.g., $Na_2S_2O_4$). In certain other embodiments, the in vivo methods for producing a reaction product provided herein comprise providing whole cells such as E. coli cells expressing a heme enzyme, variant, or homolog thereof.

In some embodiments, the heme enzyme, variant, or homolog thereof is recombinantly expressed and optionally isolated and/or purified for carrying out the in vitro sulfimidation or sulfoximidation reactions of the disclosure. In other embodiments, the heme enzyme, variant, or homolog thereof is expressed in whole cells such as *E. coli* cells, and these cells are used for carrying out the in vivo nitrene insertion activity and/or nitrene transfer activity of the disclosure.

In certain embodiments, the heme enzyme, variant, or homolog thereof comprises or consists of the same number of amino acid residues as the wild-type enzyme (i.e., a full-length polypeptide). In some instances, the heme enzyme, variant, or homolog thereof comprises or consists of an amino acid sequence without the start methionine (e.g., P450BM3 amino acid sequence set forth in SEQ ID NO:1). In other embodiments, the heme enzyme comprises or consists of a heme domain fused to a reductase domain. In yet other embodiments, the heme enzyme does not contain a reductase domain, e.g., the heme enzyme contains a heme domain only or a fragment thereof such as a truncated heme domain.

In some embodiments, the heme enzyme, variant, or homolog thereof has an enhanced nitrene insertion activity and/or nitrene transfer activity of about 1.5, 2, 3, 4, 5, 6, 7, 8, 9, 10, 15, 20, 25, 30, 35, 40, 45, 50, 55, 60, 65, 70, 75, 80, 85, 90, 95, or 100 fold compared to the corresponding wild-type heme enzyme.

In some embodiments, the heme enzyme comprises a heme domain fused to a reductase domain. In other embodiments, the heme enzyme does not comprise a reductase domain, e.g., a heme domain only or a fragment thereof.

In one embodiment, the disclosure provides a method for catalyzing a nitrene insertion into a —S— bond to produce a product having a new S—N bond. The method comprises the steps of: providing a —S— containing substrate, a nitene precursor and an engineered heme enzyme; and allowing the reaction to proceed for a time sufficient to form a product having a new S—N bond.

In particular embodiments, the heme enzyme comprises a cyctochrome P450 enzyme. Cytochrome P450 enzymes constitute a large superfamily of heme-thiolate proteins involved in the metabolism of a wide variety of both exogenous and endogenous compounds. Usually, they act as the terminal oxidase in multicomponent electron transfer chains, such as P450-containing monooxygenase systems. Members of the cytochrome P450 enzyme family catalyze myriad oxidative transformations, including, e.g., hydroxylation, epoxidation, oxidative ring coupling, heteroatom release, and heteroatom oxygenation (E. M. Isin et al., Biochim. Biophys. Acta 1770, 314 (2007)). The active site of these enzymes contains a $Fe^{III}$-protoporphyrin IX cofactor (heme) ligated proximally by a conserved cysteine thiolate (M. T. Green, Current Opinion in Chemical Biology 13, 84 (2009)). The remaining axial iron coordination site is occupied by a water molecule in the resting enzyme, but during native catalysis, this site is capable of binding molecular oxygen. In the presence of an electron source, typically provided by NADH or NADPH from an adjacent fused reductase domain or an accessory cytochrome P450 reductase enzyme, the heme center of cytochrome P450 activates molecular oxygen, generating a high valent iron (IV)-oxo porphyrin cation radical species intermediate and a molecule of water.

In some embodiments, the engineered heme enzyme is a cytochrome P450 enzyme or a variant thereof. In certain embodiments, the P450 enzyme is a member of one of the classes shown in Table 2 (see, e.g., http[://www].icegeb.org/~p450srv/P450enzymes.html), the disclosure of which is incoproated herein by reference in its entirety.

TABLE 2

Heme enzymes identified by their enzyme classification number (EC number) and classification name.

| EC | Recommended name | Family/gene |
|---|---|---|
| 1.3.3.9 | secologanin synthase | CYP72A1 |
| 1.14.13.11 | trans-cinnamate 4-monooxygenase | CYP73 |
| 1.14.13.12 | benzoate 4-monooxygenase | CYP53 |
| 1.14.13.13 | calcidiol 1-monooxygenase | CYP27 |
| 1.14.13.15 | cholestanetriol 26-monooxygenase | CYP27 |
| 1.14.13.17 | cholesterol 7α-monooxygenase | CYP7 |
| 1.14.13.21 | flavonoid 3'-monooxygenase | CYP75 |
| 1.14.13.28 | 3,9-dihydroxypterocarpan 6a-monooxygenase | CYP93A1 |
| 1.14.13.30 | leukotriene-$B_4$ 20-monooxygenase | CYP4F |
| 1.14.13.37 | methyltetrahydroprotoberberine 14-monooxygenase | CYP93A1 |
| 1.14.13.41 | tyrosine N-monooxygenase | CYP79 |
| 1.14.13.42 | hydroxyphenylacetonitrile 2-monooxygenase | — |
| 1.14.13.47 | (−)-limonene 3-monooxygenase | — |
| 1.14.13.48 | (−)-limonene 6-monooxygenase | — |
| 1.14.13.49 | (−)-limonene 7-monooxygenase | — |
| 1.14.13.52 | isoflavone 3'-hydroxylase | — |
| 1.14.13.53 | isoflavone 2'-hydroxylase | — |
| 1.14.13.55 | protopine 6-monooxygenase | — |
| 1.14.13.56 | dihydrosanguinarine 10-monooxygenase | — |
| 1.14.13.57 | dihydrochelirubine 12-monooxygenase | — |
| 1.14.13.60 | 27-hydroxycholesterol 7α-monooxygenase | — |
| 1.14.13.70 | sterol 14-demethylase | CYP51 |
| 1.14.13.71 | N-methylcoclaurine 3'-monooxygenase | CYP80B1 |
| 1.14.13.73 | tabersonine 16-hydroxylase | CYP71D12 |
| 1.14.13.74 | 7-deoxyloganin 7-hydroxylase | — |
| 1.14.13.75 | vinorine hydroxylase | — |
| 1.14.13.76 | taxane 10β-hydroxylase | CYP725A1 |
| 1.14.13.77 | taxane 13α-hydroxylase | CYP725A2 |
| 1.14.13.78 | ent-kaurene oxidase | CYP701 |
| 1.14.13.79 | ent-kaurenoic acid oxidase | CYP88A |
| 1.14.14.1 | unspecific monooxygenase | multiple |
| 1.14.15.1 | camphor 5-monooxygenase | CYP101 |
| 1.14.15.3 | alkane 1-monooxygenase | CYP4A |
| 1.14.15.4 | steroid 11β-monooxygenase | CYP11B |
| 1.14.15.5 | corticosterone 18-monooxygenase | CYP11B |
| 1.14.15.6 | cholesterol monooxygenase (side-chain-cleaving) | CYP11A |
| 1.14.21.1 | (S)-stylopine synthase | — |
| 1.14.21.2 | (S)-cheilanthifoline synthase | — |
| 1.14.21.3 | berbamunine synthase | CYP80 |
| 1.14.21.4 | salutaridine synthase | — |
| 1.14.21.5 | (S)-canadine synthase | — |
| 1.14.99.9 | steroid 17α-monooxygenase | CYP17 |
| 1.14.99.10 | steroid 21-monooxygenase | CYP21 |
| 1.14.99.22 | ecdysone 20-monooxygenase | — |
| 1.14.99.28 | linalool 8-monooxygenase | CYP111 |
| 4.2.1.92 | hydroperoxide dehydratase | CYP74 |
| 5.3.99.4 | prostaglandin-I synthase | CYP8 |
| 5.3.99.5 | thromboxane-A synthase | CYP5 |

In some embodiments, the heme enzyme variant comprises a mutation at the axial position of the heme coordination site. In some instances, the mutation is an amino acid substitution of the naturally occuring residue at this position with Ala, Asp, Arg, Asn, Cys, Glu, Gln, Gly, His, Ile, Lys, Leu, Met, Phe, Pro, Ser, Thr, Trp, Tyr or Val at the axial position. In other instances, the mutation is an amino acid substitution of Cys with Asp or Ser at the axial position.

In some embodiments, the engineered heme enzyme is expressed in a bacterial, archaeal or fungal host organism.

In some embodiments, the cytochrome P450 enzyme is a P450 BM3 enzyme or a variant thereof. In some instances, the P450 BM3 enzyme comprises the amino acid sequence set forth in SEQ ID NO: 1 or a variant thereof.

In some embodiments, the P450 enzyme variant comprises a mutation at the axial position of the heme coordination site. In some instances, the mutation is an amino acid substitution of Cys with Ala, Asp, Arg, Asn, Glu, Gln, Gly, His, Ile, Lys, Leu, Met, Phe, Pro, Ser, Thr, Trp, Tyr or Val at the axial position. In other instances, the mutation is an amino acid substitution of Cys with Asp or Ser at the axial position.

In some embodiments, the P450BM3 enzyme comprises at least one, two, three, four, five, six, seven, eight, nine, ten, eleven, twelve, or all thirteen of the following amino acid substitutions in SEQ ID NO:1: V78A, F87V, P142S, T175I, A184V, S226R, H236Q, E252G, T268A, A290V, L353V, I366V, and E442K.

In some embodiments, the cytochrome P450BM3 enzyme variant comprises a T268A mutation and/or a C400X mutation in SEQ ID NO:1, wherein X is any amino acid other than Cys. In another embodiment, the cytochrome P450BM3 enzyme variant comprises a T438S mutation and/or a C400X mutation in SEQ ID NO:1, wherein X is any amino acid other than Cys.

In one embodiment, the heme enzyme variant for use in the catalysis of a nitrene insertion into a —S— bond to produce a product having a new S—N bond is a P450BM3 variant comprising the following amino acid substitutions to SEQ ID NO: 1: V78A, F87V, P142S, T175I, A184V, S226R, H236Q, E252G, T268A, A290V, L353V, I366V, and E442K. In another embodiment, the heme variant optionally comprises the following additional amino acid substitutions to SEQ ID NO:1: L75A, I263A and L437A. In yet another embodiment, the heme variant optionally comprises the additional amino acid substitution C400S to SEQ ID NO:1. In some embodiments, the heme enzyme variant is the H2-5-F10 variant (see, Table 7). In other embodiments, the heme enzyme variant is the P411-CIS variant (see, Table 4).

Table 3 below lists additional cyctochrome P450 enzymes that are suitable for use in the sulfimidation or sulfoximidation reactions of the disclosure. The accession numbers in Table 3 are incorporated herein by reference in their entirety for all purposes. The cytochrome P450 gene and/or protein sequences disclosed in the following patent documents are hereby incorporated by reference in their entirety for all purposes: WO 2013/076258; CN103160521; CN 103223219; KR 2013081394; JP 5222410; WO 2013/073775; WO 2013/054890; WO 2013/048898; WO 2013/031975; WO 2013/064411; U.S. Pat. No. 8,361,769; WO 2012/150326, CN 102747053; CN 102747052; JP 2012170409; WO 2013/115484; CN 103223219; KR 2013081394; CN 103194461; JP 5222410; WO 2013/086499; WO 2013/076258; WO 2013/073775; WO 2013/064411; WO 2013/054890; WO 2013/031975; U.S. Pat. No. 8,361,769; WO 2012/156976; WO 2012/150326; CN 102747053; CN 102747052; US 20120258938; JP 2012170409; CN 102399796; JP 2012055274; WO 2012/029914; WO 2012/028709; WO 2011/154523; JP 2011234631; WO 2011/121456; EP 2366782; WO 2011/105241; CN 102154234; WO 2011/093185; WO 2011/093187; WO 2011/093186; DE 102010000168; CN 102115757; CN 102093984; CN 102080069; JP 2011103864; WO 2011/042143; WO 2011/038313; JP 2011055721; WO 2011/025203; JP 2011024534; WO 2011/008231; WO 2011/008232; WO 2011/005786; IN 2009DE01216; DE 102009025996; WO 2010/134096; JP 2010233523; JP 2010220609; WO 2010/095721; WO 2010/064764; US 20100136595; JP 2010051174; WO 2010/024437; WO 2010/011882; WO 2009/108388; US 20090209010; US 20090124515; WO 2009/041470; KR 2009028942; WO 2009/039487; WO 2009/020231; JP 2009005687; CN 101333520; CN 101333521; US 20080248545; JP 2008237110; CN 101275141; WO 2008/118545; WO 2008/115844; CN 101255408; CN 101250506; CN 101250505; WO 2008/098198; WO 2008/096695; WO 2008/071673; WO 2008/073498; WO 2008/065370; WO 2008/067070; JP 2008127301; JP 2008054644; KR 794395; EP 1881066; WO 2007/147827; CN 101078014; JP 2007300852; WO 2007/048235; WO 2007/044688; WO 2007/032540; CN 1900286; CN 1900285; JP 2006340611; WO 2006/126723; KR 2006029792; KR 2006029795; WO 2006/105082; WO 2006/076094; US 2006/0156430; WO 2006/065126; JP 2006129836; CN 1746293; WO 2006/029398; JP 2006034215; JP 2006034214; WO 2006/009334; WO 2005/111216; WO 2005/080572; US 2005/0150002; WO 2005/061699; WO 2005/052152; WO 2005/038033; WO 2005/038018; WO 2005/030944; JP 2005065618; WO 2005/017106; WO 2005/017105; US 20050037411; WO 2005/010166; JP 2005021106; JP 2005021104; JP 2005021105; WO 2004/113527; CN 1472323; JP 2004261121; WO 2004/013339; WO 2004/011648; DE 10234126; WO 2004/003190; WO 2003/087381; WO 2003/078577; US 20030170627; US 20030166176; US 20030150025; WO 2003/057830; WO 2003/052050; CN 1358756; US 20030092658; US 20030078404; US 20030066103; WO 2003/014341; US 20030022334; WO 2003/008563; EP 1270722; US 20020187538; WO 2002/092801; WO 2002/088341; US 20020160950; WO 2002/083868; US 20020142379; WO 2002/072758; WO 2002/064765; US 20020076777; US 20020076774; US 20020076774; WO 2002/046386; WO 2002/044213; US 20020061566; CN 1315335; WO 2002/034922; WO 2002/033057; WO 2002/029018; WO 2002/018558; JP 2002058490; US 20020022254; WO 2002/008269; WO 2001/098461; WO 2001/081585; WO 2001/051622; WO 2001/034780; CN 1271005; WO 2001/011071; WO 2001/007630; WO 2001/007574; WO 2000/078973; U.S. Pat. No. 6,130,077; JP 2000152788; WO 2000/031273; WO 2000/020566; WO 2000/000585; DE 19826821; JP 11235174; U.S. Pat. No. 5,939,318; WO 99/19493; WO 99/18224; U.S. Pat. No. 5,886,157; WO 99/08812; U.S. Pat. No. 5,869,283; JP 10262665; WO 98/40470; EP 776974; DE 19507546; GB 2294692; U.S. Pat. No. 5,516,674; JP 07147975; WO 94/29434; JP 06205685; JP 05292959; JP 04144680; DD 298820; EP 477961; SU 1693043; JP 01047375; EP 281245; JP 62104583; JP 63044888; JP 62236485; JP 62104582; and JP 62019084.

TABLE 3

Additional cytochrome P450 enzymes of the disclosure.

| Species | Cyp No. | Accession No. | SEQ ID NO |
|---|---|---|---|
| Bacillus megaterium | 102A1 | AAA87602 | 1 |
| Bacillus megaterium | 102A1 | ADA57069 | 2 |
| Bacillus megaterium | 102A1 | ADA57068 | 3 |
| Bacillus megaterium | 102A1 | ADA57062 | 4 |
| Bacillus megaterium | 102A1 | ADA57061 | 5 |
| Bacillus megaterium | 102A1 | ADA57059 | 6 |
| Bacillus megaterium | 102A1 | ADA57058 | 7 |
| Bacillus megaterium | 102A1 | ADA57055 | 8 |
| Bacillus megaterium | 102A1 | ACZ37122 | 9 |
| Bacillus megaterium | 102A1 | ADA57057 | 10 |
| Bacillus megaterium | 102A1 | ADA57056 | 11 |
| Mycobacterium sp. HXN-1500 | 153A6 | CAH04396 | 12 |
| Tetrahymena thermophile | 5013C2 | ABY59989 | 13 |
| Nonomuraea dietziae | | AGE14547.1 | 14 |
| Homo sapiens | 2R1 | NP_078790 | 15 |
| Macca mulatta | 2R1 | NP_001180887.1 | 16 |
| Canis familiaris | 2R1 | XP_854533 | 17 |
| Mus musculus | 2R1 | AAI08963 | 18 |
| Bacillus halodurans C-125 | 152A6 | NP_242623 | 19 |

TABLE 3-continued

Additional cytochrome P450 enzymes of the disclosure.

| Species | Cyp No. | Accession No. | SEQ ID NO |
|---|---|---|---|
| Streptomyces parvus | aryC | AFM80022 | 20 |
| Pseudomonas putida | 101A1 | P00183 | 21 |
| Homo sapiens | 2D7 | AAO49806 | 22 |
| Rattus norvegicus | C27 | AAB02287 | 23 |
| Oryctolagus cuniculus | 2B4 | AAA65840 | 24 |
| Bacillus subtilis | 102A2 | O08394 | 25 |
| Bacillus subtilis | 102A3 | O08336 | 26 |
| B. megaterium DSM 32 | 102A1 | P14779 | 27 |
| B. cereus ATCC14579 | 102A5 | AAP10153 | 28 |
| B. licheniformis ATTC1458 | 102A7 | YP 079990 | 29 |
| B. thuringiensis serovar konkukian str.97-27 | X | YP 037304 | 30 |
| R. metallidurans CH34 | 102E1 | YP 585608 | 31 |
| A. fumigatus Af293 | 505X | EAL92660 | 32 |
| A. nidulans FGSC A4 | 505A8 | EAA58234 | 33 |
| A. oryzae ATCC42149 | 505A3 | Q2U4F1 | 34 |
| A. oryzae ATCC42149 | X | Q2UNA2 | 35 |
| F. oxysporum | 505A1 | Q9Y8G7 | 36 |
| G. moniliformis | X | AAG27132 | 37 |
| G. zeae PH1 | 505A7 | EAA67736 | 38 |
| G. zeae PH1 | 505C2 | EAA77183 | 39 |
| M. grisea 70-15 syn | 505A5 | XP 365223 | 40 |
| N. crassa OR74 A | 505A2 | XP 961848 | 41 |
| Oryza sativa* | 97A | | |
| Oryza sativa* | 97B | | |
| Oryza sativa | 97C | ABB47954 | 42 |

Note:
the start methionine ("M") may be present or absent from these sequences.

In some embodiments, the heme enzyme variant comprises a fragment of the cytochrome P450 enzyme or variant thereof. In some embodiments, the heme enzyme variant is a cytochrome P450 BM3 enzyme variant selected from Table 4, Table 5 and Table 6.

TABLE 4

Examplary cytochrome P450BM3 enzymes variants of the disclosure.

| P450$_{BM3}$ variants | Mutation compared to wild-type P450$_{BM3}$ (SEQ ID NO: 1) |
|---|---|
| P450$_{BM3}$ (WT-BM3; SEQ ID NO: 1) | None |
| P450$_{BM3}$-C400A (WT-C400A) | C400A |
| P450$_{BM3}$-T268A (BM3-T268) | T268A |
| P411$_{BM3}$ (ABC) | C400S |
| P411$_{BM3}$-T268A (ABC-T268A) | T268A, C400S |
| P411$_{BM3}$-T438S (ABC-T438A) | T438S, C400S |
| 9-10A | R47C, V78A, K94I, P142S, T175I, A184V, F205C, S226R, H236Q, E252G, R255S, A290V, L353V |
| B1SYN | 9-10A + C47S, N70Y, A78L, F87A, I174N, I94K, V184T, I263M, G315S, A330V |
| 9-10A TS | V78A, P142S, T175I, A184V, S226R, H236Q, E252G, A290V, L353V, I366V, E442K |
| 9-10A-TS-F87V | 9-10A TS + F87V |
| H2A10 | 9-10A TS + F87V, L75A, L181A, T268A |
| H2-5-F10 | 9-10A TS + F87V, L75A, I263A, T268A, L437A |
| H2-4-D4 | 9-10A TS + F87V, L75A, M177A, L181A, T268A, L437A |
| BM3-CIS (P450$_{BM3}$-CIS; C3C) | 9-10A TS + F87V, T268A |
| BM3-CIS-I263A | BM3-CIS + I263A |
| BM3-CIS-A328G | BM3-CIS + A328G |
| BM3-CIS-T438S | BM3-CIS + T438S |
| BM3-CIS-C400S (P411$_{BM3}$-CIS; ABC-CIS) | BM3-CIS + C400S |
| BM3-CIS-C400S-A268T (P411$_{BM3}$-CIS; ABC-CIS-A268T) | BM3-CIS + C400S + A268T (9-10A TS + P87V, C400S) |
| BM3-CIS-C400D (BM3-CIS-AxD) | BM3-CIS + C400D |
| BM3-CIS-C400Y (BM3-CIS-AxY) | BM3-CIS + C400Y |
| BM3-CIS-C400K (BM3-CIS-AxK) | BM3-CIS + C400K |
| BM3-CIS-C400H (BM3-CIS-AxH) | BM3-CIS + C400H |
| BM3-CIS-C400M (BM3-CIS-AxM) | BM3-CIS + C400M |
| WT-BM3 (heme) | WT heme domain (amino acids 1-463 of SEQ ID NO: 1) |
| WT-AxA (heme) | WT heme domain (amino acids 1-463 of SEQ ID NO: 1) + C400A |
| WT-AxD (heme) | WT heme domain (amino acids 1-463 of SEQ ID NO: 1) + C400D |
| WT-AxH (heme) | WT heme domain (amino acids 1-463 of SEQ ID NO: 1) + C400H |
| WT-AxK (heme) | WT heme domain (amino acids 1-463 of SEQ ID NO: 1) + C400K |
| WT-AxM (heme) | WT heme domain (amino acids 1-463 of SEQ ID NO: 1) + C400M |
| WT-AxN (heme) | WT heme domain (amino acids 1-463 of SEQ ID NO: 1) + C400N |
| WT-AxS (heme) | WT heme domain (amino acids 1-463 of SEQ ID NO: 1) + C400S |
| WT-AxY (heme) | WT heme domain (amino acids 1-463 of SEQ ID NO: 1) + C400Y |
| BM3-CIS-T438S-AxA | BM3-CIS-T438S + C400A |
| BM3-CIS-T438S-AxD | BM3-CIS-T438S + C400D |
| BM3-CIS-T438S-AxM | BM3-CIS-T438S + C400M |
| BM3-CIS-T438S-AxY | BM3-CIS-T438S + C400Y |
| BM3-CIS-T438S-AxT | BM3-CIS-T438S + C400T |
| 7-11D | R47C, V78A, K94I, P142S, T175I, A184V, F205C, S226R, H236Q, E252G, R255S, A290V, L353V, A82F, A328V |

One skilled in the art will understand that any of the mutations listed in Table 4 can be introduced into any cytochrome P450 enzyme of interest by locating the segment of the DNA sequence in the corresponding cytochrome P450 gene which encodes the conserved amino acid residue as described above for identifying the conserved cysteine residue in a cytochrome P450 enzyme of interest that serves as the heme axial ligand. In certain instances, this DNA segment is identified through detailed mutagenesis studies in a conserved region of the protein (see, e.g., Shimizu et al., Biochemistry 27, 4138-4141, 1988). In other instances, the conserved amino acid residue is identified through crystallographic study (see, e.g., Poulos et al., J. Mol. Biol 195: 687-700, 1987). In yet other instances, protein sequence alignment algorithms can be used to identify the conserved amino acid residue. For example, BLAST alignment with the P450 BM3 amino acid sequence as the query sequence can be used to identify the heme axial ligand site and/or the equivalent T268 residue in other cytochrome P450 enzymes.

Table 5 below provides non-limiting examples of cytochrome P450 BM3 variants of the disclosure. Each P450 BM3 variant comprises one or more of the listed mutations (Variant Nos. 1-31), wherein a "+" indicates the presence of that particular mutation in the variant. Any of the variants listed in Table 4 can further comprise an I263A and/or an A328G mutation and/or at least one, two, three, four, or five of the following alanine substitutions, in any combination, in the P450 BM3 enzyme active site: L75A, M177A, L181A, I263A, and L437A. In particular embodiments, the P450 BM3 variant comprises or consists of the heme domain of any one of Variant Nos. 1-31 listed in Table 5 or a fragment thereof, wherein the fragment is capable of carrying out the nitrene transfer/sulfimidation of the disclosure.

subtillis or variants. As a non-limiting example, site-directed recombination of three bacterial cytochrome P450s can be performed with sequence crossover sites selected to minimize the number of disrupted contacts within the protein structure. In some embodiments, seven crossover sites can be chosen, resulting in eight sequence blocks. One skilled in the art will understand that the number of crossover sites can be chosen to produce the desired number of sequence blocks, e.g., 1, 2, 3, 4, 5, 6, 7, 8, or 9 crossover sites for 2, 3, 4, 5, 6, 7, 8, 9, or 10 sequence blocks, respectively. In other embodiments, the numbering used for the chimeric P450 refers to the identity of the parent sequence at each block. For example, "12312312" refers to a sequence containing block 1 from P450 #1, block 2 from P450 #2, block 3 from P450 #3, block 4 from P450 #1, block 5 from P450 #2, and so on. A chimeric library useful for generating the chimeric heme enzymes of the invention can be constructed as described in U.S. Pat. Publ. No. US-2012-0171693-A1 to Arnold et al., the disclosure of which is incorporated herein for all purposes.

As a non-limiting example, chimeric P450 proteins comprising recombined sequences or blocks of amino acids from CYP102A1 (Accession No. J04832), CYP102A2 (Accession No. CAB12544), and CYP102A3 (Accession No. U93874) can be constructed. In certain instances, the CYP102A1 parent sequence is assigned "1", the CYP102A2 parent sequence is assigned "2", and the CYP102A3 is parent sequence assigned "3". In some instances, each parent sequence is divided into eight sequence blocks containing the following amino acids (aa): block 1: aa 1-64; block 2: aa 65-122; block 3: aa 123-166; block 4: aa 167-216; block 5: aa 217-268; block 6: aa 269-328; block 7: aa 329-404; and block 8: aa 405-end. Thus, in this example, there are eight blocks of amino acids and three fragments are possible at each block. For instance, "12312312" refers to a chimeric P450 protein of the invention containing block 1 (aa 1-64) from CYP102A1, block 2 (aa 65-122) from CYP102A2, block 3 (aa 123-166) from CYP102A3, block 4 (aa 167-216) from CYP102A1, block 5 (aa 217-268) from CYP102A2, and so on. Non-limiting examples of chimeric P450 proteins include those set forth in Table 6 (C2G9, X7, X7-12, C2E6, X7-9, C2B12, TSP234). In some embodiments, the chimeric heme enzymes of the invention can comprise at least one or more of the mutations described herein.

TABLE 5

Exemplary cytochrome P450 BM3 enzyme variants of the disclosure.

| | $P450_{BM3}$ variant | | | | | | | | | | | | | | | |
| --- | --- | --- | --- | --- | --- | --- | --- | --- | --- | --- | --- | --- | --- | --- | --- | --- |
| Mutation | 1 | 2 | 3 | 4 | 5 | 6 | 7 | 8 | 9 | 10 | 11 | 12 | 13 | 14 | 15 | 16 |
| C400X | + | | | | + | + | + | + | | | | | | | | + |
| T268A | | + | | | | + | | | | + | + | + | | | | + |
| F87V | | | + | | | | + | | | + | | | + | + | | + |
| 9-10A-TS | | | | + | | | | + | | | + | | + | | + | |
| T438Z | | | | | + | | | | + | | | + | | + | + | |

| | $P450_{BM3}$ variant | | | | | | | | | | | | | | |
| --- | --- | --- | --- | --- | --- | --- | --- | --- | --- | --- | --- | --- | --- | --- | --- |
| Mutation | 17 | 18 | 19 | 20 | 21 | 22 | 23 | 24 | 25 | 26 | 27 | 28 | 29 | 30 | 31 |
| C400X | + | + | + | + | + | | | | | + | + | + | + | | + |
| T268A | + | + | | | | + | + | + | | + | + | + | | + | + |
| F87V | | | + | + | | + | + | | + | + | + | | | + | + |
| 9-10A-TS | + | | + | | + | + | | + | + | + | | | + | + | + |
| T438Z | | + | | + | + | | + | + | | + | + | + | + | + | |

Mutations relative to the wild-type $P450_{BM3}$ amino acid sequence (SEQ ID NO: 1); "X" is selected from Ala, Asp, Arg, Asn, Glu, Gln, Gly, His, Ile, Lys, Leu, Met, Phe, Pro, Ser, Thr, Trp, Tyr, and Val; "Z" is selected from Ala, Ser, and Pro; "9-10A-TS" includes the following amino acid substitutions in SEQ ID NO: 1: V78A, P142S, T175I, A184V, S226R, H236Q, E252G, A290V, L353V, I366V, and E442K.

In other aspects, the disclosure provides chimeric heme enzymes such as, e.g., chimeric P450 polypeptides comprised of recombined sequences from P450 BM3 and at least two, or more distantly related P450 enzymes from Bacillus

TABLE 6

Exemplary preferred chimeric cytochrome P450 enzymes of the invention.

| Chimeric P450s | Heme domain block sequence | SEQ ID NO |
|---|---|---|
| C2G9 | 22223132 | 43 |
| X7 | 22312333 | 44 |
| X7-12 | 12112333 | 45 |
| C2E6 | 11113311 | 46 |
| X7-9 | 32312333 | 47 |
| C2B12 | 32313233 | 48 |
| TSP234 | 22313333 | 49 |

In another embodiment, the disclosure provides a method for catalyzing a nitrene insertion or transfer into a —S— bond to produce a product with a new S—N bond. The method comprising: providing a —S— containing substrate, a nitrene precursor and an engineered P450 enzyme as described herein and above; and allowing the reaction to proceed for a time sufficient to form a product having a new S—N bond.

In some embodiments, the engineered P450 enzyme is expressed in a bacterial, archaeal or fungal host organism.

In some embodiments, the cytochrome P450 enzyme is a P450 BM3 enzyme or a variant thereof. In some instances, the P450 BM3 enzyme comprises the amino acid sequence set forth in SEQ ID NO: 1 or a variant thereof.

An enzyme's total turnover number (or TTN) refers to the maximum number of molecules of a substrate that the enzyme can convert before becoming inactivated. In general, the TTN for the heme enzymes of the disclosure range from about 1 to about 100,000 or higher. For example, the TTN can be from about 1 to about 1,000, or from about 1,000 to about 10,000, or from about 10,000 to about 100,000, or from about 50,000 to about 100,000, or at least about 100,000. In particular embodiments, the TTN can be from about 100 to about 10,000, or from about 10,000 to about 50,000, or from about 5,000 to about 10,000, or from about 1,000 to about 5,000, or from about 100 to about 1,000, or from about 250 to about 1,000, or from about 100 to about 500, or at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, or more. In certain embodiments, the variant or chimeric heme enzymes of the disclosure have higher TTNs compared to the wild-type sequences. In some instances, the variant or chimeric heme enzymes have TTNs greater than about 100 (e.g., at least about 100, 150, 200, 250, 300, 325, 350, 400, 450, 500, or more) in carrying out in vitro sulfimidation reactions. In other instances, the variant or chimeric heme enzymes have TTNs greater than about 1000 (e.g., at least about 1000, 2500, 5000, 10,000, 25,000, 50,000, 75,000, 100,000, or more) in carrying out in vivo whole cell reactions.

In general, the term "mutant" or "variant" as used herein with reference to a molecule such as polynucleotide or polypeptide, indicates that has been mutated from the molecule as it exits in nature. In particular, the term "mutate" and "mutation" as used herein indicates any modification of a nucleic acid and/or polypeptide which results in an altered nucleic acid or polypeptide. Mutations include any process or mechanism resulting in a mutant protein, enzyme, polynucleotide, gene, or cell. This includes any mutation in which a polynucleotide or polypeptide sequence is altered, as well as any detectable change in a cell wherein the mutant polynucleotide or polypeptide is expressed arising from such a mutation. Typically, a mutation occurs in a polynucleotide or gene sequence, by point mutations, deletions, or insertions of single or multiple nucleotide residues. A mutation in a polynucleotide includes mutations arising within a protein-encoding region of a gene as well as mutations in regions outside of a protein-encoding sequence, such as, but not limited to, regulatory or promoter sequences. A mutation in a coding polynucleotide such as a gene can be "silent", i.e., not reflected in an amino acid alteration upon expression, leading to a "sequence-conservative" variant of the gene. A mutation in a polypeptide includes but is not limited to mutation in the polypeptide sequence and mutation resulting in a modified amino acid. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

A mutant or engineered protein or enzyme is usually, although not necessarily, expressed from a mutant polynucleotide or gene. Engineered cells can be obtained by introduction of an engineered gene or part of it in the cell. The terms "engineered cell", "mutant cell" or "recombinant cell" as used herein refer to a cell that has been altered or derived, or is in some way different or changed, from a parent cell, including a wild-type cell. The term "recombinant" as used herein with reference to a cell in alternative to "wild-type" or "native", indicates a cell that has been engineered to modify the genotype and/or the phenotype of the cell as found in nature, e.g., by modifying the polynucleotides and/or polypeptides expressed in the cell as it exists in nature. A "wild-type cell" refers instead to a cell which has not been engineered and displays the genotype and phenotype of said cell as found in nature.

The term "engineer" refers to any manipulation of a molecule or cell that result in a detectable change in the molecule or cell, wherein the manipulation includes but is not limited to inserting a polynucleotide and/or polypeptide heterologous to the cell and mutating a polynucleotide and/or polypeptide native to the cell. Engineered cells can also be obtained by modification of the cell' genetic material, lipid distribution, or protein content. In addition to recombinant production, the enzymes may be produced by direct peptide synthesis using solid-phase techniques, such as Solid-Phase Peptide Synthesis. Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer Variants of naturally-occurring sequences can be generated by site-directed mutagenesis (Botstein and Shortie 1985; Smith 1985; Carter 1986; Dale and Felix 1996; Ling and Robinson 1997), mutagenesis using uracil containing templates (Kunkel, Roberts et al. 1987; Bass, Sorrells et al. 1988), oligonucleotide-directed mutagenesis (Zoller and Smith 1983; Zoller and Smith 1987; Zoller 1992), phosphorothioate-modified DNA mutagenesis (Taylor, Schmidt et al.

1985; Nakamaye and Eckstein 1986; Sayers, Schmidt et al. 1988), mutagenesis using gapped duplex DNA (Kramer, Drutsa et al. 1984; Kramer and Fritz 1987), point mismatch, mutagenesis using repair-deficient host strains, deletion mutagenesis (Eghtedarzadeh and Henikoff 1986), restriction-selection and restriction-purification (Braxton and Wells 1991), mutagenesis by total gene synthesis (Nambiar, Stackhouse et al. 1984; Grundstrom, Zenke et al. 1985; Wells, Vasser et al. 1985)], double-strand break repair (Mandecki 1986), and the like. Additional details on many of the above methods can be found in Methods in Enzymology Volume 154, which also describes useful controls for trouble-shooting problems with various mutagenesis methods.

Additional details regarding the methods to generate variants of naturally-occurring sequences can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter.

In particular, in some embodiments, site-directed mutagenesis can be performed on predetermined residues of a heme containing enzyme or P450 polypeptide. These predetermined sites can be identified using the crystal structure of the heme or P450 enzyme if available or a crystal structure of a homologous protein that shares at least 20% sequence identity with a heme or P450 enzyme of the disclosure and an alignment of the polynucleotide or amino acid sequences and its homologous protein. Mutagenesis of the predetermined sites can be performed changing one, two or three of the nucleotides in the codon that encodes for each of the predetermined amino acids. Mutagenesis of the predetermined sites can be performed in the described way so that each of the predetermined amino acid is mutated to any of the other 19 natural amino acids. Substitution of the predetermined sites with unnatural amino acids can be performed using methods established in vivo (Wang, Xie et al. 2006), in vitro (Shimizu, Kuruma et al. 2006), semisynthetic (Schwarzer and Cole 2005) or synthetic methods (Camarero and Mitchell 2005) for incorporation of unnatural amino acids into polypeptides.

In still further embodiments, libraries of engineered variants can be obtained by laboratory evolutionary methods and/or rational design methods, using one or a combination of techniques such as random mutagenesis, site-saturation mutagenesis, site-directed mutagenesis, DNA shuffling, DNA recombination, and the like and targeting one or more of the amino acid residues, one at a time or simultaneously. Said libraries can be arrayed on multi-well plates and screened for activity on the target molecule using a colorimetric, fluorimetric, enzymatic, or luminescence assay and the like. For example a method for making libraries for directed evolution to obtain P450s with new or altered properties is recombination, or chimeragenesis, in which portions of homologous P450s are swapped to form functional chimeras, can use used. Recombining equivalent segments of homologous proteins generates variants in which every amino acid substitution has already proven to be successful in one of the parents. Therefore, the amino acid mutations made in this way are less disruptive, on average, than random mutations. A structure-based algorithm, such as SCHEMA, can be used to identify fragments of proteins that can be recombined to minimize disruptive interactions that would prevent the protein from folding into its active form.

In some embodiments, activation of a target site in an organic molecule can be performed in a whole-cell system. To prepare the whole-cell system, the encoding sequence can be introduced into a host cell using a suitable vector, such as a plasmid, a cosmid, a phage, a virus, a bacterial artificial chromosome (BAC), a yeast artificial chromosome (YAC), or the like, into which the said sequence of the disclosure has been inserted, in a forward or reverse orientation. In some embodiments, the construct further comprises regulatory sequences, including, for example, a promoter linked to the sequence. Large numbers of suitable vectors and promoters are known to those of skill in the art, and are commercially available.

Accordingly, in other embodiments, vectors that include a nucleic acid molecule of the disclosure are provided. In other embodiments, host cells transfected with a nucleic acid molecule of the disclosure, or a vector that includes a nucleic acid molecule of the disclosure, are provided. Host cells include eucaryotic cells such as yeast cells, insect cells, or animal cells. Host cells also include procaryotic cells such as bacterial cells.

In other embodiments, methods for producing a cell for carrying out or producing an enzyme catalyst of the disclosure are provided. Such methods generally include: (a) transforming a cell with an isolated nucleic acid molecule encoding a polypeptide having the enzymatic activity that transfers or inserts a nitrene into a —S— target site; (b) transforming a cell with an isolated nucleic acid molecule encoding a polypeptide of the disclosure; or (c) transforming a cell with an isolated nucleic acid molecule of the disclosure.

The terms "vector", "vector construct" and "expression vector" as used herein refer to a vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" refers to allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used.

Vectors can be employed to transform an appropriate host to permit the host to express a protein or polypeptide. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; or plant cells or explants, etc.

In bacterial systems, a number of expression vectors may be selected depending upon the use intended for the polypeptide. For example, such vectors include, but are not limited to, multifunctional *E. coli* cloning and expression vectors such as BLUESCRIPT (Stratagene), in which the coding sequence may be ligated into the vector in-frame with sequences for the amino-terminal Met and the subsequent 7 residues of beta-galactosidase so that a hybrid protein is produced; pIN vectors; pET vectors; and the like.

Similarly, in the yeast *Saccharomyces cerevisiae* a number of vectors containing constitutive or inducible promoters such as alpha factor, alcohol oxidase and PGH may be used for production of an enzyme catalyst of the disclosure.

In order to perform the sulfimidation reactions described herein, a nitrene precursor is used. The nitrene precursor can be an azide. For example, the nitrene precursor can have the general formula: $R^1$—$N_3$, wherein $R^1$ is:

(i) a substituted or unsubstituted aryl, a substitute or unsubstituted alkyl, —$OR^2$, or —$NR^2$, wherein $R^2$ is a substituted or unsubstituted aryl, a substitute or unsubstituted alkyl;

(ii) —$SO_2R^3$, wherein $R^3$ a substituted or unsubstituted aryl, a substitute or unsubstituted alkyl, —$OR^2$ or $NR^2$, wherein $R^2$ are any alkyl or aryl;

(iii) —$COR^4$ wherein $R^4$ is a substituted or unsubstituted aryl, a substitute or unsubstituted alkyl, —$OR^2$ or $NR^2$, wherein $R^2$ are any alkyl or aryl; or (iv) —$P(O)(OR^5)(OR^6)$, wherein $R^5$ and $R^6$ are independently H, a substituted or unsubstituted aryl, a substitute or unsubstituted alkyl.

In another embodiment, the azide has a structure selected from the group consisting of:

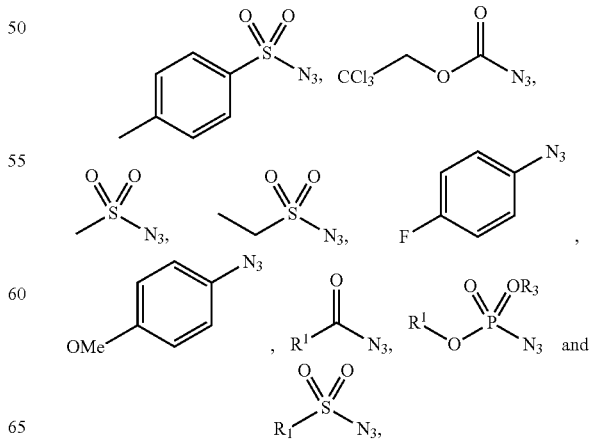

wherein $R^1$ is any alkyl, aryl, —OR, $NR^2$, wherein R, $R^2$ and $R^3$ are any alkyl, or aryl. In a specific embodiment, the azide is a tosyl azide.

The nitrene precursor can also be is selected from the group consisting of:

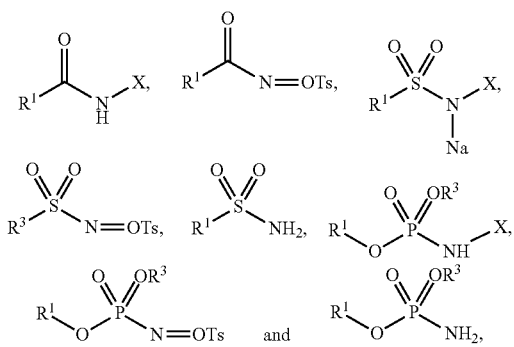

wherein $R^1$ is any alkyl, aryl, —OR, $NR^2$, wherein R, $R^2$ and $R^3$ are any alkyl, or aryl and wherein —OTs can be ITs. In certain aspects, the nitrene precursor contains a leaving group. Suitable leaving groups include, but are not limited to, OTs (tosylates), OMs (mesylates), halogen, $N_2$, $H_2$ and ITs (N-tosylimine).

In certain aspects, the disclosure provides methods and systems for heme-containing enzymes to catalyze nitrogen transfer to a sulfur in an organosulfur compound, also known as sulfimidation or sulfoximidation. The reactions can be intermolecular, intramolecular and a combination thereof. These heme containing enzymes catalyze the sulfimidation or sulfoximidation via nitrene transfer or insertion, which allows the generation of a new S—N bond. The reactions proceed with high regio, chemo, and/or diastereoselectivity as a result of uing a heme containing enzyme.

In one embodiment, the disclosure provides a method for catalyzing a nitrene insertion or transfer to a sulfur atom targe in an oranosulfur compound to produce a product having a new S—N bond. The method comprises: providing a sulfur containing substrate, a nitrene precursor and an engineered heme enzyme; and allowing the reaction to proceed for a time sufficient to form a product having a new S—N bond. In other embodiments, the disclosure provides a product of the methods herein.

In certain embodiments, the nitrene precursor contains an azide functional group. In one embodiment, a product obtained from the methods of the disclosure comprises a compound of Formula 1a:

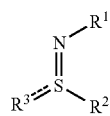

Formula 1a wherein $R^1$ is a sulfoxide, a carbonyl or a phosphonate; wherein $R^2$ is H or any alkyl or aryl; and wherein $R^3$ is H, O or an optionally substituted aryl group. In one embodiment, $R^1$ is a sulfoxide of formula $SO_2R^5$, wherein $R^5$ any alkyl, any aryl, —$OR^6$ or $NR^7$, wherein $R^6$ and $R^7$ are any alkyl, any aryl, —$OR^6$ or $NR^7$, wherein $R^6$ and $R^7$ are any alkyl or any aryl. IN a further embodiment, $R^2$ is any alkyl or aryl. In still a further or alternative embodiment, $R^3$ is H. In another embodiment, $R^1$ is a phosphonate of formula $P(O)(OR^8)(OR^9)$, wherein $R^8$ and $R^9$ are independently any aryl or any alkyl. In a further embodiment, $R^2$ is any alkyl or any aryl. In still a further embodiment, $R^3$ is any alkyl or aryl. In another embodiment, $R^1$ is a carbonyl group. In a further embodiment, $R^2$ is any alkyl or any aryl. In still a further embodiment, $R^3$ is any alkyl or any aryl. In another embodiment, $R^3$ is an optionally substituted aryl group. In a further embodiment, $R^1$ is any alkyl or any aryl. In still a further embodiment, $R^2$ is H or any alkyl or any aryl. In another embodiment, $R^1$ is a carbonyl group. In a further embodiment, $R^2$ is any alkyl or any aryl. In still a further embodiment, $R^3$ is O.

The methods of the disclosure include forming reaction mixtures that contain the heme enzymes described herein. The heme enzymes can be, for example, purified prior to addition to a reaction mixture or secreted by a cell present in the reaction mixture. The reaction mixture can contain a cell lysate including the enzyme, as well as other proteins and other cellular materials. Alternatively, a heme enzyme can catalyze the reaction within a cell expressing the heme enzyme. Any suitable amount of heme enzyme can be used in the methods of the disclosure. In general, the reaction mixtures contain from about 0.01 mol % to about 10 mol % heme enzyme with respect to the nitrene precursor and/or substrate. The reaction mixtures can contain, for example, from about 0.01 mol % to about 0.1 mol % heme enzyme, or from about 0.1 mol % to about 1 mol % heme enzyme, or from about 1 mol % to about 10 mol % heme enzyme. The reaction mixtures can contain from about 0.05 mol % to about 5 mol % heme enzyme, or from about 0.05 mol % to about 0.5 mol % heme enzyme. The reaction mixtures can contain about 0.1, 0.2, 0.3, 0.4, 0.5, 0.6, 0.7, 0.8, 0.9, or about 1 mol % heme enzyme.

The concentration of the organosulfur substrate and nitrene precursor are typically in the range of from about 100 µM to about 1 M. The concentration can be, for example, from about 100 µM to about 1 mM, or about from 1 mM to about 100 mM, or from about 100 mM to about 500 mM, or from about 500 mM to 1 M. The concentration can be from about 500 µM to about 500 mM, 500 µM to about 50 mM, or from about 1 mM to about 50 mM, or from about 15 mM to about 45 mM, or from about 15 mM to about 30 mM. The concentration of organosulfur substrate and nitrene precursor can be, for example, about 100, 200, 300, 400, 500, 600, 700, 800, or 900 µM. The concentration of organosulfur substrate and nitrene precursor can be about 1, 5, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional components. As non-limiting examples, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$, and salts of $Mn^{2+}$ and $Mg^{2+}$), denaturants (e.g., urea and guandinium hydrochloride), detergents (e.g., sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N,N-tetraacetic acid (BAPTA)), sugars (e.g., glucose, sucrose, and the like), and reducing agents (e.g., sodium dithionite, NADPH, NADH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the organosulfur substrate and nitrene precursor. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of the desired products. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 6 to about 10. The reactions can be conducted, for example, at a pH of from about 6.5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the cyclopropanation occurs in the aqueous phase. In some embodiments, the heme enzyme is located in the aqueous layer whereas the substrates and/or products occur in an organic layer. Other reaction conditions may be employed in the methods of the disclosure, depending on the identity of a particular heme enzyme, organosulfur substrate and nitrene precursor.

Reactions can be conducted in vivo with intact cells expressing a heme enzyme of the disclosure. The in vivo reactions can be conducted with any of the host cells used for expression of the heme enzymes, as described herein. A suspension of cells can be formed in a suitable medium supplemented with nutrients (such as mineral micronutrients, glucose and other fuel sources, and the like). Nitrene transfer or insertion yields from reactions in vivo can be controlled, in part, by controlling the cell density in the reaction mixtures. Cellular suspensions exhibiting optical densities ranging from about 0.1 to about 50 at 600 nm can be used for nitrene transfer reactions. Other densities can be useful, depending on the cell type, specific heme enzymes, or other factors.

The methods of the disclosure can be assessed in terms of the diastereoselectivity and/or enantioselectivity of sulfimidation or sulfoximidatino reaction—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30%>diastereoselective.

In general, the methods of the invention include reactions that are from about 1% to about 99% diastereoselective. The reactions are from about 1% to about 99% enantioselective. The reaction can be, for example, from about 10% to about 90% diastereoselective, or from about 20%> to about 80%>diastereoselective, or from about 40%> to about 60%) diastereoselective, or from about 1% to about 25% diastereoselective, or from about 25% o to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly some embodiments of the disclosure provide methods wherein the reaction is at least 30% to at least 90% diastereoselective. In some embodiments, the reaction is at least 30% to at least 90% enantioselective. As described herein, the ratios and reactants (e.g., the type of nitrene precursor the heme variant and cofactors) can be modified to yield a desired ratio of enantiomers.

One of skill in the art will appreciate that stereochemical configuration of certain of the products herein will be determined in part by the orientation of the product of the enzymatic step. Certain of the products herein will be "cis" compounds or "Z" compounds. Other products will be "trans" compounds or "E" compounds.

In certain instances, two cis isomers and two trans isomers can arise from the reaction of an organosulfur substrate and a nitrene precursor. The two cis isomers are enantiomers with respect to one another, in that the structures are non-superimposable mirror images of each other. Similarly, the two trans isomers are enantiomers. One of skill in the art will appreciate that the absolute stereochemistry of a product—that is, whether a given chiral center exhibits the right-handed "R" configuration or the left-handed "S" configuration—will depend on factors including the structures of the particular substrate and nitrene precursor used in the reaction, as well as the identity of the enzyme. The relative stereochemistry—that is, whether a product exhibits a cis or trans configuration—as well as for the distribution of product mixtures will also depend on such factors.

In certain instances, the product mixtures have cis:trans ratios ranging from about 1:99 to about 99:1. The cis:trans ratio can be, for example, from about 1:99 to about 1:75, or from about 1:75 to about 1:50, or from about 1:50 to about 1:25, or from about 99:1 to about 75:1, or from about 75:1 to about 50:1, or from about 50:1 to about 25:1. The cis:trans ratio can be from about 1:80 to about 1:20, or from about 1:60 to about 1:40, or from about 80:1 to about 20:1 or from about 60:1 to about 40:1. The cis:trans ratio can be about 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, or about 1:95. The cis:trans ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

The distribution of a product mixture can be assessed in terms of the enantiomeric excess, or "% ee," of the mixture. The enantiomeric excess refers to the difference in the mole fractions of two enantiomers in a mixture. In certain instances, as a non-limiting example, for instance, the enantiomeric excess of the "E" or trans (R,R) and (S,S) enantiomers can be calculated using the formula: %>eeE= [(% R,R−% s,s/(% R,R+% s,s)]×100%), wherein χ is the mole fraction for a given enantiomer. The enantiomeric excess of the "Z" or cis enantiomers (% eez) can be calculated in the same manner.

In certain instances, product mixtures exhibit % ee values ranging from about 1% to about 99%, or from about −1% to about −99%. The closer a given % ee value is to 99% (or −99%), the purer the reaction mixture is. The % ee can be, for example, from about −90% to about 90%), or from about −80% to about 80%, or from about −70% to about 70%, or from about −60%) to about 60%, or from about −40% to about 40%, or from about −20% to about 20%). The % ee can be from about 1% to about 99%, or from about 20% to about 80%, or from about 40% to about 60%, or from about 1% to about 25%, or from about 25% to about 50%), or from about 50% to about 75%. The % ee can be from about −1% to about −99%, or from about −20% to about −80%, or from about −40% to about −60%, or from about −1% to about −25%), or from about −25% to about −50%, or from about −50% to about −75%. The % ee can be about −99%, −95%, −90%, −85%, −80%, −75%, −70%, −65%, −60%, −55%, −50%, −45%, −40%, −35%, −30%, −25%, −20%, −15%, −10%, 10%, 15%, 20%, 25%, 30%, 35%, 40%, 45%, 50%, 55%, 60%, 65%, 70%, 75%, 80%, 85%, 90%, or about 95%. Any of these values can be % eeE values or % eez values.

Accordingly, some embodiments of the disclosure provide methods for producing a plurality of products having a % eez of from about −90% to about 90%. In some embodiments, the % eez is at least 90%. In some embodiments, the % eez is at least −99%. In some embodiments, the % eeE is from about −90% to about 90%. In some embodiments, the % eeE is at least 90%. In some embodiments, the % eeE is at least −99%.

EXAMPLES

The present disclosure is further illustrated in the following examples, which are provided by way of illustration and are not intended to be limiting.

Figure 6:
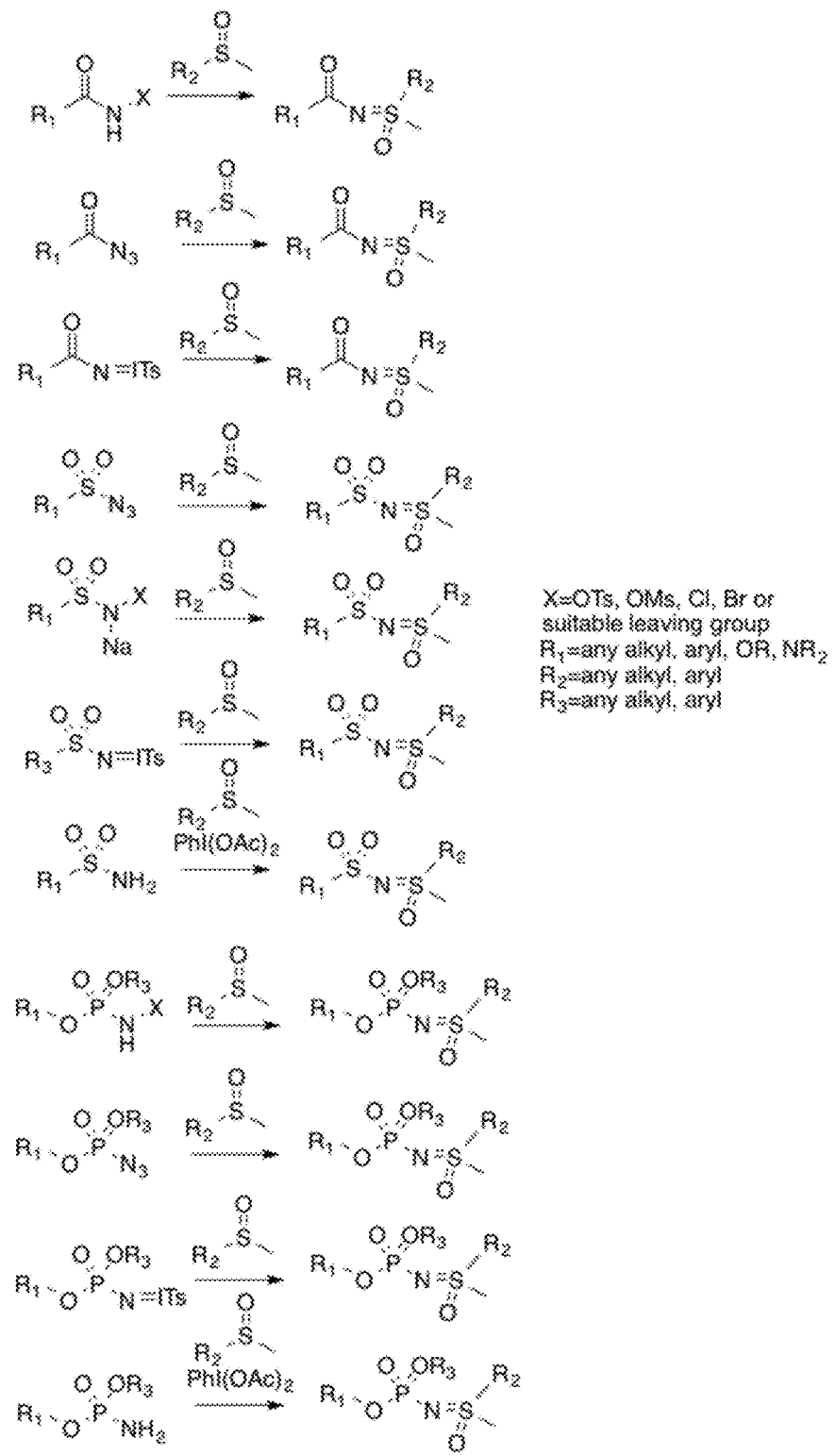
FIG. 6 shows examples of appropriate nitrene sources and generalized reactions for the formation of sulfoximines.

Work on intramolecular C—H amination was limited to aryl sulfonylazide substrates as nitrene precursors. Despite the success with this substrate class, research was performed to assess the influence of the R-group on the nitrenoid transfer and thus a series of substrates displaying a range of stereoelectronic properties that have been shown to be effective nitrene precursors in other contexts were tested (FIG. 5-6).

For the thioether acceptor substrate thioanisole was chosen, which has been used in enzymatic sulfoxidation by cytochrome P450s and other oxygenase enzymes. As a catalyst, P411$_{BM3}$-CIS T438S, a variant of cytochrome P450$_{BM3}$, possessing the aforementioned C400S mutation was used. This enzyme, which contains 14 mutations relative to wild-type P450$_{BM3}$ (Table A), was previously shown to be a good catalyst in the activation of azides for intramolecular C—H insertion. Reaction conditions were similar to those reported for intramolecular C—H amination (see, e.g., International Application Publication No. WO 2014/058729, incorporated herein by reference for all purposes) under anaerobic conditions with nicotine adenine dinucleotide phosphate (NADPH) supplied as a reductant.

TABLE A

Mutations present in P450 BM3 variants used in the disclosure

| Enzyme | Mutations relative to wild-type P450$_{BM3}$ |
|---|---|
| P450$_{BM3}$ | none |
| P450$_{BM3}$-T268A | T268A |
| P411$_{BM3}$ | C400S |
| P411$_{BM3}$-T268A | T268A, C400S |
| P450$_{BM3}$-CIS T438S | V78A, F87V, P142S, T175I, A184V, S226R, H236Q, E252G, A290V, L353V, I366V, T438S, E442K |
| P411$_{BM3}$-CIS T438S | P450BM3-CIS C400S, T438S |
| P411$_{BM3}$-CIS A268T T438S | P450BM3-CIS, A268T, C400S, T438S |
| P411$_{BM3}$ H2-A-10 | P450BM3-CIS, L75A, L181A, C400S, |
| P411$_{BM3}$ H2-5-F10 | P450BM3-CIS, L75A, I263A, C400S, L437A |
| P411$_{BM3}$ H2-4-D4 | P450BM3-CIS, L75A, M177A, L181A, C400S, L437A, T438S |

Considering the small size of reactive oxygen species naturally produced by P450s, it was anticipated that smaller azides, such as mesyl azide would be less sterically demanding than aryl or arylsulfonyl azides and thus a more suitable partner for reaction with thioanisole. Tosyl azide was shown to be an exception precursor for sulfimidation.

Control experiments confirmed that enzyme was necessary for sulfimide formation (Table 7). Free hemin showed no activity in this transformation.

In other non-natural P450 reactions reported to date, it was shown that amino acid substitutions could alter both the activity and stereoselectivity of the enzymes. Thus, mutation of conserved residues C400 and T268 and other active-site residues were tested to determine their effect on sulfimidation activity (Table B). For these experiments we used the more reactive sulfide 4-methoxythioanisole, for which we measured 300 TTN with P411BM3-CIS T438S (see below for more discussion of the effect of sulfide substituents on reactivity).

TABLE B

Sulfimidation Activity and Selectivity of BM3 Variants using Substrates and Reaction Conditions Shown$^a$

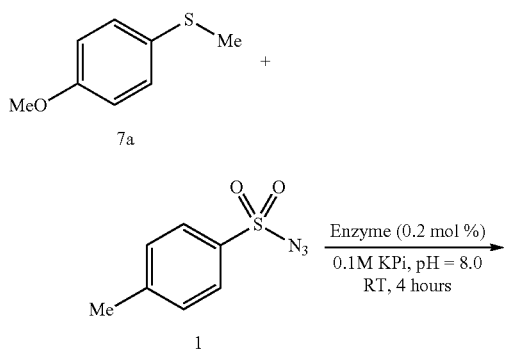

TABLE B-continued

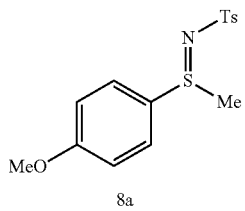 [SMILES: COc1ccc(/S(C)=N/S(=O)(=O)c2ccc(C)cc2)cc1]

8a

| entry | enzyme | TTN | er |
|---|---|---|---|
| 1 | P411$_{BM3}$-CIS T438S | 300 | 74:26 |
| 2 | P450$_{BM3}$-CIS T438S | 7 | nd |
| 3 | P411$_{BM3}$-CIS A268T T438S | 19 | nd |
| 4 | P411$_{BM3}$-H2-5-F10 | 140 | 29:71 |
| 5 | P411$_{BM3}$-H2-A-10 | 84 | 57:43 |
| 6 | P411$_{BM3}$-H2-4-D4 | 32 | 70:30 |
| 7 | P450$_{BM3}$ | 10 | nd |
| 8 | P411$_{BM3}$ | 11 | nd |
| 9 | P450$_{BM3}$-T268A | 19 | nd |
| 10 | P411$_{BM3}$-T268A | 17 | nd |
| 11 | P411$_{BM3}$-CIS I263A T438S | 320 | 18:82 |

[a]"P411" denotes Ser-ligated (C400S) variant of cytochrome P450BM3. Variant IDs and specific amino acid substitutions in each can be found in Table A. TTN—total turnover number, er = enantiomeric ratio, nd = not determined.

Since activating mutations T268A and C400S were already present in P411$_{BM3}$-CIS T438S, the effects of reverting each mutation to the wild-type residue (Table B, entries 1-3) were tested. Each revertant was much less active than the parent, supporting the benefit of having the C400S and T268A mutations for effective nitrene-transfer chemistry. Given the bulky nature of the aryl sulfonylazide nitrene sources and aryl thioethers, the C400S mutants of several P450BM3 variants that had been engineered via combinatorial alanine scanning to hydroxylate large substrates were tested (Table B, entries 4-6). While P411$_{BM3}$-H2-5-F10 displayed comparably high levels of activity to P411$_{BM3}$-CIS T438S (>100 TTN), the other mutants we tested from this library were less productive. The effects of introducing the activating mutations into wild-type P450BM3 was also tested. Although these wild-type derivatives were highly active and stereoselective for intramolecular C—H amination, neither single mutant (T268A or C400S) nor the double mutant (T268A+C400S) were as active for intermolecular sulfimidation.

Figure 7:
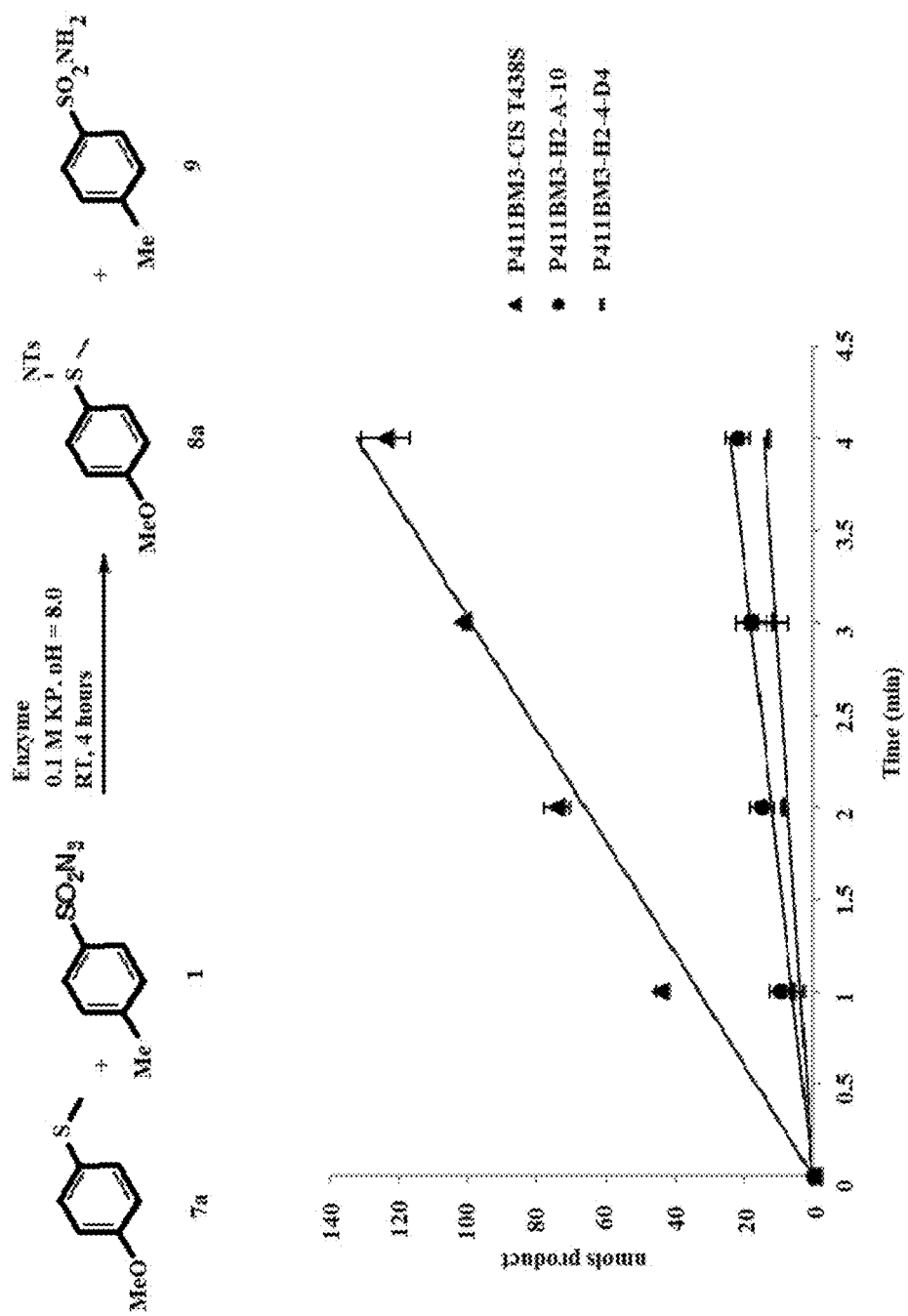
FIG. 7 shows data used to determine initial rates of the reaction depicted in scheme above the graph for the enzymes listed in figure legend.

The turnover data presented above demonstrate the sequence dependence of sulfimidation productivity. The effects, however, could be due to changes in stability of the enzymes that lead to degradation over the course of the reaction. To address this possibility, the initial rates of reaction using the most productive enzyme in terms of total turnover were compared, P411BM3-CIS T438S, and the less productive P411BM3-H2-A-10 and P411BM3-H2-4-D4 enzymes (FIG. 7). Differences in the total productivity (i.e., TTN) for each enzyme are mirrored in the initial rates of reaction, suggesting that specific amino acids proximal to the heme influence binding and orientation of the substrates to effect catalytic rate enhancement.

Figure 8:
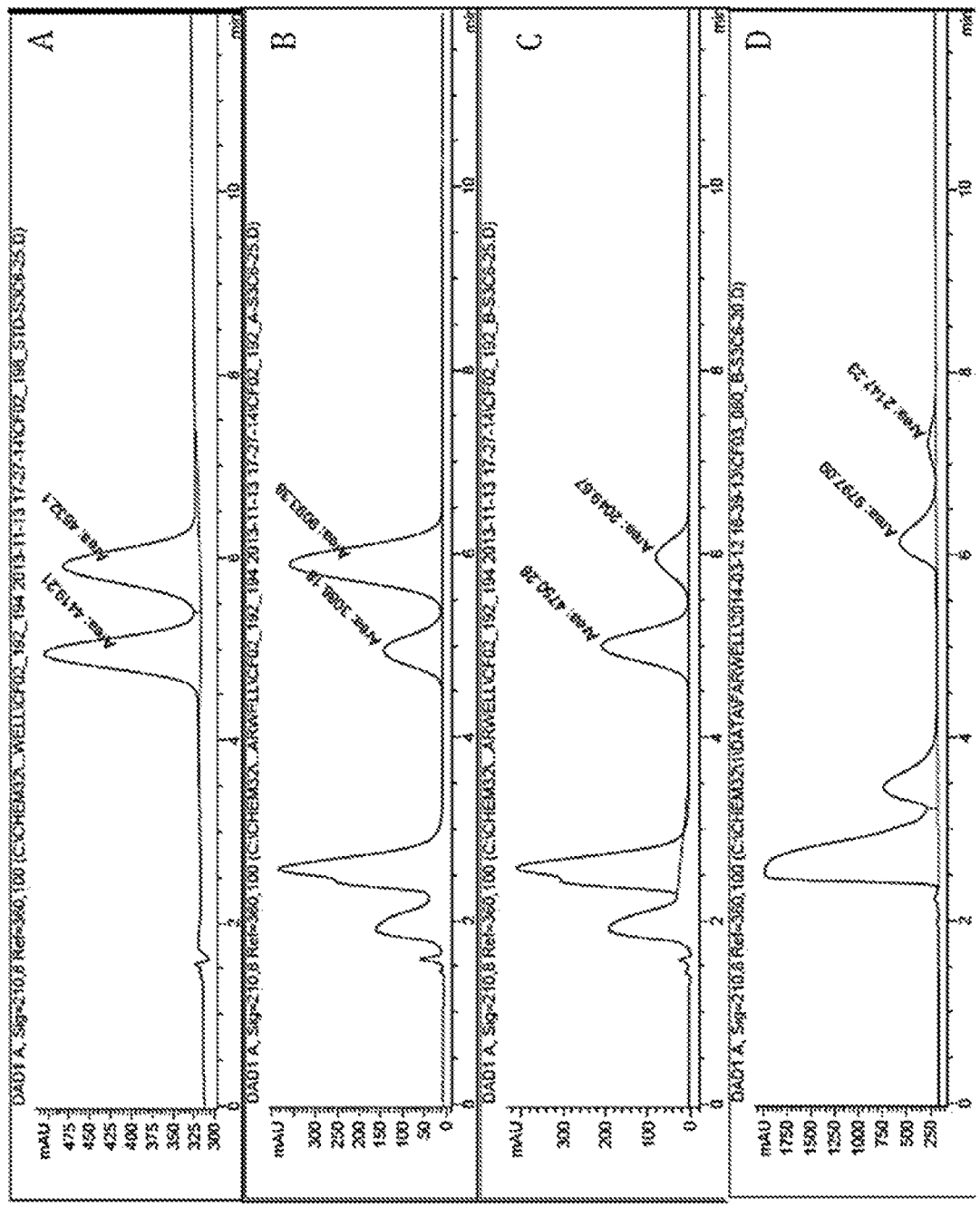
FIG. 8A-D shows traces of (A) SFC trace of synthetic standard of 8a using Chiralpak OD-H column with 25% isopropanol/75% supercritical $CO_2$ mobile phase. (B) Trace of $P411_{BM3}$-CIS T438S produced 8a under same conditions as synthetic standard. (C) Trace of $P411_{BM3}$-H2-5-F10 produced 8a. (D) Trace of $P411_{BM3}$-CIS I263A T438S produced 8a, using 20% isopropanol/80% supercritical $CO_2$ mobile phase.
Figure 9:
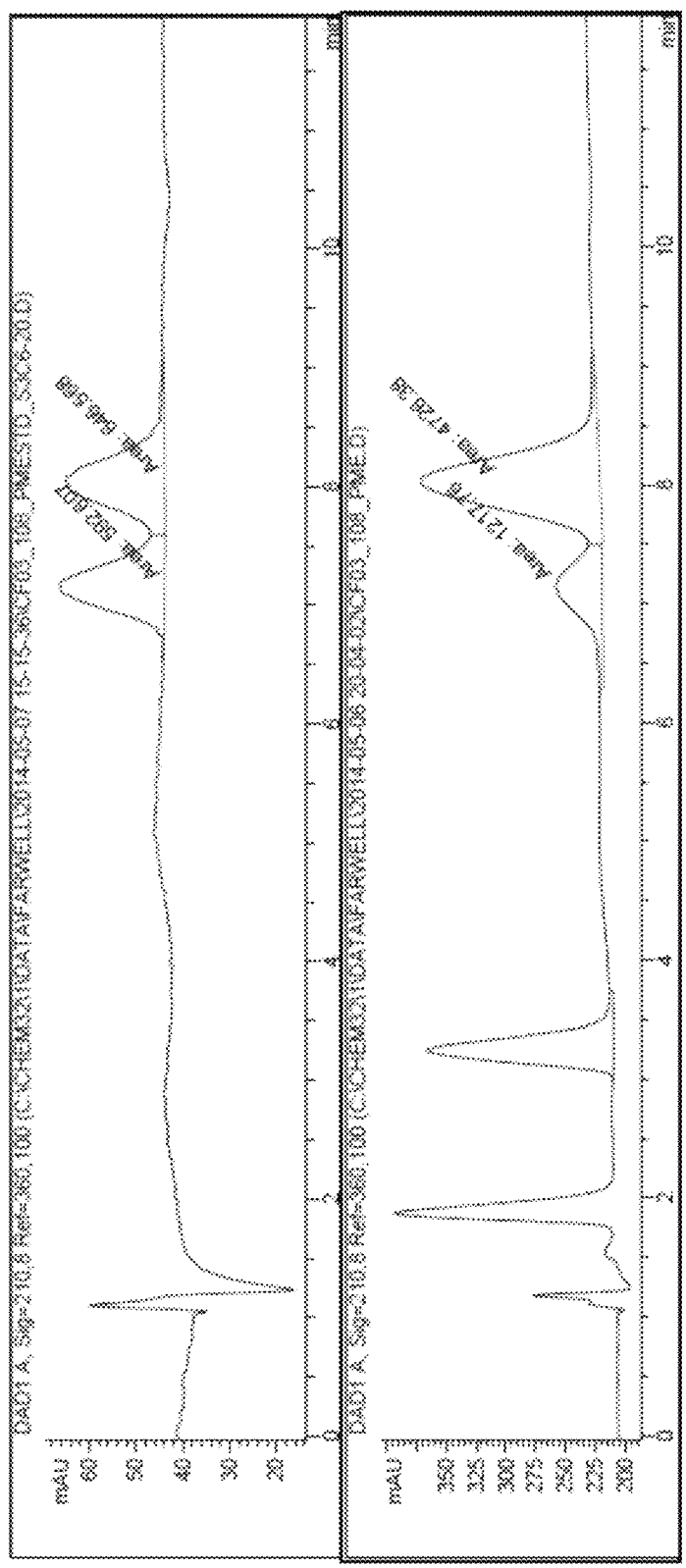
FIG. 9 shows: Top: SFC trace of 8b synthetic standard using Chiralpak OD-H column with 20% isopropanol/80% supercritical $CO_2$ mobile phase. Bottom: Trace of enzyme produced 8b.
Figure 10:
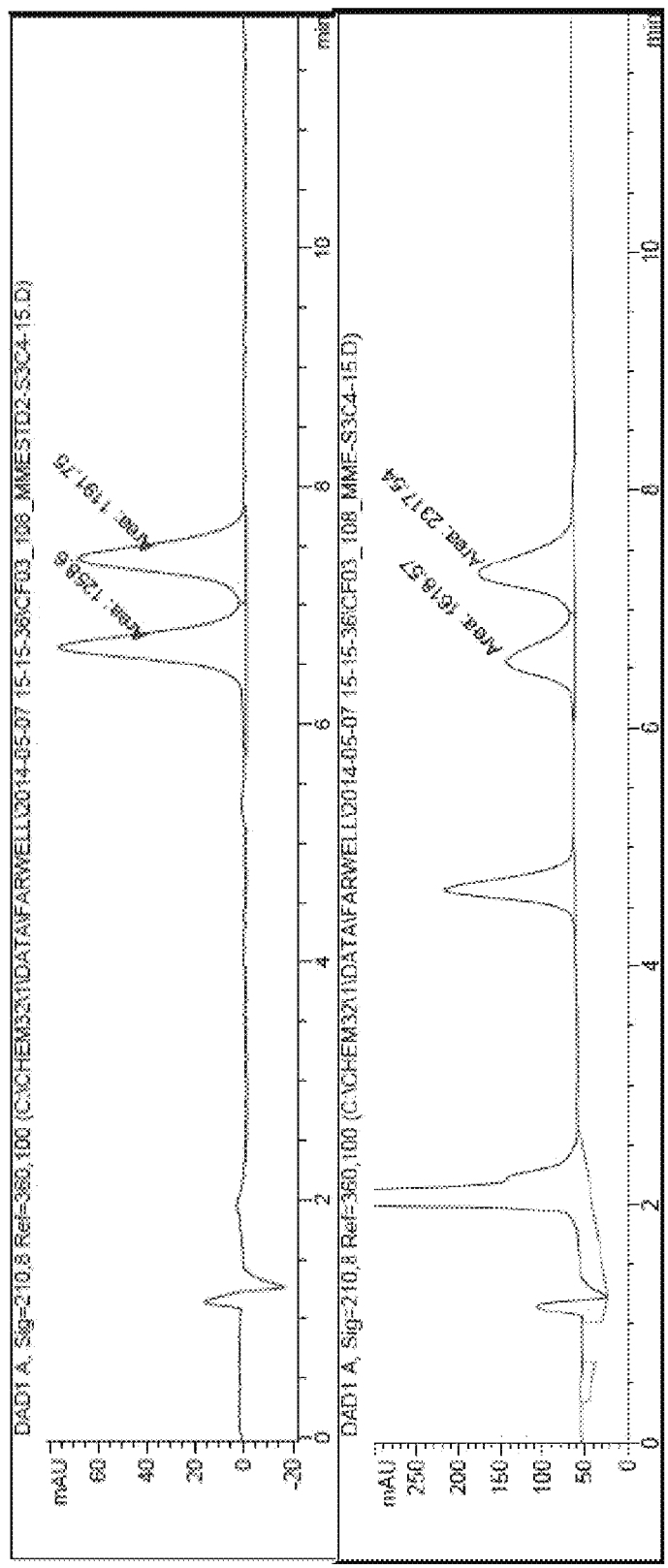
FIG. 10 shows: Top: SFC trace of 8c synthetic standard using Chiralpak OJ column with 15% isopropanol/85% supercritical $CO_2$ mobile phase. Bottom: Trace of enzyme produced 8c.
Figure 11:
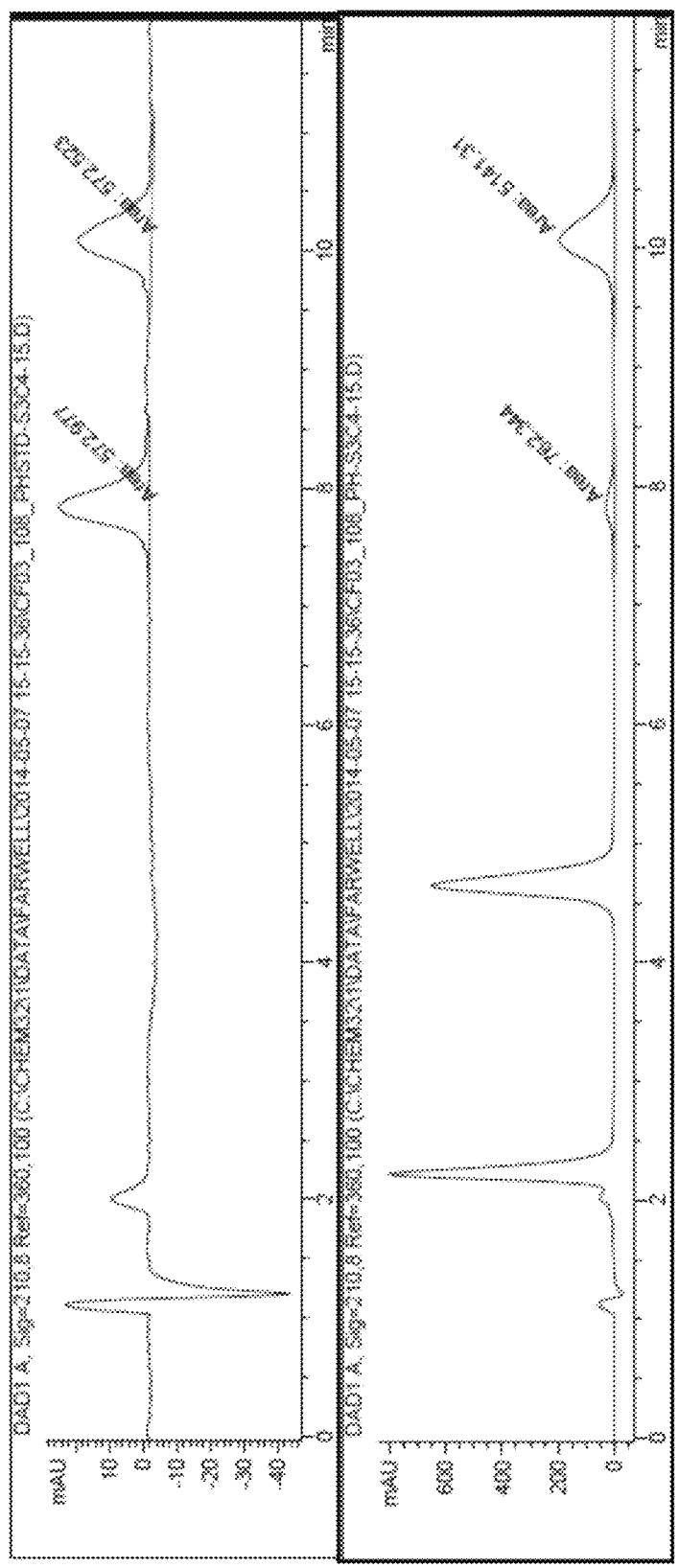
FIG. 11 shows: Top: SFC trace of 8d synthetic standard using Chiralpak OJ column with 15% isopropanol/85% supercritical $CO_2$ mobile phase. Bottom: Trace of enzyme produced 8d.

The key role of active site architecture in guiding reaction trajectory is further supported by the effects of amino acid substitutions on the reaction stereochemistry. Experiments shows that enzymes capable of producing an excess of either sulfimide enantiomer: e.g., P411BM3-CIS T438S gave an er of 74:26, while expanded active site variant P411BM3-H2-5-F10 exhibited the opposite selectivity, giving 29:71 (FIG. 8). Among the H2 mutants (which differ from P411BM3-CIS T438S by 3-5 amino acid substitutions, Table A), H2-5-F10 was alone in containing the I263A mutation, suggesting this mutation is relevant for enantiomeric inversion observed in the P411$_{BM3}$-H2-5-F10 variant. When the I263A mutation was placed in the P411BM3-CIS background, an even more pronounced inversion in selectivity was observed (er=18:82 for the P411$_{BM3}$-CIS I263A T438S variant, compared to 74:26 for P411$_{BM3}$-CIS T438S). This enzymatic system not only induces asymmetry in sulfimide products but also provides tunability in which selectivity can be switched with just a few mutations.

Previous studies of P450-catalyzed sulfoxidation as well as rhodium-catalyzed C—H amination suggest that the electronic properties of sulfide or alkyl acceptor substrates significantly impact reactivity. Thus, to better understand the mechanism of this new enzyme reaction, experiments were performed to establish how thioether electronic properties affected enzyme-catalyzed sulfimidation. A set of aryl sulfide substrates with substituents encompassing a range of electronic properties, from strongly donating to weakly withdrawing, were selected. As a first approximation of the effect of sulfide electronics, the total number of turnovers catalyzed by P411$_{BM3}$-CIS T438S was determined in the reactions of different sulfides with tosyl azide (Table C). In general, sulfides containing electron-donating substituents on the aryl sulfide ring were better substrates for sulfimidation. For example, the enzyme reaction containing 4-methoxythioanisole methoxythioanisole (7a) gave the highest levels of activity (300 TTN). In contrast, the electron-deficient p-aldehyde substrate (7e) gave only trace amounts of sulfimide product. Further, some azides that initially appeared entirely inactive gave small amounts of sulfimide products when reacted with 4-methoxythioanisole, underscoring the importance of sulfide electronics in this reaction (Table S4). The identity of substrates also exerted a modest influence on the enantioselectivity of sulfimidation. In particular, P411BM3-CIS T438S gave er values for substrates 8a-8d that ranged from 59:41 for 8c to 87:13 for 8d (Table S5, FIGS. S4-S6). While it is possible that some sulfides were poorer substrates due to the steric influence of the para substituent, the overall trend is strongly suggestive of electron induction to the aryl sulfide being a major contributor to activity. One notable aspect of these reactions is that significantly more sulfonamide (9) was produced when less reactive sulfides were used.

TABLE C

Impact of Sulfide Substituents on Sulfimidation Activity with P411$_{BM3}$-CIS T438S.

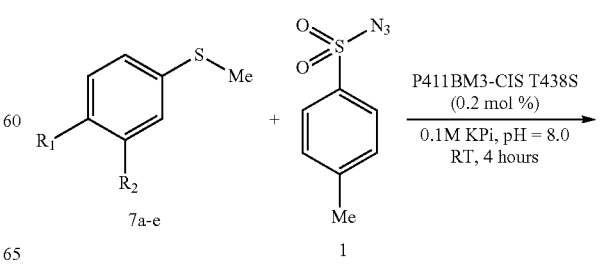

TABLE C-continued

[Structures: 8a-e showing tosyl sulfimide with R₁, R₂ substituents and Me group; 9 showing sulfonamide with Me group]

| entry | R₁ in 7 | R₂ in 7 | TTN 8 | TTN 9 |
|---|---|---|---|---|
| a | —OMe | —H | 300 | 270 |
| b | —Me | —H | 190 | 400 |
| c | —H | —Me | 100 | 390 |
| d | —H | —H | 30 | 500 |
| e | —CHO | —H | <1[a] | 510 |

[a]Trace product observed by liquid chromatography-mass spectrometry (LC-MS).

Figure 12:
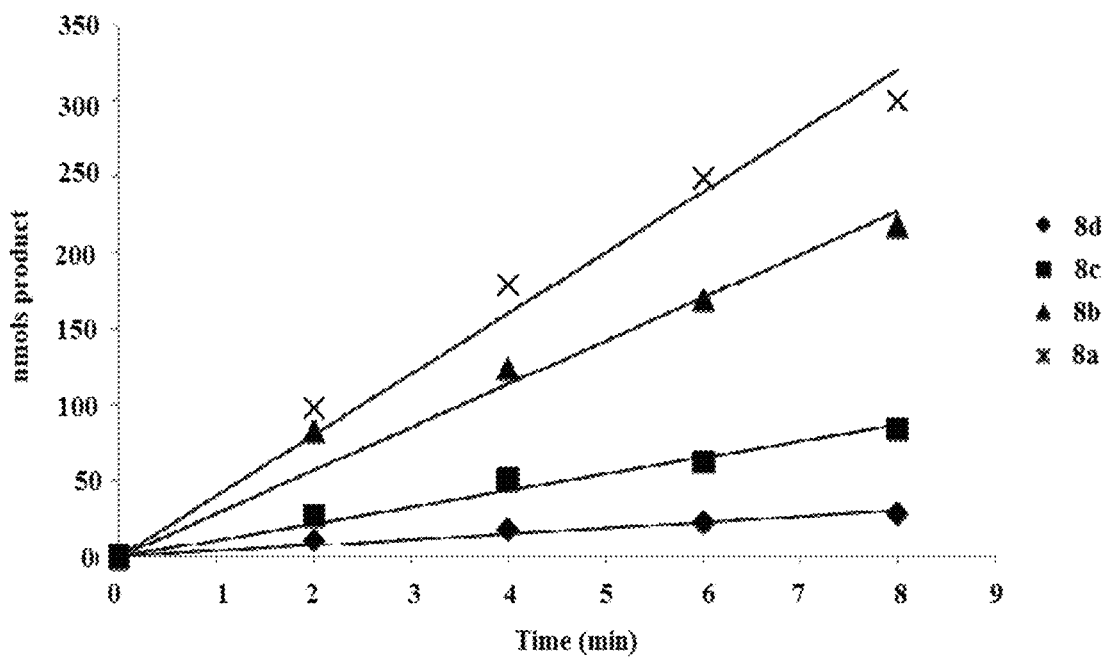
FIG. 12 shows Data used to determine initial rates for reaction of substituted aryl sulfides with tosyl azide, using $P411_{BM3}$-CIS T438S as catalyst. Sulfimide products measured are as listed in Table 2.

Although the total turnover data suggest that sulfide electronics influence reactivity, this result could also be due to other factors, such as substrate-dependent enzyme inactivation. To assess the effect of sulfide substituents on reactivity more directly, the initial rates of reaction of tosyl azide with the sulfides 7a-7d in Table 2 were measured. The initial rates correlated well with the total turnover data presented above, with p-OMe showing the highest rate of reaction (FIG. 12). Given this correlation, more mechanistic information was obtained by fitting the data to a Hammett plot that correlates the observed rates with each substituent's Hammett parameter. There was a strong, linear relationship with a Hammett value of p=−4.0 (FIG. 2), which suggests that during the rate-limiting step there is a buildup of positive charge on the sulfide that is stabilized by electron-donating substituents. This observation is consistent with Hammett values obtained for the oxidation of thioanisoles in P450-catalyzed sulfoxidation reactions, though the magnitude of p for sulfimidation is significantly greater than for sulfoxidation (−4.0 versus −0.2). One possible explanation for this difference is that the presumed nitrenoid intermediate of this reaction (FIG. 1) is a weaker oxidant than compound I, making the nucleophilicity of sulfur an important contributor to the rate of nitrenoid transfer. The large difference in the magnitude of p could also indicates a change in mechanism relative to P450 sulfoxidation: whereas sulfimidation may occur via direct nucleophilic attack of the thioether on the nitrenoid intermediate.

As noted above, a greater proportion of sulfonamide side product was formed when less reactive sulfides were used. The varying amounts of this side product prompted an examination of how sulfonamide might be produced. Experiments were performed to test the possibility that azide is reduced by some additive in the reactions (i.e., glucose oxidase, catalase, NADPH, etc.) by simply omitting the P450 enzyme from the reactions (Table 7). No-enzyme controls yielded very little reduced sulfonamide product (more than 10-fold lower than with enzyme present). While these experiments showed that enzyme was likely involved in azide reduction, this still left several possibilities. Since P411$_{BM3}$'s heme domain is fused to a reductase, there was the possibility that azide reduction occurs via direct hydride transfer from the reductase, as has been observed for aldehyde reductions. Thus, a carbon monoxide-inhibited reactions was used to investigate this possibility, since CO binding to the heme iron should have no effect on the reductase domain. In the presence of CO, there was a significant decrease in the sulfonamide produced, suggesting that azide reduction occurs at the heme. Furthermore, only trace sulfonamide was observed when reactions were conducted in the presence of oxygen, further supporting the involvement of reduced heme in azide reduction. Since all the available evidence suggests that azide reduction and sulfimide formation both occur at the heme, the most parsimonious explanation is that both reactions stem from a common intermediate that can give rise to both sulfonamide and sulfimide products.

A proposed mechanism of sulfonamide and sulfimide formation begins with the iron(III) heme gaining an electron from NADPH via the flavin cofactors of the reductase domain (FIG. 3). Addition of azide substrate results in formation of a formal iron(IV) nitrenoid, which can either be reduced by subsequent electron transfer or "trapped" by sulfide to form sulfimide product. A second electron transfer followed by protonation of the nitrenoid is proposed to generate sulfonamide which restores the heme iron to its ferric state, and additional reductant is required to return to the catalytically active ferrous state (FIG. 3, unproductive pathway).

To test whether ferric heme is involved in the unproductive pathway, the change in the visible absorbance spectrum of the reduced holoenzyme P411$_{BM3}$-CIS I263A T438S was monitored upon addition of NADPH followed by azide. The Ser-ligated P411 proteins exhibit different absorbance properties in the ferric and ferrous states compared with their Cys-ligated counterparts, such that the ferric, ferrous, and CO-ferrous Soret bands are shifted from 418, 408, and 450 nm to 405, 422, and 411 nm, respectively (FIG. 12). When NADPH was added to a solution of enzyme under an anaerobic atmosphere, a reduction of the heme from the ferric to the ferrous state was observed. When a degassed solution of azide was added to the ferrous protein, an immediate shift back to the ferric state was observed, with concomitant production of sulfonamide, verified by high-performance liquid chromatography (HPLC). This observation suggests that the unproductive azide reduction pathway occurs readily in the absence of sulfide and that, when provided only with azide, the catalyst rests in the ferric state.

Figure 14:
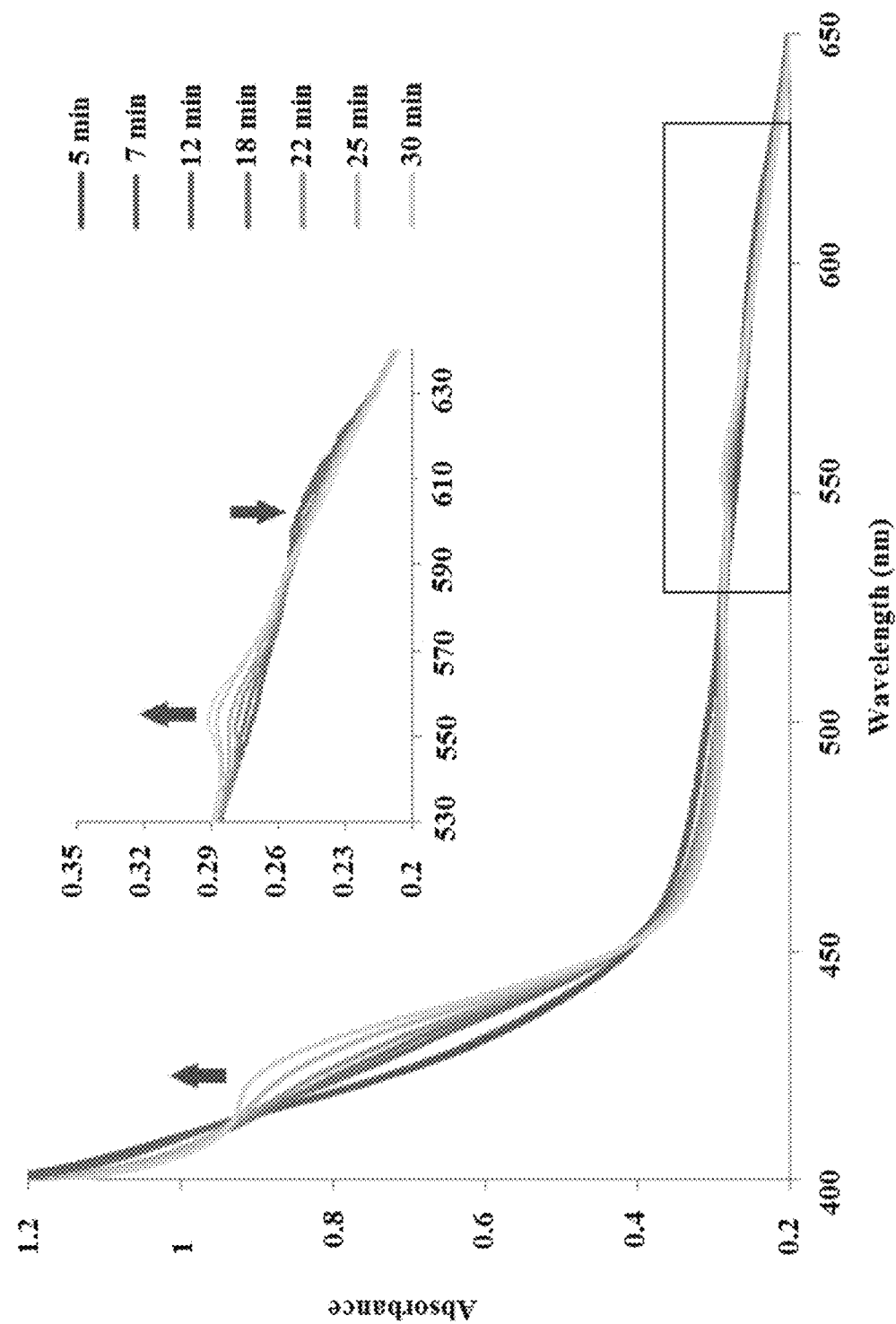
FIG. 14 shows the monitoring the iron heme during the sulfimidation reaction with azide and sulfide.

To determine the resting state of the P411 catalyst in sulfimidation, the above experiment were repeated in the presence of both sulfide and azide. Addition of sulfide to a solution of enzyme and NADPH results in no change in the Q or Soret bands, with the iron heme remaining in the ferrous state. However, addition of azide to this solution causes the iron heme to shift to the ferric state. After 10 min, peaks corresponding to the ferrous heme begin to grow until the ferrous heme becomes the dominant species at 30 min (FIG. 14). Both sulfonamide and sulfimide products are formed throughout the course of the reaction. The observations are consistent with the competing reaction pathways outlined in FIG. 3 and suggest that the catalyst rests as a mixture of ferric and ferrous hemes during sulfimidation. When the concentration of azide is high, as it is at the beginning of the reaction, the unproductive pathway is favored, and a ferric resting state dominates. As azide is consumed, both the ferric and ferrous resting states can be observed.

P450 monooxygenases are known to undergo an "oxidase uncoupling" side reaction in which compound I is reduced by two electrons to give water, which bears some similarity to the process of azide reduction observed here. One difference, however, is that only a single electron transfer is required to attain a reactive state in nitrene-transfer chemistry. This stands in contrast to P450 monooxygenase chemistry, where the generation of compound I from $O_2$ requires the transfer of two electrons. Thus, one explanation for the relatively high proportion of reduced azide in these reactions is that the electron-transfer machinery in $P450_{BM3}$ is evolved to carry out two-electron reductions. In the case of nitrene transfer chemistry, reducing the ferric heme to the +2 state allows nitrenoid formation, but a second electron transfer would generate an unreactive iron(III) sulfonamide complex, as proposed for intramolecular C—H amination. Coupled with the fact that lower sulfide concentrations and less-reactive sulfides lead to increased azide reduction, these observations are consistent with the mechanism discussed above in which sulfimide formation competes with azide reduction. Since electron transfers from the reductase domain are quite rapid, relatively reactive sulfides can successfully compete with reduction to form sulfimide.

Figure 15:
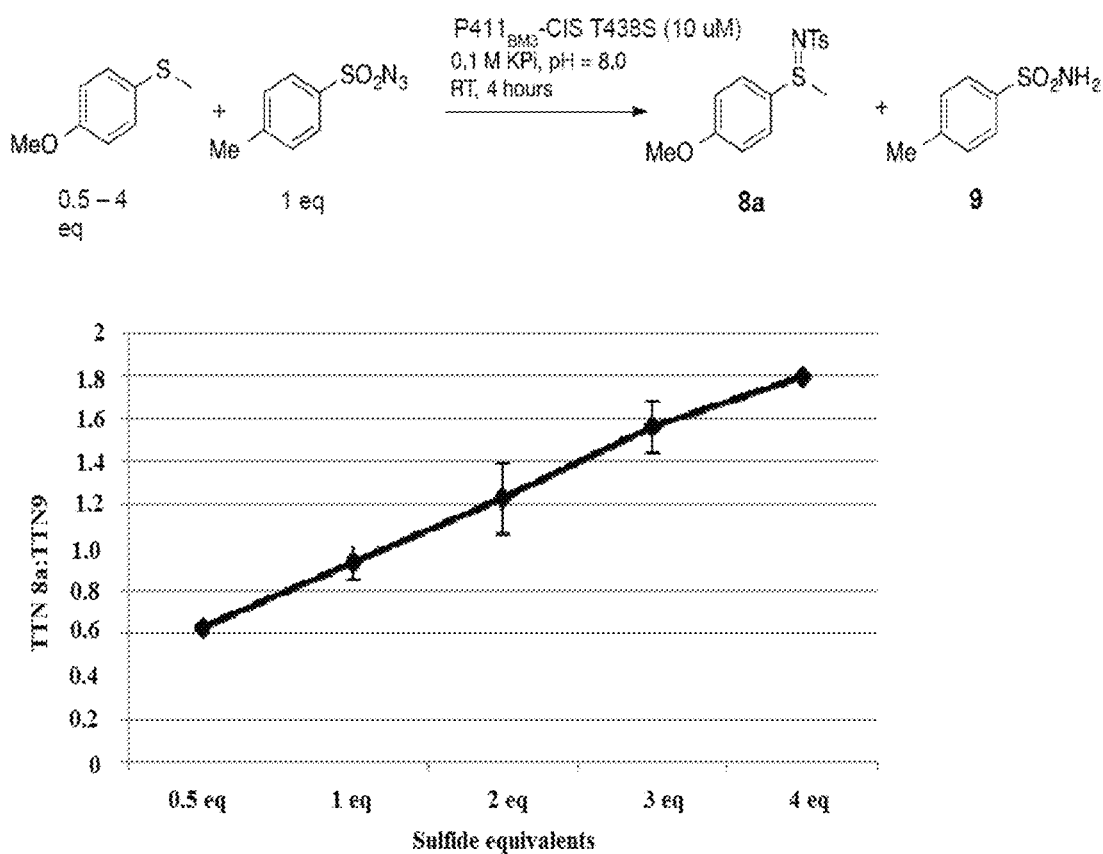
FIG. 15 shows the ratio of sulfimide TTN to sulfonamide TTN as sulfide concentration is varied, using $P411_{BM3}$-CIS T438S enzyme, as shown in the scheme. Reactions were prepared with azide concentration held constant at 1 mM and sulfide concentration varied from 0.5 mM to 4 mM.
Figure 16:
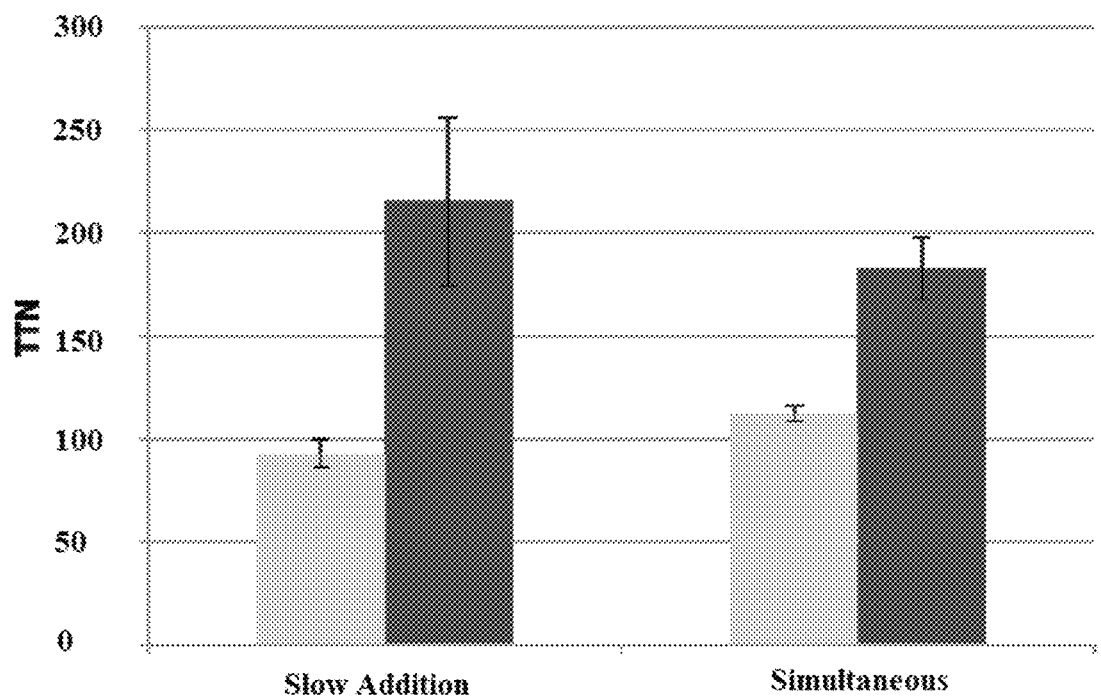
Figure 17:
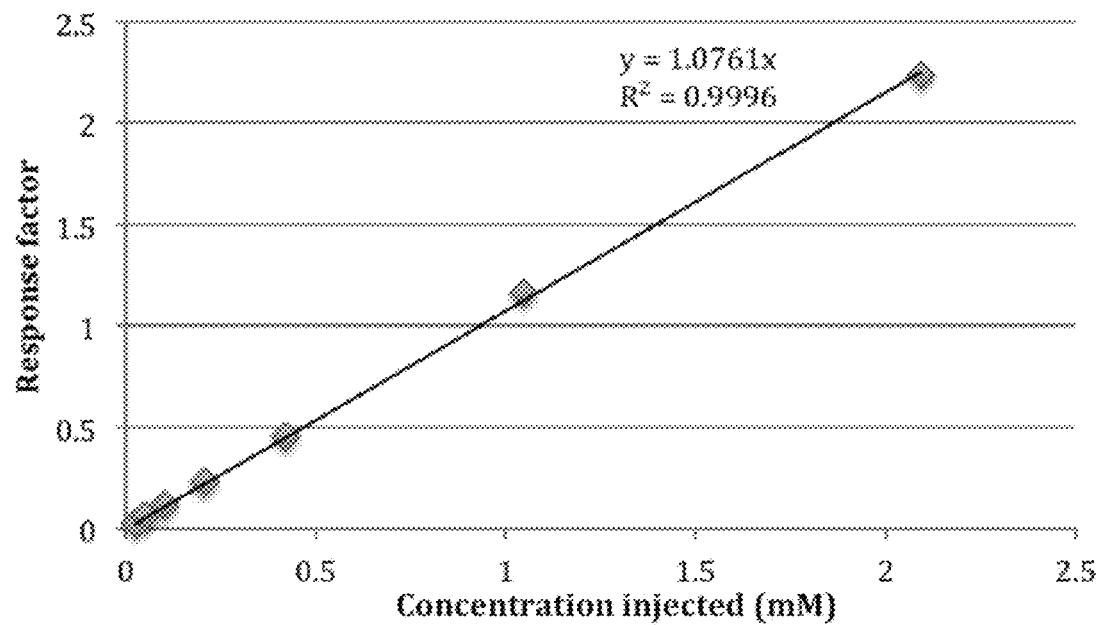
FIG. 17 shows a standard curve for product 8a, shows in response factor as ratio of product area to internal standard area.
Figure 18:
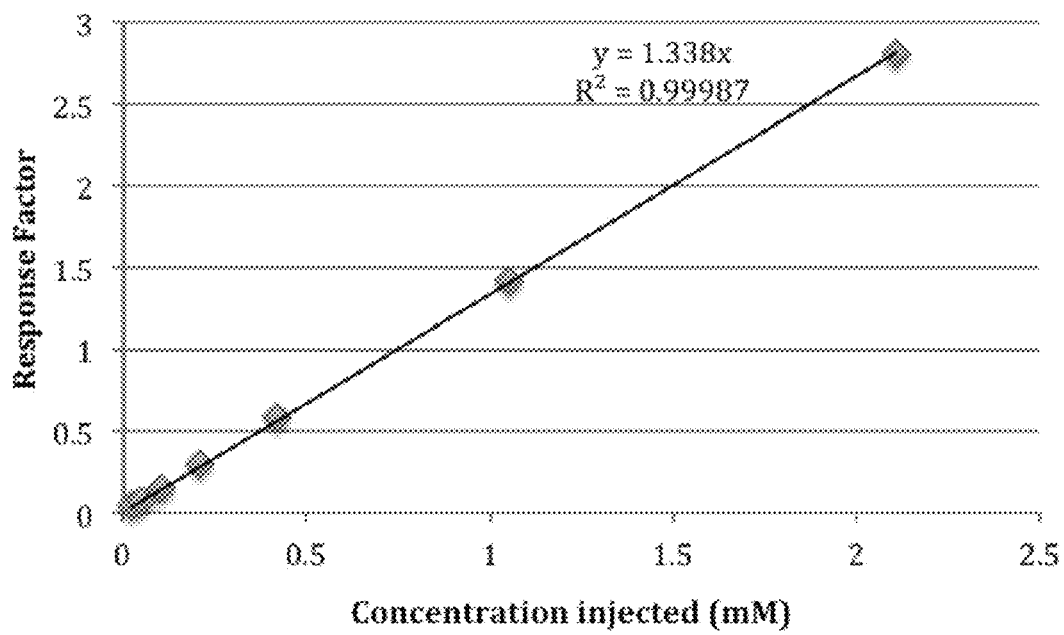
FIG. 18 shows the standard curve for product 8b.
Figure 19:
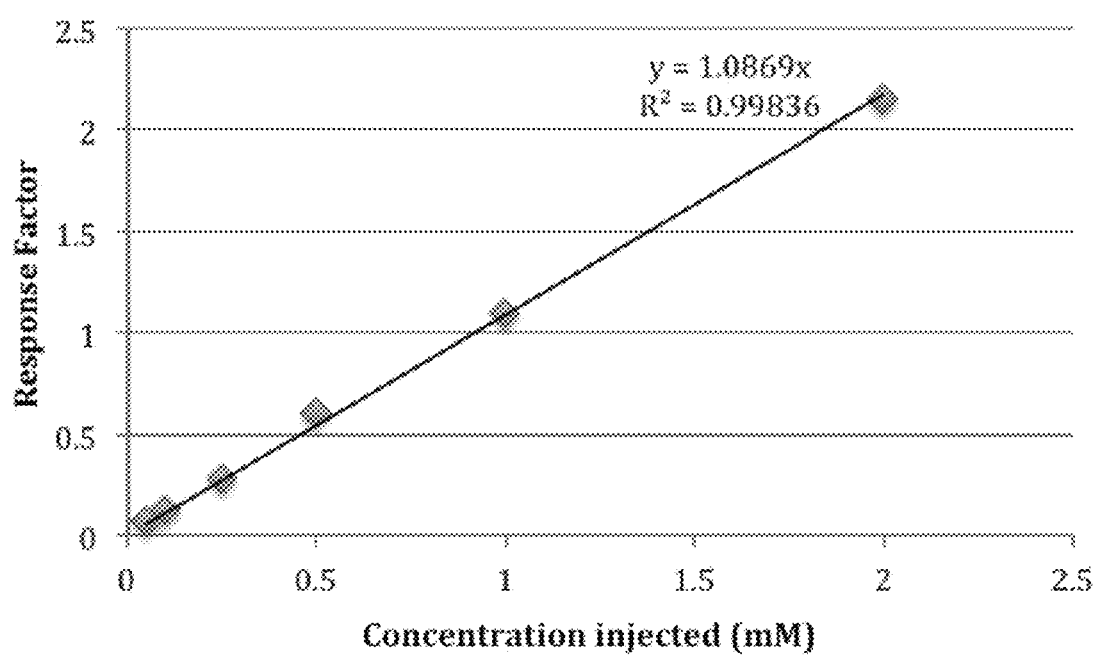
FIG. 19 shows the standard curve for product 8c.
Figure 20:
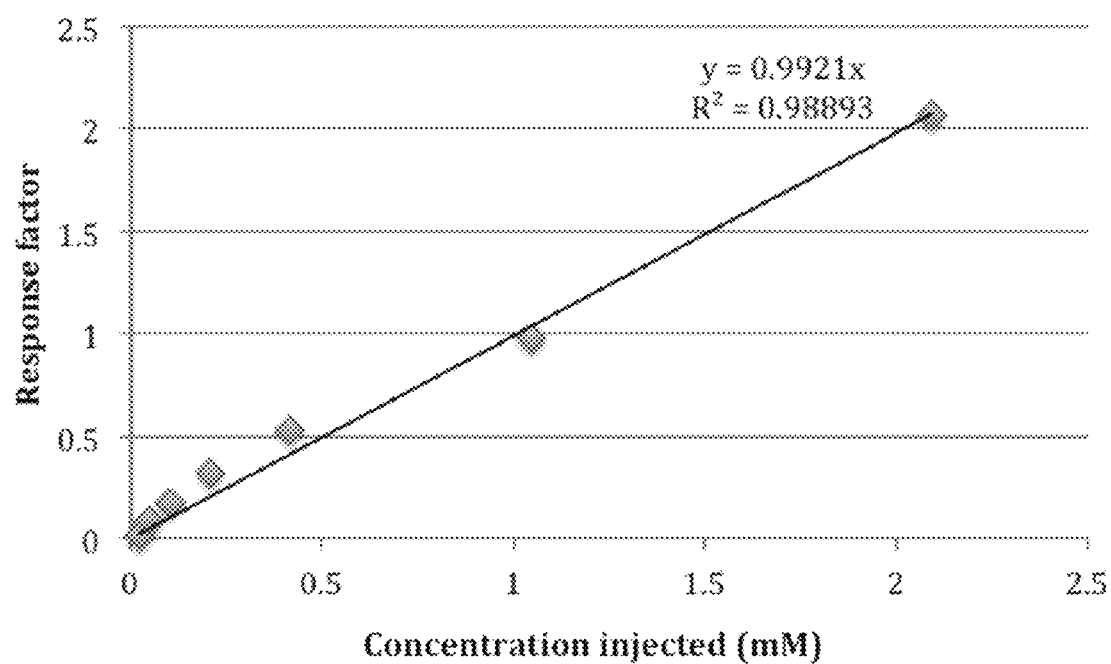
FIG. 20 shows the standard curve for product 8d.
Figure 21:
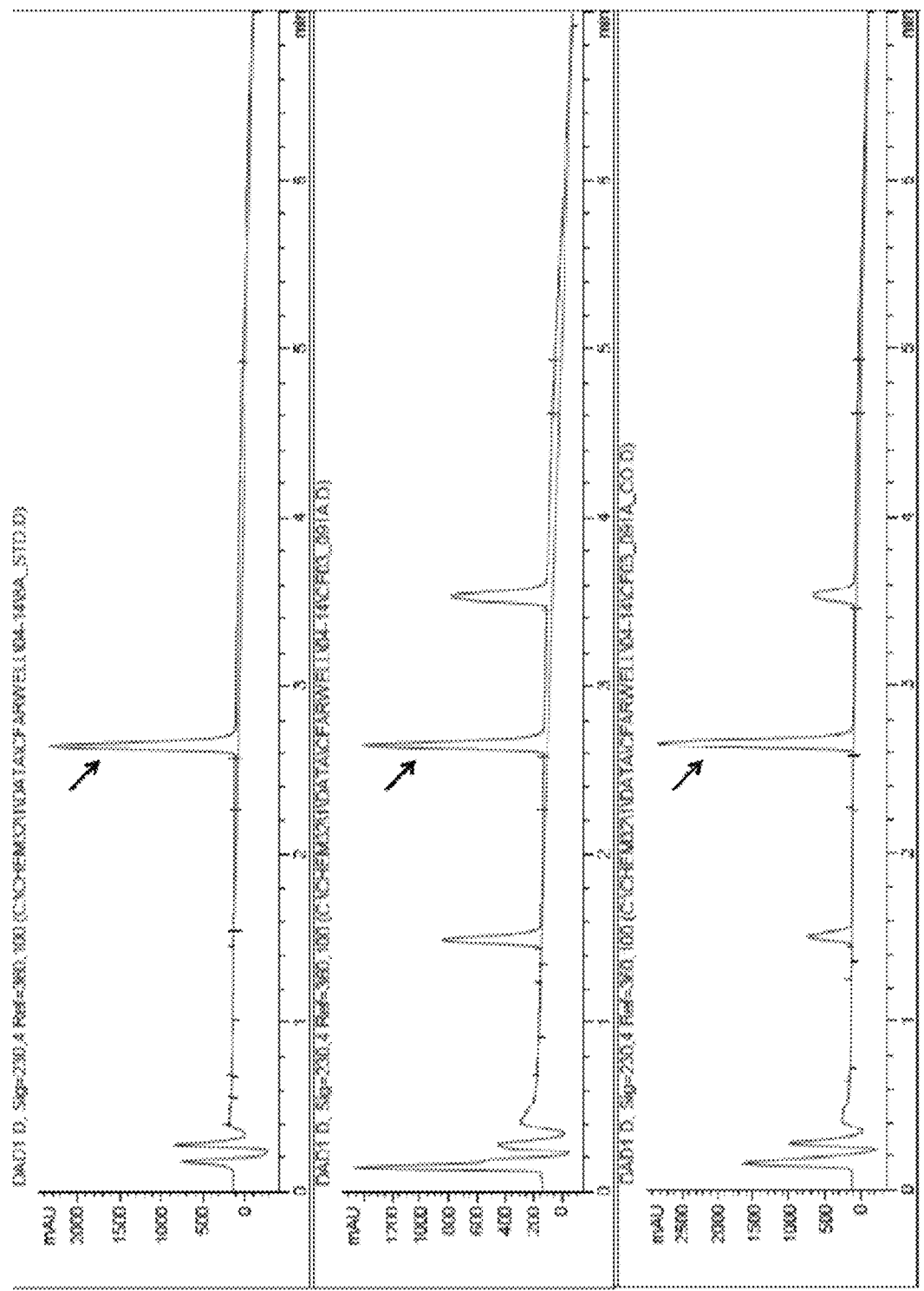
FIG. 21 shows a demonstration of enzymatic production of 8a. Top: LC-MS 230 nm chromatogram of synthetic standard of 8a, confirmed by NMR. Middle: Enzyme reaction containing putative 8a. Bottom: Mixture of enzyme reaction and synthetic 8a, showing coelution.
Figure 22:
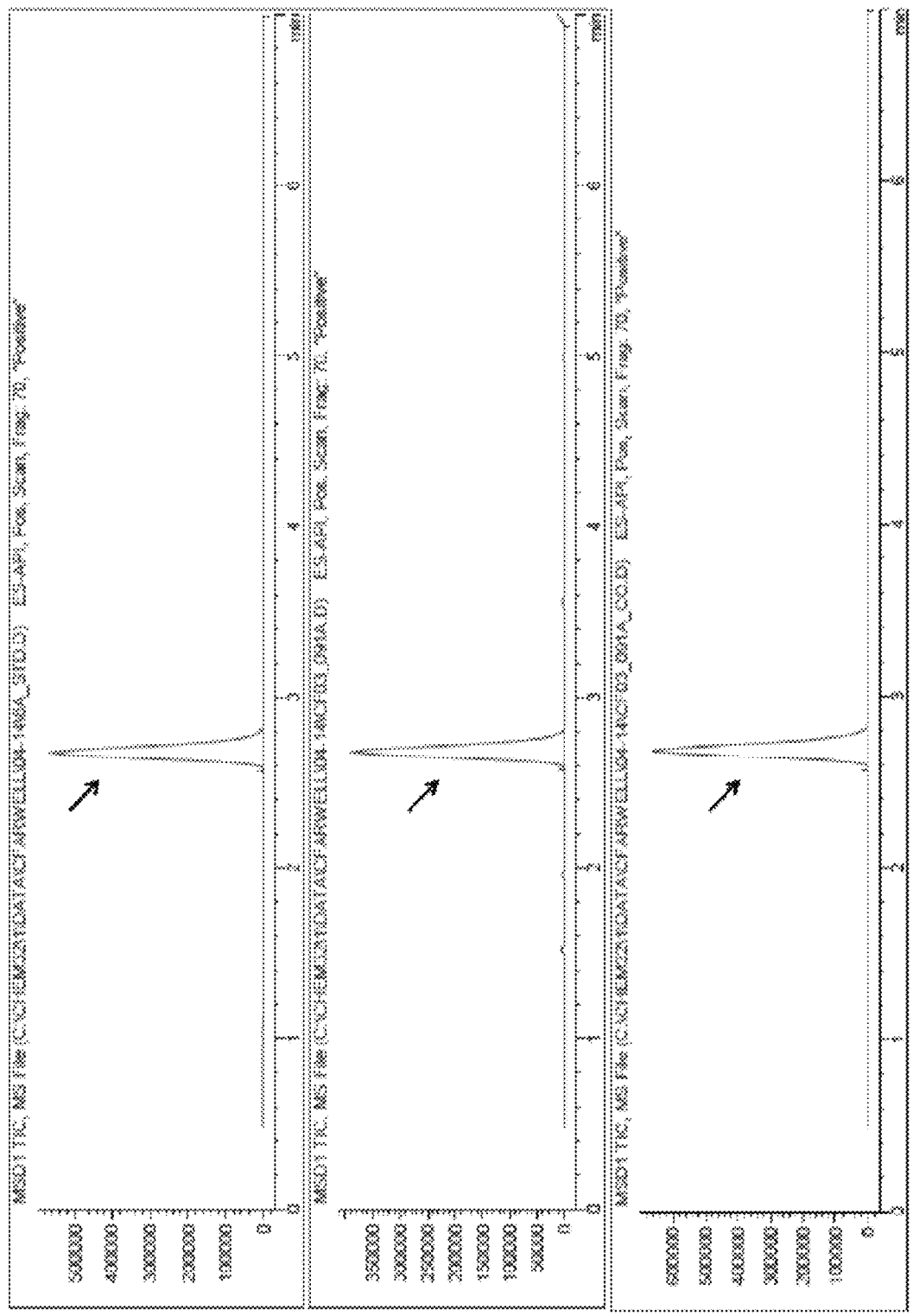
FIG. 22 shows LC runs from FIG. 21 showing ESI-MS-(+) detection of total ion chromatogram (TIC) (major peak=324, corresponding to 8a M+H+).
Figure 23:
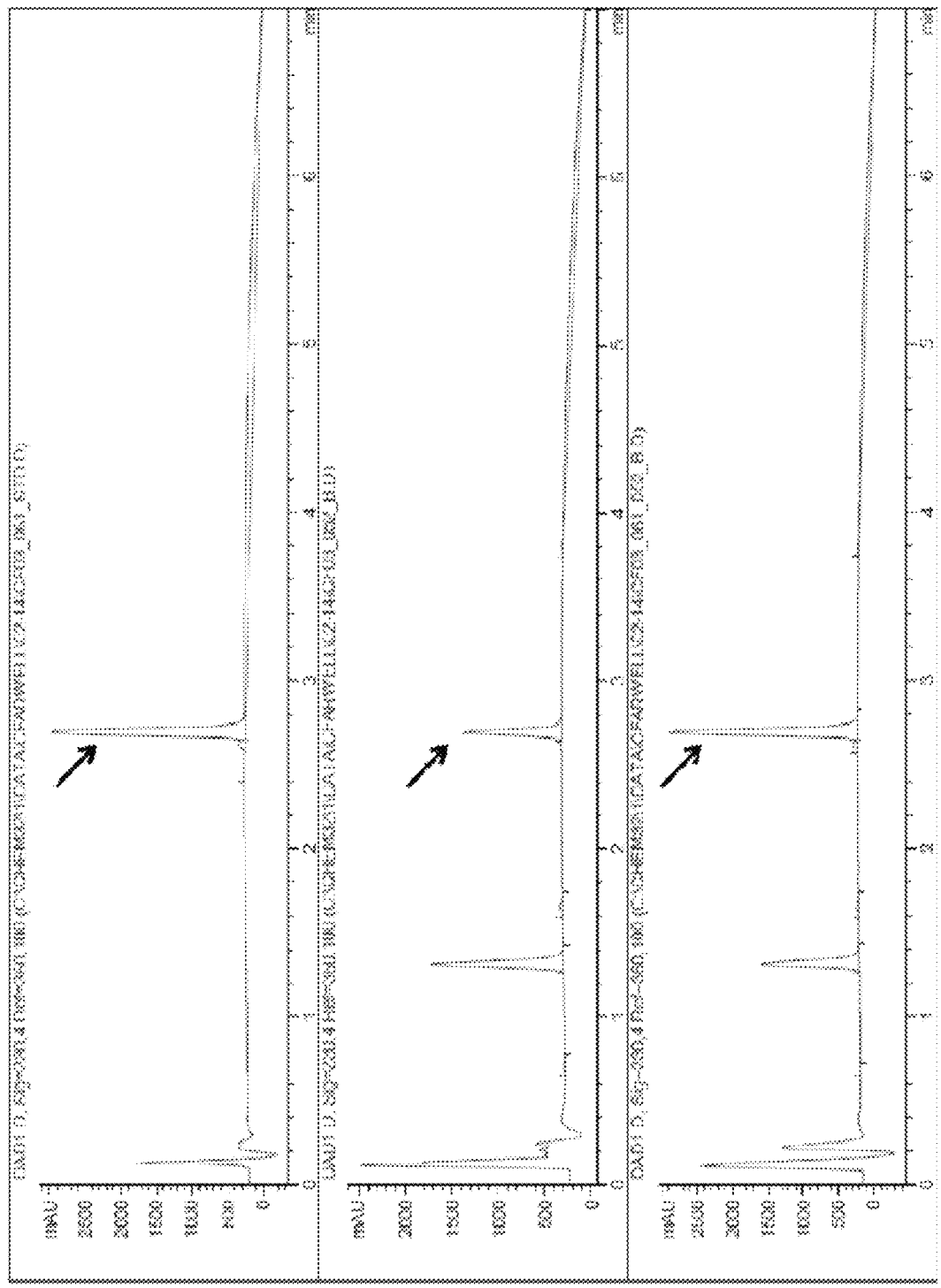
FIG. 23 shows a demonstration of enzymatic production of 8b. Top: LC-MS 230 nm chromatogram of synthetic standard of 8b, confirmed by NMR. Middle: Enzyme reaction containing putative 8b. Bottom: Mixture of enzyme reaction and synthetic 8b, showing coelution.
Figure 24:
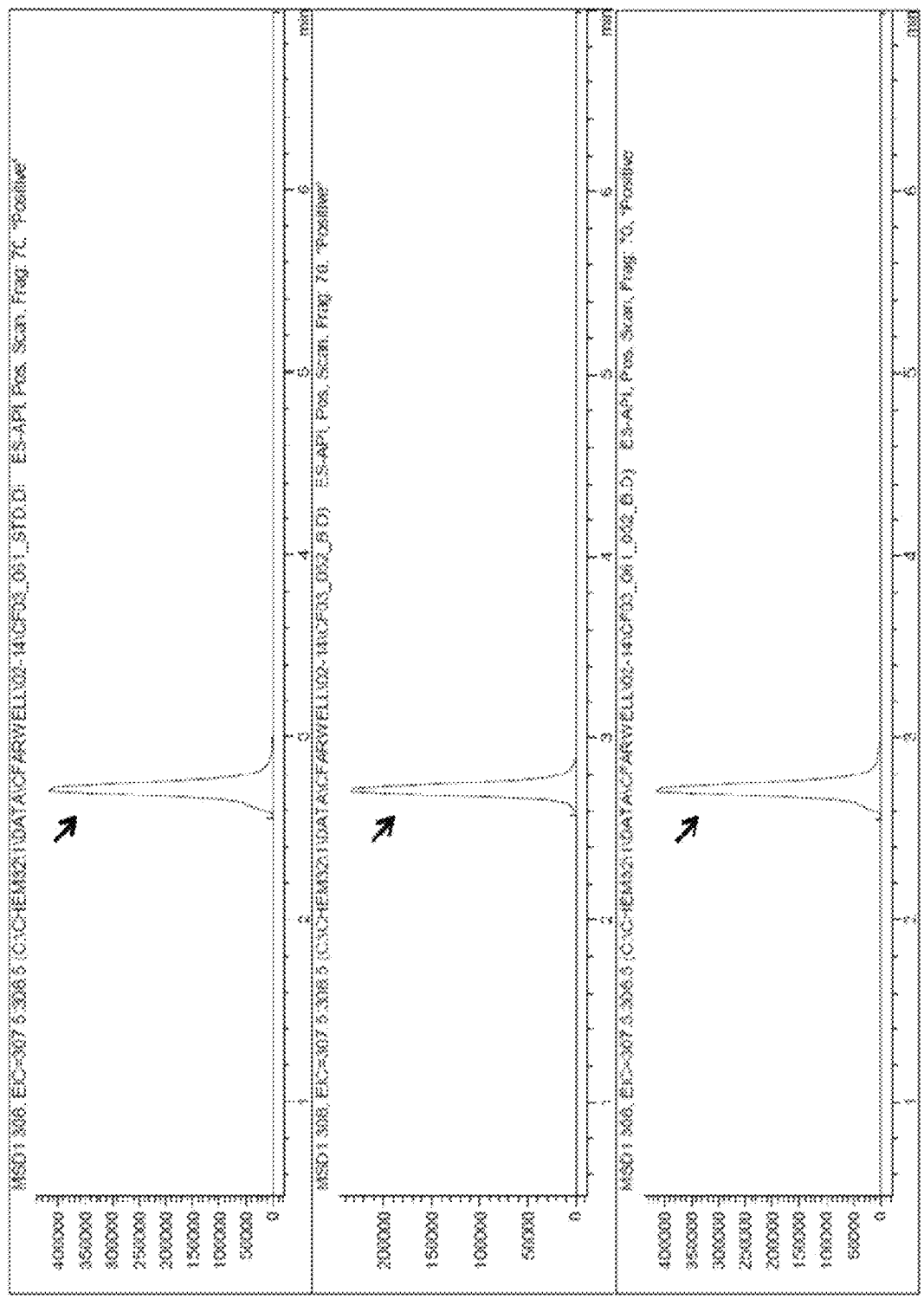
FIG. 24 shows LC runs from FIG. 23 showing ESI-MS-(+) detection of selected ions (mass window 307.5-308.5).
Figure 25:
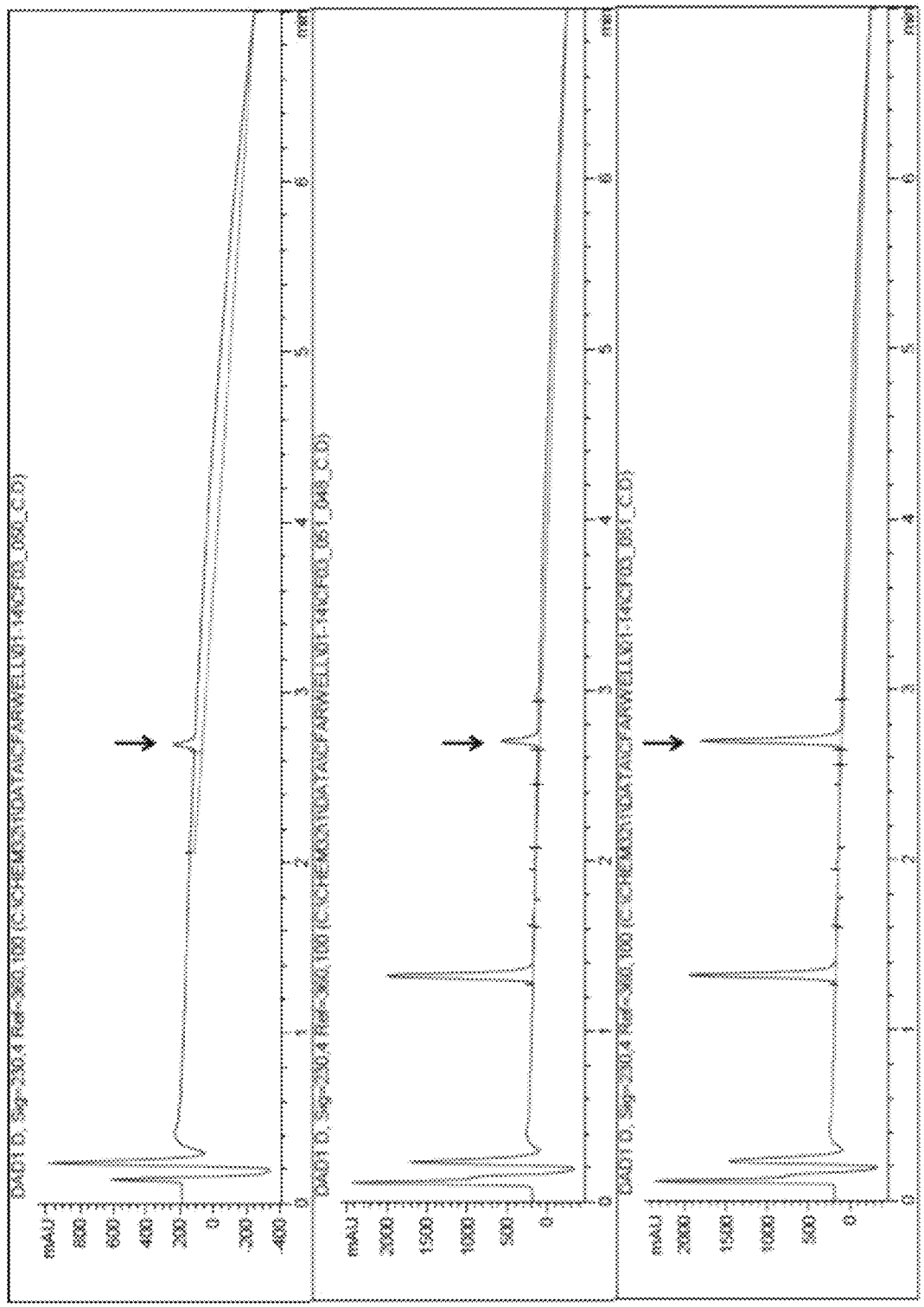
FIG. 25 shows a demonstration of enzymatic production of 8c. Top: LC-MS 230 nm chromatogram of synthetic standard of 8c, confirmed by NMR. Middle: Enzyme reaction containing putative 8c. Bottom: Mixture of enzyme reaction and synthetic 8c, showing coelution.
Figure 26:
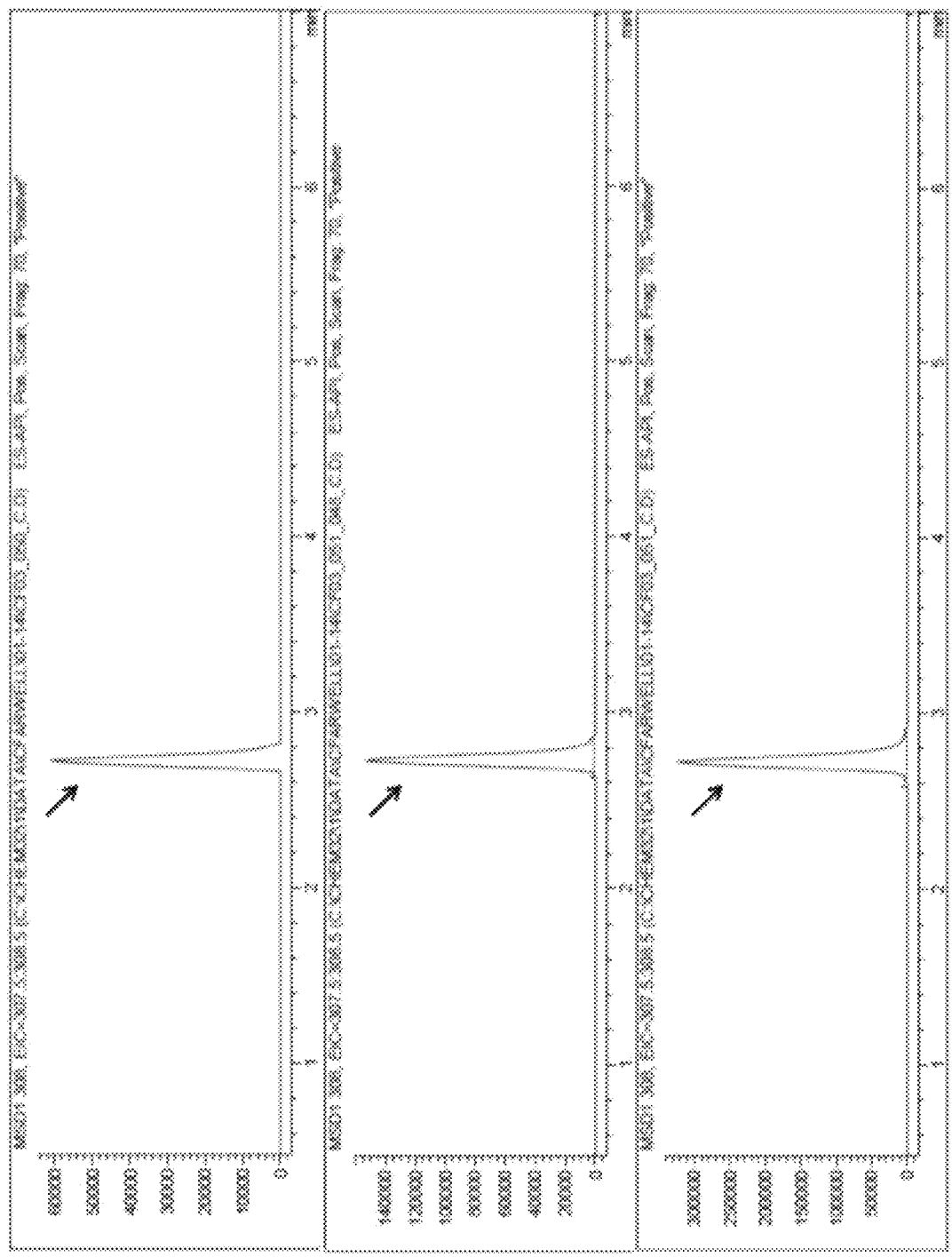
FIG. 26 shows LC runs from FIG. 25 showing ESI-MS-(+) detection of selected ions (mass window 307.5-308.5).
Figure 27:
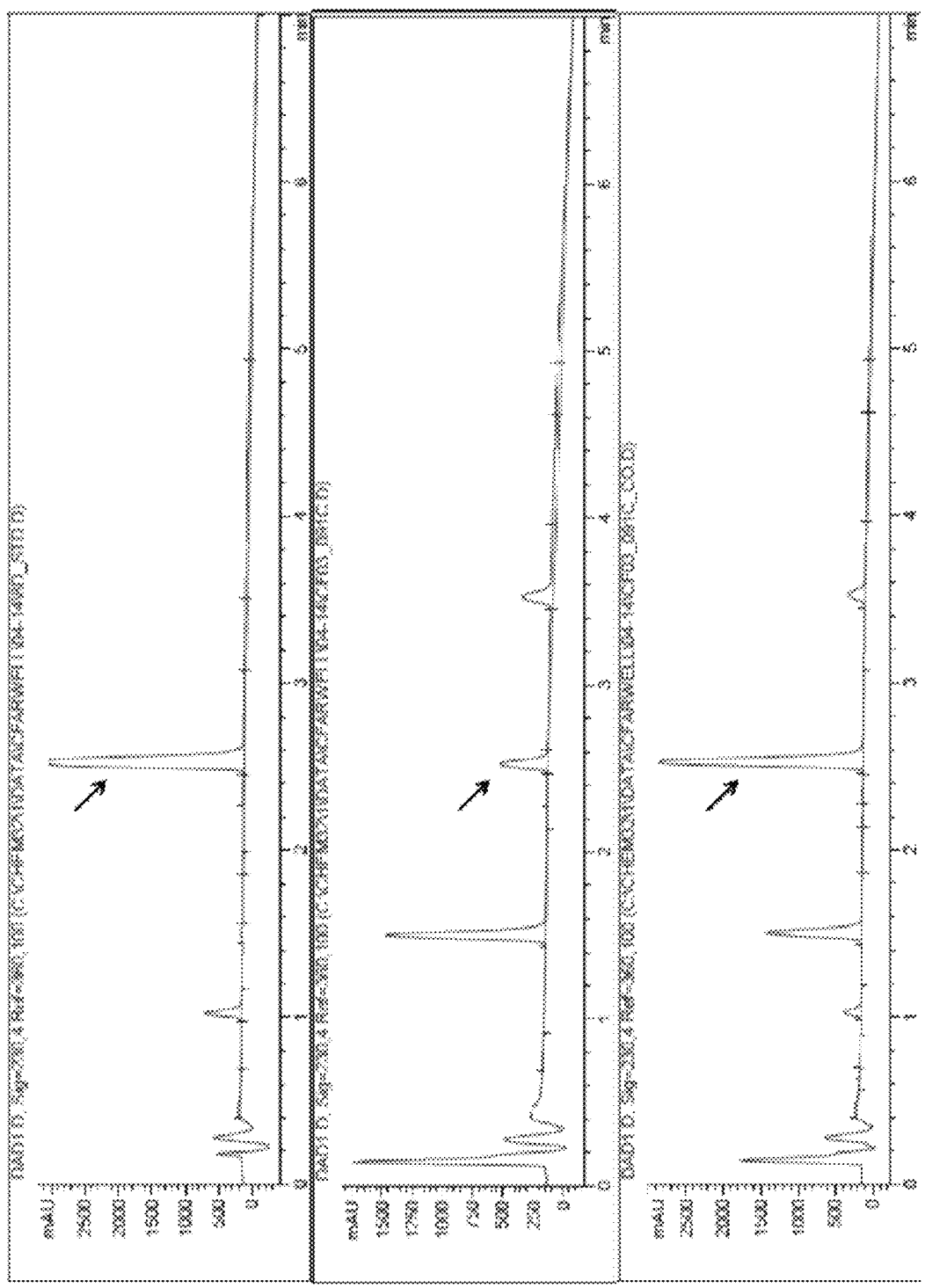
FIG. 27 shows a demonstration of enzymatic production of 8d. Top: LC-MS 230 nm chromatogram of synthetic standard of 8d, confirmed by NMR. Middle: Enzyme reaction containing putative 8d. Bottom: Mixture of enzyme reaction and synthetic 8d, showing coelution.
Figure 28:
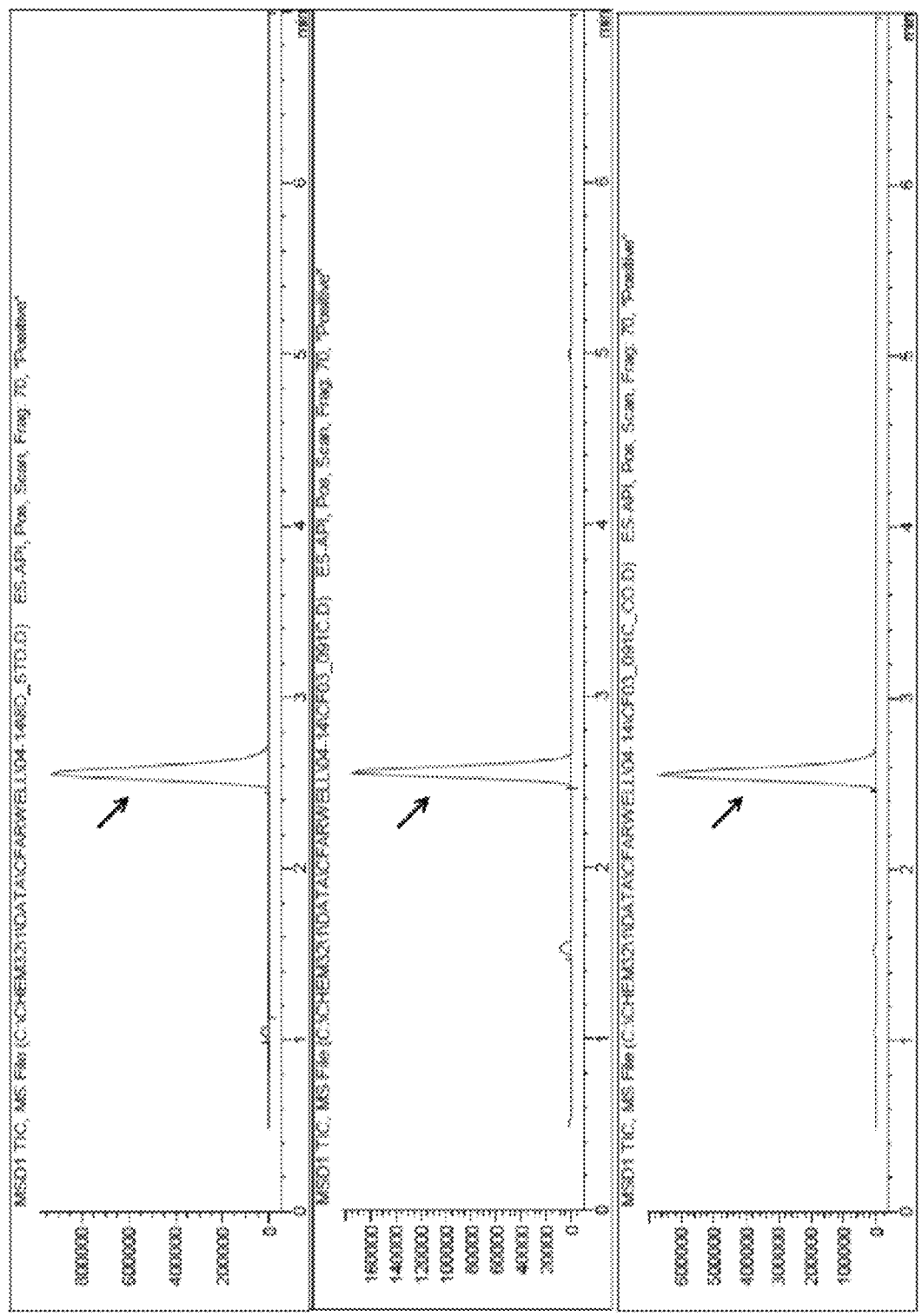
FIG. 28 shows LC runs from FIG. 27 showing ESI-MS-(+) detection of total ion chromatogram (TIC) (major peak=294 m/z, corresponding to 8d M+H+).
Figure 29:
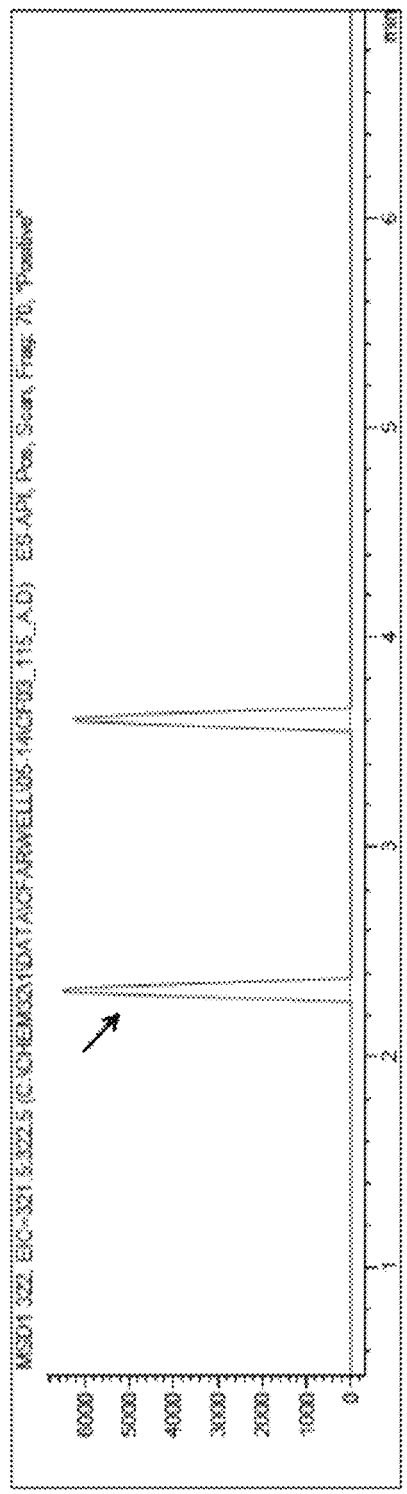
FIG. 29 shows LC runs from reaction with $P411_{BM3}$-CIS T438S with substrate 7e showing ESIMS-(+) detection of selected ions (mass window 321.5-322.5 m/z), demonstrating production of 8e.
Figure 30:
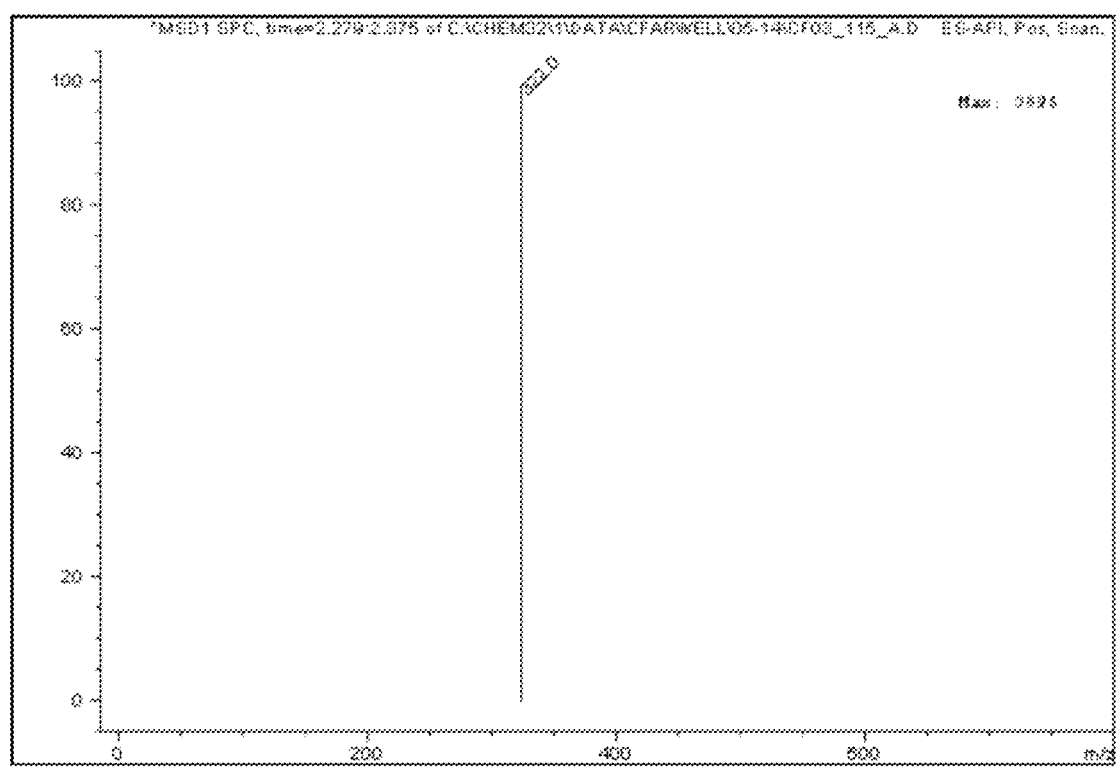
FIG. 30 shows a mass spectrum of peak identified in FIG. 29, showing M+H+ of product 8e.
Figure 31:
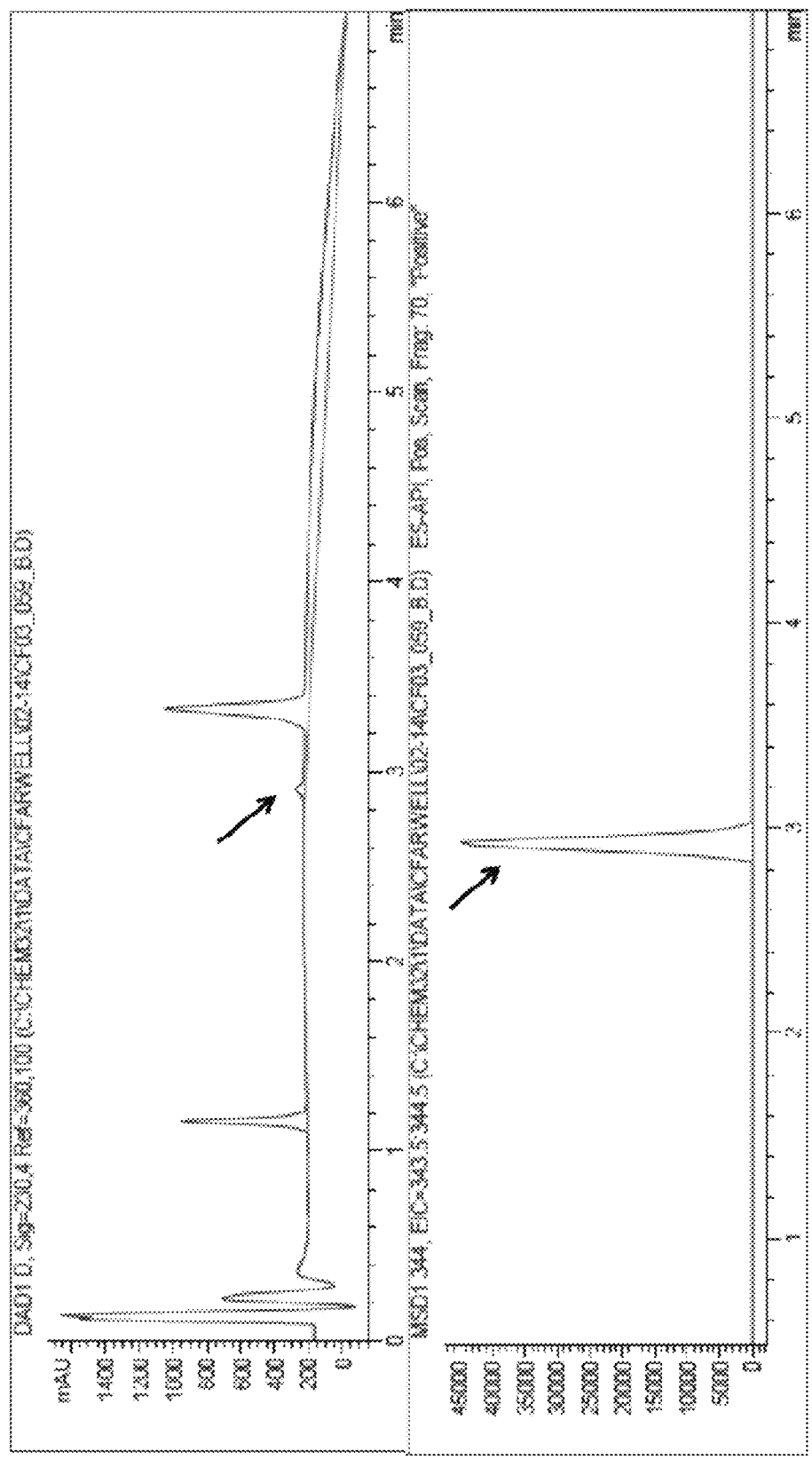
FIG. 31 shows an LC-MS chromatogram showing UV trace at 230 nm (top) and selected ions for 344 m/z, corresponding to the M+H+ mass of the product of azide 2 with sulfide 7a. Note TIC timescale differs due to instrument solvent delay.
Figure 32:
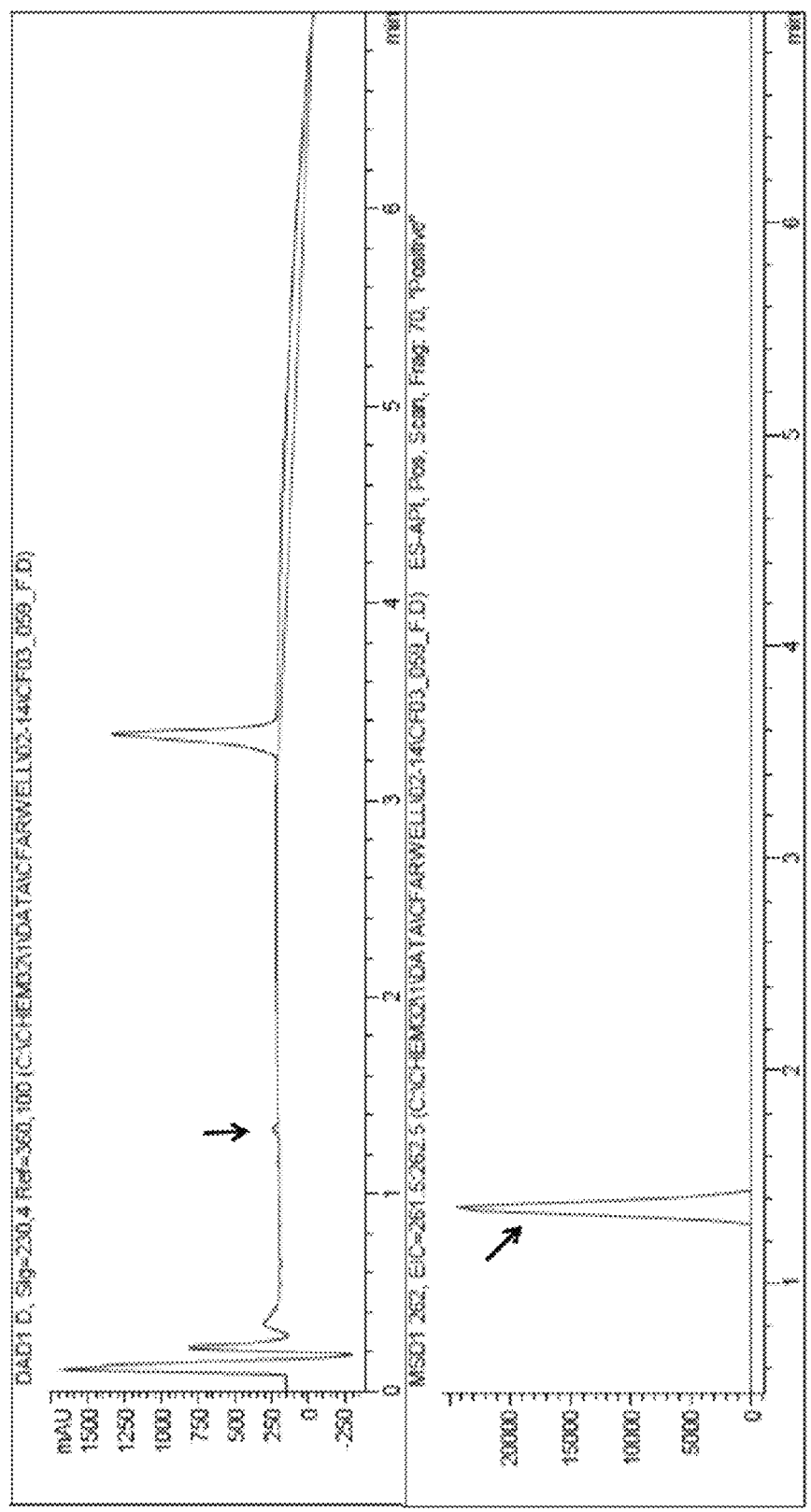
FIG. 32 shows an LC-MS chromatogram showing UV trace at 230 nm (top) and selected ions for 262 m/z, corresponding to the M+H+ mass of the product of azide 4 with sulfide 7a. Note TIC timescale differs due to instrument solvent delay.

The mechanistic picture described above suggests that achieving higher levels of sulfide occupancy in the active site should favor sulfimide formation and inhibit azide reduction. This could be achieved with tighter binding of the sulfide acceptor substrate or by increasing the concentration of sulfide relative to azide. Accordingly, experiments were performed with excess sulfide or slow addition of azide to determine if increased sulfimide formation could be obtained relative to sulfonamide. Increasing the sulfide concentration decreased reduction of azide to sulfonamide and improved the ratio of sulfimide to sulfonamide, from 0.6 (with 0.5 equiv sulfide) to 1.8 (with 4 equiv sulfide) (FIG. 15, Table D). Slow azide addition slightly increased the TTN for sulfimide and decreased sulfonamide formation in a 2 h reaction (FIG. 16). That higher concentrations of sulfide substrate improve sulfimide production suggests that protein engineering can be used to improve the binding of sulfide acceptor substrates and could also produce strong gains in the desired activity. Indeed, the specific activities of the enzyme catalysts reported here compare favorably with enantioselective iron-based catalysts, which routinely require catalyst loadings of 10 mol %. Furthermore, engineering the holoenzyme or reductase domain to favor one electron transfers might improve the proportion of desired product relative to azide reduction, which could allow reaction with more challenging organic acceptor substrates.

TABLE D

Production of sulfimide 8a and sulfonamide 9 in the presence of varying levels of sulfide acceptor substrate.

| Sulfide | Azide | TTN 8a | TTN 9 |
|---|---|---|---|
| 0.5 eq | 1 eq | 71 | 110 |
| 1 eq | 1 eq | 97 | 100 |
| 2 eq | 1 eq | 110 | 93 |
| 3 eq | 1 eq | 130 | 85 |
| 4 eq | 1 eq | 140 | 80 |

A C400S mutation (as described herein) for sulfimidation can be rationalized that the less electron-donating axial serine ligand in P411 enzymes likely makes the nitrenoid species a more potent oxidant. The impact of sulfide substituents on sulfimide formation is also reflected in the generation of sulfonamide side product, suggesting the nitrenoid undergoes rapid reduction and can be productively insert into reactive sulfides. Characterization of the redox state of the heme iron in the presence and absence of nitrene source and sulfide acceptor supports the proposal that nitrenoid "overreduction" competes with productive sulfimide formation and that the former is a two-electron process resulting in regeneration of ferric heme. Another interesting aspect of this enzyme reaction is the use of an aryl sulfonylazide nitrene source. The ability of the enzyme to accept larger aryl substrates may be beneficial for development of enantioselective intermolecular nitrene-transfer catalysts. Intermolecular nitrene transfer in the form of sulfimidation can now be added to the impressive array of cytochrome P450 enzymes.

General.

Unless otherwise noted, all chemicals and reagents for chemical reactions were obtained from commercial suppliers (Sigma-Aldrich, VWR, Alfa Aesar) and used without further purification. Silica gel chromatography purifications were carried out using AMD Silica Gel 60, 230-400 mesh. 1H spectra were recorded on a Varian Inova 500 MHz instrument in CDCl3, and are referenced to the residual solvent peak. Synthetic reactions were monitored using thin layer chromatography (Merck 60 gel plates) using an UV-lamp for visualization.

Chromatography.

Analytical high-performance liquid chromatography (HPLC) was carried out using an Agilent 1200 series, and a Kromasil 100 C18 column (Peeke Scientific, 4.6×50 mm, 5 µm). Semi-preparative HPLC was performed using an Agilent XDB-C18 (9.4×250 mm, 5 µm). Analytical chiral HPLC was conducted using a supercritical fluid chromatography (SFC) system with isopropanol and liquid $CO_2$ as the mobile phase. Chiralcel OB-H and OJ columns were used to separate sulfimide enantiomers (4.6×150 mm, 5 µM). Sulfides were all commercially available and sulfimide standards were prepared as reported. e.r. values determined by dividing the major peak area by the sum of the peak areas determined by SFC chromatography.

Cloning and Site-Directed Mutagenesis.

pET22b(+) was used as a cloning and expression vector for all enzymes described in this study. Site-directed mutagenesis on P411BM3-CIS T438S to generate P411BM3-CIS I263A T438S was performed using a modified QuickChange™ mutagenesis protocol. The PCR products were gel purified, digested with DpnI, and directly transformed into E. coli strain BL21 (DE3).

Determination of P450 Concentration.

Concentration of P450/P411 enzymes was accomplished by quantifying the amount of free hemin present in purified protein using the pyridine/hemochrome assay.

Protein Expression and Purification.

Enzymes used in purified protein experiments were expressed in BL21(DE3) E. coli cultures transformed with plasmid encoding P450 or P411 variants. Expression and purification was performed as described elsewhere, except that the shake rate was lowered to 130 RPM during expression. Following expression, cells were pelleted and frozen at −20° C. For purification, frozen cells were resuspended in buffer A (20 mM tris, 20 mM imidazole, 100 mM NaCl, pH 7.5, 4 mL/g of cell wet weight) and disrupted by sonication (2×1 min, output control 5, 50% duty cycle; Sonicator 3000, Misonix, Inc.). To pellet insoluble material, lysates were centrifuged at 24,000×g for 0.5 h at 4° C. Proteins were expressed in a construct containing a 6×-His tag and were consequently purified using a nickel NTA column (5 mL HisTrap HP, GE Healthcare, Piscataway, N.J.) using an AKTAxpress purifier FPLC system (GE healthcare). P450 or P411 enzymes were then eluted on a linear gradient from 100% buffer A 0% buffer B (20 mM tris, 300 mM imidazole, 100 mM NaCl, pH 7.5) to 100% buffer B over 10 column volumes (P450/P411 enzymes elute at around 80 mM imidazole). Fractions containing P450 or P411 enzymes were pooled, concentrated, and subjected to three exchanges of phosphate buffer (0.1 M KPi pH 8.0) to remove excess salt and imidazole. Concentrated proteins were aliquoted, flash-frozen on powdered dry ice, and stored at −20° C. until later use.

Typical Procedure for Small-Scale Sulfimidation Bioconversions Under Anaerobic Conditions Using Purified Enzymes.

Small-scale reactions (400 μL) were conducted anaerobically in 2 mL crimp vials. A solution of aryl sulfide in DMSO or methanol (100 mM, 10 μL) was added to the reaction vial via syringe, followed by arylsulfonyl azide (100 mM, 10 μL, DMSO). Final concentrations of the reagents were typically: 2.5 mM aryl sulfide, 2.5 mM arylsulfonyl azide, 10 mM NADPH, 25 mM glucose, 5-20 μM P450. To the vials were then added acetonitrile (460 μL) and internal standard (1,3,5 trimethoxybenzene, 10 mM in 10% DMSO/90% acetonitrile, 1 mM final concentration). This mixture was then transferred to a microcentrifuge tube, and centrifuged at 17,000×g for 5 minutes. A portion (20 μL) of the supernatant was then analyzed by HPLC. Sulfimide formation was quantified by comparison of integrated peak areas of internal standard (1,3,5-trimethoxy benzene, 1 mM or 1,3,5-trichlorobenzene, 1 mM) and sulfimide at 220 nm to a calibration curve made using synthetically produced sulfimide and internal standard. Coefficients determined from standard curves were multiplied by a dilution factor in order to obtain sulfimide concentrations in the reaction mixture. Standard curves and response factors for products 8a-8d are presented in FIGS. 17-20. For chiral HPLC, the quenched reaction mixture was extracted twice with ethyl acetate (2×350 μL), dried under a light argon stream and resuspended in acetonitrile (100 μL).

Controls to Confirm the Enzymatic Sulfimidation Activity of Variant P411$_{BM3}$CIS T438S.

Small-scale reactions (400 μL total volume) were set up and worked up as described above. For the reaction containing hemin as catalyst, 10 μL of a hemin solution (1 mM in 50% DMSOH2O) was added to a final concentration of 25 TTNs were determined as described above and are presented in Table 7. CS denotes 'complete system' in which all components of the reactions as described above are present. Variations from the complete system are denoted with a "-X" where X is the component removed.

TABLE 7

Control experiments using substrate 7c yielding products 8c (sulfimide) and 9 (sulfonamide). CS = complete system.

| Condition | TTN 8c | TTN 9 |
| --- | --- | --- |
| P411$_{BM3}$-CIS T438S (CS) | 90 | 300 |
| CS-NADPH | 1 | 2 |
| CS + Na$_2$S$_2$O$_4$ + CO | 2 | 40 |
| CS boiled enzyme | 1 | 53 |
| CS aerobic | 2.3 | 16 |
| Hemin + Na$_2$S$_2$O$_4$ | 0 | 42 |
| CS-P411$_{BM3}$-CIS T438S | 0 | 21 |

Synthesis of Substrates and Standards.

All sulfimides presented in Table 8 were obtained form commercial sources (Sigma Aldrich, Alfa Aesar). Sulfmide standards were synthesized using known techniques.

TABLE 8

Impact of sulfide substituents on Sulfimidation activity with P411$_{BM3}$-CIS T438S.

| entry | R$_1$ in 7 | R$_2$ in 7 | TTN 8 | TTN 9 |
| --- | --- | --- | --- | --- |
| a | —OMe | —H | 300 | 270 |
| b | —Me | —H | 190 | 400 |
| c | —H | —Me | 100 | 390 |
| d | —H | —H | 30 | 500 |
| e | —CHO | —H | <1$^a$ | 510 |

$^a$Trace product observed by liquid chromatography-mass spectrometry (LC-MS).

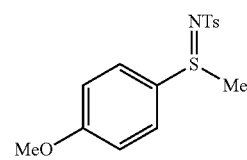

8a $_1$H NMR (500 MHz; CDCl$_3$): δ=7.71 (d, J=8.0 Hz, 2H), 7.61 (d, J=8.9 Hz, 2H), 7.15 (d, J=8.35 Hz, 2H), 6.96 (d, J=8.9 Hz, 2H), 3.83 (s, 3H), 2.81 (s, 3H), 2.34 (s, 3H).

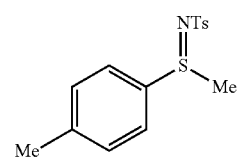

8b

1H NMR (500 MHz; CDCl3): δ=7.72 (d, J=8.2 Hz, 2H), 7.57 (d, J=8.2 Hz, 2H), 7.28 (d, J=7.3 Hz, 2H), 7.16 (d, J=8.1 Hz, 2H), 2.82 (s, 3H), 2.39 (s, 3H), 2.35 (s, 3H)

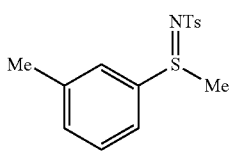

8c

1H NMR (500 MHz; CDCl3): δ=7.73 (d, J=8.0 Hz, 2H), 7.48-7.33 (m, 4H), 7.17 (d, J=8.1 Hz, 2H), 2.82 (s, 3H), 2.36 (s, 3H), 2.35 (s, 3H)

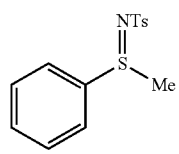

8d

1H NMR (500 MHz; CDCl3): δ=7.72 (d, J=7.8 Hz, 2H), 7.55-7.46 (m, 5H), 7.16 (d, J=8.1 Hz, 2H), 2.83 (s, 3H), 2.34 (s, 3H)

The 1H NMR listings above for products 8a-8d matched those of characterized compounds.

Determination of Initial Rates.

Four 2-ml vials were charged with a stir bar, 10× oxygen depletion system (40 μL), and a solution of enzyme prior to crimp sealing with a silicon septum. Once sealed, the headspace was flushed with argon for at least 10 minutes. Concurrently, a sealed 6-mL vial charged with glucose (250 mM, 400 μL), NADPH (20 mM, 400 μL), and KPi (pH=8.0, 0.1 M, 2.6 mL) was sparged for 10 minutes with argon. After degassing was complete, 340 μL of the reaction solution was transferred to the 2-mL vial via syringe. Sulfide (100 mM, 10 μL) was added to all four 2-mL vials followed quickly (less than 20 seconds) by tosyl azide (100 mM, 10 μL). The reactions were quenched at 1-2 minute intervals over 5-10 minutes by decapping and adding acetonitrile (460 μL). After 5 minutes of stirring, the vials were charged with internal standard and the reaction mixtures were transferred to 1.8 mL tubes, which were vortexed and centrifuged (14,000×g, 5 min). The supernatant was transferred to a vial for analysis by HPLC. Initial rates are plotted for individual enzymes referenced in FIG. 7, and for various substituted aryl sulfides in FIG. 12.

Visible Absorbance Spectroscopy and Observation of Resting States.

Figure 13:
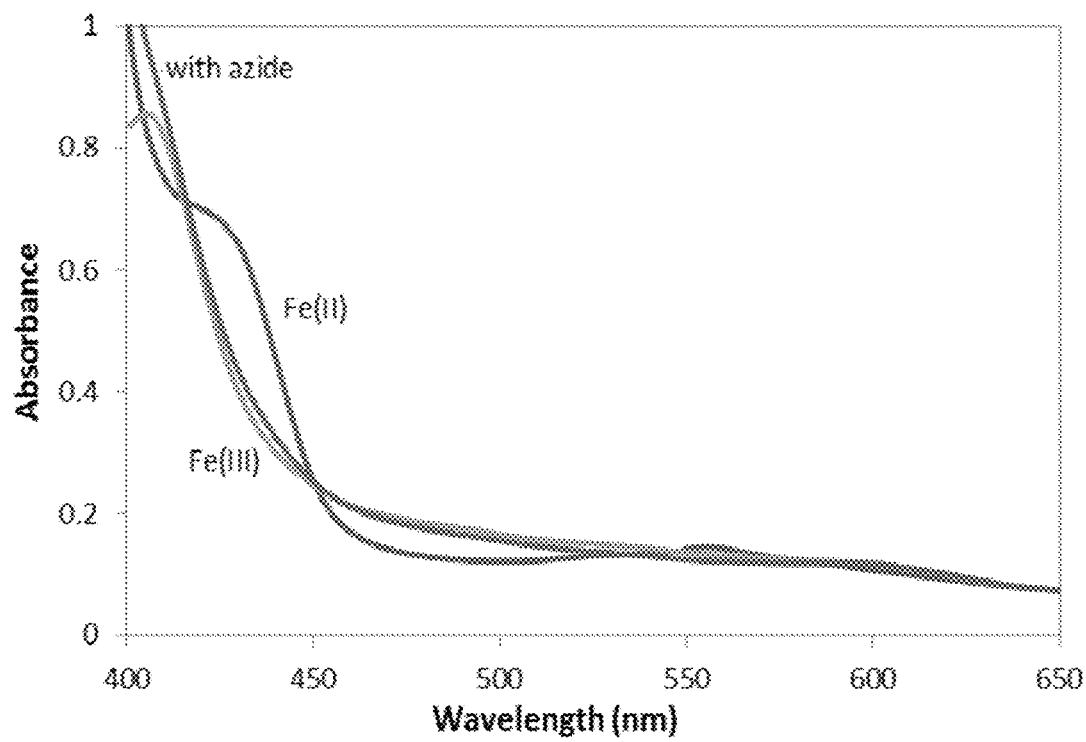
FIG. 13 shows visible spectroscopy of Fe(III) and Fe(II)-$P411_{BM3}$CIS I263A T438S in the presence of NADPH, followed by azide addition.

To a semi-micro anaerobic cuvette, 8 μL of P411$_{BM3}$CIS I263A T438S (400 μM) was added. To obtain a spectrum of the ferric protein, 0.5 mL of degassed phosphate buffer was added to the cuvette and the visible spectrum was recorded from 650 to 400 nm. To obtain a spectrum of the ferrous protein, the cuvette was sealed with a cap equipped with rubber septa and the headspace of the cuvette was purged with a gentle stream of Ar for 3 min. A solution of NADPH (5 mM) was added to a 6 mL crimp vial and made anaerobic by sparging with Ar for 5 min. The NADPH solution (0.5 mL) was then added to the anaerobic cuvette containing protein. Visible spectra of the protein sample are recorded until a stable ferrous state is reached. Representative spectra of the Fe(III)- and Fe(II)-protein are shown below (FIG. 13).

To determine the resting state of the protein in the unproductive catalytic cycle, a degassed solution of tosyl azide (2 μL, 400 mM in DMSO) was added to a fully reduced sample of ferrous protein. The visible spectrum of the protein shifted to the ferric heme immediately and remained unchanged for 20 min. Addition of an aliquot of organic solvent of similar volume did not cause the observed change in iron oxidation state. At the end of 20 minutes (FIG. 13), the cuvette was uncapped and the reaction mixture was worked up following the general procedure for small scale reactions. HPLC of the resulting solution confirmed that a substantial amount of azide is reduced to the corresponding sulfonamide.

To determine the resting state of the protein during the sulfimidation reaction, a degassed solution of sulfide 7a (2 μL, 400 mM in DMSO) was added to the cuvette containing P411BM3CIS I263A T438S in the presence of NADPH. A visible absorbance spectrum of the mixture was recorded to ensure that the oxidation state of iron heme is unchanged. Next, a degassed solution of tosyl azide (2 μL, 400 mM in DMSO) was added to the cuvette. Visible absorbance spectra of the solution were recorded at 5, 7, 12, 18, 22, 25 and 30 min (FIG. 14). The appearance of ferrous heme is observed over time. HPLC confirmed formation of both sulfimide and sulfonamide.

Excess Sulfide and Azide Slow Addition Experiments.

To assess the impact of sulfide concentration on overall productivity of reaction, sulfide was added to reaction ranging from 0.5 eq to 4 eq relative to azide. 1 eq of azide denotes 1 mM in the small scale reactions described above. Results are plotted in FIG. S10 below as a ratio of the TTN for sulfimide vs. TTN for sulfonamide. Slow addition was accomplished by adding 1 μL of a 100 mM (100 nmol) tosyl azide solution (DMSO) at 15 minute intervals to a reaction set up as described previously with 0.4% catalyst loading, containing 2.5 mM 7a. Azide was added over 150 minutes until equimolar final concentrations of sulfide and azide were achieved. Results of the slow addition are presented in FIG. 16.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method for catalyzing the intermolecular insertion of nitrogen into organosulfur substrates to produce a product having a new S-N bond, the method comprising:

providing a mixture comprising a nitrene source, an organosulfur substrate and a heme enzyme comprising the amino acid sequence of SEQ ID NO: 1 or an engineered heme enzyme comprising the amino acid sequence of SEQ ID NO: 1 with the exception of at least one, two, three, four, five, six, seven, eight, nine, ten, eleven, twelve, or all of the following amino acid substitutions in the amino acid sequence of SEQ ID NO: $1_L$ V78A, F87C, P142S, T175I, A184V, S226R, H236Q, T438S, E252G, A290V, L353V, I366V, C400X, T438S and E442K, wherein "X" is any amino acid other than Cys; and reacting said mixture for a time sufficient to form a product having a new S-N bond.

2. The method of claim 1, wherein said nitrene source is an azide.

3. The method of claim 2, wherein said azide has the general formula $R^1$—$N_3$, wherein $R^1$ is:
(i) a substituted or unsubstituted aryl, a substituted or unsubstituted aryl, —$OR^2$, or —$NR^2$, wherein $R^2$ is a substituted or unsubstituted aryl, a substituted or unsubstituted alkyl;
(ii) —$SO_2R^3$, wherein $R^3$ is a substituted or unsubstituted aryl, a substituted or unsubstituted alkyl, —$OR^2$, or —$NR^2$, wherein $R^2$ are any alkyl or aryl;
(iii) —$COR^4$, wherein $R^4$ is a substituted or unsubstituted aryl, a substituted or unsubstituted alkyl, —$OR^2$, or —$NR^2$, wherein $R^2$ are any alkyl or aryl; or
(iv) —$P(O)(OR^5)(OR^6)$, wherein $R^5$ and $R^6$ are independently H, a substituted or unsubstituted aryl, a substituted or unsubstituted alkyl.

4. The method of claim 3, wherein said azide has a structure selected from the group consisting of:

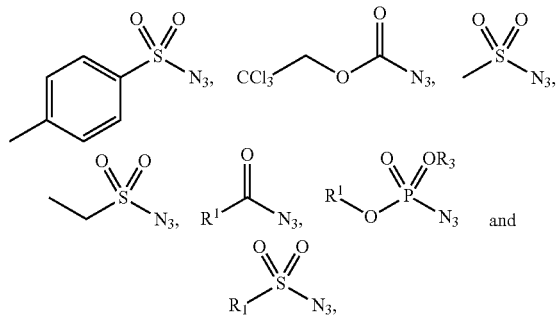

wherein $R^1$ is any alkyl, aryl, —OR, $NR^2$, wherein R, $R^2$ and $R^3$ are any alky, or aryl.

5. The method of claim 1, wherein said nitrene source is selected from the group consisting of:

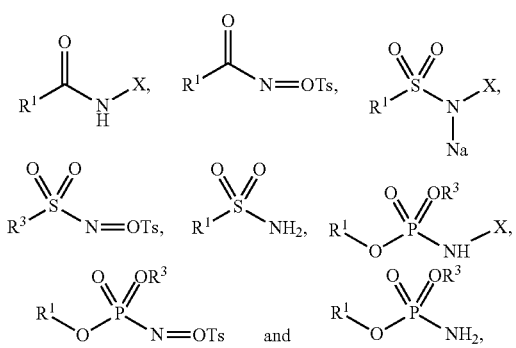

wherein $R^1$ is any alkyl, aryl, —OR, $NR^2$, wherein R, $R^2$ and $R^3$ are any alkyl, or aryl.

6. The method of claim 1, wherein said product having a new S-N bond is an aliphatic amine and said nitrene source is tosyl azide.

7. The method of claim 1, wherein said product having a new S-N bond is generated through a nitrenoid intermediate.

8. The method of claim 1, further comprising expressing said heme enzyme in a bacterial, archaeal or fungal host organism.

9. The method of claim 1, wherein said engineered heme enzyme comprises a T268A mutation, a T438S mutation and/or a C400X mutation in the amino acid sequence of SEQ ID NO: 1, wherein X is any amino acid other than Cys.

10. The method of claim 1, wherein said product having a new S-N bond is a compound of Formula Ia:

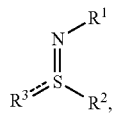

Formula Ia wherein $R^1$ is a sulfoxide, a carbonyl or a phosphonate;
wherein $R^2$ is H or any alkyl or aryl; and
wherein $R^3$ is H, O or an optionally substituted aryl group.

11. The method of claim 10, wherein $R^1$ is a sulfoxide of formula $SO_2R^5$, wherein $R^5$ is any alkyl, any aryl, —$OR^6$ or $NR^7$, wherein $R^6$ and W are any alkyl or any aryl.

12. The method of claim 10, wherein W is a phosphonate of formula $P(O)(OR^8)(OR^9)$, wherein $R^8$ and $R^9$ are independently any aryl or any alkyl.

* * * * *